United States Patent
Peters et al.

(10) Patent No.: US 12,018,258 B2
(45) Date of Patent: Jun. 25, 2024

(54) MOBILE-CRISPRi PLASMIDS AND RELATED METHODS

(71) Applicants: CZ Biohub SF, LLC, San Francisco, CA (US); The Regents of the University of California, Oakland, CA (US)

(72) Inventors: Jason Peters, Madison, WI (US); Carol Gross, Berkeley, CA (US); Oren Rosenberg, San Francisco, CA (US); Neha Prasad, San Francisco, CA (US)

(73) Assignees: CZ Biohub SF, LLC, San Francisco, CA (US); The Regents of the University of California, Oakland, CA (US)

(*) Notice: Subject to any disclaimer, the term of this patent is extended or adjusted under 35 U.S.C. 154(b) by 433 days.

(21) Appl. No.: 17/012,486

(22) Filed: Sep. 4, 2020

(65) Prior Publication Data

US 2021/0071179 A1 Mar. 11, 2021

Related U.S. Application Data

(60) Provisional application No. 62/897,162, filed on Sep. 6, 2019.

(51) Int. Cl.
*C12N 15/113* (2010.01)
*C12N 9/22* (2006.01)
*C12N 15/70* (2006.01)

(52) U.S. Cl.
CPC .............. *C12N 15/113* (2013.01); *C12N 9/22* (2013.01); *C12N 15/70* (2013.01); *C12N 2310/20* (2017.05)

(58) Field of Classification Search
CPC ........ C12N 15/113; C12N 9/22; C12N 15/70; C12N 2310/20; C12N 2330/31; C12N 2330/51; C12N 15/1093; C12N 15/111; C12N 15/63; C12N 15/74
See application file for complete search history.

(56) References Cited

PUBLICATIONS

Altschul et al., "Basic local alignment search tool", J. Mol. Biol., Oct. 1990, pp. 403-410, vol. 215, Issue 3.
Altschul et al., "Gapped BLAST and PSI-BLAST: a new generation of protein database search programs", Nucleic Acids Res., 1997, pp. 3389-3402, vol. 25, No. 17.
Auchtung et al. "Identification and characterization of the immunity repressor (ImmR) that controls the mobile genetic element ICEBs1 of Bacillus subtilis", Mol. Microbiol., May 18, 2007, pp. 1515-1528, 64 (6).
Auchtung et al. "Regulation of a Bacillus subtilis mobile genetic element by intercellular signaling and the global DNA damage response", Proc. Natl. Acad. Sci. U. S. A, Aug. 30, 2005, pp. 12554-12559, vol. 102, No. 35.
Baccanari et al. "Purification and properties of *Escherichia coli* dihydrofolate reductase", Biochemistry, Dec. 1, 1975, pp. 5267-5273, 14(24).
Bokulich et al., "Facility-specific 'house' microbiome drives microbial landscapes of artisan cheesemaking plants", Appl. Environ. Microbiol., Sep. 2013, pp. 5214-5223, vol. 79 No. 17.
Brophy et al., "Engineered integrative and conjugative elements for efficient and inducible DNA transfer to undomesticated bacteria", Nat. Microbiol. Aug. 20, 2018, pp. 1043-1053, 3.
Cardona et al., "Genomic tools to profile antibiotic mode of action", Crit. Rev. Microbiol. 2015, pp. 465-472, vol. 41, Issue 4.
Choi et al., "mini-Tn7 insertion in bacteria with single attTn7 sites: example Pseudomonas aeruginosa", Nat. Protoc. 1, Jun. 27, 2006, pp. 153-161, 1.
Choi et al., "A Tn7-based broad-range bacterial cloning and expression system", Nat. Methods, May 20, 2005, pp. 443-448, 2.
Choi et al., "Genetic Tools for Select-Agent-Compliant Manipulation of Burkholderia pseudomallei", Appl. Environ. Microbiol., 2008, pp. 1064-1075 (74).
Ferrières et al., "Silent Mischief: Bacteriophage Mu Insertions Contaminate Products of *Escherichia coli* Random Mutagenesis Performed Using Suicidal Transposon Delivery Plasmids Mobilized by Broad-Host-Range RP4 Conjugative Machinery", J. Bacteriol. 2010, pp. 6418-6427 (192).
Gilbert et al., "CRISPR-mediated modular RNA-guided regulation of transcription in eukaryotes", Cell, Jul. 18, 2013, pp. 442-451, vol. 154, Issue 2.
Gilbert et al., "Genome-Scale CRISPR-Mediated Control of Gene Repression and Activation", Cell, Oct. 23, 2014, pp. 647-661, vol. 159, Issue 3.
Ji et al., "Specific gene repression by CRISPRi system transferred through bacterial conjugation", ACS Synth. Biol., Nov. 19, 2014, pp. 929-931 (3).
Johnson et al., "Integrative and Conjugative Elements (ICEs): What They Do and How They Work", Annu. Rev. Genet., 2015, pp. 577-601 (49).
Jost et al., "Combined CRISPRi/a-Based Chemical Genetic Screens Reveal that Rigosertib Is a Microtubule-Destabilizing Agent", Mol. Cell, Oct. 5, 2017, pp. 210-223.e6, vol. 68, Issue 1.
Karlin et al., "Methods for assessing the statistical significance of molecular sequence features by using general scoring schemes", Proc. Natl. Acad. Sci. USA, Mar. 1990, pp. 2264-2268 (87).

(Continued)

*Primary Examiner* — James D Schultz
*Assistant Examiner* — Eric J Rogers
(74) *Attorney, Agent, or Firm* — Kilpatrick Townsend & Stockton LLP

(57) ABSTRACT

Described in this disclosure are CRISPRi systems and methods, along with the related compositions and kits, that combine modularity, stable genomic integration, and ease of transfer to diverse bacteria by conjugation. CRISPRi compositions, methods, systems and kits described herein allow for genetic dissection of bacteria, facilitating analyses of microbiome function, antibiotic resistances and sensitivities, as well as comprehensive screening for host-microbe interactions. Embodiments of the invention comprise compositions, methods, systems, and kits for CRISPRi-based repression of gene expression in bacteria.

29 Claims, 10 Drawing Sheets

Specification includes a Sequence Listing.

(56) References Cited

PUBLICATIONS

Karlin et al., "Applications and statistics for multiple high-scoring segments in molecular sequences", Proc. Natl. Acad. Sci. USA, Jun. 15, 1993, pp. 5873-5877, 90 (12).

Koo et al., "Construction and Analysis of Two Genome-Scale Deletion Libraries for Bacillus subtilis", Cell Syst., Mar. 22, 2017, pp. 291-305.e7, vol. 4, Issue 3.

Kritikos et al., "A tool named Iris for versatile high-throughput phenotyping in microorganisms", Nat. Microbiol., Feb. 17, 2017 pp. 1-24 (2).

Liberati et al., "An ordered, nonredundant library of Pseudomonas aeruginosa strain PA14 transposon insertion mutants", Proc. Natl. Acad. Sci. U.S.A., Feb. 21, 2006, pp. 2833-2838, 103 (8).

Liu et al., "High-throughput CRISPRi phenotyping identifies new essential genes in *Streptococcus pneumoniae*", Mol. Syst. Biol., 2017, pp. 1-18, 13.

McMahon et al., "Extensive DNA mimicry by the ArdA anti-restriction protein and its role in the spread of antibiotic resistance", Nucleic Acids Res., Aug. 1, 2009, pp. 4887-4897, vol. 37, Issue 15.

Mimee et al., "Programming a Human Commensal Bacterium, Bacteroides thetaiotaomicron, to Sense and Respond to Stimuli in the Murine Gut Microbiota", Cell Syst., Jul. 29, 2015, pp. 62-71, vol. 1, Issue 1.

Peters et al., "Enabling genetic analysis of diverse bacteria with Mobile-CRISPRi", Nature Microbiology, Feb. 2019, pp. 244-250, 4 (2).

Peters et al., "Recruitment of CRISPR-Cas systems by Tn7-like transposons", Proc. Natl. Acad. Sci., Aug. 29, 2017, pp. E7358-E7366, 114.

Peters, "Tn7", Microbiol. Spectr., 2014, pp. 1-20, 2.

Peters et al., "A Comprehensive, CRISPR-based Functional Analysis of Essential Genes in Bacteria", Cell, Jun. 2, 2016, pp. 1493-1506, vol. 165, Issue 6.

Qi et al., "Repurposing CRISPR as an RNA-guided platform for sequence-specific control of gene expression", Cell, Feb. 28, 2013, pp. 1173-1183, vol. 152, Issue 5.

Qu et al., "Modulating pathogenesis with Mobile-CRISPRi", Journal of Bacteriology, Nov. 2019, pp. 1-9, e00319, 22(201).

Rock et al., "Programmable transcriptional repression in mycobacteria using an orthogonal CRISPR interference platform", Nat. Microbiol. Feb. 6, 2017, pp. 1-21, 2.

Tan et al., "A Robust CRISPR Interference Gene Repression System in Pseudomonas", J. Bacteriol., 2018, pp. 1-12, 200.

van Opijnen et al., "Tn-seq: high-throughput parallel sequencing for fitness and genetic interaction studies in microorganisms", Nat. Methods, Sep. 20, 2009, pp. 767-772 (6).

Zhao et al., "Depletion of Undecaprenyl Pyrophosphate Phosphatases Disrupts Cell Envelope Biogenesis in Bacillus subtilis", J. Bacteriol., Nov. 2016, pp. 2925-2935, 198 (21).

Peters et al., Mobile-CRISPRi: Enabling Genetic Analysis of Diverse Bacteria, bioRxiv preprint, Available online at https://www.biorxiv.org/content/10.1101/315499v1.full.pdf, May 5, 2018, 25 pages.

MOBILE-CRISPRi PLASMIDS AND RELATED METHODS

CROSS REFERENCE TO RELATED APPLICATION

This application claims the benefit of U.S. Provisional Application No. 62/897,162, filed Sep. 6, 2019, which is incorporated by reference in its entirety herein.

STATEMENT AS TO RIGHTS TO INVENTIONS MADE UNDER FEDERALLY SPONSORED RESEARCH OR DEVELOPMENT

This invention was made with government support under Grant Nos R01 AI128214 and R35 GM118061 awarded by the National Institutes of Health. The government has certain rights in the invention.

FIELD

The invention relates to the fields of microbiology, molecular biology, genetic engineering and other related fields and subfields, such as compositions, methods, systems and kits for CRISPRi-based stable genomic integration of nucleic acid sequences into bacteria.

BACKGROUND

The vast majority of bacteria, including human pathogens and microbiome species, lack genetic tools needed to systematically associate genes with phenotypes. This is the major impediment to understanding the fundamental contributions of genes and gene networks to bacterial physiology and human health. CRISPRi, a versatile method of blocking gene expression using a catalytically inactive Cas9 protein (dCas9) and programmable single guide RNAs (sgRNAs), has emerged as a powerful genetic tool to dissect the functions of essential and non-essential genes in species ranging from bacteria to humans, as discussed, for example, in the following publications: Qi, L. S. et al. Repurposing CRISPR as an RNA-guided platform for sequence-specific control of gene expression. *Cell* 152, 1173-1183 (2013) (1); Gilbert, L. A. et al. CRISPR-mediated modular RNA-guided regulation of transcription in eukaryotes. *Cell* 154, 442-451 (2013) (2); Mimee, M., et al. Programming a Human Commensal Bacterium, *Bacteroides* thetaiotaomicron, to Sense and Respond to Stimuli in the Murine Gut Microbiota. *Cell Syst.* 1, 62-71 (2015) (3); Peters, J. M. et al. A Comprehensive, CRISPR-based Functional Analysis of Essential Genes in Bacteria. *Cell* 165, 1493-1506 (2016) (4); Rock, J. M. et al. Programmable transcriptional repression in mycobacteria using an orthogonal CRISPR interference platform. *Nat. Microbiol.* 2, 16274 (2017) (5); and Tan, S. Z. et al. A Robust CRISPR Interference Gene Repression System in *Pseudomonas. J. Bacteriol.* 200, (2018) (6). However, the difficulty of establishing effective CRISPRi systems that can be used across bacteria is a major barrier to its widespread use to dissect bacterial gene function. Accordingly, CRISPRi systems and methods that combine modularity, stable genomic integration, and ease of transfer to diverse bacteria are needed.

SUMMARY

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are described and illustrated in the present document and the accompanying figures. This summary is not intended to identify key or essential features of the claimed subject matter, nor is it intended to be used in isolation to determine the scope of the claimed subject matter. The subject matter should be understood by reference to appropriate portions of the entire specification, any or all figures and each claim.

Described in this disclosure are CRISPRi systems and methods, along with the related compositions and kits, that combine modularity, stable genomic integration and ease of transfer to diverse bacteria by conjugation. The disclosure demonstrates the efficacy of CRISPRi compositions, methods, systems and kits described herein in Gammaproteobacteria and Bacillales Firmicutes at the both individual gene scale by examining drug-gene synergies and at the library scale by systematically phenotyping conditionally essential genes involved in amino acid biosynthesis. CRISPRi compositions, methods, systems and kits described herein allow for genetic dissection of bacteria, facilitating analyses of microbiome function, antibiotic resistances and sensitivities, as well as comprehensive screening for host-microbe interactions. Embodiments of the invention comprise devices, compositions, methods, systems, and kits for CRISPRi-based stable genomic integration of nucleic acid sequences into bacteria. The invention may be embodied in a variety of ways.

Among the exemplary embodiments of the present invention are artificial DNA constructs comprising (i) a nucleotide sequence encoding a single guide RNA (sgRNA) targeting a bacterial gene of interest and a first promoter operably linked thereto or a restriction site for insertion of the nucleotide sequence encoding the sgRNA alone or together with the first promoter operably linked thereto, (ii) a second promoter and a ribosome binding site operably linked to a nucleotide sequence encoding a catalytically inactive variant of CRISPR-associated protein 9 (dCas9), or one or more restriction sites for insertion of the nucleotide sequence encoding dCas9 and one or both of the second promoter and the ribosome binding site such that, when inserted, the second promoter and/or the ribosome binding site are operably linked to the sequence encoding dCas9, (iii) a nucleotide sequence of a gene conferring resistance to an antibiotic, or a restriction site for insertion of the gene conferring resistance to the antibiotic, and (iv) nucleotide transfer sequences comprising Tn7L and Tn7R transposon sequences or sequences encoding bacterial integrative and conjugative elements (ICE sequences), the nucleotide transfer sequences flanking elements (i)-(iii) of the artificial DNA construct, wherein the artificial DNA construct comprises at least one of the nucleotide sequence encoding a sgRNA and a first promoter operably linked to the nucleotide sequence encoding the sgRNA as (i) or the second promoter and the ribosome binding site operably linked to a nucleotide sequence encoding a dCas9 as (ii). The artificial DNA construct may comprise the restriction site for insertion of the nucleotide sequence encoding the sgRNA alone or together with a first promoter operably linked thereto, the second promoter and the ribosome binding site operably linked to the nucleotide sequence encoding dCas9, and the nucleotide sequence of the gene conferring resistance to the antibiotic. For example, the artificial DNA construct may comprise the nucleotide sequence encoding the sgRNA, the first promoter operably linked to the nucleotide sequence encoding the sgRNA, the second promoter and the ribosome binding site operably linked to the nucleotide sequence encoding dCas9, and the nucleotide sequence of the gene conferring resistance to the antibiotic. In some embodiments of the artificial DNA construct, the nucleotide transfer sequences are Tn7L and Tn7R transposon sequences. In some embodiments of the artificial DNA construct, the nucleotide transfer sequences are ICE sequences. In some embodiments of the artificial DNA construct, the nucleotide transfer sequences are integrative and conjugative elements from *Bacillus subtilis* (ICEBs1). The artificial DNA construct may further comprise a nucleotide sequence of a reporter gene or a restriction site for insertion of the nucleotide sequence of the reporter gene. The artificial DNA construct may further comprise a nucleotide sequence of a regulatory gene upstream of (i). In some examples, the artificial DNA construct may comprise a nucleic acid sequence having at least 90% identity to nucleotides to nucleotides 1501-10310 of SEQ ID NO:2, nucleotides 1501-11673 of SEQ ID NO:3, nucleotides 152-8155 of SEQ ID NO:4, nucleotides 152-8155 of SEQ ID NO:5, nucleotides 152-8155 of SEQ ID NO:6, nucleotides 2517-9310 of SEQ ID NO:7, nucleotides 2517-11688 of SEQ ID NO:8, nucleotides 2517-11688 of SEQ ID NO:9, nucleotides 2517-11836 of SEQ ID NO:10, nucleotides 2517-11650 of SEQ ID NO:11, nucleotides 2517-11710 of SEQ ID NO:12, nucleotides 2517-11710 of SEQ ID NO:13, nucleotides 2517-10705 of SEQ ID NO:14, nucleotides 152-8321 of SEQ ID NO:15, nucleotides 1-8272 of SEQ ID NO:16, nucleotides 1-10636 of SEQ ID NO:17, nucleotides 1-9813 of SEQ ID NO:18, nucleotides 152-8733 of SEQ ID NO:19, nucleotides 152-8714 of SEQ ID NO:20, nucleotides 152-8714 of SEQ ID NO:21, nucleotides 152-8714 of SEQ ID NO:22, nucleotides 152-8420 of SEQ ID NO: 37, nucleotides 152-8608 of SEQ ID NO:24, nucleotides 152-8846 of SEQ ID NO:25, nucleotides 152-8586 of SEQ ID NO:26, nucleotides 2517-4992 of SEQ ID NO:27, or nucleotides 8574 to 6498 of SEQ ID NO:28.

Among the embodiments of the present invention are DNA vectors comprising: (a) an artificial DNA construct comprising (i) a nucleotide sequence encoding a single guide RNA (sgRNA) targeting a bacterial gene of interest and a first promoter operably linked to the nucleotide sequence encoding the sgRNA, or a restriction site for insertion of a nucleotide sequence encoding the sgRNA alone or together with the first promoter operably linked thereto, (ii) a second promoter and a ribosome binding site operably linked to a nucleotide sequence encoding a catalytically inactive variant of CRISPR-associated protein 9 (dCas9), or one or more restriction sites for insertion of the nucleotide sequence encoding dCas9 and one or both of the second promoter and the ribosome binding site such that, when inserted, the second promoter and/or the ribosome binding site are operably linked to the sequence encoding dCas9, (iii) a nucleotide sequence of a gene conferring resistance to a first antibiotic, or a restriction site for insertion of the gene conferring resistance to the first antibiotic, and (iv) nucleotide transfer sequences comprising Tn7L and Tn7R transposon sequences or sequences comprising bacterial integrative and conjugative elements (ICE sequences), the nucleotide transfer sequences flanking elements (i)-(iii) of the artificial DNA construct; (b) a nucleotide sequence of a gene conferring resistance to a second antibiotic, the nucleotide sequence located outside the artificial DNA construct; (c) a conditional origin of replication located outside the artificial DNA construct; and (d) an origin of transfer site located outside the artificial DNA construct. In some examples of the DNA vector, the conditional origin of replication is R6K γ origin of replication. In some examples of the DNA vector, the artificial DNA construct may further comprise a nucleotide sequence of a reporter gene or a restriction site for insertion of the nucleotide sequence of the reporter gene. In some examples of the DNA vector, the artificial DNA construct may further comprise a nucleotide sequence of a regulatory gene upstream of (i). In some examples of the DNA vector, the nucleotide transfer sequences are Tn7L and Tn7R transposon sequences. In some examples of the DNA vector, the nucleotide transfer sequences are ICE sequences. In some examples of the DNA vector, the nucleotide transfer sequences are integrative and conjugative elements from *Bacillus subtilis* (ICEBs1). In some examples of the DNA vector, the artificial DNA construct comprises the restriction site for insertion of the nucleotide sequences encoding the sgRNA and the first promoter operably linked to the nucleotide sequence encoding the sgRNA, the second promoter and the ribosome binding site operably linked to the nucleotide sequence encoding the dCas9, and the nucleotide sequence of the gene conferring resistance to the first antibiotic. In some examples of the DNA vector, the artificial DNA construct comprises the nucleotide sequence encoding the sgRNA, the first promoter operably linked to the nucleotide sequence encoding the sgRNA, the second promoter and the ribosome binding site operably linked to the nucleotide sequence encoding dCas9, and the nucleotide sequence of the gene conferring resistance to the first antibiotic. In some examples of the DNA vector, the artificial DNA construct comprises the nucleic acid sequence having at least 90% or at least 95% identity to nucleotides 1501-10310 of SEQ ID NO:2, nucleotides 1501-11673 of SEQ ID NO:3, nucleotides 152-8155 of SEQ ID NO:4, nucleotides 152-8155 of SEQ ID NO:5, nucleotides 152-8155 of SEQ ID NO:6, nucleotides 2517-9310 of SEQ ID NO:7, nucleotides 2517-11688 of SEQ ID NO:8, nucleotides 2517-11688 of SEQ ID NO:9, nucleotides 2517-11836 of SEQ ID NO:10, nucleotides 2517-11650 of SEQ ID NO:11, nucleotides 2517-11710 of SEQ ID NO:12, nucleotides 2517-11710 of SEQ ID NO:13, nucleotides 2517-10705 of SEQ ID NO:14, nucleotides 152-8321 of SEQ ID NO:15, nucleotides 1-8272 of SEQ ID NO:16, nucleotides 1-10636 of SEQ ID NO:17, nucleotides 1-9813 of SEQ ID NO:18, nucleotides 152-8733 of SEQ ID NO:19, nucleotides 152-8714 of SEQ ID NO:20, nucleotides 152-8714 of SEQ ID NO:21, nucleotides 152-8714 of SEQ ID NO:22, nucleotides 152-8420 of SEQ ID NO: 37, nucleotides 152-8608 of SEQ ID NO:24, nucleotides 152-8846 of SEQ ID NO:25, nucleotides 152-8586 of SEQ ID NO:26, nucleotides 2517-4992 of SEQ ID NO:27, or nucleotides 8574 to 6498 of SEQ ID NO:28. In some examples, the DNA vector has at least 90% or at least 95% identity to SEQ ID NO:14, SEQ ID NO:18, SEQ ID NO:19 or SEQ ID NO:28. DNA vectors having at least 90% or at least 95% sequence identity to SEQ ID NO:1, SEQ ID NO:14, SEQ ID NO:18, SEQ ID NO:19, or SEQ ID NO:28 are also included among the exemplary embodiments of the present invention.

Also among the embodiments of the present invention are engineered bacterial cells comprising a DNA vector according to the embodiments of the present invention. In some examples, an engineered bacterial cell may comprise a DNA vector in which the artificial DNA construct comprises a restriction site for insertion of the nucleotide sequences encoding the sgRNA, the second promoter and the ribosome binding site operably linked to the nucleotide sequence encoding dCas9, and the nucleotide sequence of the gene conferring resistance to the first antibiotic. In some examples, an engineered bacterial cell may comprise a DNA vector in which the artificial DNA construct comprises the nucleotide sequence encoding the sgRNA, the first promoter operably linked to the nucleotide sequence encoding the sgRNA, the second promoter and the ribosome binding site operably linked to the nucleotide sequence encoding dCas9, and the nucleotide sequence of the gene conferring resistance to the first antibiotic. In some examples of an engineered bacterial cell, the nucleotide transfer sequences in the DNA vector are Tn7L and Tn7R transposon sequences. Such an engineered bacterial cell may be an *Escherichia coli* bacterial cell. In some examples of an engineered bacterial cell, the nucleotide transfer sequences in the DNA vector are integrative and conjugative elements from *Bacillus subtilis* (ICEBs1). Such an engineered bacterial cell may be a *B. subtilis* bacterial cell.

Among the embodiments of the present invention are methods of producing engineered bacterial cells, comprising the steps of: (a) transforming a bacterial cell with the DNA vector according to the embodiments of the present invention, thereby creating the engineered bacterial cells comprising the DNA vector; and (b) growing the engineered bacterial cell in or on a growth medium comprising the second antibiotic under growth conditions leading to growth of the engineered bacterial cell. In a method of producing an engineered bacterial cell, the bacterial cell being transformed in step (a) may be a bacterial cell comprising a gene whose expression permits the conditional origin of replication to be functional. In a method of producing an engineered bacterial cell, the bacterial cell being transformed is step (a) may be auxotrophic and require the presence of a nutritional substance for growth, and the growing of step (b) is then conducted in a presence of the nutritional substance. In an example of a method of producing an engineered bacterial cell, the conditional origin of replication may be R6K γ origin of replication, and the bacterial cell being transformed is step (a) be a pir+ bacterial cell. In such an exemplary method, the pir+ bacterial cell is may be pir+ cell of *Escherichia coli*. In an example of a method of producing an engineered bacterial cell, the nucleotide transfer sequences in the DNA vector according to the embodiments of the present invention may be Tn7L and Tn7R transposon sequences. In such an exemplary method, the engineered bacterial cell may be an *Escherichia coli* bacterial cell. In an example of a method of producing an engineered bacterial cell, the nucleotide transfer sequences may be integrative and conjugative elements from *Bacillus subtilis* (ICEBs1). In such an exemplary method, the engineered bacterial cell may be a *B. subtilis* cell.

Also among the embodiments of the present invention are methods of generating engineered bacterial cells. An exemplary method of generating an engineered bacterial cell comprises the steps of: (a) providing a first donor engineered bacterial cell comprising RP4 transfer machinery and the DNA vector according to the embodiments of the present invention, in which the artificial DNA construct comprises the nucleotide sequence encoding the sgRNA, the first promoter operably linked to the nucleotide sequence encoding the sgRNA, the second promoter and the ribosome binding site operably linked to the nucleotide sequence encoding dCas9, and the nucleotide sequence of the gene conferring resistance to the first antibiotic, wherein the first donor engineered bacterial cell is auxotrophic and requires the presence of a nutritional substance for growth, wherein the first donor engineered bacterial cell comprises a gene allowing the conditional original of replication to be functional, and wherein the nucleotide transfer sequences are Tn7L and Tn7R transposon sequences; (b) providing a second donor engineered bacterial cell comprising a transposase gene, wherein the second donor engineered bacterial cell is auxotrophic and requires the presence of the nutritional substance for growth; (c) contacting the first donor engineered bacterial cell and the second donor engineered bacterial cell with a recipient bacterial cell under conditions allowing for mating of the first donor engineered cell, the second donor engineered cell, and the recipient bacterial cell, wherein the recipient bacterial cell does not require the presence of the nutritional substance for growth for growth; and (d) growing the contacted bacterial cells of step (c) in or on a medium comprising the first antibiotic and not including the nutritional substance thereby producing an engineered bacterial cell. In some embodiments, the transposase gene of the second donor engineered bacterial cell is located on a plasmid having at least 90% sequence identity to SEQ ID NO:1. In the above exemplary method, the recipient bacterial cell may be a Gammaproteobacteria class bacterial cell. In some examples, the Gammaproteobacteria class bacterial cell is *Escherichia coli, Enterobacter cloacae, Enterobacter aerogenes, Pseudomonas aeruginosa, Klebsiella pneumoniae, Vibrio casei, Salmonella enterica*, or *Proteus mirabilis*. In some examples, the Gammaproteobacteria class bacterial cell is *Acinetobacter baumannii*, and the method further comprises the step of providing a third donor engineered bacterial cell comprising a self-mobilizing RP4 transfer plasmid and, in the contacting step (c), contacting the first donor engineered bacterial cell, the second donor engineered bacterial cell and the third donor engineered bacterial cell with the recipient bacterial cell. In some example of the above exemplary method, the first donor engineered bacterial cell and the second donor engineered bacterial cells are engineered *Escherichia coli* cells. Another exemplary method of generating an engineered bacterial cell comprises the steps of: (a) providing a donor engineered bacterial cell comprising the DNA vector according to the embodiments of the present invention, in which the artificial DNA construct comprises the nucleotide sequence encoding the sgRNA, the first promoter operably linked to the nucleotide sequence encoding the sgRNA, the second promoter and the ribosome binding site operably linked to the nucleotide sequence encoding dCas9, and the nucleotide sequence of the gene conferring resistance to the first antibiotic, wherein the nucleotide transfer sequences are bacterial integrative and conjugative elements (ICE sequences), wherein the donor engineered bacterial cell comprises conjugation genes, and wherein the donor engineered bacterial cell comprises a gene allowing the conditional original of replication to be functional; (b) inducing expression of the conjugation genes, thereby causing excision of the artificial DNA construct from the DNA vector in the donor engineered bacterial cell; (c) after the inducing, contacting the donor engineered bacterial cell with a recipient bacterial cell under conditions allowing for mating of the donor engineered bacterial cell and the recipient bacterial cell, thereby resulting in transfer of the artificial DNA construct into the recipient bacterial cell, wherein a chromosome of the recipient bacterial cell carries a gene conferring resistance to a third antibiotic; and (d) growing the contacted bacterial cells of claim (c) in or on a medium comprising the first antibiotic and the third antibiotic thereby producing an engineered bacterial cell. In some examples of the above exemplary method, the recipient bacterial cell may be a Firmicutes bacterial cell. In some examples, the Firmicutes bacterial cell may be *Bacillus subtilis, Listeria monocytogenes, Staphylococcus aureus,* or *Enterococcus faecalis.* In some examples of the above exemplary method, the donor engineered bacterial cells may be a *B. subtilis* cell.

Among the embodiments of the present invention are engineered bacteria comprising an artificial DNA sequence integrated into a chromosome, the artificial DNA sequence comprising a nucleotide sequence encoding a single guide RNA (sgRNA) targeting a bacterial gene of interest, a first promoter operably linked to the nucleotide sequence encoding the sgRNA, a second promoter and a ribosome binding site operably linked to the nucleotide sequence encoding a catalytically inactive variant of CRISPR-associated protein 9 (dCas9), and a nucleotide sequence of a gene conferring resistance to an antibiotic. In some examples, an engineered bacterium may be engineered from a pathogenic bacterium, and wherein the bacterial gene of interest is a virulence or virulence life-style gene. In some examples, a bacterial gene of interest in an engineered bacterium may be an essential gene. An engineered bacterium may be engineered from a Gammaproteobacteria bacterium. In some examples, an engineered Gammaproteobacteria bacterium may be *Escherichia coli, Enterobacter cloacae, Enterobacter aerogenes, Pseudomonas aeruginosa, Klebsiella pneumoniae, Vibrio casei, Salmonella enterica, Acinetobacter baumannii,* or *Proteus mirabilis.* An engineered bacterium may be engineered from a Firmicutes bacterium. In some examples, an engineered Firmicutes bacterium may be *Bacillus subtilis, Listeria monocytogenes, Staphylococcus aureus,* or *Enterococcus faecalis.* Also among the embodiments of the present invention are methods of reducing expression of the bacterial gene of interest, comprising the step growing a population of the engineered bacteria according to the exemplary embodiments of the present invention, which comprise an artificial DNA sequence integrated into a chromosome, in the presence of the antibiotic and under conditions allowing for transcription of the sgRNA. In an exemplary method of reducing expression of the bacterial gene of interest, an artificial DNA construct according to the embodiments of the present invention may comprise a sequence encoding a regulator gene upstream of the nucleotide sequence encoding the sgRNA, and wherein the conditions allowing for the transcription of the sgRNA comprise conditions inducing expression of the regulator gene.

Among the embodiments of the present invention are vector libraries comprising a plurality of DNA vectors according to the embodiments of the present invention, wherein the plurality of vectors comprise a plurality of different sgRNAs comprising different targeting sequences. In an exemplary vector library, the different targeting sequences may target different bacterial genes of interest. Also among the embodiments of the present invention, are methods of constructing a knockdown library of bacterial cells. An exemplary method of constructing a knockdown library of bacterial cells comprises the steps of: (a) cloning a plurality of sgRNAs targeting a plurality of genes of interest into a plurality of DNA vectors according to the embodiments of the present invention, in which the artificial DNA construct comprises the restriction site for insertion of the nucleotide sequences encoding the sgRNA, the second promoter and the ribosome binding site operably linked to the nucleotide sequence encoding the dCas9, and the nucleotide sequence of the gene conferring resistance to the first antibiotic, wherein the nucleotide transfer sequences in the plurality of the vectors are Tn7L and Tn7R transposon sequences, thereby generating a vector library; (b) transforming a plurality of bacterial cells comprising RP4 transfer machinery with the vector library, wherein the bacterial cells are auxotrophic and require the presence of a nutritional substance for growth, and wherein the bacterial cells comprise a gene whose expression permits the conditional original of replication to be functional; (c) contacting under conditions allowing for mating (i) the plurality of transformed bacterial cells from step (b), (ii) a plurality of engineered bacterial cells comprising a transposase plasmid, wherein the engineered bacterial cells are auxotrophic and require the presence of the nutritional substance for growth, and (iii) a plurality of recipient bacterial cells not requiring the presence of the nutritional substance for growth; and (d) growing the contacted bacterial cells of step (c) in or on a medium comprising the first antibiotic and not including the nutritional substance thereby generating the knockdown library of bacterial cells. In the above exemplary method, in step (a), the plurality of sgRNAs may be cloned as a pool to generate the vector library, or each of sgRNA of the plurality of sgRNAs may cloned individually and then pooled to generate the vector library. Another exemplary method of constructing a knockdown library of bacterial cells, comprises the steps of: (a) transforming a plurality of bacterial cells comprising RP4 transfer machinery with a vector library according to embodiments of the present invention, wherein the bacterial cells are auxotrophic and require the presence of a nutritional substance for growth, and wherein the bacterial cells comprise a gene whose expression permits the conditional original of replication to be functional; (b) contacting under conditions allowing for mating (i) the plurality of transformed bacterial cells from step (b), (ii) a plurality of engineered bacterial cells comprising a transposase plasmid, wherein the engineered bacterial cells are auxotrophic and require the presence of the nutritional substance for growth, and (iii) a plurality of recipient bacterial cells not requiring the presence of the nutritional substance for growth; and (c) growing the contacted bacterial cells of step (c) in or on a medium comprising the first antibiotic and not including the nutritional substance thereby generating the knockdown library of bacterial cells. Another exemplary method of constructing a knockdown library of bacterial cells, comprises the steps of: (a) cloning a plurality of sgRNAs into a plurality of DNA vectors according to the embodiments of the present invention, in which the artificial DNA construct comprises the restriction site for insertion of the nucleotide sequences encoding the sgRNA, the second promoter and the ribosome binding site operably linked to the nucleotide sequence encoding the dCas9, and the nucleotide sequence of the gene conferring resistance to the first antibiotic, wherein the nucleotide transfer sequences in the plurality of the vectors are the bacterial integrative and conjugative elements (ICE), thereby generating a vector library; (b) transforming a plurality of bacterial cells with the vector library, wherein the bacterial cells comprise conjugation genes and a gene whose expression permits the conditional original of replication to be functional; (c) inducing expression of the conjugation genes in the transformed bacterial cells, thereby promoting the excision of the artificial DNA constructs from the vector library; (d) after the inducing, contacting transformed bacterial cells with a plurality of recipient bacterial cells under conditions allowing for mating of the transformed bacterial cells and the recipient bacterial cells, thereby resulting in transfer of the artificial DNA constructs into the recipient bacterial cells; and (e) growing the contacted bacterial cells in or on a medium comprising the first antibiotic thereby generating the knockdown library of bacterial cells. In the above exemplary method, in step (a), the plurality of sgRNAs may be cloned as a pool to generate the vector library, or each of the sgRNAs of the plurality of sgRNAs is cloned individually and then pooled to generate the vector library. Another exemplary method of constructing a knockdown library of bacterial cells comprises the steps of: (b) transforming a plurality of bacterial cells with the vector library according to the embodiments of the present invention, wherein the bacterial cells comprise conjugation genes and a gene whose expression permits the conditional original of replication to be functional; (c) inducing expression of the conjugation genes in the transformed bacterial cells, thereby promoting the excision of the artificial DNA constructs from the vector library; (d) after the inducing, contacting transformed bacterial cells with a plurality of recipient bacterial cells under conditions allowing for mating of the transformed bacterial cells and the recipient bacterial cells, thereby resulting in transfer of the artificial DNA constructs into the recipient bacterial cells; and (e) growing the contacted bacterial cells in or on a medium comprising the first antibiotic thereby generating the knockdown library of bacterial cells.

Among the embodiments of the present invention are systems for generating an engineered bacterium. An exemplary system may comprise: (a) an artificial DNA construct according to the embodiments of the present invention, in which the nucleotide transfer sequences are Tn7L and Tn7R transposon sequences, the construct comprising the restriction site for insertion of the nucleotide sequence encoding the sgRNA; and (b) a nucleic acid sequence of a transposase gene. In the above exemplary system, the artificial DNA construct may be located on a bacterial vector comprising a nucleotide sequence of a gene conferring resistance to a second antibiotic located outside the artificial DNA construct, a conditional origin of replication located outside the artificial DNA construct, and an origin of transfer site located outside the artificial DNA construct. In the above exemplary system, the nucleic acid sequence of the transposase gene may be located on a bacterial plasmid that does not include the artificial DNA construct. Inn some embodiments, the nucleic acid sequence of the transposase gene is located on a plasmid having at least 90% sequence identity to SEQ ID NO:1. The above exemplary system may further comprise a bacterial cell comprising RP4 transfer machinery, wherein the bacterial cell is auxotrophic and requires the presence of a nutritional substance for growth, and wherein the bacterial cell comprises a gene whose expression permits the conditional original of replication to be functional. The system may further comprise a recipient bacterial cell not requiring the presence of the nutritional substance for growth for growth. Another exemplary system for generating an engineered bacterium comprises: (a) an artificial DNA construct according to the embodiments of the present invention, in which the nucleotide transfer sequences are ICE sequences, the artificial DNA construct comprising the restriction site for insertion of the nucleotide sequence encoding the sgRNA; and, (b) a bacterial cell comprising conjugation genes and a gene whose expression permits the conditional original of replication to be functional. In the above exemplary system, the artificial DNA construct may be located on a bacterial vector comprising a nucleotide sequence of a gene conferring resistance to a second antibiotic located outside the artificial DNA construct, a conditional origin of replication located outside the artificial DNA construct, and an origin of transfer site located outside the artificial DNA construct. The above exemplary system may further comprise a recipient bacterial cell having a gene of interest that is targeted by the sgRNA. A chromosome of the recipient bacterial cell may carry a gene conferring resistance to a third antibiotic. Also among the embodiments of the present invention are kits comprising the DNA vectors according to the embodiment of the present invention. An exemplary kit comprises a DNA vector according to the embodiments of the present invention, in which the nucleotide transfer sequences are Tn7L and Tn7R transposon sequences, and a bacterial plasmid encoding transposase. In some embodiments, the nucleic acid sequence of the transposase gene is located on a plasmid having at least 90% sequence identity to SEQ ID NO:1. The above exemplary kit may further comprise a self-mobilizing RP4 transfer plasmid. The above exemplary kit may further comprise a plurality of auxotrophic bacterial cells comprising a gene whose expression permits the conditional origin of replication to be functional. Another exemplary kit is a kit comprising the DNA vector according to the embodiments of the present invention, in which the nucleotide transfer sequences are ICE sequences, and a plurality of auxotrophic bacterial cells comprising a gene whose expression permits the conditional original of replication to be functional.

DETAILED DESCRIPTION

Figure 1:
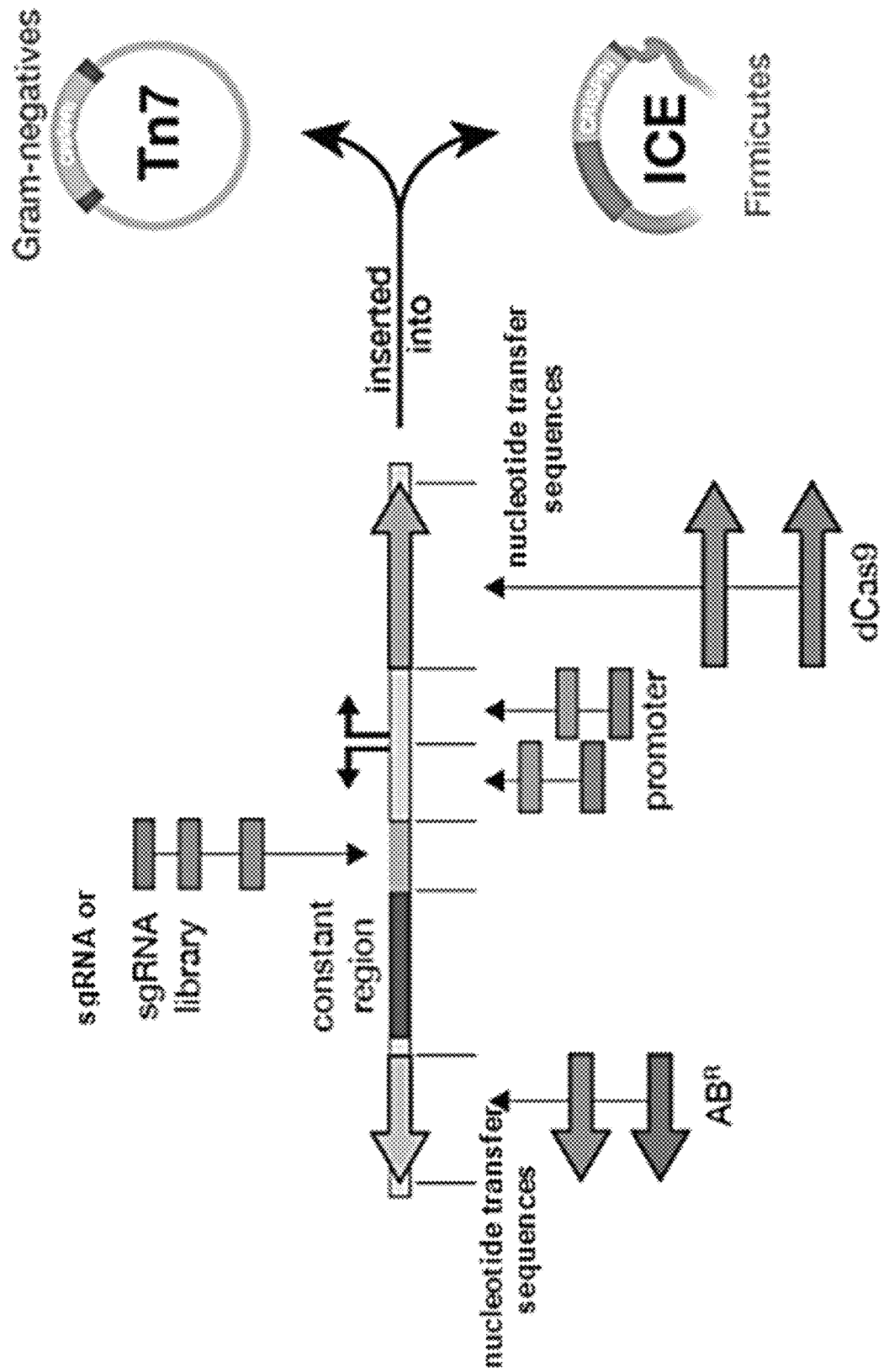
FIG. 1 schematically illustrates an artificial DNA construct encoding a single guide RNA (sgRNA) targeting a bacterial gene of interest according to aspects of this disclosure.

CRISPRi (Clustered Regularly Interspaced Short Palindromic Repeats interference) is a programmable method for controlling gene expression that has enabled systematic interrogation of gene phenotypes in diverse organisms. CRISPRi is described, for example, in the following publications: Qi, L. S. et al. Repurposing CRISPR as an RNA-guided platform for sequence-specific control of gene expression. *Cell* 152, 1173-1183 (2013) (1); Gilbert, L. A. et al. CRISPR-mediated modular RNA-guided regulation of transcription in eukaryotes. *Cell* 154, 442-451 (2013) (2); Mimee, M. et al. Programming a Human Commensal Bacterium, *Bacteroides* thetaiotaomicron, to Sense and Respond to Stimuli in the Murine Gut Microbiota. *Cell Syst.* 1, 62-71 (2015) (3); Peters, J. M. et al. A Comprehensive, CRISPR-based Functional Analysis of Essential Genes in Bacteria. *Cell* 165, 1493-1506 (2016) (4); Rock, J. M. et al. Programmable transcriptional repression in mycobacteria using an orthogonal CRISPR interference platform. *Nat. Microbiol.* 2, 16274 (2017) (5); and Tan, S. Z et al. A Robust CRISPR Interference Gene Repression System in *Pseudomonas*. *J. Bacteriol.* 200, (2018) (6).

In bacterial CRISPRi, a sgRNA-dCas9 complex binds to a target gene by base-pairing and reduces gene expression by sterically blocking transcription elongation. New CRISPRi targets are easily programmed by substituting the first 20 nt of the sgRNA sequence (spacer) to match the non-template strand of the target gene, allowing for design and construction of CRISPRi libraries that target specific sets of genes or the entire genome, as discussed, for example, in (4), Liu, X. et al. High-throughput CRISPRi phenotyping identifies new essential genes in *Streptococcus pneumoniae*. *Mol. Syst. Biol.* 13, (2017) (7), and Gilbert, L. A. et al. Genome-Scale CRISPR-Mediated Control of Gene Repression and Activation. *Cell* 159, 647-661 (2014) (8). Genetic screens using CRISPRi libraries have contributed new insights into fundamental biology and molecular medicine including identifying functions for uncharacterized essential genes and drug modes of action, a discussed, for example, in (4), (7) and Jost, M. et al. Combined CRISPRi/a-Based Chemical Genetic Screens Reveal that Rigosertib Is a Microtubule-Destabilizing Agent. *Mol. Cell* 68, 210-223.e6 (2017) (9).

CRISPRi provides several advantages over other methods for genetic manipulation in bacteria. CRISPRi knockdowns can be induced (see, e.g., (1) and (3)-(6)) and titrated/tuned (see, e.g., (4) and Vigouroux, A et al. Tuning dCas9's ability to block transcription enables robust, noiseless knockdown of bacterial genes. *Mol. Syst. Biol.* 14, e7899 (2018) (10)), allowing for depletion of essential gene products without complex strain construction strategies that remove genes from their native regulation. Dissecting genetic redundancy via multiplexed CRISPRi targeting of several genes in the same cell requires markedly less effort than construction of multiple-deletion strains. See, for example, (4) and Zhao, H. et al. Depletion of Undecaprenyl Pyrophosphate Phosphatases Disrupts Cell Envelope Biogenesis in *Bacillus subtilis*. *J. Bacteriol.* 198, 2925-2935 (2016) (11). At the genome scale, CRISPRi expands on prior transposon-based gene perturbation methods such as Tn-seq, which is described, for example, in van Opijnen, T. et al. Tn-seq: high-throughput parallel sequencing for fitness and genetic interaction studies in microorganisms. *Nat. Methods* 6, 767-772 (2009) (12), by allowing all genes-including essential genes that cannot be studied through deletion—to be systematically targeted so that a relatively small strain library provides comprehensive coverage of the genome. Moreover, the DNA sequences encoding sgRNAs serve as unique barcodes to differentiate CRISPRi strains mixed in a pool, allowing for competitive fitness measurements using next generation sequencing, as described, for example, in (8). CRISPRi blocks expression of downstream genes in operons, as described, for example, in (1) and (4), but this property can be used to further simplify libraries by targeting operons instead of genes. Despite its promise, CRISPRi has been used in only a few bacterial species both because CRISPRi has been transferred using species-specific or narrow host-range strategies, as described, for example, in (1), (3)-(6), and Ji, W. et al. Specific gene repression by CRISPRi system transferred through bacterial conjugation.

ACS Synth. Biol. 3, 929-931 (2014) (13), and because components need to be optimized for function in different species.

Figure 2:
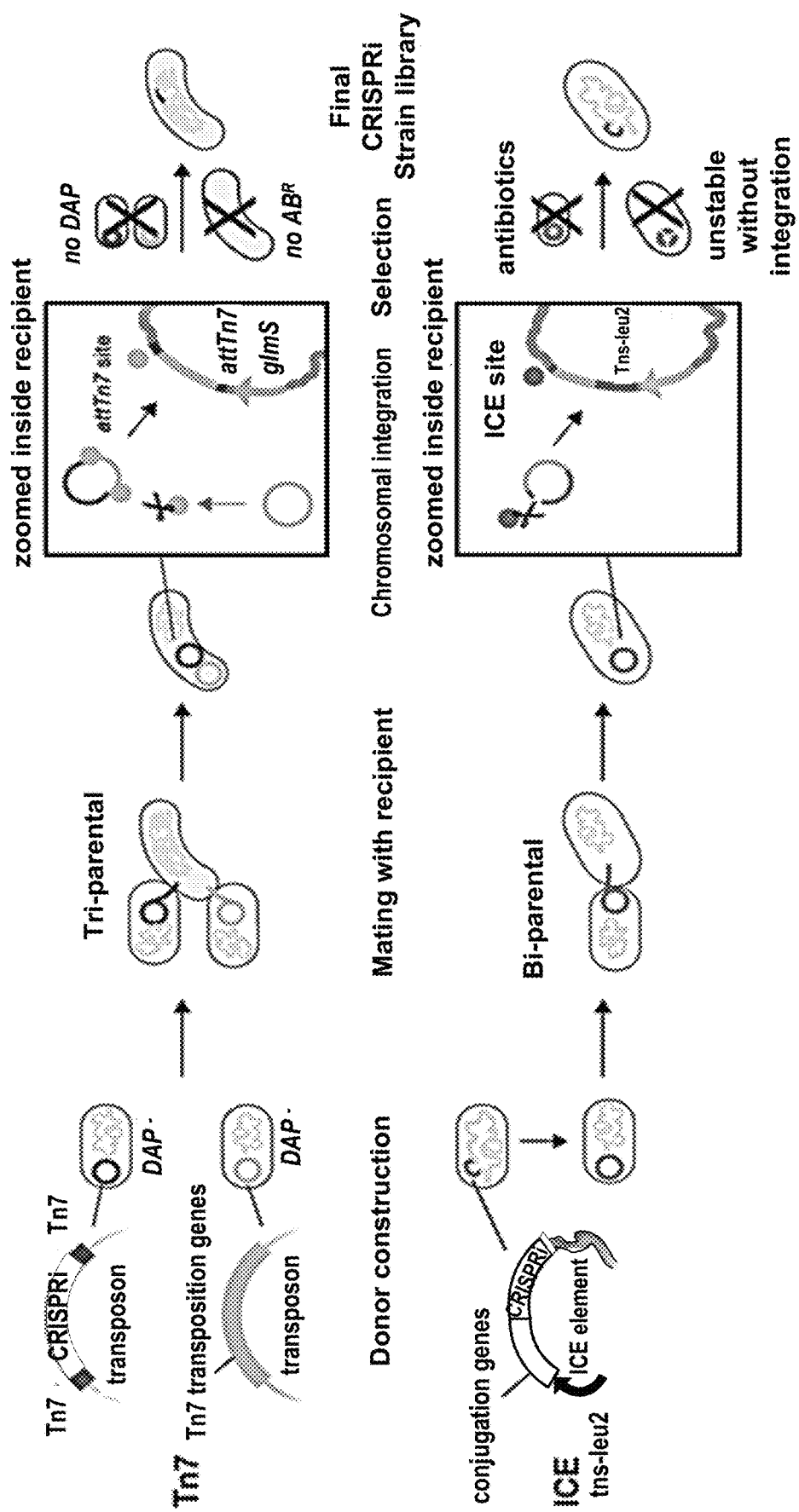
FIG. 2 schematically illustrates a process of bacterial strain construction using Mobile-CRISPRi according to aspects of this disclosure. Top: A Tn7 transposon carrying CRISPRi components and a plasmid containing Tn7 transposition genes are transferred to recipient bacteria by triparental mating. Bottom: An ICE element carrying CRISPRi components is transferred to recipient bacteria by bi-parental mating.
Figure 3:
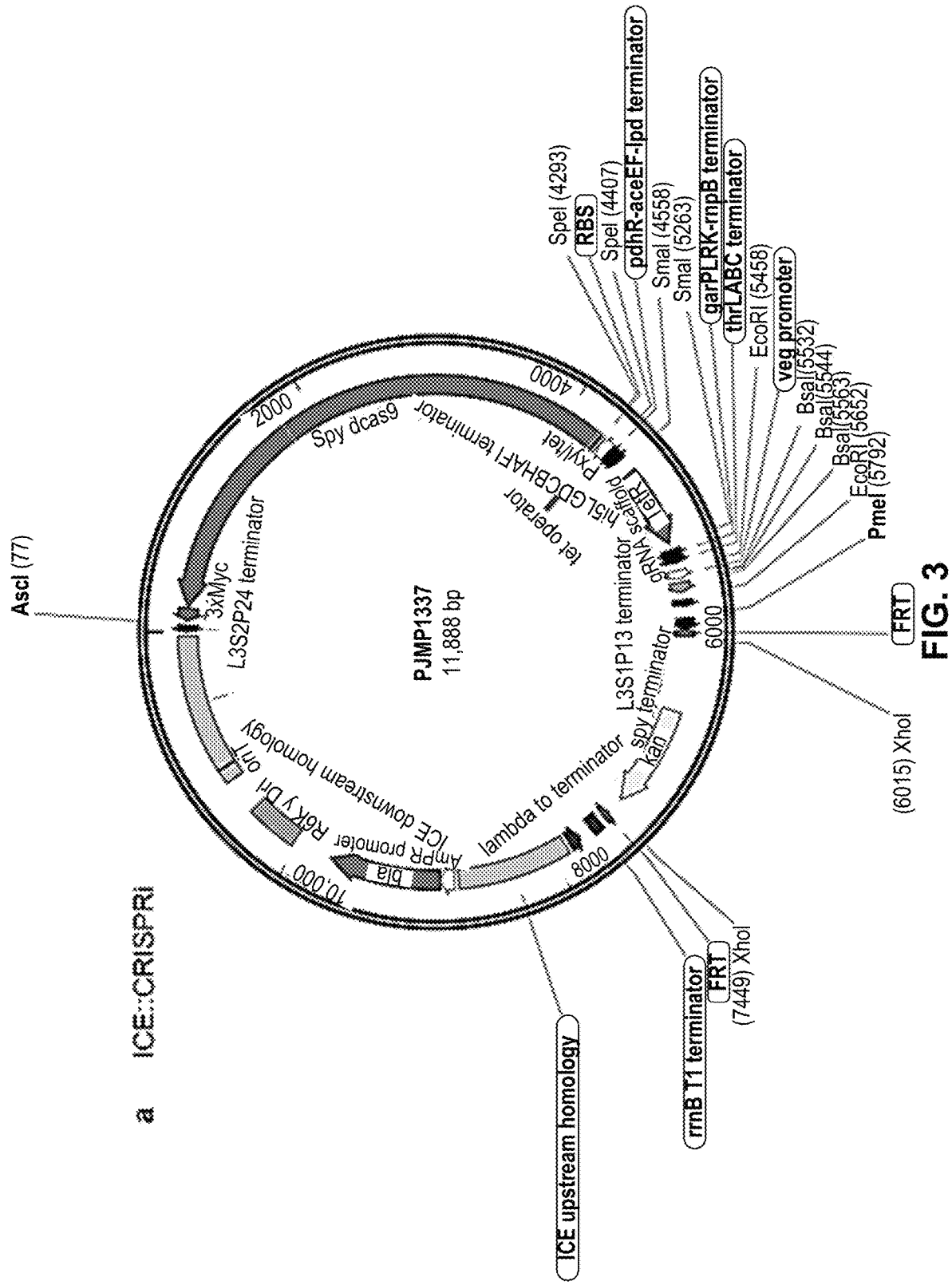
FIG. 3 is a schematic illustration of an exemplary mobile-CRISPRi vector pJMP1337 (see Table 1) including, as nucleotide transfer sequences, the sequences encoding bacterial integrative and conjugative elements (ICE) according to aspects of this disclosure. Antibiotic resistance markers and associated promoters are located between two XhoI sites—these markers can be removed from recipient cells by Flp-mediated recombination after selection as discussed in Choi, K.-H. et al. A Tn7-based broad-range bacterial cloning and expression system. *Nat. Methods* 2, 443-448 (2005) (15). PmeI is a unique site that can be used for inserting reporters, such as the rfp gene that was used in Example 1. The sgRNA and associated promoter is located between two EcoRI sites, and regulatory genes (e.g., tetR and lacI) can be cloned between two SmaI sites. The promoter and ribosome binding site (RBS) for dcas9 is located between two SpeI sites. All the cloning sites are transcriptionally-insulated by strong terminators.
Figure 4:
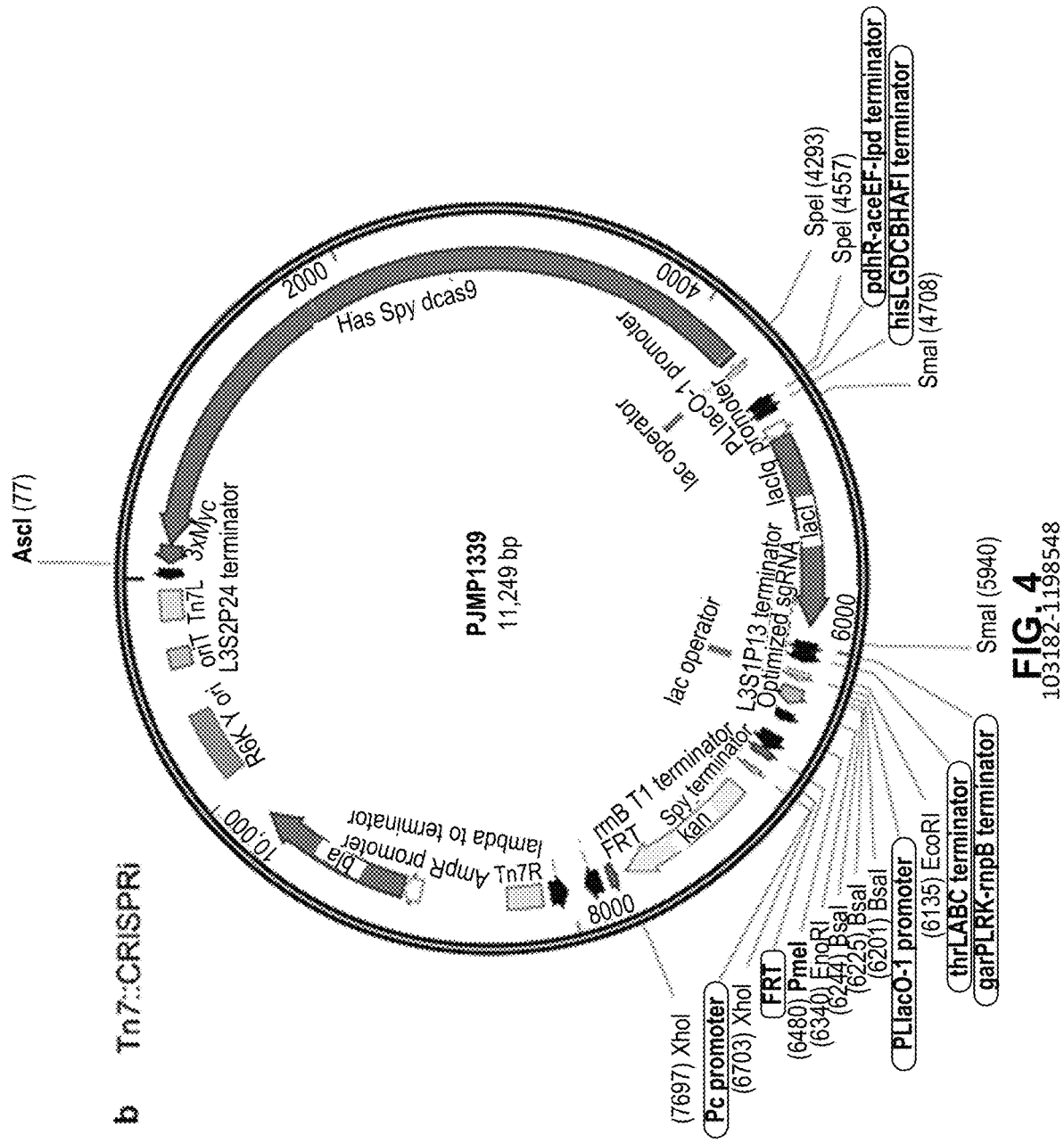
FIG. 4 is a schematic illustration of an exemplary mobile-CRISPRi vector pJMP1339 (see Table 1) including, as nucleotide transfer sequences, Tn7L and Tn7R transposon sequences according to aspects of this disclosure. Antibiotic resistance markers and associated promoters are located between two XhoI sites—these markers can be removed from recipient cells by Flp-mediated recombination after selection as discussed in (15). PmeI is a unique site that can be used for inserting reporters, such as the rfp gene that was used in this study. The sgRNA and associated promoter is located between two EcoRI sites, and regulatory genes (e.g., tetR and lacI) can be cloned between two SmaI sites. The promoter and ribosome binding site (RBS) for dcas9 is located between two SpeI sites. All the cloning sites are transcriptionally-insulated by strong terminators.

Described in the present disclosure is so-called "Mobile-CRISPRi," a term that refers to a suite of modular and transferable CRISPRi components that can stably integrate into the genomes of diverse bacteria, as well as to the associated artificial DNA constructs, vectors, methods, systems and kits. An example of an artificial DNA construct used in Mobile-CRISPRi is schematically illustrated in FIG. 1. Examples of the vectors used in Mobile-CRISPRi are illustrated in FIGS. 3 and 4. Mobile-CRISPRi achieves transfer and genomic integration by distinct mechanisms for Gammaproteobacteria and Firmicutes. For Gammaproteobacteria, Mobile-CRISPRi is transferred from *Escherichia coli* using the broad host range RP4 plasmid conjugation machinery, and is integrated into the recipient genome downstream of the highly conserved glmS gene using the extensively characterized Tn7 transposition system described, for example, in Peters, J. E. Tn7. *Microbiol. Spectr.* 2, (2014) (14) and Choi, K.-H. et al. A Tn7-based broad-range bacterial cloning and expression system. *Nat. Methods* 2, 443-448 (2005) (15). A process of Gammaproteobacteria strain construction using Mobile-CRISPRi is schematically illustrated in FIG. 2, top. The above strategy was previously unsuccessful in Bacillales Firmicutes, as discussed, for example, in (15). As described in the present disclosure, Mobile-CRISPRi is transferred into Bacillales Firmicutes using nucleic acid sequences encoding bacterial integrative and conjugative elements (ICE), for example, ICEs from *Bacillus subtilis* (ICEBs). A process of Bacillales Firmicutes strain construction using Mobile-CRISPRi is schematically illustrated in FIG. 2, bottom.

Mobile-CRISPRi components, artificial DNA constructs, vectors, methods, systems and kits, as well as bacterial cells engineered using Mobile-CRISPRi, as described herein possess a number of advantages over previously known CRISPRi constructs and associated methods. The modularity of every component of Mobile-CRISPRi artificial DNA constructs and vectors makes it straightforward to clone in organism-specific sgRNA libraries and other components. Mobile-CRISPRi also achieves transfer and genomic integration into a broad range of bacteria. Mobile-CRISPRi integrations do not disrupt transferred of the native bacterial genes, and they occur in a specified orientation and are stable and functional in the absence of selection for many (≥50) generations. Mobile-CRISPRi allows for studies of gene and antibiotic function in organisms in which maintaining selection is problematic or impossible. The stability of Mobile-CRISPRi in the absence of selection makes a valuable tool for dissecting the genetics of host-microbe interactions in both pathogenic and microbiome contexts and facilitates studies of the mode of action of antibiotics in pathogenic bacteria. Mobile-CRISPRi allows for both polled and arrayed library construction and assaying of phenotypes. Mobile-CRISPRi allows for studies of various bacteria, including those lacking genetic tools (such as bacteria isolated from the environment). Mobile-CRISPRi facilitates cross-species genetic analysis. Mobile-CRISPRi allows for interrogation of essential genes and double mutant combinations, as well as construction of parsimonious genome-scale knockdown libraries. The modularity of Mobile-CRISPRi makes it straightforward to expand the range of bacterial host species, for example, by combining different transfer and integration functions, anti-restriction proteins (such as those described in McMahon, S. A. et al. Extensive DNA mimicry by the ArdA anti-restriction protein and its role in the spread of antibiotic resistance. *Nucleic Acids Res.* 37, 4887-4897 (2009) (21)). The modularity of Mobile-CRISPRi also allows for easy testing and increasing knockdown efficiency by incorporation of different versions of dcas9 genes. In addition to the present disclosure, Mobile-CRISPRi is described in Peters et al. Enabling genetic analysis of diverse bacteria with Mobile-CRISPRi, *Nature Microbiology* 4, 244-250 (2019) (36) and Qu et al. Modulating pathogenesis with Mobile-CRISPRi. *bioRxiv preprint* posted online Apr. 25, 2019 (37).

A. Terms and Concepts

A number of terms and concepts are discussed below. They are intended to facilitate the understanding of various embodiments of the invention in conjunction with the rest of the present document and the accompanying figures. These terms and concepts may be further clarified and understood based on the accepted conventions in the fields of the present invention. the description provided throughout the present document and/or the accompanying figures. Some other terms can be explicitly or implicitly defined in other sections of this document and in the accompanying figures, and may be used and understood based on the accepted conventions in the fields of the present invention, the description provided throughout the present document and/or the accompanying figures. The terms not explicitly defined can also be defined and understood based on the accepted conventions in the fields of the present invention and interpreted in the context of the present document and/or the accompanying figures.

Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry are those well-known and commonly used. Known methods and techniques are generally performed according to conventional methods well known and as described in various general and more specific references that are discussed throughout the present disclosure, unless otherwise indicated. Enzymatic reactions and purification techniques are performed according to manufacturer's specifications, as commonly accomplished. The nomenclatures used in connection with the laboratory procedures and techniques described in the present disclosure are those well-known and commonly used.

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "about" may be used to indicate that a value includes the inherent variation of error for the device, the method being employed to determine the value, or the variation that exists among samples.

The "CRISPR/Cas" system refers to a widespread class of bacterial systems for defense against foreign nucleic acid. CRISPR/Cas systems are found in a wide range of eubacterial and archaeal organisms. CRISPR/Cas systems include various types and subtypes based on shared characteristics and evolutionary similarity. These are grouped into two large classes based on the structure of the effector complex that cleaves genomic DNA. The Type II CRISPR/Cas system was the first used for genome engineering, with Type V following. Wild-type type II CRISPR/Cas systems utilize an RNA-mediated nuclease Cas protein or homolog complex with guide RNA to recognize and cleave foreign nucleic acid. The term "Cas nuclease" or "Cas" refers to CRISPR associated protein, an RNA-guided nuclease that introduces a double stranded break in nucleic acid. The Cas nuclease can be CRISPR associated protein 9 ("Cas9 nuclease" or "Cas9"). Cas9 proteins also use an activating RNA (also referred to as a transactivating or tracr RNA). Guide RNAs can have activity of either a guide RNA or both a guide RNA and an activating RNA, depending on the type of CRISPR-associated endonuclease used. Dual activity guide RNAs are referred to as a single guide RNA (sgRNA). In this disclosure, the term "sgRNA" is used to refer to an RNA molecule that complexes with a CRISPR-associated endonuclease and localizes the ribonucleoprotein complex to a target DNA sequence. Typically, an sgRNA comprises a "scaffold" sequence for binding the nuclease and a "targeting" sequence that defines the target nucleic acid site (for example, a genomic DNA site). "Activity" in the context of CRISPR/Cas activity, CRISPR-associated endonuclease activity, sgRNA activity, sgRNA:CRISPR-associated endonuclease nuclease activity and the like refers to the ability to bind to a target genetic element. Typically, activity also refers to the ability of the sgRNA:CRISPR-associated endonuclease nuclease complex to make double-strand breaks at a target genomic region. A catalytically inactive variant of Cas endonuclease, such as a catalytically inactive variant of Cas9, which is referred to as "dead Cas9" or "dCas9" in the present disclosure, lacks endonuclease activity. For example, dCas9 is a mutant form of Cas9 whose endonuclease activity is eliminated through point mutations in its endonuclease domains. When coexpressed with a guide RNA, such as an sgRNA, the guide RNA and dCas9 generate a DNA recognition complex that can specifically interfere with transcription of a nucleotide sequence, to which the guide RNA is targeted. CRISPR interference (CRISPRi) methods and systems use dCAS9 paired with sgRNA to hinder transcription of a target gene.

The terms "nucleic acid" and "polynucleotide," as well as the related terms, interchangeably refer to DNA, RNA, and polymers thereof in single-stranded, double-stranded, or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term includes, for example, a recombinant DNA which is incorporated into a vector, into an autonomously replicating plasmid or virus, or into the genomic DNA of a prokaryote or eukaryote, or which exists as a separate molecule (for example, as a cDNA or a genomic or cDNA fragment produced by PCR or restriction enzyme digestion) independent of other sequences. It also includes a recombinant DNA which is part of a hybrid gene encoding additional polypeptide sequence.

The term "oligonucleotide" typically refers to short polynucleotides, generally no greater than about 50 nucleotides.

It is understood that when a nucleotide sequence is represented by a DNA sequence denoted, for example, by A, T, G, C notation of bases, the nucleotide sequence also includes a corresponding RNA sequence denoted by A, U, G, C notation of bases, in which "U" replaces "T".

As used herein, the terms "identity" or "percent (%) identity" when used with respect to a particular pair of aligned nucleic acid sequences, refers to the percent nucleic acid sequence identity that is obtained by counting the number of identical matches in the alignment and dividing such number of identical matches by the length of the aligned sequences. As used herein, the terms "similarity" or "percent (%) similarity" when used with respect to a particular pair of aligned nucleic acid sequences, refers to the sum of the scores that are obtained from a scoring matrix for each amino acid pair in the alignment divided by the length of the aligned sequences. Mathematical algorithms are known can be utilized for the comparison of nucleic acid sequences. See, for example, the algorithm of Karlin and Altschul, S. F. Methods for assessing the statistical significance of molecular sequence features by using general scoring schemes. *Proc. Nat. Acad. Sci. USA* 87:2264-2268 (1990) (31), modified as in Karlin, S. and Altschul, S. F. Applications and statistics for multiple high-scoring segments in molecular sequences. *Proc. Nat. Acad. Sci. USA* 90:5873-5877 (1993) (32). Such an algorithm is incorporated into the BLAST programs of Altschul, S. F. et al. Basic local alignment search tool. *J. Mol. Biol.* 215:403 (1990) (33). BLAST nucleotide searches can be performed with the BLASTN program (nucleotide query searched against nucleotide sequences) to obtain nucleotide sequences homologous to a particular sequence. To obtain gapped alignments for comparison purposes, Gapped BLAST (in BLAST 2.0) can be utilized as described in Altschul, S. F. et al. Gapped BLAST and PSI-BLAST: a new generation of protein database search programs. *Nucleic Acids Res.* 25:3389 (1997) (34). Alternatively, PSI-Blast can be used to perform an iterated search that detects distant relationships between molecules. When utilizing BLAST, Gapped BLAST, and PSI-Blast programs, the default parameters of the respective programs (e.g., BLASTX and BLASTN) can be used. Alignment may also be performed manually by inspection. Two sequences are "optimally aligned" when they are aligned for similarity scoring using a defined nucleic acid substitution matrix, gap existence penalty and gap extension penalty so as to arrive at the highest score possible for that pair of sequences. The gap existence penalty is imposed for the introduction of a single nucleic acid gap in one of the aligned sequences, and the gap extension penalty is imposed for each additional empty nucleic acid position inserted into an already opened gap. The alignment is defined by the nucleic acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, such as gapped BLAST 2.0. Optimal alignments, including multiple alignments, can be prepared using, e.g., PSI-BLAST, available through www.ncbi.nlm.nih.gov and described in (34). Algorithms and programs equivalent to those discussed above can also be utilized, meaning any sequence comparison programs and/or algorithms that, for any two sequences in question, can generate an alignment having identical nucleotide residue matches and an identical percent sequence identity.

The term "variant" or "variants" is intended to mean substantially similar sequences. Percent sequence identity or similarity between any two polynucleotides can be calculated using sequence alignment algorithms and/or programs and parameters described elsewhere in this disclosure. Where any given pair of polynucleotides of the disclosure is evaluated by comparison of the percent sequence identity, the percent sequence identity or percent sequence similarity between the two substantially similar sequences is at least 60%, 65%, 70%, 75%, 80%, 85%, 86%, 87%, 88%, 89%, 90%, 91%, 92%, 93%, 94%, 95%, 96%, 97%, 98%, 99%, or more. Variants may differ by as few as 1-15 nucleic acid residues, as few as 1-10, such as 6-10, as few as 5, as few as 4, as few as 3, as few as 2, or as few as 1 nucleic acid residues. Variant polynucleotides can comprise an 3' or a 5' end truncation, which can comprise at least a deletion of 10, 15, 20, 25, 30, 35, 40, 45, or 50 nucleic acids or more from either the 3' or a 5' end of the polynucleotide used for comparison.

A "recombinant nucleic acid" or "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides include chemical synthesis or by the manipulation of isolated segments of polynucleotides by genetic engineering techniques. A recombinant polynucleotide can comprise a recombinant DNA sequence or a recombinant RNA sequence. A "fragment of a recombinant polynucleotide or nucleic acid" comprises at least one of a combination of two or more chemically linked amino acid segments which are not found directly joined in nature.

The term "promoter" refers to regions or sequence located upstream and/or downstream from the start of transcription and which are involved in recognition and binding of RNA polymerase and other proteins to initiate transcription. A promoter directs a transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription. Bacterial promoters can consist of two short DNA sequences that are separated by a defined number of bases. The two short DNA sequences are positioned at roughly −10 and −35 in relation to the start position of transcription that they initiate. The −10 box is sometimes referred to as the "Pribnow box." Bacterial promoters can also include other sequences that can either repress or activate gene expression. For example, A/T rich sequences that can be found upstream of some strong bacterial promoters at an approximate position of −47 to −57 bp and allow the C-terminal domain of the alpha subunit of RNA polymerase to bind to the DNA with greater affinity, thereby increasing transcription. Bacterial promoters include constitutive promoters and those that are responsive under certain conditions. The latter promoters include regulated promoters. Examples regulated promoters include the AraBAD promoter and the Lac promoter, which use repressors (AraC and LacI, respectively) to silence transcription. Bacterial cell can contain a plasmid which encoding a nucleic acid sequence downstream of a promoter that contains a repressor binding site. The promoter is prevented from expressing the gene of interest by the repressor. When induction of the promoter is desirable, it is possible to add an inducing agent (for example, IPTG for Lac regulated promoters), which allows the nucleic acid to be transcribed.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A term "vector" refers to a polynucleotide that, when independent of a host chromosome, can be capable replication in a host organism. Vectors include circular vectors, which can be termed "plasmids" and typically have an origin of replication. Vectors can comprise transcription and translation terminators, transcription and translation initiation sequences, and promoters useful for regulation of the expression of the particular nucleic acid. The term "vector" can also refer to a polynucleotide used to deliver an isolated nucleic acid included in the polynucleotide to the interior of a cell.

A "restriction site" is term used to denote a region of a nucleic acid (for example, a vector) that is a sequence of nucleotides that is recognized by at least one restriction enzyme. The term "restriction site" can be used interchangeably with the term "cloning site." A "multiple cloning site" as the term is used herein is a region of a nucleic acid or a vector that contains more than one sequence of nucleotides that is recognized by at least one restriction enzyme.

An "antibiotic resistance marker" or "antibiotic resistance gene" is the term used to refer to a sequence of nucleotides that encodes a protein that, when expressed in a living cell, confers to that cell the ability to live and grow in the presence of a particular antibiotic.

The term "ribosome binding site" refers to a sequence of nucleotides upstream of the start codon of an mRNA transcript. A ribosome binding site is responsible for the recruitment of a ribosome during the initiation of protein translation. One example of a ribosome binding site is a so-called Shine-Dalgarno sequence, although some bacterial translations of initiation regions lack identifiable Shine-Dalgarno sequences.

The term "gene" refers to a nucleotide sequence containing a sequence or sequences (which can be discontinuous) encoding a polypeptide or a nucleic acid (in case of RNA-encoding gene). In addition to coding sequence or sequences, a gene can contain other elements, such as nucleotide sequences that are not transcribed, nucleotide sequences corresponding to untranslated regions of the RNA, promoters, and regulatory sequences. A gene can have more than one promoter. Regulatory sequences include enhancers, which can increase transcription by binding an activator protein, and silencers, that can bind repressor proteins. The untranslated regions of RNA, with the corresponding sequences included in a gene, can contain a ribosome binding site, a terminator, start and stop codons.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (in case of RNA) or a defined sequence of amino acids (in the case of polypeptides) and the resulting biological properties. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. For gene encoding an RNA (for example, an sgRNA in the context of the present disclosure), the coding strand encodes the RNA. Unless otherwise specified, a "nucleotide sequence encoding an amino acid sequence" includes all nucleotide sequences that are degenerate versions of each other and that encode the same amino acid sequence. Nucleotide sequences that encode proteins and/or RNA may include introns. In the context of the present disclosure, the nucleotide sequences that encode sgRNAs do not include introns.

A "coding region" of a gene consists of the nucleotide residues of the coding strand of the gene and the nucleotides of the non-coding strand of the gene that are homologous with or complementary to, respectively, the coding region of an mRNA molecule that is produced by transcription of the gene. A "coding region" of an mRNA molecule also consists of the nucleotide residues of the mRNA molecule that are matched with an anticodon region of a transfer RNA molecule during translation of the mRNA molecule or which encode a stop codon. The coding region may thus include nucleotide residues corresponding to amino acid residues that are not present in the mature protein encoded by the mRNA molecule (e.g., amino acid residues in a protein export signal sequence).

A "reporter gene" or "reporter" is a gene containing a nucleic acid sequence encoding molecules, such as polypeptides or proteins, that are readily detectable due to their biochemical characteristics, such as enzymatic activity or chemifluorescent features. These reporter proteins can be used as selectable markers. One specific example of such a reporter is red fluorescent protein (RFP). Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, chloramphenicol acetyl transferase (CAT); luciferase (lux); 0-galactosidase; LacZ; 0-glucuronidase; and alkaline phosphatase. Other suitable reporters include those that encode for a particular epitope that can be detected with a labeled antibody that specifically recognizes the epitope.

An "origin of replication" (which can also be called "replication origin") is a particular sequence in a genome at which replication is initiated.

B. Mobile-CRISPRi Artificial Nucleotide Sequences and Vectors

Provided in this disclosure are artificial DNA constructs used in Mobile-CRISPRi vectors, methods, systems and kits according to the embodiments of the present invention. Some embodiments of the artificial DNA constructs include one or more nucleotide sequences each encoding a single guide RNA (sgRNA) targeting a bacterial gene or genes of interest. A bacterial gene of interest, which can also be referred to as a "target gene," is a bacterial gene of which the function is to be disrupted or interfered using Mobile-CRISPRi vectors, methods, systems, and kits according to the embodiments of the present disclosure. For example, a target gene can be, but is not limited to, an essential bacterial gene underpinning core cellular processes, a virulence or virulence life-style gene (VLG) of a pathogenic bacterium, a gene encoding an antibiotic target, a gene encoding an antibiotic resistance factor or a gene encoding an antibiotic permeability factor.

In some embodiments, an artificial DNA construct includes one nucleotide sequence encoding a sgRNA targeting a bacterial gene of interest. In some other embodiments, an artificial DNA construct can include a plurality, such as two or more (for example, 2-10, 2-9 or 2-8, such as 2, 3, 4, 5, 6, 7, 8, 9 or 10) nucleotide sequences encoding a plurality of sgRNAs targeting a bacterial gene or genes of interest. In Mobile-CRISPRi methods according to the embodiments of the present disclosure, a sgRNA-dCas9 complex binds to a target gene by base-pairing via the sgRNA and reduces gene expression by sterically blocking transcription elongation. As discussed above, a sgRNA comprises a "scaffold" sequence for binding the nuclease and a "targeting" sequence that defines and interacts with the target sequence within a gene of interest. Accordingly, the nucleotide sequences encoding sgRNA sequences are designed so that the first ~20 nucleotides of the sgRNA sequence match the non-template strand of the target sequence in the gene of interest. In some embodiments of artificial DNA construct according to the embodiments of the present disclosure, a sgRNA can have a length of 70-130 base pairs, such as 86-113 base-pairs. In some embodiments, the sgRNA includes a targeting sequence that has a length of about 10 to 30 nucleotides, such as 10-20 oligonucleotides.

A promoter is operably linked to the nucleotide sequence encoding the sgRNA in artificial DNA constructs according to the embodiments of the present disclosure. The promoter is generally a bacterial promoter. The promoter can be a constitutive or a regulated promoter. Some non-limiting examples of the regulated promoters that can be used in this context are a trp promoter, a lac promoter, an araBAD, a trc promoter, a Pxyl oromoter, a Pxyl/tet promoter, a PLlacO-1 promoter, a PLtetO-1 promoter or a PtetA promoter. Regulated promoters included in the embodiments of the present disclosure operate in concert with regulatory sequences, such as operators (segments of DNA to which a repressor molecule binds). Another example of a regulatory sequence is a sequence encoding a regulatory protein, for example, a repressor, such as a LacI gene encoding lac repressor protein. A sequence encoding a regulatory protein can be referred to as a "regulatory gene." Regulatory sequences associated with the operators operably linked to the nucleotide sequence encoding the sgRNA can also be included in artificial DNA constructs according to the embodiments of the present disclosure. Regulatory sequences, such as the nucleotide sequence of a regulatory gene or genes, may be inserted upstream of the nucleotide sequence encoding the sgRNA. Some non-limiting examples of constitutive promoters are a pveg promoter, a P23119 promoter, and derivatives of PlacUV5 and Ptrc promoters that lack LacI operator sites. In some embodiments, a promoter can be an engineered promoter, such as a regulated promoter altered to become a constitutive promoter by removing an operator sequence. Some embodiments of artificial DNA constructs do not include a nucleotide sequence encoding the sgRNA and instead include a restriction site for insertion of one or more nucleotide sequences encoding sgRNAs. In such embodiments, the artificial DNA constructs may or may not include the corresponding promoter sequence(s) for the one or more nucleotide sequences encoding sgRNAs. If the promoter sequences are not included, they can be inserted into the restriction site together with the nucleotide sequence encoding the sgRNA or inserted into a separately provided restriction site upstream of the nucleotide sequence encoding the sgRNA. If the promoter sequences are included, the nucleotide sequence encoding the sgRNA may be inserted in the restriction site under the control of the provided promoter. It is also possible to insert the nucleotide sequence encoding the sgRNA with an operably linked promoter other than the promoter provided in the artificial DNA construct. For example, a nucleotide sequence may be generated that contains both the promoter other than the promoter already provided in the artificial DNA construct ("new promoter), the new promoter operably linked the sgRNA. The nucleotide sequence then may be inserted into the restriction site in the artificial DNA construct. Embodiments of artificial DNA constructs may or may not include regulatory sequences associated with the operators operably linked to the one or more nucleotide sequences encoding the sgRNAs. If a regulatory sequence is not included, a separate restriction site may be provided for a regulatory sequence to be inserted.

Artificial DNA constructs according to the embodiments of the present disclosure include a nucleotide sequence encoding a catalytically inactive variant of CRISPR-associated protein 9 (dCas9). A catalytically inactive dCas9 lacks endonuclease activity and, when coexpressed with a sgRNA, generates a DNA recognition complex interfering with binding and function of transcriptional machinery (such as transcriptional elongation, RNA polymerase binding and/or transcription factor binding, as discussed, for example, in (1)). Some examples of catalytically inactive dCas9 are listed in Table 1. Some embodiments of artificial DNA constructs do not include a nucleotide sequence encoding a catalytically inactive dCas9 and instead a restriction site for inserting such a nucleotide sequence is provided. A promoter and a ribosome binding site is operably linked to the nucleotide sequence encoding a catalytically inactive dCas9 included in the artificial DNA constructs according to the embodiments of the present disclosure.

A promoter operably linked to the nucleotide sequence encoding a catalytically inactive dCas9 can be a constitutive or a regulated promoter. Some non-limiting examples of the regulated promoters that can be used in this context are a trp promoter, a lac promoter, an araBAD promoter, a Pxyl/tet promoter, a trc promoter, a Pxyl promoter, a PLacO-1 promoter, a PLtetO-1 promoter or a PtetA promoter. Regulated promoter include in the embodiments of the present disclosure operate in concert with regulatory sequences, such as operators (segments of DNA to which a repressor molecule binds). Another example of a regulatory sequence is a sequence encoding a regulatory protein, for example, a repressor, such as a LacI gene encoding lac repressor protein. A sequence encoding a regulatory protein can be referred to as a "regulatory gene." Such regulatory sequences associated with the operators operably linked to the nucleotide sequence encoding the encoding a catalytically inactive dCas9 can also be included in artificial DNA constructs according to the embodiments of the present disclosure. A regulatory nucleotide sequence may be inserted upstream of the nucleotide sequence encoding the nucleotide sequence encoding a catalytically inactive dCas9. Some non-limiting examples of constitutive promoters are a pveg promoter, a P23119 promoter, or derivatives of PlacUV5 and Ptrc promoters that lack LacI operator sites. In some embodiments, a promoter can be an engineered promoter, such as a regulated promoter altered to become a constitutive promoter by removing an operator sequence.

Some embodiments of artificial DNA constructs do not include a nucleotide sequence encoding a catalytically inactive dCas9 and instead include a restriction site for insertion of the nucleotide sequence encoding the catalytically inactive dCas9. Such embodiments of artificial DNA constructs may or may not include the corresponding promoter sequences. If the promoter sequence operably linked to the catalytically inactive dCas9 is not included in the artificial DNA construct, it can be inserted into the restriction site together with the nucleotide sequence encoding dCas9 or inserted into a separately provided restriction site upstream of the nucleotide sequence encoding the dCas9. Embodiments of artificial DNA constructs may or may not include regulatory sequences associated with the operators operably linked to the nucleotide sequence encoding the catalytically inactive dCas9. If a regulatory sequence is not included, a separate restriction site may be provided for including a regulatory sequence. Embodiments of artificial DNA constructs may or may not include a ribosome binding sequence operably linked to the nucleotide sequence encoding the catalytically inactive dCas9. If a ribosome binding sequence is not included, a separate restriction site may be provided for a regulatory sequence to be inserted.

Artificial DNA constructs according to the embodiments of the present disclosure may include a nucleotide sequence of a selectable marker. One example of such a selectable marker is a gene conferring resistance to an antibiotic, which can be referred to as an "antibiotic resistance marker." An antibiotic resistance marker is a gene that confers a resistance to an antibiotic. An antibiotic resistance marker typically encodes a protein that provides cells expressing the protein with resistance to an antibiotic. Examples include beta-lactamase, which confers ampicillin resistance to bacterial cells; the neo gene that confers resistance to kanamycin to bacterial cells, and the cat gene, which confers chloramphenicol resistance to bacterial cells. Some non-limiting examples of antibiotic resistance genes that may be used in artificial DNA constructs according to the embodiments of the present disclosure are ampicillin resistance genes, chloramphenicol resistance genes, gentamicin resistance genes, trimethoprim resistance genes, streptomycin resistance genes, tetracycline resistance genes, kanamycin resistance genes and spectinomycin resistance genes.

Another example of a selectable marker is a prototrophic marker, which is a gene that confers an ability to synthetize a compound (for example, diaminopimelic acid (DAP) or D-alanine) needed for growth of an auxotrophic bacterium, meaning a bacterium unable to synthesize a particular organic compound required for its growth. In some embodiments, artificial DNA constructs may not include a nucleotide sequence of a selectable marker and instead may include a restriction site for insertion of the nucleotide sequence of a selectable marker. For example, some embodiments of the artificial DNA constructs may include restriction site for insertion of a gene conferring resistance to an antibiotic and/or a prototrophic marker.

Artificial DNA constructs according to embodiments of the present disclosure may include a nucleotide sequence of a reporter gene or a restriction site for insertion of the nucleotide sequence of the reporter gene. In some embodiments, the reporter gene encodes a reporter protein. One example of a suitable reporter gene is a gene encoding red fluorescent protein (RFP), although other suitable reporter genes may also be used. In some embodiments, a reporter protein is expressed from a constitutive promoter. In some embodiments, a reporter protein is expressed from a regulated promoter. Generally, the promoter is a bacterial promoter. Some embodiments of the artificial DNA constructs are constructed so that the reporter gene and the nucleotide sequence encoding the sgRNA are a part of the same operon under control of a single promoter. In this arrangement, the reporter gene may be inserted downstream of the nucleotide sequence encoding sgRNA, which has the advantage that the detectable reporter signal indicates transcription of the nucleotide sequence encoding sgRNA. When the single promoter is a regulated promoter, a nucleotide sequence of a regulatory gene or genes may be inserted upstream of the nucleotide sequence encoding the sgRNA and the reporter gene.

Artificial DNA constructs according to the embodiments of the present disclosure include bacterial nucleotide transfer sequences, which flank the other elements of the artificial DNA constructs, including but not limited to those elements described above. Some examples of such nucleotide transfer sequences include transposon sequences, insertion sequences, site-specific phage integration sequences (e.g., phage lambda (int)), sequences encoding bacterial integrative and conjugative elements (ICE), or other site-specific integration sequences. One example of transposon sequences are Tn7L and Tn7R sequences. ICE, which can also be referred to as "conjugative transposons," are modular mobile genetic elements and are integrative to the bacterial chromosome, passively propagated during chromosomal replication and cell division. ICE transfer sequences need certain genes for integration and excision for transfer ("ICE genes"). Induction of the expression of ICE genes, leads to excision of ICE elements, production of the conserved conjugation machinery, and the transfer of the excised DNA to recipient bacterial cells upon conjugation. In some embodiments of the artificial DNA constructs, the nucleotide transfer sequences are integrative and conjugative elements from *Bacillus subtilis* (ICEBs1).

Some embodiments of the artificial DNA constructs are schematically illustrated in FIG. 1. Some exemplary embodiments of the artificial DNA constructs include a restriction site for insertion of a nucleotide sequence encoding a sgRNA, a first promoter operably linked to the nucleotide sequence encoding a sgRNA, a second promoter and a ribosome binding site operably linked to a nucleotide sequence encoding the catalytically inactive variant of Cas9 (dCas9), and a nucleotide sequence of a gene conferring resistance to an antibiotic. Some exemplary embodiments of the artificial DNA constructs include a nucleotide sequence encoding a sgRNA, a first promoter operably linked to the nucleotide sequence encoding the sgRNA, a second promoter and a ribosome binding site operably linked to the nucleotide sequence encoding the catalytically inactive dCas9, and a nucleotide sequence of a gene conferring resistance to an antibiotic. Some embodiments of the artificial DNA constructs include nucleic acid sequences having at least 60%, 65%, 70%, 75%, 80%, 85%, 86%, 87%, 88%, 89%, 90%, 91%, 92%, 93%, 94%, 95%, 96%, 97%, 98%, or 99% identity to nucleotides 1501-10310 of SEQ ID NO:2, nucleotides 1501-11673 of SEQ ID NO:3, nucleotides 152-8155 of SEQ ID NO:4, nucleotides 152-8155 of SEQ ID NO:5, nucleotides 152-8155 of SEQ ID NO:6, nucleotides 2517-9310 of SEQ ID NO:7, nucleotides 2517-11688 of SEQ ID NO:8, nucleotides 2517-11688 of SEQ ID NO:9, nucleotides 2517-11836 of SEQ ID NO:10, nucleotides 2517-11650 of SEQ ID NO:11, nucleotides 2517-11710 of SEQ ID NO:12, nucleotides 2517-11710 of SEQ ID NO:13, nucleotides 2517-10705 of SEQ ID NO:14, nucleotides 152-8321 of SEQ ID NO:15, nucleotides 1-8272 of SEQ ID NO:16, nucleotides 1-10636 of SEQ ID NO:17, nucleotides 1-9813 of SEQ ID NO:18, nucleotides 152-8733 of SEQ ID NO:19, nucleotides 152-8714 of SEQ ID NO:20, nucleotides 152-8714 of SEQ ID NO:21, nucleotides 152-8714 of SEQ ID NO:22, nucleotides 152-8420 of SEQ ID NO: 37, nucleotides 152-8608 of SEQ ID NO:24, nucleotides 152-8846 of SEQ ID NO:25, nucleotides 152-8586 of SEQ ID NO:26, nucleotides 2517-4992 of SEQ ID NO:27, or nucleotides 8574 to 6498 of SEQ ID NO:28.

Provided in this disclosure are DNA vectors used in Mobile-CRISPRi methods, systems, and kits according to the embodiments of the present invention. The DNA vectors according to some embodiments of the present invention are plasmids, meaning circular DNA constructs. A DNA vector according to some embodiments of the present invention includes embodiments of an artificial DNA construct as described above. In addition, a DNA vector according to the embodiments of the present invention includes other elements described below.

A DNA vector according to the embodiments of the present disclosure includes a nucleotide sequence of a selectable marker outside of the artificial DNA construct sequence, which is different from the selectable marker encoded by a nucleotide sequence within the artificial DNA construct. Accordingly, a selectable marker included in the vector and located within the artificial DNA construct may be described as a "first," whereas a selectable marker included in the vector and located outside the artificial DNA construct may be described as "second." For example, in some embodiments of the vectors, a nucleotide sequence of a gene conferring resistance to an antibiotic located within the artificial DNA construct may be referred to as a nucleotide sequence of a gene conferring resistance to a first antibiotic, whereas a nucleotide sequence of a gene conferring resistance to an antibiotic located outside the artificial DNA construct may be referred to as a nucleotide sequence of a gene conferring resistance to a second antibiotic. In a non-limiting example, in some embodiments of the vectors, the first antibiotic may be ampicillin, and the second embodiments may be trimethoprim, kanamycin, gentamicin, chloramphenicol, or spectinomycin. Two different selectable markers are included in the vector, one within and one outside of the artificial DNA construct, in order to exercise appropriate selection procedures during Mobile-CRISPRi methods of transferring the artificial DNA constructs from a donor bacterium, in which the vectors are replicated, to a chromosome of a recipient bacterium. Such Mobile-CRISPRi methods are described further in the present disclosure.

A DNA vector according to the embodiments of the present disclosure includes a conditional origin of replication located outside the artificial DNA construct. Conditional origins of replication require additional genes in order to be functional. Some non-limiting examples of conditional origins of replication are R6K, oriV or temperature-sensitive pSC101 origins of replication. An R6K origin of replication (which includes R6K α, β and γ R6K origins of replication) requires expression of a pir gene encoding replication initiator protein pi to be functional. Bacterial strains that express pi protein (pir+ strains) can replicate R6K origins. An oriV origin of replication requires the expression of trfA gene for replication. Some embodiments of the DNA vectors of the present disclosure include R6K γ origin of replication. Accordingly, such vectors require a pir+ bacterial strain, such as a pir+ strain of *Escherichia coli*, to replicate.

A DNA vector according to the embodiments of the present invention can also include an origin of transfer site located outside the artificial DNA construct. An origin of transfer, which is typically denoted oriT, is a nucleic acid sequence usually of up to approximately 500 bp in length that is required for transfer of the DNA that contains it from a bacterial host cell to recipient cell during bacterial conjugation. An origin of transfer is cis-acting, meaning that it is found on the same DNA that is being transferred, and it is transferred along with the DNA. In some embodiments, DNA vectors that comprise Tn7 transposon sequences also comprise an origin as transfer. Such DNA vectors have utility in tri-parental mating in which RP4 transfer machinery is employed for DNA transfer as discussed below in this disclosure.

Some embodiments of the DNA vectors are illustrated in FIG. 3 and FIG. 4. Some embodiments of the DNA vectors are described in Table 1, for example, the vectors named pJMP1055, pJMP1067, pJMP1069, pJMP1159, pJMP1161, pJMP1170, pJMP1171, pJMP1183, pJMP1185, pJMP1187, pJMP1189, pJMP1217, pJMP1219, pJMP1221, pJMP1223, pJMP1237, pJMP1333, pJMP1335, pJMP1337, pJMP1339, pJMP1354, pJMP1356, pJMP1358 or pJMP1360. Some embodiments of the DNA vectors include nucleic acid sequence having at least 60%, 65%, 70%, 75%, 80%, 85%, 86%, 87%, 88%, 89%, 90%, 91%, 92%, 93%, 94%, 95%, 96%, 97%, 98%, or 99% identity to pJMP1055, pJMP1067, pJMP1069, pJMP1159, pJMP1161, pJMP1170, pJMP1171, pJMP1183, pJMP1185, pJMP1187, pJMP1189, pJMP1217, pJMP1219, pJMP1221, pJMP1223, pJMP1237, pJMP1333, pJMP1335, pJMP1337, pJMP1339, pJMP1354, pJMP1356, pJMP1358 or pJMP1360. In some embodiments, the artificial DNA vectors include nucleic acid sequences having at least 90% or at least 95% identity to nucleotides nucleotides 1501-10310 of SEQ ID NO:2, nucleotides 1501-11673 of SEQ ID NO:3, nucleotides 152-8155 of SEQ ID NO:4, nucleotides 152-8155 of SEQ ID NO:5, nucleotides 152-8155 of SEQ ID NO:6, nucleotides 2517-9310 of SEQ ID NO:7, nucleotides 2517-11688 of SEQ ID NO:8, nucleotides 2517-11688 of SEQ ID NO:9, nucleotides 2517-11836 of SEQ ID NO:10, nucleotides 2517-11650 of SEQ ID NO:11, nucleotides 2517-11710 of SEQ ID NO:12, nucleotides 2517-11710 of SEQ ID NO:13, nucleotides 2517-10705 of SEQ ID NO:14, nucleotides 152-8321 of SEQ ID NO:15, nucleotides 1-8272 of SEQ ID NO:16, nucleotides 1-10636 of SEQ ID NO:17, nucleotides 1-9813 of SEQ ID NO:18, nucleotides 152-8733 of SEQ ID NO:19, nucleotides 152-8714 of SEQ ID NO:20, nucleotides 152-8714 of SEQ ID NO:21, nucleotides 152-8714 of SEQ ID NO:22, nucleotides 152-8420 of SEQ ID NO: 37, nucleotides 152-8608 of SEQ ID NO:24, nucleotides 152-8846 of SEQ ID NO:25, nucleotides 152-8586 of SEQ ID NO:26, nucleotides 2517-4992 of SEQ ID NO:27, or nucleotides 8574 to 6498 of SEQ ID NO:28.

In one aspect, provided in this disclosure is a bacterial expression vector comprising a transposase gene. Such transposase vectors are used in Mobile-CRISPRi methods according to embodiments as described in this disclosure. One such plasmid, for example, is the pJMP1039 plasmid (SEQ ID NO:1). In some embodiments, the bacterial expression vector comprising a transposase gene comprises at least 90% or at least 95% identity to the nucleotide sequence of SEQ ID NO:1.

In another aspect, provided in this disclosure is a bacterial vector pJMP1055 (SEQ ID NO:27). This bacterial vector is the backbone sequence used for construction of various other DNA vectors described in this disclosure. In some embodiments, provided is a bacterial vector comprising at least 90% or at least 95% identity to the nucleotide sequence of SEQ ID NO:27.

C. Engineered Bacterial Cells Containing Mobile-CRISPRi Vectors and Related Methods Provided in this disclosure are engineered bacterial cells comprising DNA vectors according to the embodiments of the present invention and described above. The provided engineered bacterial cells comprising the DNA vectors can be used for vector production, as well as Mobile-CRISPRi methods, and in systems and kits described elsewhere in the present disclosure. In some embodiments, an engineered bacterial cell contains a DNA vector according to the embodiments of the present disclosure. Such an engineered bacterial cell may be generated by transforming an appropriate bacterial strain with the DNA vector or by reproducing bacterial cells already containing the DNA vector. In some embodiments, an engineered bacterial cell is an *Escherichia coli* bacterial cell. For example, if the artificial DNA construct of the vector comprises Tn7L and Tn7R transposon sequences as the nucleotide transfer sequences, then the engineered bacterial cell useful for vector production and/or in Mobile-CRISPRi methods may be an *Escherichia coli* bacterial cell. In other embodiments, an engineered bacterial cell is a *Bacillus subtilis* bacterial cell. For example, if the nucleotide transfer sequences in the artificial DNA construct included in the vector are integrative and conjugative elements from *Bacillus subtilis* (ICEBs1), then the engineered bacterial cell useful for vector production and/or in Mobile-CRISPRi methods may be a *Bacillus subtilis* bacterial cell. It is to be understood that the engineered bacterial cells are not limited to *Escherichia coli* and *Bacillus subtilis* bacterial cells, and that other bacteria may be used for generating bacterial cells for vector production and/or in Mobile-CRISPRi methods. In particular, there are many possible bacterial strain recipients.

Also provided in the present disclosure are methods of producing engineered bacterial cells comprising DNA vectors as described above. In some embodiments, a method of producing an engineered bacterial cell may include the step of transforming a bacterial cell with the DNA vector according to the embodiments of the present disclosure, and growing the transformed bacterial cell under growth conditions leading to growth of the engineered bacterial cell containing the DNA vector. For example, the transformed bacterial cells are grown in or on a growth medium requiring, for bacterial growth, the selectable marker included in the DNA vector outside of the artificial DNA construct (that is, the second selectable marker). In some embodiments the transformed bacterial cell is grown in or on a growth medium comprising a second antibiotic in order for the engineered bacterial cells being grown to maintain the DNA vector. In another example, due to the conditional origin of replication being present in the DNA vector, in order for the transformed bacterial cell to grow, the transformed bacterial cell includes and expresses a gene allowing the conditional origin of replication to be functional. When the conditional origin of replication is R6K γ origin of replication, the cell being transformed is a pir+ bacterial cell, which allows R6K γ origin of replication to function. In some embodiments of the methods of producing engineered bacterial cells comprising DNA vectors according to the embodiments of the present disclosure, the bacterial cell being transformed is auxotrophic and requires the presence of a nutritional substance for growth, in such case the growing of the bacterial cell (before and/or after transformation) is conducted in the presence of the required nutritional substance. This feature is advantageous when the engineered bacterial cells are used in certain Mobile-CRISPRi methods described below in this disclosure, in which the artificial DNA construct includes Tn7 transposon nucleotide transfer sequences, and which employ the selection on growth media lacking the nutritional substance to eliminate the engineered bacterial cells that are the donors of the artificial DNA constructs from a culture also containing the engineered bacterial cells that are the recipients of the artificial DNA construct, which is integrated into the recipient cells by Mobile-CRISPRi methods.

D. Mobile-CRISPRi Methods and Bacteria Engineered with Mobile-CRISPRi

Provided in this disclosure are methods of producing or generating engineered bacteria using DNA vectors described in the present disclosure. Such methods may be referred to as "Mobile-CRISPRi methods." Mobile-CRISPRi methods involve a transfer of an artificial DNA construct included in a DNA vector, each described elsewhere in the present disclosure, from a donor bacterial cell to a recipient bacterial cell and subsequent integration of the artificial DNA construct into the genome of the bacterial cell. The transfer and integration process is accomplished by different variations of Mobile-CRISPRi methods, depending on whether the Tn7 transposon sequences or ICE are used as nucleotide transfer sequences in the artificial DNA construct. The transfer of the artificial DNA construct using Tn7 transposon sequences may be accomplished by tri-parent bacterial conjugation employing RP4 transfer machinery in the donor engineered bacterial cell and a second donor engineered bacterial cell providing a transposase gene. The transfer of the artificial DNA construct using ICE may be accomplished by excision of the artificial DNA construct by the proteins expressed from conjugation genes (ICE genes) in the donor engineered bacterial cell, followed by bi-parental mating resulting in the transfer and integration of the artificial DNA construct into the genome of the recipient cell.

An example of a Mobile-CRISPRi method according to embodiments of the present disclosure is a method of generating an engineered bacterium using a first donor engineered bacterial cell comprising RP4 transfer machinery and the DNA vector including an artificial DNA construct with Tn7L and Tn7R transposon sequences as the nucleotide transfer sequence. The Tn7 transposition system is described, for example, in Peters, J. E. Tn7. *Microbiol. Spectr.* 2, (2014) (14) and Choi, K.-H. et al. A Tn7-based broad-range bacterial cloning and expression system. *Nat. Methods* 2, 443-448 (2005) (15). The artificial DNA construct includes a nucleotide sequence encoding a sgRNA, a first promoter operably linked to the nucleotide sequence encoding the sgRNA, a second promoter and a ribosome binding site operably linked to the nucleotide sequence encoding the catalytically inactive variant of Cas9 (dCas9), and the nucleotide sequence of the gene conferring resistance to the first antibiotic. The first donor engineered bacterial cell is auxotrophic and requires the presence of a nutritional substance for growth. For example, the first donor engineered bacterial cell can be diaminopimelic acid (DAP) auxotrophic. The first donor engineered bacterial cell also has a gene allowing the conditional origin of replication in the DNA vector to be functional. For example, when the conditional origin of replication is R6K γ, then the first donor engineered bacterial cell is pyr+. This exemplary Mobile-CRISPRi method also uses a second donor engineered bacterial cell comprising a transposase gene, with the second donor engineered bacterial cell also being auxotrophic and requiring the presence of the nutritional substance for growth. For example, the second donor engineered bacterial cell can also be DAP auxotrophic. The transposase gene in the second donor engineered bacterial cell may be located on a plasmid. The first donor engineered bacterial cell and the second donor engineered bacterial cell are contacted with a recipient bacterial cell under conditions allowing for mating of the first donor engineered cell, the second donor engineered cell, and the recipient bacterial cell. The recipient bacterial cell does not require the presence of the nutritional substance for growth for growth. After the tri-parental mating occurs, the bacterial cells are grown in or on a medium comprising the first antibiotic and not including the nutritional substance. For example, when DAP auxotrophy is used for counterselection, the bacterial cells are grown in or on the medium lacking DAP following the tri-parent mating. The selective pressure exerted by the medium eliminates the donor bacterial cells and retains only the recipient cells that integrated the artificial DNA construct with the gene conferring resistance to the first antibiotic.

The above exemplary method may be useful for generating engineered Gammaproteobacteria, in which case the recipient bacterial cell is a Gammaproteobacteria class bacterial cell. In some examples, the Gammaproteobacteria class bacterial cell is *Escherichia coli, Enterobacter cloacae, Enterobacter aerogenes, Pseudomonas aeruginosa, Klebsiella pneumoniae, Vibrio casei, Salmonella enterica*, or *Proteus mirabilis*. In some examples, the first and the second donor engineered bacterial cells are *Escherichia coli* cells. In variations of the above exemplary method, the RP4 transfer machinery may be provided by the genome of the donor engineered bacterial cells and/or may be supplied on a plasmid. For example, a self-mobilizing RP4 transfer plasmid may be employed. A self-mobilizing RP4 transfer plasmid may be provided in a third donor cell. In one example, when the recipient cell is *Acinetobacter baumannii*, a third donor engineered bacterial cell comprising a self-mobilizing RP4 transfer plasmid is used.

Another example of a Mobile-CRISPRi method according to embodiments of the present disclosure is a method of generating an engineered bacterium using a donor engineered bacterial cell the DNA vector including an artificial DNA construct with ICE as the nucleotide transfer sequence. The artificial DNA construct includes a nucleotide sequence encoding a sgRNA, a first promoter operably linked to the nucleotide sequence encoding the sgRNA, a second promoter and a ribosome binding site operably linked to the nucleotide sequence encoding the catalytically inactive variant of Cas9 (dCas9), and the nucleotide sequence of the gene conferring resistance to a first antibiotic. The donor engineered bacterial cell has a gene allowing the conditional origin of replication to be functional. For example, when the conditional origin of replication is R6K γ, then the first donor engineered bacterial cell is pyr+. The exemplary methods involves inducing expression of the conjugation genes in the donor engineered bacterial cells, which promotes the excision of the artificial DNA construct from the vector in the donor engineered bacterial cell. ICE elements are described, for example, in Johnson, C. M. & Grossman, A. D. Integrative and Conjugative Elements (ICEs): What They Do and How They Work. *Annu. Rev. Genet.* 49:577-601 (2015) (16). After inducing the expression of the conjugation genes in the donor bacterial cell, it is contacted with a recipient bacterial cell under conditions allowing for mating of the donor engineered bacterial cell and the recipient bacterial cell to occur, which results in transfer of the artificial DNA construct into the recipient bacterial cell. In this exemplary method, the chromosome of the recipient bacterial carries a gene conferring resistance to a third antibiotic. After the mating, the bacterial cells are grown in or on a medium containing the first antibiotic and the third antibiotic. The pressure exerted by the medium containing two antibiotics selects the engineered bacterial cells with the artificial DNA constructs integrated into the chromosome of the recipient bacterial cells. The above exemplary method may be useful for generating engineered Firmicutes bacteria, in which case the recipient bacterial cell is a Firmicutes bacterial cell. In some examples, the Firmicutes bacterial cell is *Bacillus subtilis, Listeria monocytogenes, Staphylococcus aureus*, or *Enterococcus faecalis*. In some examples, the donor engineered bacterial cells is a *Bacillus subtilis* cell.

Also provided in this disclosure are engineered bacterial produced by Mobile-CRISPRi methods according to the embodiments of the present disclosure. One example of such an engineered bacterium is an engineered bacterium comprising an artificial DNA sequence integrated into a chromosome, the artificial DNA sequence comprising a nucleotide sequence encoding a single guide RNA (sgRNA) targeting a bacterial gene of interest, a first promoter operably linked to the nucleotide sequence encoding the sgRNA, a second promoter and a ribosome binding site operably linked to the nucleotide sequence encoding a catalytically inactive variant of Cas9 (dCas9), and a nucleotide sequence of a gene conferring resistance to an antibiotic. An exemplary engineered bacterium can be a bacterium, in which a bacterial gene of interest targeted by a Mobile-CRISPRi method is an essential gene. An exemplary engineered bacterium can be engineered from a pathogenic bacterium. In some instances, the gene of interest in a pathogenic bacterium targeted by a Mobile-CRISPRi method is a virulence or virulence life-style gene In some examples, an engineered bacterium is engineered from a Gammaproteobacteria bacterium, such as, but not limited to, *Escherichia coli, Enterobacter cloacae, Enterobacter aerogenes, Pseudomonas aeruginosa, Klebsiella pneumoniae, Vibrio casei, Salmonella enterica, Acinetobacter baumannii,* or *Proteus mirabilis*. In some examples, an engineered bacterium is engineered from a Firmicutes bacterium, such as, but not limited to, *Bacillus subtilis, Listeria monocytogenes, Staphylococcus aureus,* or *Enterococcus faecalis*.

Also provided in this disclosure are methods for reducing expression of the bacterial gene of interest, which may be accomplished by growing a population of the engineered bacteria produced by Mobile-CRISPRi methods according to the embodiments of the present invention in the presence of the antibiotic, and under conditions allowing for transcription of the sgRNA. In such engineered bacteria, the DNA construct may include a sequence encoding a regulator gene upstream of the nucleotide sequence encoding the sgRNA.

E. Vector Libraries and Methods of Constructing Knockdown Libraries

Provided in this disclosure are methods and compositions for constructing knockdown libraries of bacteria using Mobile-CRISPRi methods according to the embodiments of the present disclosure. Such knockdown libraries of bacteria are constructed using vector libraries. Such vector libraries include a plurality of bacterial DNA vectors according to the embodiments of the present invention and described elsewhere in the present disclosure. In such vector libraries, different DNA vectors have artificial DNA constructs that each include different sgRNAs that have different targeting sequences. In some embodiments, different targeting sequences target different bacterial genes of interest.

An exemplary method for constructing a knockdown library of bacterial cells may involve cloning multiple sgRNAs into multiple DNA vectors, in which the nucleotide transfer sequences of the artificial DNA construct are Tn7L and Tn7R transposon sequences, to generate a vector library. The cloning to generate the vector library may involve cloning a pool of sgRNAs, or, alternatively, each sgRNAs may be cloned individually into a DNA vector and the individual vectors then pooled. The vector library is transformed into bacterial cells comprising RP4 transfer machinery and also including a gene allowing for the conditional original of replication of the DNA vector to be functional. The above bacterial cells are also auxotrophic and require the presence of a nutritional substance for growth. The transformed bacterial cells and an engineered bacterial including a transposase plasmid, which are also auxotrophic and require the presence of the nutritional substance for growth, are contacted with recipient bacterial cells that do not require the presence of the nutritional substance for growth for growth, under conditions allowing for mating between the contacted bacterial cells. The contacted bacterial cells are then grown on a medium comprising the first antibiotic and not including the nutritional substance. As in the Mobile-CRISPRi methods described elsewhere in the present disclosure, the selective pressure exerted by the medium eliminates the donor bacterial cells and retains only the recipient cells that integrated the artificial DNA construct with the gene conferring resistance to the first antibiotic into their genome.

Another exemplary method for constructing a knockdown library of bacterial cells may involve cloning multiple sgRNAs into multiple DNA vectors, in which the nucleotide transfer sequences of the artificial DNA construct are ICE, to generate a vector library. The cloning to generate the vector library may involve cloning a pool of sgRNAs, or, alternatively, each sgRNAs may be cloned individually into a DNA vector and the individual vectors then pooled. The vector library is transformed into bacterial cells that comprise conjugation genes and a gene allowing the conditional original of replication to be functional. In the exemplary method, expression of the conjugation genes is induced in the transformed bacterial cells, thereby promoting the excision of the artificial DNA constructs from the vectors of the vector library. After the induction, the transformed bacterial cells are contacted with a plurality of recipient bacterial cells under conditions allowing for mating of the transformed bacterial cells and the recipient bacterial cells, resulting in transfer of the artificial DNA constructs into the recipient bacterial cells. In this exemplary method, the chromosome of the recipient bacterial carries a gene conferring resistance to a third antibiotic. After mating, the bacterial cells are grown in or on a medium comprising the first antibiotic and the third antibiotic. The pressure exerted by the medium containing the two antibiotics selects the engineered bacterial cells with the artificial DNA constructs integrated into the chromosome of the engineered bacterial cells.

F. Systems and Kits

Provided in this disclosure are systems and kits for producing engineered bacteria using Mobile-CRISPRi methods according to the embodiments of the present disclosure. An exemplary system for generating an engineered bacterium may include an artificial DNA construct including Tn7L and Tn7R transposon sequences as the nucleotide transfer sequences. The artificial DNA construct also includes the restriction site for insertion of the nucleotide sequence encoding the sgRNA. The exemplary system also includes a nucleic acid sequence of a transposase gene. In such an exemplary sequence, the artificial DNA construct may be located on a bacterial vector including a nucleotide sequence of a gene conferring resistance to a second antibiotic and located outside the artificial DNA construct, a conditional origin of replication located outside the artificial DNA construct, and an origin of transfer site that is also located outside the artificial DNA construct. The nucleic acid sequence of the transposase gene may be located on a second plasmid that does not include the artificial DNA construct. In addition to the above components, an exemplary system may also include a bacterial cell comprising RP4 transfer machinery, the bacterial cell being auxotrophic and requiring the presence of a nutritional substance for growth, and also including a gene allowing the conditional original of replication to be functional. An exemplary system may also include recipient bacterial cell that is intended to be modified by integration of the artificial DNA construct and does not require the presence of the nutritional substance for growth.

Another exemplary system for generating an engineered bacterium may include an artificial DNA construct including ICE as the nucleotide transfer sequences. The artificial DNA construct also includes a restriction site for insertion of the nucleotide sequence encoding the sgRNA. In such an exemplary sequence, the artificial DNA construct may be located on a bacterial vector including a nucleotide sequence of a gene conferring resistance to a second antibiotic and located outside the artificial DNA construct, a conditional origin of replication located outside the artificial DNA construct, and an origin of transfer site that is also located outside the artificial DNA construct. The exemplary system may also include a bacterial cell, comprising conjugation genes and a gene allowing the conditional original of replication to be functional (a donor bacterial cell). In addition to the above components, the exemplary system may include a recipient bacterial cell capable of receiving the artificial DNA construct from the vector transformed into a donor bacterial cell and excised upon induction of the conjugation genes in the donor bacterial cell after the transformation.

An exemplary kit for producing engineered bacteria using Mobile-CRISPRi methods according to the embodiments of the present invention may include a DNA vector according to the embodiments of the present invention in which the nucleotide transfer sequences are the Tn7L and Tn7R transposon sequences. The exemplary kit may also include a bacterial DNA vector encoding transposase. The exemplary kit may also include a self-mobilizing RP4 transfer plasmid. In addition, the kit may include auxotrophic bacterial cells including a gene allowing the conditional original of replication to be functional. Another exemplary kit for producing engineered bacteria using Mobile-CRISPRi methods according to the embodiments of the present invention may include a DNA vector according to the embodiments of the present invention in which the nucleotide transfer sequences are ICE sequences and a plurality of auxotrophic bacterial cells that have a gene allowing the conditional original of replication to be functional.

EXAMPLES

The following examples are offered to illustrate, but not to limit the claimed invention.

Example 1: Materials and Methods Used in the Examples

A. Construction of Mobile-CRISPRi Vectors

A complete list of Mobile-CRISPRi vectors is provided in Table 1. All plasmids were constructed by restriction enzyme digestion of vector DNA followed by either ligation or NEBuilder HiFi DNA Assembly with insert DNA (all enzymes were purchased from New England Biolabs®, Ipswich, Massachusetts). To generate the Mobile-CRISPRi vectors, the pUC origin of replication in the Tn7 transposon plasmid pTJ1 was replaced with the R6K γ origin that requires the π protein (encoded by the pir gene) for replication, generating pJMP1050, and ensuring that Mobile-CRISPRi vectors cannot replicate in recipient cells. Mobile-CRISPRi "backbone" DNA containing unique restriction sites that flank the cloning modules was synthesized as a gBlock (IDT), and inserted into a pJMP1050 derivative (pJMP1054) that lacked those restriction sites, generating pJMP1055. pJMP1055 served as a base for all Tn7-based Mobile-CRISPRi derivatives. Derivatives were constructed by inserting components into the following modules/restriction sites: antibiotic markers/XhoI, reporter genes (e.g., rfp)/PmeI, sgRNA promoters and sgRNAs/EcoRI, sgRNA spacers (for creating sgRNA libraries)/BsaI, regulatory genes (e.g., lacI)/SmaI, dcas9 promoters and ribosome binding sites/SpeI, and dcas9/SpeI-AscI. To create a Mobile-CRISPRi plasmid that integrates into the ICEBs1 element, two ~1 kb DNA fragments flanking the rapI gene were amplified from B. subtilis 168 gDNA and used to replace the Tn7 transposon ends in a pJMP1055 derivative (pJMP1106), generating pJMP1290. pJMP1290 served as a base for all ICE-based Mobile-CRISPRi derivatives and has the same unique restriction sites listed for the modules above. sgRNAs were cloned into the BsaI sites of Mobile-CRISPRi plasmids by ligating annealed oligonucleotides. Oligonucleotides were designed to include overlaps that were complementary to the sticky ends generated by BsaI. Oligonucleotides were added to 1×NEB buffer 4 at 5 µM concentration, denatured for 5 min at 95° C., and then annealed by transferring the reactions to room temperature. Annealed oligonucleotides were then diluted 1:20, 2 µl of the dilution was ligated to 100 ng of BsaI-digested vector for 1 hr at room temperature. sgRNAs were designed as previously described in Peters, J. M. et al. A Comprehensive, CRISPR-based Functional Analysis of Essential Genes in Bacteria. *Cell* 165, 1493-1506 (2016) (4).

TABLE 1

Plasmids

| Name and SEQ ID NO | Tn7 or ICE[a] | Origin[b] | E. coli resistance[c] | Recipient resistance[d] | Reporter[e] | sgRNA promoter[f] | dcas9 promoter[g] | dcas9 variant[h] |
|---|---|---|---|---|---|---|---|---|
| pJMP1039[i] SEQ ID NO: 1 | Tn7 | R6K | AMP | Not applicable (NA) | none | none | none | none |
| pJMP1050[j] | Tn7 | R6K | AMP | TMP | none | none | none | none |
| pJMP1054[j] | Tn7 | R6K | AMP | TMP | none | none | none | none |
| pJMP1055[j] SEQ ID NO: 27 | Tn7 | R6K | AMP | TMP | none | trc (no operator) | none | none |
| pJMP1067[k] | Tn7 | R6K | AMP | TMP | PJ23119-rfp | trc (no operator) | none | none |
| pJMP1069[k] SEQ ID NO: 2 | Tn7 | R6K | AMP | TMP | PJ23119-rfp | trc (no operator) | PBAD | Spy dcas9::3X myc |
| pJMP1071 SEQ ID NO: 3 | Tn7 | R6K | AMP | TMP | PJ23119-rfp | trc (no operator) | PBAD | Hsa Spy dcas9::3X myc |
| pJMP1102 SEQ ID NO:4 | Tn7 | R6K | AMP | TMP | none | trc (no operator) | PBAD | Spy dcas9::3X myc |
| pJMP1103 SEQ ID NO: 5 | Tn7 | R6K | AMP | TMP | none | trc (no operator) | PBAD | Spy dcas9::3X myc |
| pJMP1104 SEQ ID NO: 6 | Tn7 | R6K | AMP | TMP | none | trc (no operator) | PBAD | Spy dcas9::3X myc |
| pJMP1106 SEQ ID NO: 7 | Tn7 | R6K | AMP | TMP | none | trc (no operator) | none | Spy dcas9::3X myc |
| pJMP1159[k] SEQ ID NO: 8 | Tn7 | R6K | AMP | GEN | PJ23119-rfp | PLlacO1 | PLlacO-1 | Spy dcas9::3X myc |
| pJMP1161[k] | Tn7 | R6K | AMP | GEN | PJ23119-rfp | none | PLlacO-1 | Spy dcas9::3X myc |
| pJMP1170[k] SEQ ID NO: 9 | Tn7 | R6K | AMP | GEN | PJ23119-rfp | PLlacO1 | PLlacO-1 | Hsa Spy dcas9::3X myc |
| pJMP1171[k] | Tn7 | R6K | AMP | GEN | PJ23119-rfp | none | PLlacO-1 | Hsa Spy dcas9::3X myc |
| pJMP1183[k] SEQ ID NO: 10 | Tn7 | R6K | AMP | KAN | PJ23119-rfp | PLlacO1 | PLlacO-1 | Spy dcas9::3X myc |
| pJMP1185[k] | Tn7 | R6K | AMP | KAN | PJ23119-rfp | none | PLlacO-1 | Spy dcas9::3X myc |
| pJMP1187[k] SEQ ID NO: 11 | Tn7 | R6K | AMP | KAN | PJ23119-rfp | PLlacO1 | PLlacO-1 | Hsa Spy dcas9::3X myc |
| pJMP1189[k] SEQ ID NO: 35 | Tn7 | R6K | AMP | KAN | PJ23119-rfp | none | PLlacO-1 | Hsa Spy dcas9::3X myc |
| pJMP1217[k] SEQ ID NO: 12 | Tn7 | R6K | AMP | CHL | PJ23119-rfp | PLlacO1 | PLlacO-1 | Spy dcas9::3X myc |
| pJMP1219[k] | Tn7 | R6K | AMP | CHL | PJ23119-rfp | none | PLlacO-1 | Spy dcas9::3X myc |
| pJMP1221[k] SEQ ID NO: 13 | Tn7 | R6K | AMP | CHL | PJ23119-rfp | PLlacO1 | PLlacO-1 | Hsa Spy dcas9::3X myc |
| pJMP1223[k] | Tn7 | R6K | AMP | CHL | PJ23119-rfp | none | PLlacO-1 | Hsa Spy dcas9::3X myc |
| pJMP1237[l] SEQ ID NO: 14 | Tn7 | R6K | AMP | GEN | none | trc (no operator) | PBAD | Hsa Spy dcas9::3X myc |
| pJMP1239 SEQ ID NO: 15 | Tn7 | R6K | AMP | GEN | none | trc (no operator) | PBAD | Hsa Spy dcas9::3X myc |
| pJMP1263[m] | Tn7 | pACYC | CHL | NA | none | none | none | none |
| pJMP1273[n] | Tn7 | pACYC | CHL | NA | none | none | none | none |
| pJMP1274[o] | Tn7 | pACYC | CHL | NA | none | none | none | none |
| pJMP1290[j] | ICE | R6K | AMP | NA | none | trc (no operator) | none | Spy |

TABLE 1-continued

Plasmids

| Name and SEQ ID NO | Tn7 or ICE[a] | Origin[b] | E. coli resistance[c] | Recipient resistance[d] | Reporter[e] | sgRNA promoter[f] | dcas9 promoter[g] | dcas9 variant[h] |
|---|---|---|---|---|---|---|---|---|
| SEQ ID NO: 16 | | | | | | operator) | | dcas9::3X myc |
| pJMP1333[k] SEQ ID NO: 17 | ICE | R6K | AMP | KAN(Gram+) | Pveg-rfp | Pveg | Pxyl/tet | Spy dcas9::3X myc |
| pJMP1335[k] | ICE | R6K | AMP | KAN(Gram+) | Pveg-rfp | none | Pxyl/tet | Spy dcas9::3X myc |
| pJMP1337[l] SEQ ID NO: 18 | ICE | R6K | AMP | KAN(Gram+) | none | Pveg | Pxyl/tet | Spy dcas9::3X myc |
| pJMP1339[l] SEQ ID NO: 19 | Tn7 | R6K | AMP | KAN | none | PLlacO1 | PLlacO-1 | Hsa Spy dcas9::3X myc |
| pJMP1341 SEQ ID NO: 20 | Tn7 | R6K | AMP | KAN | none | PLlacO1 | PLlacO-1 | Hsa Spy dcas9::3X myc |
| pJMP1344 SEQ ID NO: 21 | Tn7 | R6K | AMP | KAN | none | PLlacO1 | PLlacO-1 | Hsa Spy dcas9::3X myc |
| pJMP1346 SEQ ID NO: 22 | Tn7 | R6K | AMP | KAN | none | PLlacO1 | PLlacO-1 | Hsa Spy dcas9::3X myc |
| pJMP1354[l] SEQ ID NO: 23 | Tn7 | R6K | AMP | TMP | none | PLlacO1 | PLlacO-1 | Hsa Spy dcas9::3X myc |
| pJMP1356[l] SEQ ID NO: 24 | Tn7 | R6K | AMP | CHL | none | PLlacO1 | PLlacO-1 | Hsa Spy dcas9::3X myc |
| pJMP1358[l] SEQ ID NO: 25 | Tn7 | R6K | AMP | SPT | none | PLlacO1 | PLlacO-1 | Hsa Spy dcas9::3X myc |
| pJMP1360[l] SEQ ID NO: 26 | Tn7 | R6K | AMP | GEN | none | PLlacO1 | PLlacO-1 | Hsa Spy dcas9::3X myc |
| pJMP1363[p] SEQ ID NO: 28 | ICE | R6K | AMP | CHL(Gram+) | none | none | none | Spy dcas9::3X myc |

[a]Denotes whether the plasmid was associated with Tn7 or ICE experiments.
[b]Plasmid replication origin in E. coli donors.
[c]Antibiotic resistance gene used for selection in E. coli donors (AMP = ampicillin; CHL = chloramphenicol).
[d]Antibiotic resistance used for selection in recipient strains (KAN = kanamycin; CHL = chloramphenicol; GEN = gentamicin; TMP = trimethoprim; SPT = spectinomycin).
[e]Reporter gene and associated promoter inserted into Mobile-CRISPRi.
[f]Promoter driving sgRNA expression; trc promoters with no LacI operator site are constitutive.
[g]Promoter driving dcas9 expression.
[h]dcas9 sequence variants; "Spy" has the original S. pyogenes sequences; "Hsa Spy" is human codon optimized and works better in some species (for example, P. aeruginosa).
[i]This plasmid is a transposase expression vector and contains no Tn7 ends.
[j]Construction intermediate;
[k]rfp "test" strain;
[l]a vector for cloning new sgRNAs;
[m]B. subtilis attTn7 site and flanking sequence cloned into pACYC;
[n]E. coli attTn7 site with B. subtilis flanking sequence cloned into pACYC;
[o]B. subtilis ΔattTn7 site and flanking sequence cloned into pACYC;
[p]a vector for stabilizing ICE in the presence of rapI expression.

B. Construction of Mobile-CRISPRi Strains and Mating Assays

A complete list of strains used in the study can be found in Table 2. In nature, CRISPR systems can be transferred by transposons related to Tn7, as discussed, for example, in Peters, J. E. et al. Recruitment of CRISPR-Cas systems by Tn7-like transposons. *Proc. Nat. Acad. Sci.* 114, E7358-E7366 (2017) (22). Tn7-based Mobile-CRISPRi strains were constructed by tri- or quad-parental mating as previously described in Choi, K.-H. et al. A Tn7-based broad-range bacterial cloning and expression system. *Nat. Methods* 2, 443-448 (2005) (15) and Choi, K.-H. & Schweizer, H. P. mini-Tn7 insertion in bacteria with single attTn7 sites: example *Pseudomonas aeruginosa*. *Nat. Protoc.* 1, 153-161 (2006) (23), with several modifications. All Tn7 matings used MFDpir (a pir+ strain that is dependent on DAP for growth and contains the RP4 transfer machinery; see, for example, Ferrières, L. et al. Silent Mischief: Bacteriophage Mu Insertions Contaminate Products of *Escherichia coli* Random Mutagenesis Performed Using Suicidal Transposon Delivery Plasmids Mobilized by Broad-Host-Range RP4 Conjugative Machinery. *J. Bacteriol.* 192, 6418-6427 (2010) (24)) transformed with either a Tn7 transposase plasmid (pJMP1039—a derivative of pTNS3—see, for example, Choi, K.-H. et al. Genetic Tools for Select-Agent-Compliant Manipulation of *Burkholderia pseudomallei*. *Appl. Environ. Microbiol.* 74, 1064-1075 (2008) (25)—with a spontaneous small deletion upstream of the $P_t$ promoter) or transposon plasmid (various pJMP1055 derivatives) as mating donors. Matings with *Acinetobacter baumannii* ATCC19606 required the presence of a third donor strain containing the self-mobilizing RP4 transfer plasmid pRK2013 (described in 15) for unknown reasons. Cultures of the two *E. coli* donor strains (transposon and transposase donors) were grown overnight (~16 hrs) at 37° C. in Lysogeny Broth (LB)+300 µM DAP (Alfa Aesar B22391)+ 100 µg/ml ampicillin. Recipient strains assayed here also grew to saturation in LB after incubation at 37° C. for ~16 hrs. 100 µl of each donor and recipient strain was added to 700 µl of LB and mixed by pipetting. Mixes of donor and recipient strains were pelleted for 2 min at 7000×g, washed twice with 1 ml of LB, resuspended in 30 µl of LB after the final wash, pipetted onto a cellulose filter (MF-Millipore HAWG01300) placed on a pre-warmed LB+300 µM DAP plate, and incubated at 37° C. for 6 hrs. Filters were then transferred to microcentrifuge tubes containing 200 µl of PBS and vortexed to liberate the cells. Cells were spread onto on media that selects for the Mobile-CRISPRi plasmid and recipient (e.g., LB+ kanamycin) without DAP (the absence of DAP will select against donor *E. coli*). Antibiotic concentrations used for selection were: 30 µg/ml kanamycin, and 30 µg/ml gentamicin (for *P. aeruginosa*).

ICE-based Mobile-CRISPRi strains were constructed by bi-parental mating as previously described in Auchtung, J. M. et al. Regulation of a *Bacillus subtilis* mobile genetic element by intercellular signaling and the global DNA damage response. *Proc. Natl. Acad. Sci. U.S.A* 102, 12554-12559 (2005) (26) and Auchtung, J. M. et al. Identification and characterization of the immunity repressor (ImmR) that controls the mobile genetic element ICEBs1 of *Bacillus subtilis*. *Mol. Microbiol.* 64, 1515-1528 (2007) (27) with modifications. ICE donor strains were generated by transformation of *B. subtilis* with Mobile-CRISPRi integration plasmids using natural competence as previously described in Peters, J. M. et al. A Comprehensive, CRISPR-based Functional Analysis of Essential Genes in Bacteria. *Cell* 165, 1493-1506 (2016) (4). Expression of the ICE antirepressor, RapI, induces conjugation genes found on the ICE element and promotes excision, as discussed in (26). ICE excision and the large insert size of Mobile-CRISPRi plasmids resulted in very few transformants. To produce a strain with a stable ICE element in the presence of an IPTG-inducible rap gene that transformed at high efficiency, a dcas9 gene linked to a chloramphenicol-resistance marker was integrated into ICE-selection for the chloramphenicol marker and the extra homology present in the dcas9 gene improved transformation efficiency. For mating, one 3 ml LB culture of each donor and recipient strain was grown from single colonies to exponential phase (~2 hrs at 37° C.); donors were grown in LB+3.25 µg/ml kanamycin to select for ICE retention. Exponential phase cultures were then back diluted to an $OD_{600}$ of 0.02 and grown until $OD_{600}$ 0.2 before inducing rapI expression with 1 mM IPTG for 1 hr. 2.5 ml of donor and recipient cells adjusted to an $OD_{600}$ of 0.9 were mixed with 5 ml of 1× Spizizen salts and vacuum filtered using an analytical CN filter (Nalgene 145-0020). Filters were transferred to Spizizen agar plates and incubated for 3 hrs at 37° C. Transconjugants were selected for plating on kanamycin+streptomycin plates as all recipient strains were streptomycin resistant. The ICE mating procedure used was the same for all Bacillales Firmicutes in this study. Antibiotic concentrations used for selection were: 6 µg/ml (*B. subtilis*) chloramphenicol, 7.5/50/1000 µg/ml kanamycin (*B. subtilis/S. aureus* and *L. monocytogenes/E. faecalis*), and 100 µg/ml streptomycin.

TABLE 2

Bacterial strains.

| Systematic Name | Other Name | Organism | Genotype |
|---|---|---|---|
| CAG74136 | CAG74136 | *Escherichia coli* K-12 DH10B F' | F'[::Tn10(TetR), proAB+, lacIq, lacZΔM15], endA1, recA1, galE15, galK16, nupG, rpsL, ΔlacX74, Φ80[lacZΔM15], araD139, Δ(araleu)7697, mcrA, Δ(mrr-hsdRMS-mcrBC) λ- |
| CAG74168 | 168 | *Bacillus subtilis* 168 | wild-type, trpC2 |
| CAG74538 | BW25113 | *Escherichia coli* K-12 BW25113 | wild-type, Δ(araD-araB)567 Δ(rhaD-rhaB)568 ΔlacZ4787(::rrnB-3) hsdR514 rph-1 |
| CAG80640 | RAU150 | *Listeria monocytogenes* 10403s | Ø cure, Δcas9, streptomycin-resistant |
| CAG81205 | ATCC13047 | *Enterobacter cloacae* ATCC13047 | wild-type |
| CAG81206 | ATCC13048 | *Enterobacter aerogenes* ATCC13048 | wild-type |
| CAG80303 | MR-1 | *Shewanella oneidensis* MR-1 | wild-type |
| CAG80049 | UCBPP-PA14 | *Pseudomonas aeruginosa* UCBPP-PA14 | wild-type |
| CAG80988 | ATCC43816 KPPR1 | *Klebsiella pneumoniae* KPPR1 | wild-type, rifampicin-resistant |
| CAG81207 | JB196 | *Vibrio casei* JB196 | wild-type |
| CAG81208 | ATCC19606 | *Acinetobacter baumannii* ATCC19606 | wild-type |
| CAG81209 | 14028s | *Salmonella enterica* 14028s | wild-type |
| CAG80990 | HI4320 | *Proteus mirabilis* HI4320 | wild-type |
| CAG80688 | RN4220 | *Staphylococcus aureus* RN4220 | wild-type, hsdR, essC, mntH |
| CAG80728 | CAG80728 | *Staphylococcus aureus* RN4220 | hsdR, essC, mntH, spontaneous streptomycin-resistant mutant |
| CAG80280 | MFDpir | *Escherichia coli* K-12 MFDpir | RP4-2-Tc::ΔMu1::aac(3)IV-ΔaphA-Δnic35-ΔMu2::zeo, ΔdapA::(erm-pir), ΔrecA |

TABLE 2-continued

Bacterial strains.

| Systematic Name | Other Name | Organism | Genotype |
|---|---|---|---|
| CAG74195 | BW25141 | *Escherichia coli* K-12 BW25141 | Δ(araD-araB)567, ΔlacZ4787(::rrnB-3), Δ(phoB-phoR)580, λ-, galU95, ΔuidA3::pir+, recA1, endA9(del-ins)::FRT, rph-1, Δ(rhaD-rhaB)568, hsdR514 |
| CAG75134 | BW29427 | *Escherichia coli* K-12 BW29427 | RP4-2(TetS, kan1360::FRT), thrB1004, lacZ58(del)(M15), dapA1341::[erm pir+], rpsL(strR), thi-, hsdS-, pro- |
| CAG75376 | CAG75376 | *Escherichia coli* K-12 | pRK2013(KanR) |
| CAG80068 | CAG80068 | *Escherichia coli* K-12 BW29427 | RP4-2(TetS, kan1360::FRT), thrB1004, lacZ58(del)(M15), dapA1341::[erm pir+], rpsL(strR), thi-, hsdS-, pro-, pRK2013(KanR) |
| CAG80612 | CAL89 | *Bacillus subtilis* CAL89 | ΔICE, rpsL(streptomycin-resistant), ΔcomK::spc(SpcR) |
| CAG80614 | JMA183 | *Bacillus subtilis* JMA183 | trpC2, pheA1, amyE::Pspank-rapI(SpcR) |
| CAG81072 | CAG81072 | *Bacillus subtilis* JMA183 | trpC2, pheA1, amyE::Pspank-rapI(SpcR), ICE::pJMP1363(CmR) |
| CAG80448 | CAG80448 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1039(AmpR, GenR) |
| CAG80452 | CAG80452 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1159(AmpR, GenR) |
| CAG80456 | CAG80456 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1161 (AmpR, GenR) |
| CAG80460 | CAG80460 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1170(AmpR, GenR) |
| CAG80464 | CAG80464 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1171 (AmpR, GenR) |
| CAG80486 | CAG80486 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1183(AmpR, KanR) |
| CAG80488 | CAG80488 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1185(AmpR, KanR) |
| CAG80490 | CAG80490 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1187(AmpR, KanR) |
| CAG80492 | CAG80492 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1189(AmpR, KanR) |
| CAG80112 | CAG80112 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1067(AmpR, TmpR) |
| CAG80113 | CAG80113 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1069(AmpR, TmpR) |
| CAG80114 | CAG80114 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1071(AmpR, TmpR) |
| CAG81113 | CAG81113 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1341(AmpR, KanR) |
| CAG81118 | CAG81118 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1344(AmpR, KanR) |
| CAG81119 | CAG81119 | *Escherichia coli* K-12 MFDpir | RP4-2-Tc::ΔMu1::aac(3)IV-ΔaphA-Δnic35-ΔMu2::zeo, ΔdapA::(erm-pir), ΔrecA, pJMP1346(AmpR, KanR) |
| CAG80900 | CAG80900 | *Bacillus subtilis* JMA183 | trpC2, pheA1, amyE::Pspank-rapI(SpcR), ICE::pJMP1333(KanR) |
| CAG80902 | CAG80902 | *Bacillus subtilis* JMA183 | trpC2, pheA1, amyE::Pspank-rapI(SpcR), ICE::pJMP1335(KanR) |
| CAG80998 | CAG80998 | *Bacillus subtilis* CAL89 | rpsL(streptomycin-resistant), ΔcomK::spc(SpcR), ICE::pJMP1333(KanR) |
| CAG81002 | CAG81002 | *Bacillus subtilis* CAL89 | rpsL(streptomycin-resistant), ΔcomK::spc(SpcR), ICE::pJMP1335(KanR) |
| CAG81043 | CAG81043 | *Staphylococcus aureus* RN4220 | hsdR, essC, mntH, streptomycin-resistant, ICE::pJMP1333(KanR) |
| CAG81047 | CAG81047 | *Staphylococcus aureus* RN4220 | hsdR, essC, mntH, streptomycin-resistant, ICE::pJMP1335(KanR) |

TABLE 2-continued

Bacterial strains.

| Systematic Name | Other Name | Organism | Genotype |
|---|---|---|---|
| CAG80904 | CAG80904 | *Escherichia coli* K-12 BW25113 | Δ(araD-araB)567 Δ(rhaD-rhaB)568 ΔlacZ4787(::rrnB-3) hsdR514 rph-1, attTn7::pJMP1183(KanR) |
| CAG80908 | CAG80908 | *Escherichia coli* K-12 BW25113 | Δ(araD-araB)567 Δ(rhaD-rhaB)568 ΔlacZ4787(::rrnB-3) hsdR514 rph-1, attTn7::pJMP1185(KanR) |
| CAG80912 | CAG80912 | *Escherichia coli* K-12 BW25113 | Δ(araD-araB)567 Δ(rhaD-rhaB)568 ΔlacZ4787(::rrnB-3) hsdR514 rph-1, attTn7::pJMP1187(KanR) |
| CAG80916 | CAG80916 | *Escherichia coli* K-12 BW25113 | Δ(araD-araB)567 Δ(rhaD-rhaB)568 ΔlacZ4787(::rrnB-3) hsdR514 rph-1, attTn7::pJMP1189(KanR) |
| CAG80920 | CAG80920 | *Salmonella enterica* 14028s | attTn7::pJMP1183(KanR) |
| CAG80924 | CAG80924 | *Salmonella enterica* 14028s | attTn7::pJMP1185(KanR) |
| CAG80928 | CAG80928 | *Salmonella enterica* 14028s | attTn7::pJMP1187(KanR) |
| CAG80932 | CAG80932 | *Salmonella enterica* 14028s | attTn7::pJMP1189(KanR) |
| CAG80936 | CAG80936 | *Enterobacter cloacae* ATCC13047 | attTn7::pJMP1183(KanR) |
| CAG80940 | CAG80940 | *Enterobacter cloacae* ATCC13047 | attTn7::pJMP1185(KanR) |
| CAG80944 | CAG80944 | *Enterobacter cloacae* ATCC13047 | attTn7::pJMP1187(KanR) |
| CAG80948 | CAG80948 | *Enterobacter cloacae* ATCC13047 | attTn7::pJMP1189(KanR) |
| CAG80952 | CAG80952 | *Enterobacter aerogenes* ATCC13048 | attTn7::pJMP1183(KanR) |
| CAG80956 | CAG80956 | *Enterobacter aerogenes* ATCC13048 | attTn7::pJMP1185(KanR) |
| CAG80960 | CAG80960 | *Enterobacter aerogenes* ATCC13048 | attTn7::pJMP1187(KanR) |
| CAG80964 | CAG80964 | *Enterobacter aerogenes* ATCC13048 | attTn7::pJMP1189(KanR) |
| CAG81139 | CAG81139 | *Proteus mirabilis* HI4320 | attTn7::pJMP1183(KanR) |
| CAG81140 | CAG81140 | *Proteus mirabilis* HI4320 | attTn7::pJMP1185(KanR) |
| CAG81141 | CAG81141 | *Proteus mirabilis* HI4320 | attTn7::pJMP1187(KanR) |
| CAG81142 | CAG81142 | *Proteus mirabilis* HI4320 | attTn7::pJMP1189(KanR) |
| CAG81132 | CAG81132 | *Klebsiella pneumoniae* KPPR1 | rifampicin-resistant, attTn7::pJMP1183(KanR) |
| CAG81133 | CAG81133 | *Klebsiella pneumoniae* KPPR1 | rifampicin-resistant, attTn7::pJMP1185(KanR) |
| CAG81134 | CAG81134 | *Klebsiella pneumoniae* KPPR1 | rifampicin-resistant, attTn7::pJMP1187(KanR) |
| CAG81135 | CAG81135 | *Klebsiella pneumoniae* KPPR1 | rifampicin-resistant, attTn7::pJMP1189(KanR) |
| CAG81019 | CAG81019 | *Acinetobacter baumannii* ATCC19606 | attTn7::pJMP1183(KanR) |
| CAG81023 | CAG81023 | *Acinetobacter baumannii* ATCC19606 | attTn7::pJMP1185(KanR) |
| CAG81027 | CAG81027 | *Acinetobacter baumannii* ATCC19606 | attTn7::pJMP1187(KanR) |
| CAG81031 | CAG81031 | *Acinetobacter baumannii* ATCC19606 | attTn7::pJMP1189(KanR) |
| CAG80130 | CAG80130 | *Pseudomonas aeruginosa* UCBPP-PA14 | attTn7::pJMP1067(TmpR) |
| CAG80132 | CAG80132 | *Pseudomonas aeruginosa* UCBPP-PA14 | attTn7::pJMP1068(TmpR) |
| CAG80134 | CAG80134 | *Pseudomonas aeruginosa* UCBPP-PA14 | attTn7::pJMP1069(TmpR) |
| CAG81203 | CAG81203 | *Pseudomonas aeruginosa* UCBPP-PA14 | attTn7::pJMP1237(GenR) |
| CAG81204 | CAG81204 | *Pseudomonas aeruginosa* UCBPP-PA14 | attTn7::pJMP1239(GenR) |
| CAG81130 | CAG81130 | *Klebsiella pneumoniae* KPPR1 | rifampicin-resistant, attTn7::pJMP1341(KanR) |
| CAG81131 | CAG81131 | *Klebsiella pneumoniae* KPPR1 | rifampicin-resistant, attTn7::pJMP1346(KanR) |
| CAG81128 | CAG81128 | *Enterobacter aerogenes* ATCC13048 | attTn7::pJMP1341(KanR) |
| CAG81129 | CAG81129 | *Enterobacter aerogenes* ATCC13048 | attTn7::pJMP1346(KanR) |

C. Transfer Efficiency Assays

Tn7 or ICE mating experiments were carried out in triplicate (n=3 matings). Transfer efficiency was calculated by taking the ratio of transconjugants (antibiotic-resistant Dap$^+$ colonies for Tn7 matings, and KanR/StrR colonies for ICE matings) to viable cells (LB colonies for Tn7 matings, and StrR colonies for ICE matings). For Tn7 transfer to the B. subtilis attTn7 site in E. coli, the native attTn7 site in E. coli K-12 DH10B was occupied by an unmarked Tn7 to prevent chromosomal transposition, while test attTn7 sites were cloned onto a chloramphenicol resistant plasmid.

D. Mobile-CRISPRi Stability Assays

Four independently generated isolates (n=4 isolates) of E. coli K-12 BW25113 and B. subtilis 168 containing Mobile-CRISPRi systems targeting rfp were grown to saturation overnight at 37° C. in LB+ kanamycin (30 µg/ml for E. coli, E. cloacae, and K. pneumoniae and 7.5 µg/ml for B. subtilis) to select for retention of the of the Tn7 or ICE element containing CRISPRi. One ml of each culture was centrifuged at 6000×g for 3 min and washed twice with LB to remove any residual kanamycin. The washed cells were diluted 1:1000 in LB and grown to saturation. The procedure of dilution and growth to saturation was repeated a total of 5 times for ~50 generations of growth. Cells were then serially diluted and plated on selective (LB+kanamycin) and non-selective plates (LB). The ratio between colony counts on LB and LB+ kanamycin was used to determine the fraction of cells that retained the Tn7 or ICE element.

E. RFP Knockdown Assays

RFP knockdown was measured using flow cytometry or a plate reader (for A. baumannii and V. casei; n=4 independently constructed isolates for all strains except P. mirabilis [n=3 isolates] and V. casei [n=3 isolates]). Flow cytometry was performed by diluting overnight cultures of Mobile-CRISPRi rfp knockdown strains 1:10,000 into fresh media (LB for Gammaproteobacteria and B. subtilis, Brain Heart Infusion broth for S. aureus) containing CRISPRi inducer (1 mM IPTG for all Gammaproteobacteria except P. aeruginosa, 1% arabinose for P. aeruginosa, and 0.1 µg/ml anhydrotetracycline for Firmicutes) and incubating cultures at 37° C. with rotation until the cultures reached mid-log phase (OD$_{600}$ 0.3-0.6). Cultures were then cross-linked with 1% formaldehyde [final] for 10 min, followed by quenching for 10 min with 0.5 M glycine [final]. Cross-linked cells were then diluted 1:10 in phosphate buffered saline and flowed on a BD LSRII using 610/20 BP filter (PE-Texas-Red fluorochrome). Data for at least 10,000 cells was collected for four independently constructed strain isolates. In all cases, data for 100% of the cells collected were used in the analysis. For V casei, overnight cultures were normalized to 2.0 OD$_{600}$ and then diluted 1:200 in LB with or without 0.5 mM IPTG. After 6 hours growth post-induction the strains were normalized to 0.2 OD$_{600}$ and washed once in 1×PBS. The samples were then transferred to a 96-well plate (200 µl in each well) in triplicate and measured for ds-Red fluorescence (Ex 557 nm Em 592 nm) using a bottom-read plate reader (Tecan). For A. baumannii, overnight cultures were diluted 1:10,000 into fresh LB with or without 0.1 mM IPTG. Cells were grown in a 96 well plate with measurements of OD$_{600}$ and RFP every 10 min. The values reported reflect the RFP knockdown at mid-log growth. The values reported are mean values and error bars reflect the standard deviation from the mean.

F. Pyocyanin Knockdown Assays

Strains were grown overnight in Kings Medium A Base (HiMedia M1543) to induce pyocyanin and pyorubin production and 1% arabinose to fully induce dcas9 expression. Growth was repeated 3 times (n=3); representative results are shown.

G. Antibiotic Sensitivity Assays

MIC assays were performed using the broth microdilution method as previously described in Wiegand et al. Agar and broth dilution methods to determine the minimal inhibitory concentration (MIC) of antimicrobial substances. Nat. Protoc. 3, 163 (2008) (28), except that 0.1% arabinose (for P. aeruginosa) or 100 µM IPTG (for E. aerogenes) was added to induce dcas9 expression, and K. pneumoniae cultures were shaken to reduce clumping. Three biological replicates were grown for MIC assays. Growth curves shown in FIG. 3 were set up in exactly the same manner as the MIC assays, except that cultures were grown with agitation in a plate reader (BioTek) for ~16 hrs. P-values for comparing MICs between control sgRNA and folA sgRNA strains were obtained using an unpaired two-tailed t-test with Welch's correction to account for unequal variances between samples and calculated using GraphPad Prism 7.0e.

H. Construction of Mobile-CRISPRi Strains and Mating Assays

Pooled Tn7-based Mobile-CRISPRi libraries for E. cloacae were constructed by following the procedure for single gene CRISPRi strain construction with several modifications. Equal concentration of annealed oligonucleotides for each sgRNA were pooled and ligated into a BsaI digested plasmid. Ligation product was transformed into an E. coli pir+ strain. Colonies on selection plates (LB+100 µg/ml ampicillin) were collected and resuspended in LB and plasmids were purified from of pooled transformants. Purified pooled plasmids were transformed into donor strain, MFDpir. Transformants were collected and resuspended in LB+300 µM DAP+100 µg/ml ampicillin+12.5% glycerol and stored at −80° C. For comparison, the other donor was prepared by transformation of a pool of individually cloned plasmids with equal concentration. Tri-parental mating and selection were performed as described above and selected colonies of E. cloacae CRISPRi strains were collected and resuspended in MOPS salts solution (as described in Koo, B.-M. et al. Construction and Analysis of Two Genome-Scale Deletion Libraries for Bacillus subtilis. Cell Syst. 4, 291-305.e7 (2017) (28))+12.5% glycerol and stored at −80° C. after measurement of OD$_{450}$ of stock. In order to prepare inoculum of library to screen fitness of library in minimal media, frozen stock was diluted in glucose minimal medium to OD$_{450}$ of 5 and incubated for recovery for 1 hr. Recovered cell culture was mixed with a 100-fold excess wild-type E. cloacae, then diluted to an OD$_{450}$ of 0.01 in 30 ml glucose minimal media with or without IPTG, then grown in 125 ml flasks at 30° C. with shaking (250 rpm). When the culture reached OD$_{450}$ of 0.64, 1 ml of culture was collected for preparation of sequencing library of 6 doubling sample. For 12 doubling sample, this culture was diluted to an OD$_{450}$ of 0.01 in 30 ml and was grown until the culture reached OD$_{450}$ of 0.64. in order to prepare the Illumina sequencing library, genomic DNA was purified using the Qiagen DNeasy Blood & Tissue kit and sequencing region was amplified by PCR using the primers harboring indices for different sampling time and growth conditions. Differentially indexed PCR products were purified by agarose gel electrophoresis prior Illumina sequencing. Frequencies of strains in each sample were calculated by dividing the number of reads of sgRNA encoding sequence from each strain by the number of total read and used for calculation of fitness. Fitness (data not shown) was calculated as described in van Opijnen et al.

Tn-seq: high-throughput parallel sequencing for fitness and genetic interaction studies in microorganisms. *Nat. Methods* 6, 767-772 (2009) (12):

$$Wi=\ln(Ni(t2)Xd/Ni(ti))/\ln((1-Ni(t2))Xd/(1-Ni(t1))),$$

N(t) is frequency of the mutant in the population at the time points, and d represents the growth of the bacterial population during library selection (calculated using $OD_{450}$ change).

Pearson's r was calculated from a linear fit of the data using Microsoft Excel. The list of constructed in Mobile-CRISPRi *E. cloacae* strains is presented in Table 3.

were selected on LB supplemented with kanamycin two times and stored at -80° C. as a glycerol stock. To screen growth phenotype of each strain, cells were pinned from glycerol stocks onto rectangular LB agar plates in 384-format using a Singer ROTOR robot (four technical replicates on one plate in this screen). For each screen, exponentially growing cells in 384-format were then pinned to defined media plates and incubated for 16 hrs at room temperature to avoid mucoid colony formation. Plates were imaged using a Powershot G10 camera (Canon) when at a time point at which fitness differences were apparent but growth had not saturated. The calculation of relative fitness

TABLE 3

List Mobile-CRISPRi *E. cloacae* strains

| Strain | Locus tag of targeted gene | Targeted gene | product |
|---|---|---|---|
| argG_1 | ECL_04553 | argG | argininosuccinate synthase |
| argG_2 | ECL_04553 | argG | argininosuccinate synthase |
| argH_1 | ECL_05028 | argH | argininosuccinate lyase |
| argH_2 | ECL_05028 | argH | argininosuccinate lyase |
| dapE_1 | ECL_03769 | dapE | succinyl-diaminopimelate desuccinylase |
| dapE_2 | ECL_03769 | dapE | succinyl-diaminopimelate desuccinylase |
| hisD_1 | ECL_03340 | hisD | histidinol dehydrogenase |
| hisD_2 | ECL_03340 | hisD | histidinol dehydrogenase |
| hisG_1 | ECL_03339 | hisG | ATP phosphoribosyltransferase |
| hisG_2 | ECL_03339 | hisG | ATP phosphoribosyltransferase |
| ispG_1 | ECL_03857 | ispG | 4-hydroxy-3-methylbut-2-en-l-yl diphosphate synthase |
| ispG_2 | ECL_03857 | ispG | 4-hydroxy-3-methylbut-2-en-l-yl diphosphate synthase |
| ispH_1 | ECL_00837 | ispH | 4-hydroxy-3-methylbut-2-enyl diphosphate reductase |
| ispH_2 | ECL_00837 | ispH | 4-hydroxy-3-methylbut-2-enyl diphosphate reductase |
| lacZ_1 | ECL_03691 | lacZ | beta-D-galactosidase |
| lacZ_2 | ECL_03691 | lacZ | beta-D-galactosidase |
| lon_1 | ECL_01197 | lon | lon protease |
| lon_2 | ECL_01197 | lon | lon protease |
| lysA_1 | ECL_04165 | lysA | diaminopimelate decarboxylase |
| lysA_2 | ECL_04165 | lysA | diaminopimelate decarboxylase |
| mreC_1 | ECL_04633 | mreC | rod shape-determining protein MreC |
| mreC_2 | ECL_04633 | mreC | rod shape-determining protein MreC |
| mreD_1 | ECL_04632 | mreD | rod shape-determining protein MreD |
| mreD_2 | ECL_04632 | mreD | rod shape-determining protein MreD |
| nrdE_1 | ECL_04015 | nrdE | ribonucleotide-diphosphate reductase subunit alpha |
| nrdE_2 | ECL_04015 | nrdE | ribonucleotide-diphosphate reductase subunit alpha |
| nrdF_1 | ECL_04016 | nrdF | ribonucleotide-diphosphate reductase subunit beta |
| nrdF_2 | ECL_04016 | nrdF | ribonucleotide-diphosphate reductase subunit beta |
| rpoS_1 | ECL_04088 | rpoS | RNA polymerase nonessential primary-like sigma factor (SigmaS) |
| rpoS_2 | ECL_04088 | rpoS | RNA polymerase nonessential primary-like sigma factor (SigmaS) |
| thrB_1 | ECL_00815 | thrB | homoserine kinase |
| thrB_2 | ECL_00815 | thrB | homoserine kinase |
| thrC_1 | ECL_00816 | thrC | threonine synthase |
| thrC_2 | ECL_00816 | thrC | threonine synthase |
| tolC_1 | ECL_04363 | tolC | putative outer membrane channel protein |
| tolC_2 | ECL_04363 | tolC | putative outer membrane channel protein |
| trpA_1 | ECL_01725 | trpA | tryptophan synthase subunit alpha |
| trpA_2 | ECL_01725 | trpA | tryptophan synthase subunit alpha |
| trpD_1 | ECL_01728 | trpD | bifunctional glutamine amidotransferase/anthranilate phosphoribosyltransferase |
| trpD_2 | ECL_01728 | trpD | bifunctional glutamine amidotransferase/anthranilate phosphoribosyltransferase |

Ordered Tn7-based Mobile-CRISPRi libraries for *E. cloacae* were constructed by following the procedure for single gene CRISPRi strain construction with modifications for automation. Each donor Tn7::CRISPRi strains were prepared by transformation of individually cloned plasmids into MFDpir strain and arrayed in 96 well plate. Equal amount of transposase strain was added to each well and pinned to LB+300 µM DAP+2% agar plate using a Singer ROTOR robot. Wild-type *E. cloacae* cells arrayed in 96 colony format were pinned to the same plate, which was incubated for 6 hrs. Kanamycin resistant *E. cloacae* CRISPRi strains was carried out as described in (29) with minor modifications. Relative fitness (RF) was measured by the colony opacity of each mutant determined with Iris colony sizing software described in Kritikos, G. et al. A tool named Iris for versatile high-throughput phenotyping in microorganisms. *Nat. Microbiol.* 2, 17014 (2017) (30). The RF of each mutant was calculated as: RF=(average colony opacity of CRISPRi strain)/(average colony opacity of CRISPRi with no sgRNA strain); knockdown strains were grown in quadruplicate (n=4).

I. dCas9 Western Blot

Cultures of *P. aeruginosa* were diluted back from stationary phase and grown to saturation in the presence/absence of 1% arabinose at 37° C. and then 1 ml of culture was added to 0.25 ml 5×SDS-PAGE sample buffer and boiled at 100° C. for 10 min before storage. Samples were boiled at 90° C. for 2 min before running on a Bolt 10% Bis-Tris Plus gel (ThermoFisher) alongside PagerRuler Plus Protein Ladder (ThermoFisher) at 150V for 1 hr. Proteins were transferred to a nitrocellulose membrane (Bio-Rad, 0.45 µm) at 100V for 2 hr at 4° C. using the Mini Trans-Blot® Cell system (Bio-Rad). Protein amounts were checked by Ponceau staining (0.1% Ponceau S, 5% (v/v) acetic acid) for 25 min at room temperature, followed by washing in water to destain. Membranes were blocked in Odyssey Blocking Buffer (Licor) at 4° C. overnight. Each primary antibody (Anti-CRISPR-Cas9 (AbCam #191468) and c-Myc (Santa Cruz Biotechnology #9E10)) were used at 1:1000 in PBS+0.5% Tween® 80+3% BSA at room temperature for 2 hr. Secondary antibody (IRDye 680RD Goat anti-Mouse IgG, #926-68070) was used at 1:10000 in Odyssey® Blocking Buffer (Licor) at room temperature for 1 hr. All membrane washes were performed using PBS+0.5% Tween® 80. Blots were images on a Licor Odyssey© Aerius® at 700 nm.

J. Data Collection and Analysis

Flow cytometry data was collected using BD FACSDIVA v8.0.1. Data analysis was performed in Galaxy v18.01 (pooled sequencing data), FlowJo v10.4.2 and FCS Express 6 Plus (flow cytometry data), GraphPad Prism 7.0e (graphing and statistical analysis), and Microsoft Excel v16.12. Plasmid sequence maps were created using SnapGene v3.1.4.

Example 2: Construction of Mobile-CRISPRi Strains

The experiments described below showed that the Mobile-CRISPRi system was an effective genetic tool for gene knockdowns in diverse bacteria. For Gammaproteobacteria, a mobile-CRISPRi artificial DNA construct was transferred from *Escherichia coli* using the broad host range RP4 plasmid conjugation machinery, and was integrated into the recipient genome downstream of the highly conserved glmS gene using the extensively characterized Tn7 transposition system (described, for example, in (14) and (15)). The process of bacterial strain constructions using Mobile-CRISPRi DNA vectors having an artificial DNA constructs including Tn7 transposon sequences and carrying CRISPRi components and a second plasmid containing Tn7 transposition genes by tri-parental mating is schematically illustrated in FIG. 2, top. Donor cells contain a chromosomal copy of the RP4 transfer machinery were used to mobilize the Tn7 plasmids. Once inside the recipient cell, Tn7 transposition proteins integrated the CRISPRi DNA flanked by left and right Tn7 end sequences (artificial DNA construct) into the recipient genome downstream of the glmS gene. Selection on antibiotic plates lacking DAP eliminated *E. coli* donors and retained the recipients with an integrated CRISPRi system.

Figure 5:
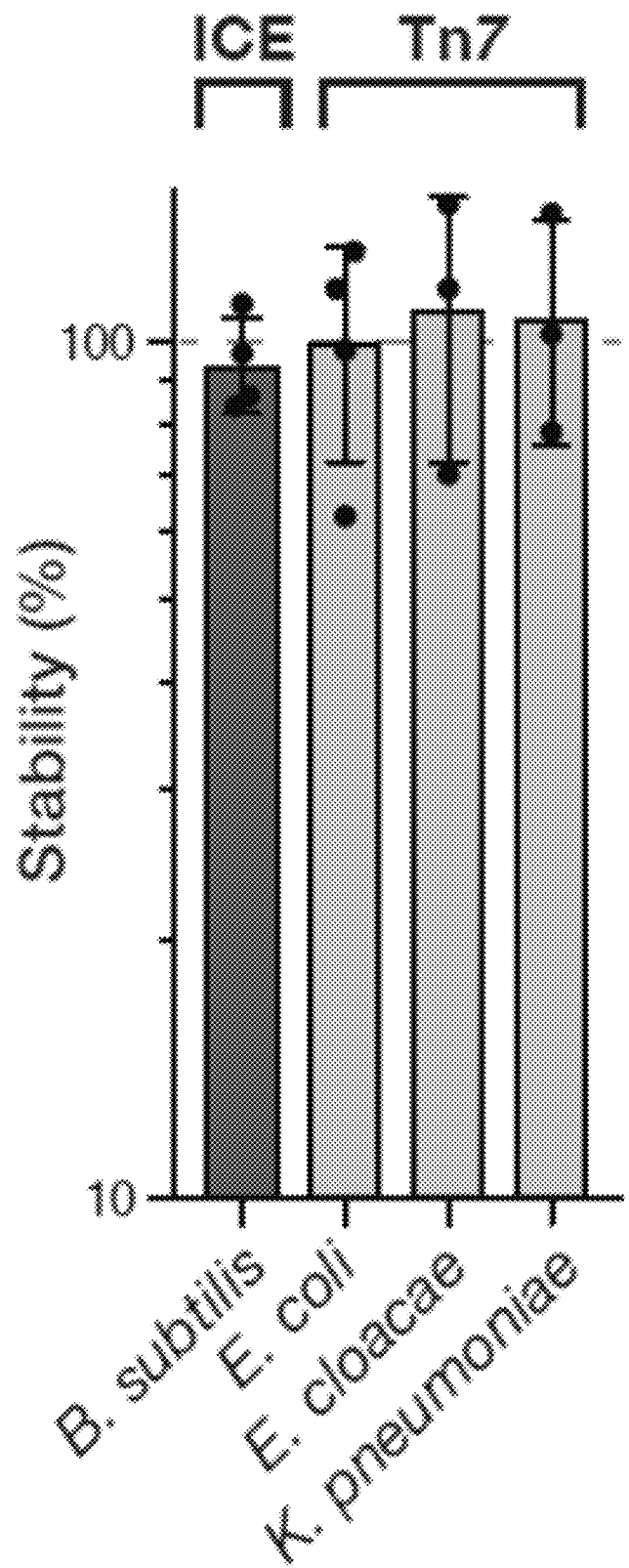
FIG. 5 shows a bar graph illustrating stability of bacteria modified with mobile-CRISPRi after 50 generations of growth in the absence of antibiotic selection in the bacterial species listed on the x-axis according to aspects of this disclosure. Stability, plotted on the y-axis, was calculated as the plating efficiency on kanamycin (the marker associated with Mobile-CRISPRi) vs. no antibiotic: n=4 for *B. subtilis* and *E. coli* and n=3 for *E. cloacae* and *K. pneumoniae*.

Because a Tn7-based strategy was previously unsuccessful in Bacillales Firmicutes, as discussed, for example, in (15), a strategy for transferring CRISPRi using the ICEBs1 conjugation and integration machinery was also developed. In this strategy, a DNA vector having an artificial DNA construct including ICE elements and carrying CRISPRi components was transferred to recipient bacteria by biparental mating, as illustrated in FIG. 2, bottom. ICE elements are described, for example, in (16). Once inside the recipient cell, the ICE integrase inserts ICE into trnS-leu2. Double antibiotic plates that select for ICE and for the intrinsic resistance of the recipient strain were used to identify recipients with an integrated CRISPRi system artificial DNA construct. Using the above strategy, mobile-CRISPRi artificial DNA construct was transferred from *B. subtilis* to other Bacillales Firmicutes (for example, *Staphylococcus aureus*) and integrated into trnS-leu2. Notably, the observed ICEBs1 host range was broader than previously thought (see, for example, Brophy, J. A. N. et al. Engineered integrative and conjugative elements for efficient and inducible DNA transfer to undomesticated bacteria. *Nat. Microbiol.* 3:1043-1053 (2018) (17)). Mobile-CRISPRi integrations either downstream of glmS (Tn7) or into trnS-leu2 (ICEBs) did not disrupt the functions of these genes, occurred in a specified orientation, and were stable and functional in the absence of selection for ≥50 generations, thus allowing for the studies of gene and antibiotic function in which maintaining selection was problematic or impossible. FIG. 5 illustrates the observed stability of *B. subtilis, E. coli, E. cloacae,* and *K. pneumoniae* modified with mobile-CRISPRi artificial DNA constructs after 50 generations of growth in the absence of antibiotic selection.

Figure 6:
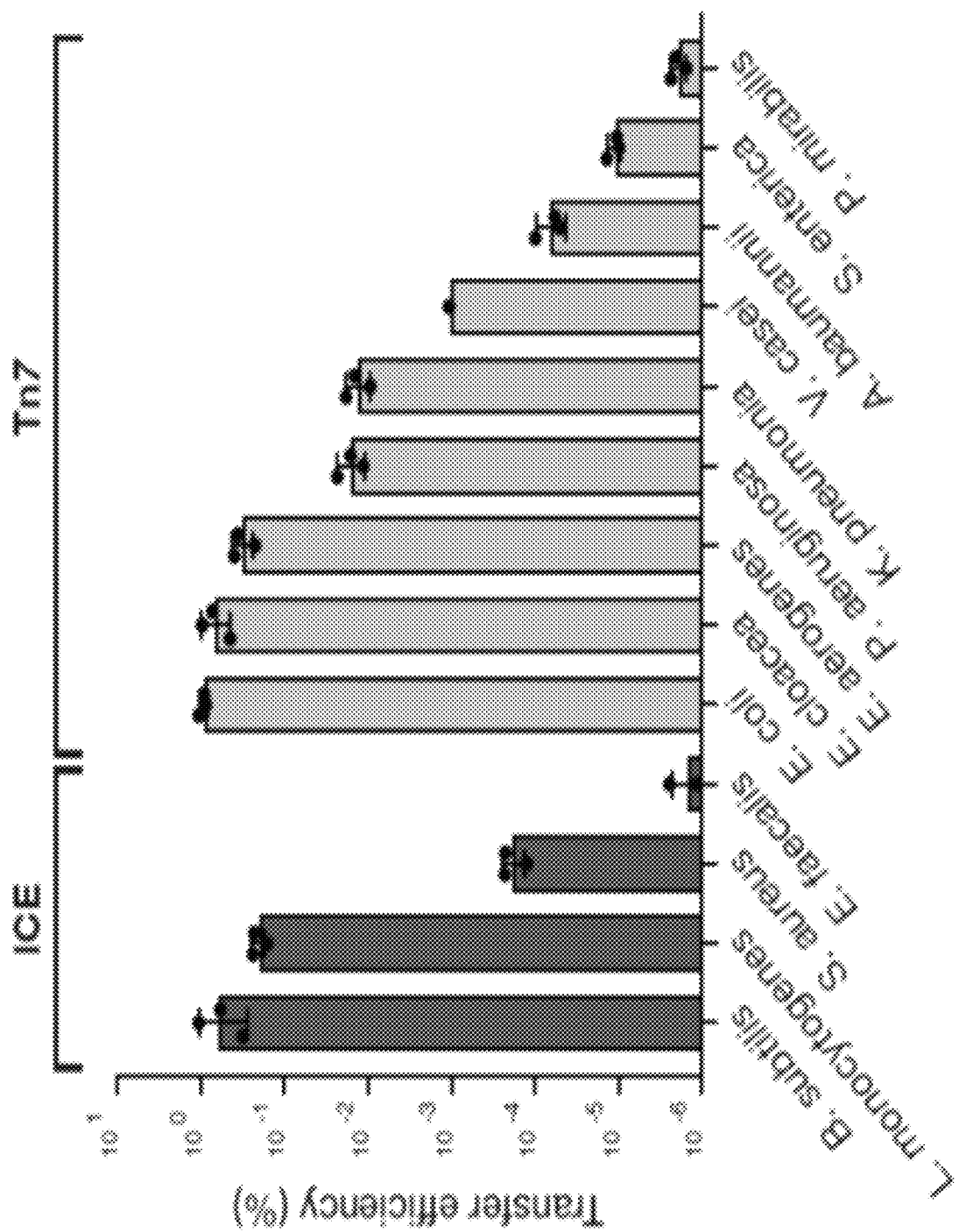
FIG. 6 shows a bar graph illustrating mobile-CRISPRi transfer and integration efficiency according to aspects of this disclosure. ICE or Tn7 containing CRISPRi was transferred to the bacterial species listed on the x-axis. Transfer efficiency, plotted on the y-axis, was calculated as: % $AB^R$/total recipients. n=3 for all strains except *V. casei* for which n=1.

The efficacy of Mobile-CRISPRi in multiple bacterial species was assessed, focusing on the bacterial species involved in human disease. CRISPRi construct transfer was measured by quantifying the number of recipient colonies (transconjugants) on selective agar plates as a fraction of total recipients. The results of the transfer and integration efficiency determination are illustrated in FIG. 6. Most of the tested bacterial species showed transfer efficiencies sufficient for genome-scale sgRNA library construction (for example, transfer efficiency for *Enterobacter* sp. was measured to be ~$10^{-2}$-$10^{-3}$%, and transfer efficiency for *L. monocytogenes* was measured to be ~$10^{-2}$%). The transfer efficiencies measured in some of the bacterial species were suited for single gene knockdown approaches (for example, the transfer efficiency in *Acinetobacter baumannii* was measured to be ~$10^{-6}$%).

Figure 7:
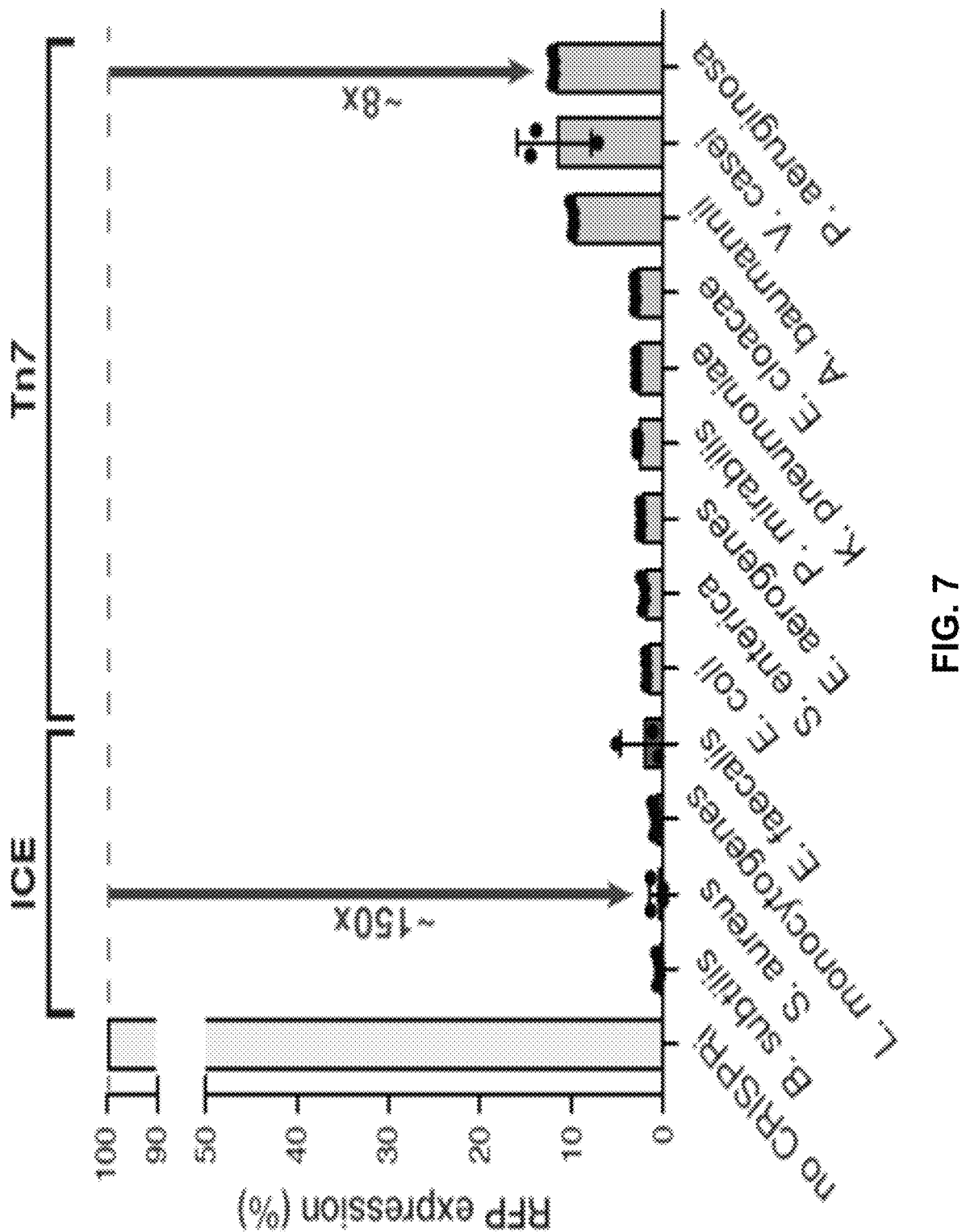
FIG. 7 shows a bar graph illustrating the efficiency of Mobile-CRISPRi knockdown in various bacterial species listed on the x-axis according to aspects of this disclosure. Knockdown was tested using a Mobile-CRISPRi variant containing a constitutively expressed red fluorescent protein (RFP) reporter and an sgRNA targeting RFP. RFP expression, plotted on the y-axis, was normalized to a strain lacking either dcas9 (for *P. aeruginosa*) or an sgRNA (all others; no sgRNA controls are recommended for future experiments). n=4 for all strains except *E. faecalis, P. mirabilis*, and *V casei* for which n=3. Data are represented as mean±s.d.

CRISPRi knockdown efficacy was assessed with a "test" version Mobile-CRISPRi DNA construct consisting of rfp gene encoding Red Fluorescent Protein (RFP) and either an sgRNA targeting rfp (to measure knockdown) or lacking an sgRNA (a control to normalize rfp expression). Quantification of rfp knockdown in single cells using flow cytometry indicated that knockdown efficiency ranged from ~8-fold in *Pseudomonas aeruginosa* (possibly due to dCas9 degradation) to ~150-fold in *S. aureus*, with a median knockdown of ~40-fold across all measured species. The results of the determination of efficiency of Mobile-CRISPRi knockdown are illustrated in FIG. 7. Additionally, knockdown was demonstrated to be titratable (data not shown). It was confirmed that CRISPRi using this system was also functional against native genes by targeting *P. aeruginosa* pyocyanin production. Mobile-CRISPRi constructs were used to target genes involved directly (phzAI and phzM) or indirectly in pyocyanin biosynthesis (pqsC). In a visual assay, the loss of blue pigment in *P. aeruginosa* suspension cultures indicated the knockdown of the pyocyanin pathway (data not shown).

To determine whether the Mobile-CRISPRi system functioned in an environmental isolate with no existing genetic system, transfer and knockdown was tested in *Vibrio casei*, a member of Gammaproteobacteria originally isolated from French wash-rind cheeses and broadly associated with cheese microbiomes (see, for example, Bokulich, N. A. & Mills, D. A. Facility-specific 'house' microbiome drives microbial landscapes of artisan cheesemaking plants. *Appl. Environ. Microbiol.* 79:5214-5223 (2013) (18)). It was found that Mobile-CRISPRi DNA constructs transferred to V *casei* with library scale efficiency ($\sim 10^{-3}$, as illustrated in FIG. 5), and a modest, but useful knockdown efficiency ($\sim$8-fold, as illustrated in FIG. 6). The modular nature of Mobile-CRISPRi vectors, which are illustrated in FIGS. 1, 3, and 4, allows for further optimization of knockdown efficiency; for instance, by using *Vibrio*-specific promoters for dcas9 and sgRNA expression.

Example 3: Use of Mobile-CRISPRi to Explore Mode of Action of Antibiotics in Pathogenic Gammaproteobacteria Associated with Antibiotic Resistance The emergence of multi-drug resistant pathogenic bacteria is an urgent threat to human health that requires both new antibiotics and a better understanding how existing antibiotics function. Knowledge of the mechanisms by which antibiotics kill bacteria—the mode of action (MOA)—is critical to advance new antibiotics from the laboratory to the clinic, as discussed, for example, in Cardona, S. T. et al. Genomic tools to profile antibiotic mode of action. *Crit. Rev. Microbiol.* 41, 465-472 (2015) (19). Because the full complement of genes in a bacterial genome (that is, genetic background) can affect antibiotic function. the MOA should ideally be determined directly in clinically relevant strains. However, most pathogenic bacterial lack genetic tools to systematically perturb the functions of essential genes that typically encode antibiotic targets. It was previously shown that the ability to titrate the knockdown level enables the systematic study of essential genes in *B. subtilis*. A low ($\sim$3-fold) level of knockdown allowed sufficient growth to determine the MOA of an uncharacterized antibiotic by virtue of its synergistic effects on growth (see (4)). The experiments described below showed that Mobile-CRISPRi targeting of essential genes can be used to generate sensitized strains for antibiotic MOA studies.

Figure 8:
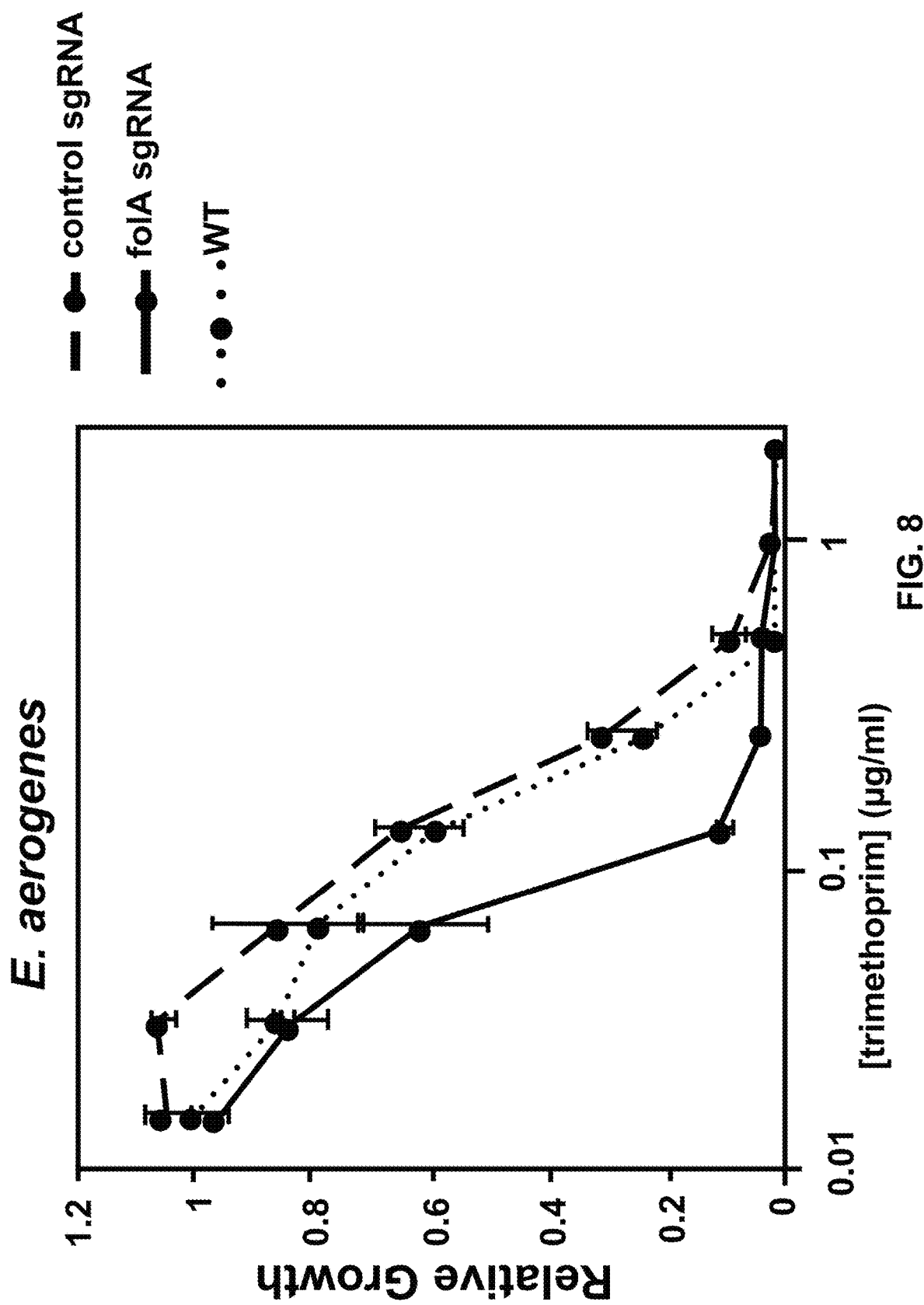
FIG. 8 shows a line graph illustrating increased sensitivity to trimethoprim in *Enterobacter aerogenes* after CRISPRi knockdown of folA according to aspects of this disclosure. Trimethoprim concentration is plotted on the x-axis. Relative growth data plotted on the y-axis was generated by MIC assay for trimethoprim sensitivity (n=3). The data are represented as mean±s.d.
Figure 9:
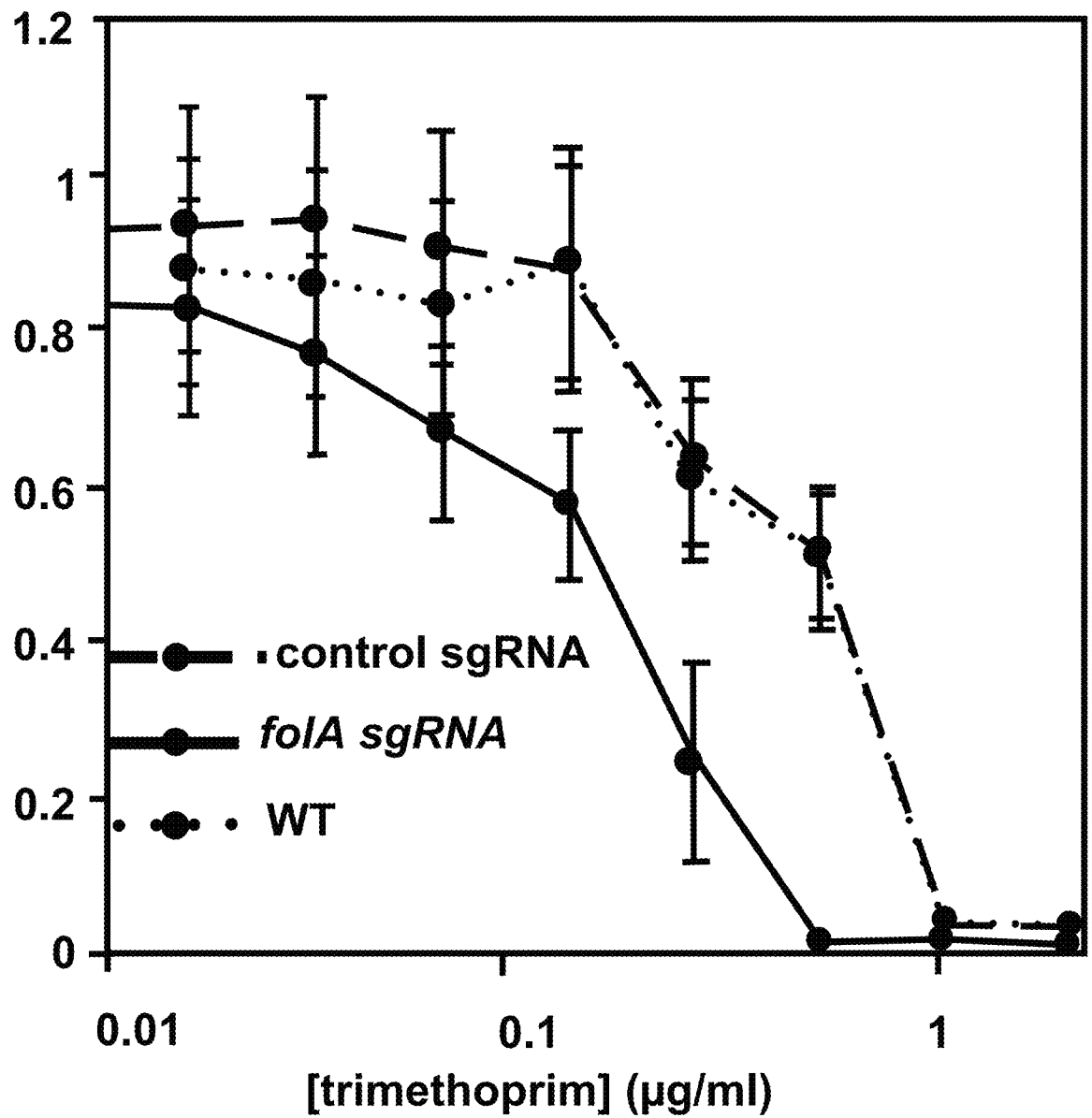
FIG. 9 shows a line graph increased sensitivity to trimethoprim in *Klebsiella pneumoniae* after CRISPRi knockdown of folA according to aspects of this disclosure. Trimethoprim concentration is plotted on the x-axis. Relative growth data plotted on the y-axis was generated by MIC assay for trimethoprim sensitivity (n=3). The data are represented as mean±s.d.
Figure 10:
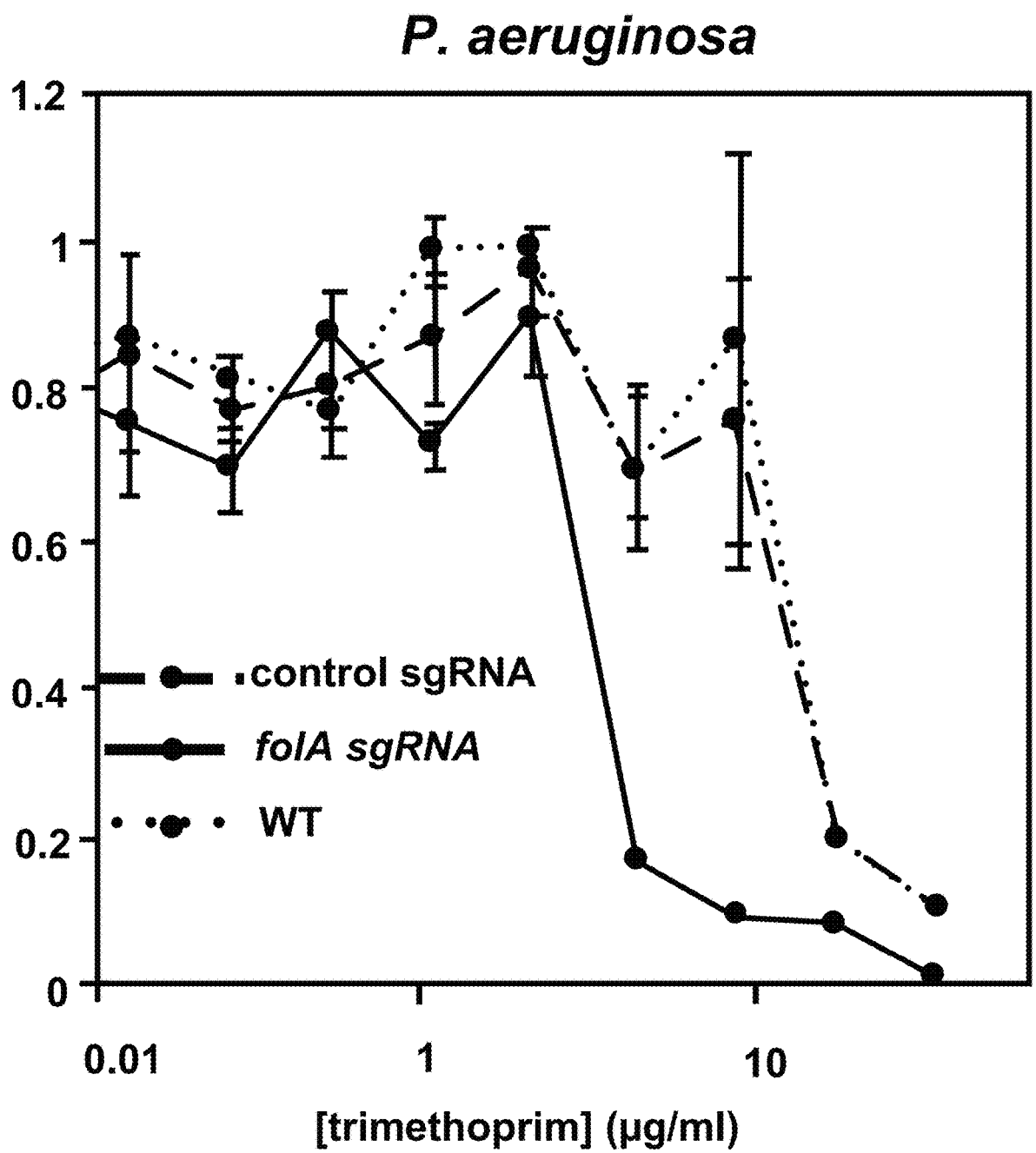
FIG. 10 shows a line graph illustrating increased sensitivity to trimethoprim in *Pseudomonas aeruginosa* after CRISPRi knockdown of folA according to aspects of this disclosure. Trimethoprim concentration is plotted on the x-axis. Relative growth data plotted on the y-axis was generated by MIC assay for trimethoprim sensitivity (n=3). The data are represented as mean±s.d.

Mobile-CRISPRi methodology and components were used to explore MOA in pathogenic Gammaproteobacteria associated with antibiotic resistance (Gram-negative rods). It was expected that strains with a small reduction in expression of the direct target of an antibiotic would be sensitized to low concentrations of that antibiotic (a phenomenon referred to as drug-gene interaction or synergy). Partial knockdown of the essential gene folA, which encodes the trimethoprim target dihydrofolate reductase (described, for example, in Baccanari, D. et al. Purification and properties of *Escherichia coli* dihydrofolate reductase. *Biochemistry* 14:5267-5273 (1975) (20)), increased sensitivity to trimethoprim, shifting the minimal inhibitory concentration (MIC) by 2-4-fold (depending on the species), which indicates synergy. The experimental results are illustrated in FIGS. 8-10. Although Mobile-CRISPRi knockdown in *Pseudomonas aeruginosa* exhibited a lower efficiency, compared to other strains, there was still a clear shift toward trimethoprim sensitivity, as illustrated in FIG. 10. Moreover, concentrations of trimethoprim below the MIC for the wild type bacteria completely inhibited growth of the folA knockdown strains, clearly demonstrating synergy (data not shown). Fully induced CRISPRi targeting of folA using the Mobile-CRISPRi methodology and components was lethal in *Enterobacter aerogenes, Klebsiella pneumoniae*, and *P. aeruginosa*.

Example 4: Use of Mobile-CRISPRi for Construction of a Knockdown Library

CRISPRi was previous used for eukaryotic pooled knockdown library construction, either for defined gene sets or at the genome scale (see, for example, Gilbert, L. A. et al. Genome-Scale CRISPR-Mediated Control of Gene Repression and Activation. *Cell* 159, 647-661 (2014) (8)). Such library construction was not previously performed in prokaryotes. The experiments described below showed that Mobile-CRISPRi methodology and components were useful for both pooled and arrayed library construction and straightforward assaying of phenotypes in prokaryotes.

A 40-member library of selected *Enterobacter cloacae* genes (see Table 3) was created. In the pooled context, each sgRNA functioned as a barcode, enabling quantification of each knockdown strain in the pool. Strain representation was evaluated by performing two different pooled experiments. In the first experiment, all steps from initial cloning to analysis were performed in a pool. The first experiment revealed that all sgRNA strains were present and had reasonable representation in the pool (31/40 sgRNA counts were within one standard deviation of the median, with a maximum 50-fold difference in representation). In the second experiment, each sgRNA plasmid was constructed individually, and an equimolar mixture of plasmids was used to transform *E. coli* and perform downstream steps. The second experiment assessed the variability of all steps downstream of cloning and revealed a maximum 2-fold difference in representation. Thus, Mobile-CRISPRi DNA construct transfer and integration was shown to be highly uniform, with essentially all variability derived from the initial cloning step.

The fitness of the strain library, which included knockdowns of 10 amino acid biosynthesis genes, 4 putative essential genes and 6 well-characterized genes, each targeted by 2 sgRNAs, was evaluated. The library was grown in glucose minimal medium in competition with a 100-fold excess of wild-type *E. cloacae*, and the relative frequency of each strain in the library was measured after 6 and 12 generations with or without Mobile-CRISPRi induction to initiate knockdown. Using the fitness calculation of van Opijnen et al. (12), it was found that fitness of strains with sgRNAs targeting amino acid biosynthesis and those targeting some putative essential genes decreased, whereas representation of non-essential genes that were unrelated to amino acid biosynthesis remained constant (data not shown). Fitness for affected strains was more pronounced at 12 doublings than at 6 doublings, suggesting that a larger number of generations was required to dilute out existing protein products. Additionally, both guides generally decreased the fitness of the essential and auxotrophic genes, but with more variability than previously observed in the study reported in (4). Finally, the fitness measurements from the completely pooled construction and those in the equal representation library were highly correlated ($R^2=0.92$), indicating that the initial frequency of the strain in the pooled library did not affect the measurement of the fitness.

An arrayed library of each individual knockdown strain was screened. The auxotrophy of amino acid biosynthesis gene knockdown strains was confirmed, finding that their poor growth in minimal medium was suppressed by relevant amino acids (data not shown). Thus, the knockdown effects were specific to the targeted gene and did not represent off-target effects of CRISPRi. It was found that knockdown of some putative essential genes (for example, mreD)

showed no apparent phenotype, possibly because of limited growth after induction or low sgRNA efficacy.

Example 4: Use of Mobile-CRISPRi for Controlling Expression of Conditionally Essential Genes in *Pseudomonas aeruginosa*

Conditionally essential genes (CE genes) are required by pathogenic bacteria to establish and maintain infections. CE genes encode for "virulence factors," such as secretion systems and effector proteins, as well as biosynthetic enzymes that produce metabolites not found in the host environment. Precise manipulation of CE gene expression in the context of infection is technically challenging, limiting the ability to understand the roles of CE genes in pathogenesis and accordingly design effective inhibitors. The experimental study described below showed the efficacy of Mobile-CRISPRi methodology and components in controlling CE gene expression in an animal infection model. The Mobile-CRISPRi methodology and components were optimized for use in *Pseudomonas aeruginosa* in a murine model of pneumonia by tuning the expression of CRISPRi components to avoid non-specific toxicity. It was demonstrated that CRISPRi-mediated knockdown of a CE gene encoding the type III secretion system (T3SS) activator ExsA blocked effector protein secretion in culture and attenuated *P. aeruginosa* virulence in mice. A detailed description of the study is found in (37).

dCas9 overexpression is known to cause non-specific toxicity in bacteria. To overcome this problem, Mobile-CRISPRi vectors were constructed that expressed dCas9$_{Spy}$ from a series of weak constitutive promoters to reduce toxicity and achieve partial knockdown. dCas9 was expressed from the arabinose-inducible PBAD promoter in vectors based on pJMP1237 (SEQ ID NO:14) and three constitutive promoters in the vectors based on pJQ47 (SEQ ID NO:29), pJQ48 (SEQ ID NO:30), and pJQ49 (SEQ ID NO:31), which were generated from pJMP1237 (SEQ ID NO:14) by replacing PBAD promoter with respective constitutive promoters Anderson BBa_J23117 (P1; SEQ ID NO:32), Anderson BBa_J23114 (P2; SEQ ID NO:33), and Anderson BBa_J23115 (P3; SEQ ID NO:34). To assess Mobile-CRISPRi efficacy using different promoters, a "test" Mobile-CRISPRi DNA vector was employed expressing monomeric Red Fluorescent Protein (mRFP) and an sgRNA targeting the mRFP gene. Knockdown levels were quantified for each promoter through comparing the mutants' fluorescence normalized to growth over time. After 12 hours, stable fluorescence ratios between mutants without and with mRFP-targeting sgRNA were identified. The gradient of knockdown ranged from 10-17-fold at the 14-hour time point, which roughly corresponded to the promoter strength used to express dCas9. RNA-seq on cells expressing dCas9 from the strongest of the three promoters was performed to confirm that CRISPRi retained specificity. The cells expressing dCas9$_{Spy}$ from all three promoters were imaged and found no apparent defects in morphology. Thus, Mobile-CRISPRi methodology and components optimized with the promoters driving dCas9$_{Spy}$ allowed for a non-toxic gradient of constitutive knockdowns in *P. aeruginosa*.

The Mobile-CRISPRi system was used to target exsA gene, which encodes the key activator of T3SS genes required for pathogenesis in *P. aeruginosa*. CRISPRi knockdown of exsA reduced expression of T3SS genes by more than 100-fold. All three promoters diving dCas9$_{Spy}$ expression were equally effective a reducing exsA transcript levels. Knockdown of exsA eliminated detectable production of T3SS pilus (PopB/D) and effector (ExoT/U) proteins. Neither the exsA knockdown nor the non-targeting control sgRNA strains showed a growth defect in rich culture medium.

To test whether Mobile-CRISPRi methodology and components can be used to probe the functions of CE genes such as exsA in a host environment, C57BL/6 mice were intratracheally instilled with a range of $10^5$ to $10^7$ CFU of wild-type (WT) *P. aeruginosa* PA14, an isogenic exsA::Tn mutant with an exsA disruption described in Liberati, N. T. et al. An ordered, nonredundant library of *P. aeruginosa* strain PA14 transposon insertion mutants. *Proc. Natl. Acad. Sci. U.S.A.* 103, 2833-2838 (2006) (35), or Mobile-CRISPRi engineered bacterial strains containing dCas9$_{Spy}$ driven by one of the promoter and either a sgRNA targeting exsA or a non-targeting control sequence. The experimental animals were sacrificed, and their lungs were collected 18 hours after infection. Lung homogenates were plated to estimate the number of viable bacteria. The strains with the exsA::Tn allele or Mobile-CRISPRi construct targeting exsA were highly attenuated for virulence and yielded similar recovery rates. Furthermore, CFU recovery was similar between WT and the control bacteria containing the non-targeting Mobile-CRISPRi construct, suggesting that non-specific toxicity of dCas9 was mitigated by reduced expression. Other general indicators of infection, including hypothermia and leukopenia, were observed for the non-targeting construct bacteria and WT bacteria controls. In contrast, both the exsA::Tn strain and strain having the Mobile-CRISPRi targeting exsA construct had similar levels of white blood cell counts (equivalent or higher than those seen in the PBS control) and similar body temperatures, indicative of reduced virulence. Consistently with the above results, WT and non-targeting construct strains showed severe lung injury not seen in the exsA::Tn and exsA targeting strains.

References cited in this disclosure:
1. Qi, L. S. et al. Repurposing CRISPR as an RNA-guided platform for sequence-specific control of gene expression. *Cell* 152, 1173-1183 (2013).
2. Gilbert, L. A. et al. CRISPR-mediated modular RNA-guided regulation of transcription in eukaryotes. *Cell* 154, 442-451 (2013).
3. Mimee, M et al. Programming a Human Commensal Bacterium, *Bacteroides* thetaiotaomicron, to Sense and Respond to Stimuli in the Murine Gut Microbiota. *Cell Syst.* 1, 62-71 (2015).
4. Peters, J. M. et al. A Comprehensive, CRISPR-based Functional Analysis of Essential Genes in Bacteria. *Cell* 165, 1493-1506 (2016).
5. Rock, J. M. et al. Programmable transcriptional repression in mycobacteria using an orthogonal CRISPR interference platform. *Nat. Microbiol.* 2, 16274 (2017).
6. Tan, S. Z. et al. A Robust CRISPR Interference Gene Repression System in *Pseudomonas*. *J. Bacteriol.* 200, (2018).
7. Liu, X. et al. High-throughput CRISPRi phenotyping identifies new essential genes in *Streptococcus pneumoniae*. *Mol. Syst. Biol.* 13, (2017).
8. Gilbert, L. A. et al. Genome-Scale CRISPR-Mediated Control of Gene Repression and Activation. *Cell* 159, 647-661 (2014).
9. Jost, M. et al. Combined CRISPRi/a-Based Chemical Genetic Screens Reveal that Rigosertib Is a Microtubule-Destabilizing Agent. *Mol. Cell* 68, 210-223.e6 (2017).
10. Vigouroux, A. et al. Tuning dCas9's ability to block transcription enables robust, noiseless knockdown of bacterial genes. *Mol. Syst. Biol.* 14, e7899 (2018).

11. Zhao, H. et al. Depletion of Undecaprenyl Pyrophosphate Phosphatases Disrupts Cell Envelope Biogenesis in *Bacillus subtilis. J. Bacteriol.* 198, 2925-2935 (2016).
12. van Opijnen, T. et al. Tn-seq: high-throughput parallel sequencing for fitness and genetic interaction studies in microorganisms. *Nat. Methods* 6, 767-772 (2009).
13. Ji, W. et al. Specific gene repression by CRISPRi system transferred through bacterial conjugation. *ACS Synth. Biol.* 3, 929-931 (2014).
14. Peters, J. E. Tn7. *Microbiol.* Spectr. 2, (2014).
15. Choi, K.-H. et al. A Tn7-based broad-range bacterial cloning and expression system. *Nat. Methods* 2, 443-448 (2005).
16. Johnson, C. M. & Grossman, A. D. Integrative and Conjugative Elements (ICEs): What They Do and How They Work. *Annu. Rev. Genet.* 49, 577-601 (2015).
17. Brophy, J. A. N. et al. Engineered integrative and conjugative elements for efficient and inducible DNA transfer to undomesticated bacteria. *Nat. Microbiol.* 3, 1043-1053 (2018).
18. Bokulich, N. A. & Mills, D. A. Facility-specific 'house' microbiome drives microbial landscapes of artisan cheesemaking plants. *Appl. Environ. Microbiol.* 79, 5214-5223 (2013).
19. Cardona, S. T. et al. Genomic tools to profile antibiotic mode of action. *Crit. Rev. Microbiol.* 41, 465-472 (2015).
20. Baccanari, D. et al. Purification and properties of *Escherichia coli* dihydrofolate reductase. *Biochemistry* 14, 5267-5273 (1975).
21. McMahon, S. A. et al. Extensive DNA mimicry by the ArdA anti-restriction protein and its role in the spread of antibiotic resistance. *Nucleic Acids Res.* 37, 4887-4897 (2009).
22. Peters, J. E. et al. Recruitment of CRISPR-Cas systems by Tn7-like transposons. *Proc. Nat. Acad. Sci.* 114, E7358-E7366 (2017).
23. Choi, K.-H. & Schweizer, H. P. mini-Tn7 insertion in bacteria with single attTn7 sites: example *Pseudomonas aeruginosa. Nat. Protoc.* 1, 153-161 (2006).
24. Ferrières, L. et al. Silent Mischief: Bacteriophage Mu Insertions Contaminate Products of *Escherichia coli* Random Mutagenesis Performed Using Suicidal Transposon Delivery Plasmids Mobilized by Broad-Host-Range RP4 Conjugative Machinery. *J. Bacteriol.* 192, 6418-6427 (2010).
25. Choi, K.-H. et al. Genetic Tools for Select-Agent-Compliant Manipulation of *Burkholderia pseudomallei. Appl. Environ. Microbiol.* 74, 1064-1075 (2008).
26. Auchtung, J. M. et al. Regulation of a *Bacillus subtilis* mobile genetic element by intercellular signaling and the global DNA damage response. *Proc. Nat. Acad. Sci. U.S.A* 102, 12554-12559 (2005).
27. Auchtung, J. M. et al. Identification and characterization of the immunity repressor (ImmR) that controls the mobile genetic element ICEBs1 of *Bacillus subtilis. Mol. Microbiol.* 64, 1515-1528 (2007).
28. Wiegand, I et al. Agar and broth dilution methods to determine the minimal inhibitory concentration (MIC) of antimicrobial substances. *Nat. Protoc.* 3, 163 (2008).
29. Koo, B.-M. et al. Construction and Analysis of Two Genome-Scale Deletion Libraries for *Bacillus subtilis. Cell Syst.* 4, 291-305.e7 (2017).
30. Kritikos, G. et al. A tool named Iris for versatile high-throughput phenotyping in microorganisms. *Nat. Microbiol.* 2, 17014 (2017).
31. Karlin and Altschul, S. F. Methods for assessing the statistical significance of molecular sequence features by using general scoring schemes. *Proc. Nat. Acad. Sci. USA* 87:2264-2268 (1990).
32. Karlin, S. and Altschul, S. F. Applications and statistics for multiple high-scoring segments in molecular sequences. *Proc. Nat. Acad. Sci. USA* 90:5873-5877 (1993).
33. Altschul, S. F. et al. Basic local alignment search tool. *J. Mol. Biol.* 215:403 (1990).
34. Altschul, S. F. et al. Gapped BLAST and PSI-BLAST: a new generation of protein database search programs. *Nucleic Acids Res.* 25:3389 (1997).
35. Liberati, N. T. et al. An ordered, nonredundant library of *Pseudomonas aeruginosa* strain PA14 transposon insertion mutants. *Proc. Nat. Acad. Sci. U.S.A.* 103, 2833-2838 (2006).
36. Peters et al. Enabling genetic analysis of diverse bacteria with Mobile-CRISPRi, *Nature Microbiology* 4:244-250 (2019).
37. Qu et al. Modulating pathogenesis with Mobile-CRISPRi. bioRxiv preprint posted online Apr. 25, 2019; *Journal of Bacteriology* 22(201): e00304-19 (2019).

REFERENCE TO A SEQUENCE LISTING SUBMITTED AS A TEXT FILE VIA EFS-WEB

The official copy of the sequence listing is submitted electronically as an ASCII formatted sequence listing with a file named 1198548 Replacement_ST25.txt, created on Sep. 13, 2023, and having a size of 463 kilobytes. The sequence listing contained in this ASCII formatted document is part of the specification and is herein incorporated by reference in its entirety.

In the foregoing description, numerous specific details are set forth to provide a more thorough understanding of the present invention. However, it will be apparent to one of skill in the art that the invention described in this disclosure may be practiced without one or more of these specific details. In other instances, well-known features and procedures well known to those skilled in the art have not been described in order to avoid obscuring the invention. Embodiments of the disclosure have been described for illustrative and not restrictive purposes. Although the present invention is described primarily with reference to specific embodiments, it is also envisioned that other embodiments will become apparent to those skilled in the art upon reading the present disclosure, and it is intended that such embodiments be contained within the present inventive methods. Accordingly, the present disclosure is not limited to the embodiments described above or depicted in the drawings, and various embodiments and modifications can be made without departing from the scope of the claims below. All publications, patents, and patent applications cited herein are hereby incorporated by reference in their entirety for all purposes.

What is claimed is:

1. An artificial DNA construct comprising (i) a nucleotide sequence encoding a catalytically inactive variant of CRISPR-associated protein 9 (dCas9) with, optionally, a second promoter and a ribosome binding site operably linked to the nucleotide sequence encoding dCas9, (ii) a nucleotide sequence of a gene conferring resistance to a first antibiotic; and (iii) two nucleotide transfer sequences, wherein the two nucleotide transfer sequences are Tn7L and Tn7R transposon sequences or sequences encoding bacterial integrative and conjugative elements (ICE sequences), one of each of the two nucleotide transfer sequences flanking a nucleotide sequence comprising elements (i) and (ii) of the artificial DNA construct; wherein the artificial DNA construct comprises a nucleic acid sequence having at least 90% sequence identity over the full-length of nucleotides 2517-11688 of SEQ ID NO:9, nucleotides 2517-11650 of SEQ ID NO:11, nucleotides 2517-10705 of SEQ ID NO:14, nucleotides 1-9813 of SEQ ID NO:18, nucleotides 152-8586 of SEQ ID NO:26, nucleotides 6498-8574 of SEQ ID NO:28, nucleotides 2517-11650 of SEQ ID NO:35, or nucleotides 2517-11502 of SEQ ID NO:36.

2. The artificial DNA construct of claim 1, wherein the two nucleotide transfer sequences are the Tn7L and Tn7R transposon sequences, and wherein the artificial DNA construct comprises the nucleic acid sequence having at least 90% sequence identity over the full-length of nucleotides 2517-11688 of SEQ ID NO:9, nucleotides 2517-11650 of SEQ ID NO:11, nucleotides 2517-10705 of SEQ ID NO:14, nucleotides 152-8733 of SEQ ID NO:19, nucleotides 152-8586 of SEQ ID NO:26, nucleotides 2517-11650 of SEQ ID NO:35, or nucleotides 2517-11502 of SEQ ID NO:36.

3. The artificial DNA construct of claim 1, wherein the two nucleotide transfer sequences are the ICE sequences, and wherein the artificial DNA construct comprises the nucleic acid sequence having at least 90% sequence identity over the full-length of nucleotides 1-9813 of SEQ ID NO:18 or nucleotides 6498-8574 of SEQ ID NO:28.

4. A DNA vector comprising: (a) the artificial DNA construct of claim 1; (b) a nucleotide sequence of a gene conferring resistance to a second antibiotic, the nucleotide sequence located outside the artificial DNA construct; (c) a conditional origin of replication located outside the artificial DNA construct; and (d) an origin of transfer site located outside the artificial DNA construct.

5. The DNA vector of claim 4, wherein the conditional origin of replication is R6K γ origin of replication.

6. The DNA vector of claim 4, wherein the two nucleotide transfer sequences are Tn7L and Tn7R transposon sequences, and wherein the artificial DNA construct comprises the nucleic acid sequence having at least 90% sequence identity over the full-length of nucleotides 2517-11688 of SEQ ID NO:9, nucleotides 2517-11650 of SEQ ID NO: 11, nucleotides 2517-10705 of SEQ ID NO:14, nucleotides 152-8733 of SEQ ID NO:19, nucleotides 152-8586 of SEQ ID NO:26, nucleotides 2517-11650 of SEQ ID NO:35, or nucleotides 2517-11502 of SEQ ID NO:36.

7. DNA vector of claim 4, wherein the two nucleotide transfer sequences are ICE sequences, and wherein the artificial DNA construct comprises nucleic acid sequence having at least 90% sequence identity over the full-length of nucleotides 1-9813 of SEQ ID NO:18 or nucleotides 6498-8574 857/1 to 6/198 of SEQ ID NO:28.

8. The DNA vector of claim 4, having at least 90% nucleic acid sequence identity over the full-length of SEQ ID NO:9, SEQ ID NO:11, SEQ ID NO:14, SEQ ID NO:18, SEQ ID NO:19, SEQ ID NO:26, SEQ ID NO:28, SEQ ID NO:35, or SEQ ID NO:36.

9. An engineered bacterial cell comprising the DNA vector of claim 4.

10. A method of producing an engineered bacterial cell, comprising: (a) transforming a bacterial cell comprising a gene whose expression permits the conditional origin of replication to be functional with the DNA vector of claim 4, thereby creating the engineered bacterial cell comprising the DNA vector; and (b) growing the engineered bacterial cell in or on a growth medium comprising the second antibiotic under growth conditions leading to growth of the engineered bacterial cell.

11. A method of constructing a knockdown library of bacterial cells, comprising: (a) cloning a plurality of nucleotide sequence encoding single guide RNA (sgRNAs) targeting a plurality of genes of interest into a plurality of vectors having at least 90% sequence identity over the full-length of SEQ ID NO:19, thereby generating a vector library; (b) transforming a plurality of bacterial cells comprising RP4 transfer machinery with the vector library, wherein the bacterial cells are auxotrophic and require presence of a nutritional substance for growth, and wherein the bacterial cells comprise a gene whose expression permits a conditional origin of replication of a vector having at least 90% sequence identity over the full-length of SEQ ID NO:19 to be functional; (c) contacting under conditions allowing for mating (i) the plurality of transformed bacterial cells from step (b), (ii) a plurality of engineered bacterial cells comprising a transposase plasmid, wherein the engineered bacterial cells are auxotrophic and require the presence of the nutritional substance for growth, and (iii) a plurality of recipient bacterial cells not requiring the presence of the nutritional substance for growth; and (d) growing the contacted bacterial cells of step (c) in or on a medium comprising ampicillin and not including the nutritional substance thereby generating the knockdown library of bacterial cells.

12. The method of claim 11, wherein, in step (a), the plurality of sgRNAs are cloned as a pool into the plurality of vectors to generate the vector library.

13. The method of claim 11, wherein, in step (a), each sgRNA of the plurality of sgRNAs is cloned individually into one of the plurality of vectors and then the plurality of vectors containing the sgRNAs are pooled to generate the vector library.

14. A method of constructing a knockdown library of bacterial cells, comprising: (a) cloning a plurality of nucleotide sequences encoding single guide RNAs (sgRNAs) into a plurality of vectors having at least 90% sequence identity over the full-length of SEQ ID NO:18, thereby generating a vector library; (b) transforming a plurality of bacterial cells with the vector library, wherein the bacterial cells comprise conjugation genes and a gene whose expression permits a conditional origin of replication of a vector having at least 90% sequence identity over the full-length of SEQ ID NO:18 to be functional; (c) inducing expression of the conjugation genes in the transformed bacterial cells, thereby promoting excision of vector modules comprising the nucleotide sequences encoding the sgRNAs from the vector library; (d) after the inducing, contacting transformed bacterial cells with a plurality of recipient bacterial cells under conditions allowing for mating of the transformed bacterial cells and the recipient bacterial cells, thereby resulting in transfer of the plurality of nucleotide sequences encoding single guide RNAs sgRNAs into the recipient bacterial cells; and (e) growing the contacted bacterial cells in or on a medium comprising ampicillin, thereby generating the knockdown library of bacterial cells.

15. The method of claim 14, wherein, in step (a), the plurality of sgRNAs are cloned as a pool into the plurality of vectors to generate the vector library.

16. The method of claim 14, wherein, in step (a), each sgRNA of the plurality of sgRNAs is cloned individually into one of the plurality of vectors and then the plurality of vectors containing the sgRNAs are pooled to generate the vector library.

17. A system for generating an engineered bacterium, comprising: (a) the artificial DNA construct of claim 2, the artificial DNA construct comprising the nucleic acid sequence having at least 90% sequence identity over the full-length of nucleotides 152-8733 of SEQ ID NO:19; and (b) a nucleic acid sequence of a transposase gene.

18. The system of claim 17, wherein the artificial DNA construct is located on a bacterial vector comprising a nucleotide sequence of a gene conferring resistance to a second antibiotic located outside the artificial DNA construct, a conditional origin of replication located outside the artificial DNA construct, and an origin of transfer site located outside the artificial DNA construct.

19. The system of claim 18, further comprising a plurality of auxotrophic bacterial cells comprising a gene whose expression permits the conditional origin of replication to be functional.

20. The system of claim 18, wherein the bacterial vector is a vector having at least 90%_sequence identity over the full-length of SEQ ID NO:19.

21. The system of claim 17, wherein the nucleic acid sequence of the transposase gene is located on a plasmid having at least 90% sequence identity over the full-length of SEQ ID NO:1.

22. The system of claim 18, further comprising a bacterial cell comprising RP4 transfer machinery, wherein the bacterial cell is auxotrophic and requires presence of a nutritional substance for growth, and wherein the bacterial cell comprises a gene whose expression permits the conditional origin of replication to be functional.

23. The system of claim 17, further comprising a self-mobilizing RP4 transfer plasmid.

24. A system for generating an engineered bacterium, comprising: (a) the artificial DNA construct of claim 3, the artificial DNA construct comprising the nucleic acid sequence having at least 90% sequence identity over the full-length of nucleotides 1-9813 of SEQ ID NO:18; and (b) a bacterial cell comprising conjugation genes.

25. The system of claim 24, wherein the artificial DNA construct is located on a bacterial vector comprising a nucleotide sequence of a gene conferring resistance to a second antibiotic located outside the artificial DNA construct, a conditional origin of replication located outside the artificial DNA construct, and an origin of transfer site located outside the artificial DNA construct.

26. The system of claim 25, wherein the bacterial cell comprises a gene whose expression permits the conditional origin of replication to be functional in the cell.

27. The system of claim 25, wherein the bacterial vector is a vector having at least 90% sequence identity over the full-length of SEQ ID NO:18.

28. A DNA vector having at least 90% sequence identity over the full-length of SEQ ID NO:1, SEQ ID NO:9, SEQ ID NO:11, SEQ ID NO:14, SEQ ID NO:18, SEQ ID NO:19, SEQ ID NO:26, SEQ ID NO:28, SEQ ID NO:35, or SEQ ID NO:36.

29. The artificial DNA construct of claim 1, further comprising (iv) a nucleotide sequence encoding a single guide RNA (sgRNA) and a first promoter operably linked thereto, or a restriction site with the first promoter optionally located upstream, wherein the one of each of the two nucleotide transfer sequences flank a nucleotide sequence comprising elements (i)-(ii) and (iv) of the artificial DNA construct.

* * * * *

UNITED STATES PATENT AND TRADEMARK OFFICE
CERTIFICATE OF CORRECTION

| | | |
|---|---|---|
| PATENT NO. | : 12,018,258 B2 | Page 1 of 1 |
| APPLICATION NO. | : 17/012486 | |
| DATED | : June 25, 2024 | |
| INVENTOR(S) | : Jason Peters et al. | |

It is certified that error appears in the above-identified patent and that said Letters Patent is hereby corrected as shown below:

In the Claims

In Column 370, Line 39:
In Claim 7, after "8574"
Delete "857/1 to 6/198".

In Column 371, Line 42:
In Claim 14, after "RNAs"
Delete ""sgRNAs".

In Column 372, Line 13:
In Claim 20, Delete "90%_sequence" and
Insert -- 90% sequence --.

Signed and Sealed this
Thirteenth Day of August, 2024

Katherine Kelly Vidal
*Director of the United States Patent and Trademark Office*

SEQUENCE LISTING

<160> NUMBER OF SEQ ID NOS: 36

<210> SEQ ID NO 1
<211> LENGTH: 9971
<212> TYPE: DNA
<213> ORGANISM: Artificial Sequence
<220> FEATURE:
<223> OTHER INFORMATION: Synthetic construct

<400> SEQUENCE: 1

```
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc attttaatt taaaaggatc taggtgaaga  1140
tcctttttga taatctcatg accaaaatcc cttaacgtga gttttcgttc cactgagcgt  1200 cagacccgt agaaaagatc aaaggatctt cttgagatcc ttttttttctg cgcgtaatct  1260 gctgcttgca acaaaaaaa ccaccgctac cagcggtggt ttgtttgccg gatcaagagc  1320
taccaactct ttttccgaag gtaactggct tcagcagagc gcagatacca aatactgtcc  1380
ttctagtgta gccgtagtta ggccaccact caagaactc tgtagcaccg cctacatacc  1440
tcgctctgct aatcctgtta ccagccggtt gtcagccgtt aagtgttcct gtgtcactca  1500
aaattgcttt gagaggctct aagggcttct cagtgcgtta catccctggc ttgttgtcca  1560
caaccgttaa accttaaaag ctttaaaagc cttatatatt ctttttttc ttataaaact  1620 taaaaccta gaggctattt aagttgctga tttatattaa ttttattgtt caaacatgag  1680
agcttagtac gtgaaacatg agagcttagt acgttagcca tgagagctta gtacgttagc  1740
catgagggtt tagttcgtta aacatgagag cttagtacgt taaacttgag agcttagtac  1800
gtgaaacatg agagcttagt acgtactatc aacaggttga actgcccatg ttcttctg    1860 cgttatcaga gcttatcggc cagcctcgca gagcaggatt cccgttgagc accgccaggt  1920
gcgaataagg gacagtgaag aaggaacacc cgctcgcggg tgggcctact tcacctatcc  1980
tgcccggctg acgccgttgg atacaccaag gaaagtctac acgaacccttt tggcaaaatc  2040
```

```
ctgtatatcg tgcgaaaaag gatggatata ccgaaaaaat cgctataatg accccgaagc    2100
agggttatgc agcggaaagt ataccttaac atgttctttc ctgcgttatc ccctgattct    2160
gtggataacc gtattaccgc ctttgagtga gctgataccg ctcgccgcag ccgaacgacc    2220
gagcgcagcg agtcagtgag cgaggaagcg gaagagcgcc caatacgcaa accgcctctc    2280
cccgcgcgtt ggccgattca ttaatgcagc tggcacgaca ggtttcccga ctggaaagcg    2340
ggcagtgagc gcaacgcaat taatgtgagt tagctcactc attaggcacc ccaggcttta    2400
cactttatgc ttccggctcg tatgttgtgt ggaattgtga gcggataaca atttcacaca    2460
ggaaacagct atgacatgat tacgaattca cgaacccagt tgacataagc ctgttcggtt    2520
cgtaaactgt aatgcaagta gcgtatgcgc tcacgcaact ggtccagaac cttgaccgaa    2580
cgcagcggtg gtaacggcgc agtggcggtt ttcatggctt gttatgactg ttttttgta    2640 cagtctatgc ctcgggcatc caagcagcaa gcgcgttacg ccgtgggtcg atgtttgatg    2700
ttatggagca gcaacgatgt tacgcagcag ggcagtcgcc ctaaaacaaa gttaggcagc    2760
cgttgtgctg gtgctttctg atagttgttg tggggtaggc agtcagagct cgatttgctt    2820
gtcgccataa tagattcaca agaaggattc gacccgggga tcctctagag tcgagatgcc    2880
gcatgtggaa gaggtgattg caccgatctt ctacaccgtt ccgctgcagc tgctggctta    2940
ccatgtcgcg ctgatcaaag gcaccgacgt tgaccagccg cgtaacctgg caaaatcggt    3000
tacggttgag taataaatgg atgccctgcg taagcgggtg tgggcggaca ataaagtctt    3060
aaagggaaca aaatagatct aaactatgac aataaagtct taaactagac agaatagttg    3120
taaactgaaa tcagtccagt tatgctgtga aaaagcatac tggactttg ttatggctaa    3180 agcaaactct tcattttctg aagtgcaaat tgcccgtcgt attaaagagg ggcgtggcca    3240
agggcatggt aaagactata ttccatggct aacagtacaa gaagttcctt cttcaggtcg    3300
ttcccaccgt atttattctc ataagacggg acgagtccat catttgctat ctgacttaga    3360
gcttgctgtt tttctcagtc ttgagtggga gagcagcgtg ctagatatac gcgagcagtt    3420
ccccttatta cctagtgata ccaggcagat tgcaatagat agtggtatta agcatcctgt    3480
tattcgtggt gtagatcagg ttatgtctac tgatttttta gtggactgca aagatggtcc    3540
ttttgagcag tttgctattc aagtcaaacc tgcagcagcc ttacaagacg agcgtacctt    3600
agaaaaacta gaactagagc gtcgctattg gcagcaaaag caaattcctt ggttcatttt    3660
tactgataaa gaaataaatc ccgtagtaaa agaaatatt gaatggcttt attcagtgaa    3720
aacagaagaa gtttctgcgg agcttttagc acaactatcc ccattggccc atatcctgca    3780
agaaaaagga gatgaaaaca ttatcaatgt ctgtaagcag gttgatattg cttatgattt    3840
ggagttaggc aaaacattga gtgagatacg agccttaacc gcaaatggtt ttattaagtt    3900
caatatttat aagtctttca gggcaaataa gtgtgcagat ctctgtatta gccaagtagt    3960
gaatatggag gagttcgcgct atgtggcaaa ttaatgaggt tgtgctattt gataatgatc    4020
cgtatcgcat tttggctata gaggatggcc aagttgtctg gatgcaaata gcgctgata    4080 aaggagttcc acaagctagg gctgagttgt tgctaatgca gtatttagat gaaggccgct    4140
tagttagaac tgatgaccct tatgtacatc ttgatttaga agagccgtct gtagattctg    4200
tcagcttcca gaagcgcgag gaggattatc gaaaaattct tcctattatt aatagtaagg    4260
atcgtttcga ccctaaagtc agaagcgaac tcgttgagca tgtggtccaa gaacataagg    4320
ttactaaggc tacagtttat aagttgttac gccgttactg gcagcgtggt caaacgccta    4380
```

```
atgcattaat tcctgactac aaaaacagcg gtgcaccagg ggaaagacgt tcagcgacag    4440
gaacagcaaa gattggccga gccagagaat atggtaaggg tgaaggaacc aaggtaacgc    4500
ccgagattga acgccttttt aggttgacca tagaaaagca cctgttaaat caaaaaggta    4560
caaagaccac cgttgcctat agacgatttg tggacttgtt tgctcagtat tttcctcgca    4620
ttccccaaga ggattaccca acactacgtc agtttcgtta tttttatgat cgagaatacc    4680
ctaaagctca gcgcttaaag tctagagtta agcaggggt atataaaaaa gacgtacgac     4740
ccttaagtag tacagccact tctcaggcgt taggccctgg gagtcgttat gagattgatg    4800
ccacgattgc tgatatttat ttagtggatc atcatgatcg ccaaaaaatc ataggaagac    4860
caacgcttta cattgtgatt gatgtgttta gtcggatgat cacgggcttt tatatcggct    4920
ttgaaaatcc gtcttatgtg gtggcgatgc aggcttttgt aaatgcttgc tctgacaaaa    4980
cggccatttg tgcccagcat gatattgaga ttagtagctc agactggccg tgtgtaggtt    5040
tgccagatgt gttgctagcg gaccgtggcg aattaatgag tcatcaggtc gaagccttag    5100
tttctagttt taatgtgcga gtggaaagtg ctccacctag acgtggcgat gctaaaggca    5160
tagtggaaag cactttaga acactacaag ccgagtttaa gtcctttgca cctggcattg      5220
tagagggcag tcggatcaaa agccatggtg aaacagacta taggttagat gcatctctgt    5280
cggtatttga gttcacacaa attattttgc gtacgatctt attcagaaat aaccatctgg    5340
tgatggataa atacgatcga gatgctgatt ttcctacaga tttaccgtct attcctgtcc    5400
agctatggca atggggtatg cagcatcgta caggtagttt aagggctgtg gagcaagagc    5460
agttgcgagt agcgttactg cctcgccgaa aggtctctat ttcttcattt ggcgttaatt    5520
tgtggggttt gtattactcg gggtcagaga ttctgcgtga gggttggttg cagcggagca    5580
ctgatatagc tagacctcaa catttagaag cggcttatga cccagtgctg gttgatacga    5640
tttatttgtt tccgcaagtt ggcagccgtg tattttggcg ctgtaatctg acggaacgta    5700
gtcggcagtt taaggtctc tcattttggg aggtttggga tatacaagca caagaaaaac     5760
acaataaagc caatgcgaag caggatgagt taactaaacg cagggagctt gaggcgttta    5820
ttcagcaaac cattcagaaa gcgaataagt taacgcccag tactactgag cccaaatcaa    5880
cacgcattaa gcagattaaa actaataaaa agaagccgt gacctcggag cgtaaaaaac      5940
gtgcggagca tttgaagcca agctcttcag gtgatgaggc taaagttatt cctttcaacg    6000
cagtggaagc ggatgatcaa aagattaca gcctacccac atacgtgcct gaattatttc      6060
aggatccacc agaaaaggat gagtcatgag tgctacccgg attcaagcag tttatcgtga    6120 tacggggta gaggcttatc gtgataatcc ttttatcgag gccttaccac cattacaaga     6180
gtcagtgaat agtgctgcat cactgaaatc ctctttacag cttacttcct ctgacttgca    6240
aaagtcccgt gttatcagag ctcataccat tgtcgtatt ccagatgact attttcagcc      6300
attaggtacg catttgctac taagtgagcg tatttcggtc atgattcgag gtggctacgt    6360
aggcagaaat cctaaaacag gagatttaca aaagcattta caaaatggtt atgagcgtgt    6420
tcaaacggga gagttggaga catttcgctt tgaggaggca cgatctacgg cacaaagctt    6480
attgttaatt ggttgttctg gtagtgggaa gacgacctct cttcatcgta ttctagccac    6540
gtatcctcag gtgatttacc atcgtgaact caatgtagag caggtggtgt atttgaaaat    6600
agactgctcg cataatggtt cgctaaaaga aatctgcttg aattttttca gagcgttgga    6660
tcgagccttg ggctcgaact atgagcgtcg ttatggctta aaacgtcatg gtatagaaac    6720
catgttggct ttgatgtcgc aaatagccaa tgcacatgct ttagggttgt tggttattga    6780
```

```
tgaaattcag catttaagcc gctctcgttc gggtggatct caagagatgc tgaacttttt    6840
tgtgacgatg gtgaatatta ttggcgtacc agtgatgttg attggtaccc ctaaagcacg    6900
agagattttt gaggctgatt tgcggtctgc acgtagaggg gcagggtttg gagctatatt    6960
ctgggatcct atacaacaaa cgcaacgtgg aaagcccaat caagagtgga tcgcttttac    7020
ggataatctt tggcaattac agcttttaca acgcaaagat gcgctgttat cggatgaggt    7080
ccgtgatgtg tggtatgagc taagccaagg agtgatggac attgtagtaa aacttttgt     7140 actcgctcag ctccgtgcgc tagctttagg caatgagcgt attaccgctg gtttattgcg    7200
gcaagtgtat caagatgagt taaagcctgt gcaccccatg ctagaggcat tacgctcggg    7260
tatcccagaa cgcattgctc gttattctga tctagtcgtt cccgagattg ataaacggtt    7320
aatccaactt cagctagata tcgcagcgat acaagaacaa acaccagaag aaaaagccct    7380
tcaagagtta gataccgaag atcagcgtca tttatatctg atgctgaaag aggattacga    7440
ttcaagcctg ttaattccca ctattaaaaa agcgtttagc cagaatccaa cgatgacaag    7500
acaaaagtta ctgcctcttg ttttgcagtg gttgatggaa ggcgaaacgg tagtgtcaga    7560
actagaaaag ccctccaaga gtaaaaaggt ttcggctata aagtagtca agcccagcga     7620 ctgggatagc ttgcctgata cggatttacg ttatatctat tcacaacgcc aacctgaaaa    7680
aaccatgcat gaacggttaa aagggaaagg ggtaatagtg gatatggcga gcttatttaa    7740
acaagcaggt tagccatgag aaactttcct gttccgtact cgaatgagct gatttatagc    7800
actattgcac gggcaggcgt ttatcaaggg attgttagtc ctaagcagct gttggatgag    7860
gtgtatggca accgcaaggt ggtcgctacc ttaggtctgc cctcgcattt aggtgtgata    7920
gcaagacatc tacatcaaac aggacgttac gctgttcagc agcttattta tgagcatacc    7980
ttattcccct tatatgctcc gtttgtaggc aaggagcgcc gagacgaagc tattcggtta    8040
atggagtacc aagcgcaagg tgcggtgcat ttaatgctag gagtcgctgc ttctagagtt    8100
aagagcgata accgctttag atactgccct gattgcgttg ctcttcagct aaataggtat    8160
ggggaagcct tttggcaacg agattggtat ttgcccgctt tgccatattg tccaaaacac    8220
ggtgctttag tcttctttga tagagctgta gatgatcacc gacatcaatt ttgggctttg    8280
ggtcatactg agctgctttc agactacccc aaagactccc tatctcaatt aacagcacta    8340
gctgcttata tagcccctct gttagatgct ccacgagcgc aagagctttc cccaagcctt    8400
gagcagtgga cgctgtttta tcagcgctta gcgcaggatc tagggctaac caaaagcaag    8460
cacattcgtc atgacttggt ggcggagaga gtgaggcaga cttttagtga tgaggcacta    8520
gagaaactgg atttaaagtt ggcagagaac aaggacacgt gttggctgaa agtatattc     8580 cgtaagcata gaaaagcctt tagttatta cagcatagta ttgtgtggca agccttattg     8640
ccaaaactaa cggttataga agcgctacag caggcaagtg ctcttactga gcactctata    8700
acgacaagac ctgttagcca gtctgtgcaa cctaactctg aagatttatc tgttaagcat    8760
aaagactggc agcaactagt gcataaatac caaggaatta aggcggcaag acagtcttta    8820
gagggtgggg tgctatacgc cttggcttta cgacatgaca gggattggct agttcactgg    8880
aatcaacagc atcaacaaga gcgtctggca cccgccccta gagttgattg gaaccaagaa    8940
gatcgaattg ctgtacgaca actattaaga atcataaagc gtctagatag tagccttgat    9000
cacccaagag cgcatcgag ctggctgtta aagcaaactc ctaacggaac ctctcttgca     9060
aaaaatctac agaaactgcc tttggtagcg ctttgcttaa agcgttactc agagagtgtg    9120
```

```
gaagattatc aaattagacg gattagccaa gcttttatta agcttaaaca ggaagatgtt      9180
gagcttaggc gctggcgatt attaagaagt gcaacgttat ctaaagagcg gataactgag      9240
gaagcacaaa gattcttgga aatggtttat ggggaagagt gagtggttag gctagctaca      9300
tttaatgaca atgtgcaggt tgtacatatt ggtcatttat tccgtaactc gggtcataag      9360
gagtggcgta ttttttgtttg gtttaatcca atgcaagaac ggaaatggac tcgatttact      9420
catttgcctt tattaagtcg agctaaggtg gttaacagta caacaaagca aataaataag      9480
gcggatcgtg tgattgagtt tgaagcatcg gatcttcaac gagccaaaat aatcggggga      9540
tcctctagag tcgacctgca ggcatgcaag cttggcactg gccgtcgttt tacaacgtcg      9600
tgactgggaa aaccctggcg ttacccaact taatcgcctt gcagcacatc cccctttcgc      9660
cagctggcgt aatagcgaag aggcccgcac cgatcgccct tcccaacagt tgcgcagcct      9720
gaatggcgaa tggcgcctga tgcggtattt tctccttacg catctgtgcg gtatttcaca      9780
ccgcatatgg tgcactctca gtacaatctg ctctgatgcc gcatagttaa gccagccccg      9840
acacccgcca cacccgctg acgcgccctg acgggcttgt ctgctcccgg catccgctta      9900
cagacaagct gtgaccgtct ccgggagctg catgtgtcag aggttttcac cgtcatcacc      9960
gaaacgcgcg a                                                          9971

<210> SEQ ID NO 2
<211> LENGTH: 11477
<212> TYPE: DNA
<213> ORGANISM: Artificial sequence
<220> FEATURE:
<223> OTHER INFORMATION: Synthetic construct

<400> SEQUENCE: 2
ttaaaaatga agtttttaaat caatctaaag tatatatgag taaacttggt ctgacagtta        60
ccaatgctta atcagtgagg cacctatctc agcgatctgt ctatttcgtt catccatagt       120
tgcctgactc cccgtcgtgt agataactac gatacgggag ggcttaccat ctggccccag       180
tgctgcaatg ataccgcggg acccacgctc accggctcca gatttatcag caataaacca       240
gccagccgga agggccgagc gcagaagtgg tcctgcaact ttatccgcct ccatccagtc       300
tattaattgt tgccgggaag ctagagtaag tagttcgcca gttaatagtt tgcgcaacgt       360
tgttgccatt gctacaggca tcgtggtgtc acgctcgtcg tttggtatgg cttcattcag       420
ctccggttcc caacgatcaa ggcgagttac atgatccccc atgttgtgca aaaaagcggt       480
tagctccttc ggtcctccga tcgttgtcag aagtaagttg gccgcagtgt tatcactcat       540
ggttatggca gcactgcata attctcttac tgtcatgcca tccgtaagat gcttttctgt       600
gactggtgag tactcaacca agtcattctg agaatagtgt atgcggcgac cgagttgctc       660
ttgcccggcg tcaatacggg ataataccgc gccacatagc agaactttaa aagtgctcat       720
cattggaaaa cgttcttcgg ggcgaaaact ctcaaggatc ttaccgctgt tgagatccag       780
ttcgatgtaa cccactcgtg cacccaactg atcttcagca tcttttactt tcaccagcgt       840
ttctgggtga gcaaaaacag gaaggcaaaa tgccgcaaaa aagggaataa gggcgacacg       900
gaaatgttga atactcatac tcttcctttt tcaatattat tgaagcattt atcagggtta       960
ttgtctcatg agcggataca tatttgaatg tatttagaaa aataaacaaa tagggggttcc      1020 gcgcacattt ccccgaaaag tgccacctga cgtctaagaa accattatta tcatgacatt      1080
aacctataaa aataggcgta tcacgaggcc ctttcgtctc gcgcgtttcg gtgatgacgg      1140
tgaaaacctc tgacacatgc agctcccgga gacggtcaca gcttgtctgt aagcggatgc      1200
```

```
cgggagcaga caagcccgtc agggcgcgtc agcgggtgtt ggcgggtgtc ggggctggct    1260
taactatgcg gcatcagagc agattgtact gagagtgcac catatgcggt gtgaaatacc    1320
gcacagatgc gtaaggagaa ataccgcat caggcgccat tcgccattca ggctgcgcaa     1380
ctgttgggaa gggcgatcgg tgcgggcctc ttcgctatta cgccagctag aggaccagcc    1440
gcgtaacctg gcaaaatcgg ttacggttga gtaataaatg gatgccctgc gtaagcgggt    1500
gtgggcggac aataaagtct taaactgaac aaaatagatc taaactatga caataaagtc    1560
ttaaactaga cagaatagtt gtaaactgaa atcagtccag ttatgctgtg aaaaagcata    1620
ctggactttt gttatggcta aagcaaactc ttcattttct gaagtgcaaa ttgcccgtcg    1680
tattaaagag gggcgtgggg ttcgaggtcg acggtatcga taagctagct taattagctg    1740
agcttggact cctgttgata gatccagtaa tgacctcaga actccatctg gatttgttca    1800
gaacgctcgg ttgccgccgg gcgttttta ttggtgagaa tccaagctag actgcgatga     1860
gtggcagggc ggggcgtaat tttttaagg cagttattgg tgcccttaaa cgcctggggt     1920
aatgactctc tagcttgagg catcaaataa aacgaaaggc tcagtcgaaa gactgggcct    1980
ttcgttttat ctgttgtttg tcggtgaacg ctctcctgag taggacaaat ccgccgctag    2040
gagcttgcgg cccggacgat gagctcgaat tgggatctt gaagtaccta ttccgaagtt     2100
cctattctct agaaagtata ggaacttcag agcgcttttg aagctgatgc tcgagtgctt    2160
aaaaacttac tcaatggaat aattctagat aattcttagg ccacacgttc aagtgcagcc    2220
acaggataaa tttgcactga gcctgggtgg gattcggact cgaccgcata gccttcagga    2280
gtgagttttg tgcaatacca accgacgact tgaccctgcc aagcggcacc agatttcttg    2340
cgtacgcgat cccctaagcc aaaggtggca ctcaggggaa gcgcaaactg ccctgcaacg    2400
ggagcgttgg cttcatcgct actttgaccc atgtcgaatc cttcttgtga atctattatg    2460
gcgacaagca aatcgagctc tgactgccta ccccacaaca actatcagaa agcaccagca    2520
caacggctgc ctaactttgt tttagggcga ctgccctgct gcgtaacatc gttgctgctc    2580
cataacatca aacatcgacc cacggcgtaa cgcgcttgct gcttggatgc ccgaggctag    2640
actgtacaaa aaaacagtca taacaagcca tgaaaaccgc cactgcgccg ttaccaccgc    2700
tgcgttcggt caaggttctg gaccagttgc gtgagcgcat acgctacttg cattacagtt    2760
tacgaaccga acaggcttat gtcaactggg ttcgtgaatt atccattgct gttgacaaag    2820
ggaatcaggc tcgagagttc aacagacagc cttcgttctt atggccgttc aggaggaagt    2880
tcctattccg aagttcctat tctctagaaa gtataggaac ttcttgagaa gagaaaagaa    2940
aaccgccgat cctgtccacc gcattactgc aaggtagtgg acaagaccgg cggtcttaag    3000
ttttttggct gaaacgaatg acgaaaaggc tgtctgagca aatccaggag gtcgttttta    3060
ttaagcaccg gtggagtgac gaccttcagc acgttcgtac tgttcaacga tggtgtagtc    3120
ttcgttgtgg gaggtgatgt ccagtttgat gtcggttttg taagcacccg gcagctgaac    3180
cggtttttta gccatgtagg tggttttaac ttcagcgtcg tagtgaccac cgtctttcag    3240
tttcagacgc attttgattt caccttcag agcaccgtct tccgggtaca tacgttcggt     3300
ggaagcttcc caacccatgg tttttttctg cataaccgga ccgtcggacg ggaagttggt    3360
accacgcagt ttaactttgt agatgaactc accgtcttgc agggaggagt cctgggtaac    3420
ggtaacaaca ccaccgtctt cgaagttcat aacacgttcc catttgaaac cttccgggaa    3480
ggacagtttc aggtagtccg ggatgtcagc cgggtgttta acgtaagctt tggaaccgta    3540
```

```
ctggaactgc ggggacagga tgtcccaagc aacggcagc ggaccacctt tggtaactttt      3600
cagtttagcg gtctgggtac cttcgtacgg acgaccttca ccttcacctt cgatttcgaa      3660
ctcgtgaccg ttaacggaac cttccatacg aactttgaaa cgcatgaact ctttgataac      3720
gtcttcgcta ctcgccatgg tacctttctc ctctttaatt aattcagatc tattataacct    3780
aggactgagc tagctgtcaa attcaccacc ctgaattgac tctcaaaccg tattagcccg      3840
gtattttgga aatagcggaa gcactgactt ttgttatcaa taaaaaaggc cccccgttag      3900
ggaggcctta ttgttcgtct actcggaaga gcgagagaca acagaacggt cagccacatg      3960
aattcaaaaa aaaagcaccg actcggtgcc acttttcaa gttgataacg gactagcctt       4020
atttaaacttt gctatgctgt ttccagcata gctcttaaac agaccgctaa actgaaagtt     4080
ccacacatta tacgagccgg atgattaatt gtcaacagct catttcagaa tatttgccag     4140
aaccggaatt ctttcagctc agtcgatagg tagtaggcaa gagtagtcgc acctttggtc     4200
gaaaaaaaaa gcccgcactg tcaggtgcgg gcttttttct gtgtttcccc aaaagtaaaa     4260
acccgccgaa gcgggttttt acgtaaaaca ggtgaaactg accagacgag aaggctttgg     4320
aggtgataat ggggctcaag gacccgggag gcagataggt aggcatggcc cccatttttca    4380
atacaagcaa cgcatgagaa agccccccgga agatcacctt ccgggggctt ttttattgcg   4440
ctccggcaat taaaaagcg gctaaccacg ccgctttttt tacgtctgca gagctcatag     4500
gcaagcgaat cgtgatgcct cttagccagt actagttttat gacaacttga cggctacatc   4560
attcactttt tcttcacaac cggcacggaa ctcgctcggg ctggccccgg tgcatttttt    4620
aaataccgcc gagaaataga gttgatcgtc aaaaccaaca ttgcgaccga cggtggcgat    4680
aggcatccgg gtggtgctca aaagcagctt cgcctggctg atacgttggt cctcgcgcca   4740
gcttaagacg ctaatcccta actgctggcg gaaaagatgt gacagacgcg acggcgacaa    4800
gcaaacatgc tgtgcgacgc tggcgatatc aaaattgctg tctgccaggt gatcgctgat   4860
gtactgacaa gcctcgcgta cccgattatc catcggtgga tggagcgact cgttaatcgc    4920
ttccatgcgc cgcagtaaca attgctcaag cagatttatc gccagcagct ccgaatagcg   4980
cccttccccct tgcccggcgt taatgatttg cccaaacagg tcgctgaaat gcggctggtg   5040
cgcttcatcc gggcgaaaga accccgtatt ggcaaatatt gacggccagt taagccattc   5100
atgccagtag gcgcgcggac gaaagtaaac ccactggtga taccattcgc gagcctccgg   5160
atgacgaccg tagtgatgaa tctctcctgg cgggaacagc aaaatatcac ccggtcggca    5220
aacaaattct cgtccctgat ttttcaccac cccctgaccg cgaatggtga gattgagaat    5280
ataacctttc attcccagcg gtcggtcgat aaaaaaatcg agataaccgt tggcctcaat    5340
cggcgttaaa cccgccacca gatgggcatt aaacagtgtat cccggcagca ggggatcatt   5400
tgcgcttca gccatacttt tcatactccc gccattcaga gaagaaacca attgtccata    5460
ttgcatcaga cattgccgtc actgcgtctt ttactggctc ttctcgctaa ccaaaccggt    5520
aaccccgctt attaaaagca ttctgtaaca aagcgggacc aaagccatga caaaaacgcg   5580
taacaaaagt gtctataatc acggcagaaa agtccacatt gattatttgc acggcgtcac   5640
actttgctat gccatagcat ttttatccat aagattagcg gatcctacct gacgcttttt    5700
atcgcaactc tctactgttt ctccataccc gttttttttgg gctagaaata attttgttta    5760
actttaagaa ggagatatac atacccatgg ataagaaata ctcaataggc ttagctatcg   5820
gcacaaatag cgtcggatgg gcggtgatca ctgatgaata aaggttccg tctaaaaagt     5880
tcaaggttct gggaaataca gaccgccaca gtatcaaaaa aatcttata ggggctcttt    5940
```

```
tatttgacag tggagagaca gcggaagcga ctcgtctcaa acggacagct cgtagaaggt   6000
atacacgtcg aagaatcgt atttgttatc tacaggagat ttttcaaat gagatggcga    6060 aagtagatga tagtttcttt catcgacttg aagagtcttt tttggtggaa gaagacaaga   6120
agcatgaacg tcatcctatt tttgaaata tagtagatga agttgcttat catgagaaat    6180
atccaactat ctatcatctg cgaaaaaat tggtagattc tactgataaa gcggatttgc    6240
gcttaatcta tttggcctta gcgcatatga ttaagtttcg tggtcatttt ttgattgagg   6300
gagatttaaa tcctgataat agtgatgtgg acaaactatt tatccagttg gtacaaacct   6360
acaatcaatt atttgaagaa aaccctatta acgcaagtgg agtagatgct aaagcgattc    6420
tttctgcacg attgagtaaa tcaagacgat tagaaaatct cattgctcag ctccccggtg   6480
agaagaaaaa tggcttattt gggaatctca ttgctttgtc attgggtttg accctaatt    6540 ttaaatcaaa ttttgatttg gcagaagatg ctaaattaca gctttcaaaa gatacttacg   6600
atgatgattt agataattta ttggcgcaaa ttggagatca atatgctgat ttgttttgg    6660 cagctaagaa tttatcagat gctattttac tttcagatat cctaagagta aatactgaaa   6720
taactaaggc tcccctatca gcttcaatga ttaaacgcta cgatgaacat catcaagact   6780
tgactctttt aaaagcttta gttcgacaac aacttccaga aaagtataaa gaaatctttt   6840
ttgatcaatc aaaaaacgga tatgcaggtt atattgatgg gggagctagc caagaagaat   6900
tttataaatt tatcaaacca atttttagaaa aaatggatgg tactgaggaa ttattggtga   6960
aactaaatcg tgaagatttg ctgcgcaagc aacggacctt tgacaacggc tctattcccc    7020
atcaaattca cttgggtgag ctgcatgcta ttttgagaag acaagaagac ttttatccat   7080
ttttaaaaga caatcgtgag aagattgaaa aaatcttgac ttttcgaatc ccttattatg   7140
ttggtccatt ggcgcgtggc aatagtcgtt ttgcatggat gactcggaag tctgaagaaa   7200
caattacccc atggaatttt gaagaagttg tcgataaagg tgcttcagct caatcattta    7260
ttgaacgcat gacaaacttt gataaaaatc ttccaaatga aaaagtacta ccaaaacata   7320
gtttgcttta tgagtatttt acggtttata acgaattgac aaaggtcaaa tatgttactg   7380
aaggaatgcg aaaaccagca tttctttcag gtgaacagaa gaaagccatt gttgatttac   7440
tcttcaaaac aaatcgaaaa gtaaccgtta agcaattaaa agaagattat ttcaaaaaaa   7500
tagaatgttt tgatagtgtt gaaatttcag gagttgaaga tagatttaat gcttcattag   7560
gtacctacca tgatttgcta aaaattatta aagataaaga ttttttggat aatgaagaaa   7620
atgaagatat cttagaggat attgttttaa cattgacctt atttgaagat agggagatga   7680
ttgaggaaag acttaaaaca tatgctcacc tctttgatga taaggtgatg aaacagctta   7740
aacgtcgccg ttatactggt tggggacgtt tgtctcgaaa attgattaat ggtattaggg   7800
ataagcaatc tggcaaaaca atattagatt ttttgaaatc agatggtttt gccaatcgca   7860
attttatgca gctgatccat gatgatagtt tgacatttaa agaagacatt caaaagcac    7920 aagtgtctgg acaaggcgat agtttacatg aacatattgc aaatttagct ggtagccctg   7980
ctattaaaaa aggtatttta cagactgtaa aagttgttga tgaattggtc aaagtaatgg   8040
ggcggcataa gccagaaaat atcgttattg aaatggcacg tgaaaatcag acaactcaaa   8100
agggccagaa aaattcgcga gagcgtatga acgaatcga agaaggtatc aaagaattag   8160 gaagtcgat tcttaaagag catcctgttg aaaatactca attgcaaaat gaaaagctct    8220
atctctatta tctccaaaat ggaagagaca tgtatgtgga ccaagaatta gatattaatc   8280
```

```
gtttaagtga ttatgatgtc gatgccattg ttccacaaag tttccttaaa gacgattcaa    8340
tagacaataa ggtcttaacg cgttctgata aaaatcgtgg taaatcggat aacgttccaa    8400
gtgaagaagt agtcaaaaag atgaaaaact attggagaca acttctaaac gccaagttaa    8460
tcactcaacg taagtttgat aatttaacga aagctgaacg tggaggtttg agtgaacttg    8520
ataaagctgg ttttatcaaa cgccaattgg ttgaaactcg ccaaatcact aagcatgtgg    8580
cacaaatttt ggatagtcgc atgaatacta aatacgatga aaatgataaa cttattcgag    8640
aggttaaagt gattacctta aaatctaaat tagtttctga cttccgaaaa gatttccaat    8700
tctataaagt acgtgagatt aacaattacc atcatgccca tgatgcgtat ctaaatgccg    8760
tcgttggaac tgctttgatt aagaaatatc aaaacttga atcggagttt gtctatggtg    8820
attataaagt ttatgatgtt cgtaaaatga ttgctaagtc tgagcaagaa ataggcaaag    8880
caaccgcaaa atatttcttt tactctaata tcatgaactt cttcaaaaca gaaattacac    8940
ttgcaaatgg agagattcgc aaacgccctc taatcgaaac taatgggaa actggagaaa    9000 ttgtctggga taagggcga gattttgcca cagtgcgcaa agtattgtcc atgccccaag    9060
tcaatattgt caagaaaaca gaagtacaga caggcggatt ctccaaggag tcaattttac    9120 caaaagaaa ttcggacaag cttattgctc gtaaaaaaga ctgggatcca aaaaaatatg    9180
gtggttttga tagtccaacg gtagcttatt cagtcctagt ggttgctaag gtggaaaaag    9240
ggaaatcgaa gaagttaaaa tccgttaaag agttactagg gatcacaatt atggaaagaa    9300
gttcctttga aaaaaatccg attgactttt tagaagctaa aggatataag gaagttaaaa    9360
aagacttaat cattaaacta cctaaatata gtcttttga gttagaaaac ggtcgtaaac    9420
ggatgctggc tagtgccgga gaattacaaa aaggaaatga gctggctctg ccaagcaaat    9480
atgtgaattt tttatattta gctagtcatt atgaaaagtt gaagggtagt ccagaagata    9540
acgaacaaaa acaattgttt gtggagcagc ataagcatta tttagatgag attattgagc    9600
aaatcagtga atttttctaag cgtgttattt tagcagatgc caatttagat aaagttctta    9660
gtgcatataa caaacataga gacaaaccaa tacgtgaaca agcagaaaat attattcatt    9720
tatttacgtt gacgaatctt ggagctcccg ctgcttttaa atattttgat acaacaattg    9780
atcgtaaacg atatacgtct acaaaagaag ttttagatgc cactcttatc catcaatcca    9840
tcactggtct ttatgaaaca cgcattgatt tgagtcagct aggaggtgac gcggccgcgg    9900
agcagaaact catctctgaa gaagatctgg aacaaaagtt gatttcagaa gaagatctgg    9960
aacagaagct catctctgag gaagatctgt aataaggcgc gcctccttaa tgggacttgc   10020
agcctcggta ccaaattcca gaaaagacac ccgaaagggt gttttttcgt tttggtccca   10080
cagaatgagc atcatggcac tagtcgacat cggagaagag tacggctctt ttaaccgcct   10140
caagaaccag ataagtgaaa tctagttcca aactattttg tcatttttaa ttttcgtatt   10200
agcttacgac gctacaccca gttcccatct attttgtcac tcttccctaa ataatccta   10260 aaaactccat ttccacccct cccagttccc aactattttg tccgcccaca gcggggcatt   10320
tttcttcctg ttatgtttgg gcgctgcatt aatgaatcgg ccaacgcgcg gggagaggcg   10380
gtttgcgtat tgggcgctct tccgcttcct cgctcactga cccgctgcgc tcggtcgttc   10440
ggctgcggcg agcggtatca gagcttatcg gccagcctcg cagagcagga ttcccgttga   10500
gcaccgccag gtgcgaataa gggacagtga agaaggaaca cccgctcgcg ggtgggccta   10560
cttcacctat cctgcccggc tgacgccgtt ggatacacca aggaaagtct acacgaaccc   10620
tttggcaaaa tcctgtatat cgtgcgaaaa aggatggata taccgaaaaa atcgctataa   10680
```

```
tgaccccgaa gcagggttat gcagcggaaa gtataccctta aggaatcccc tgataacgca    10740
ggaaagaaca tgtgagcaaa aggccagcaa aaggccagga accgtaaaaa ggccgcactc    10800
cctgcctctg tcatcacgat actgtgatgc catggctaat tcccatgtca gccgttaagt    10860
gttcctgtgt cactcaaaat tgcttttgaga ggctctaagg gcttctcagt gcgttacatc    10920
cctggcttgt tgtccacaac cgttaaacct aaaagcttt aaaagcctta tatattcttt    10980
tttttcttat aaaacttaaa accttagagg ctatttaagt tgctgattta tattaatttt    11040
attgttcaaa catgagagct tagtacgtga acatgagag cttagtacgt tagccatgag    11100
agcttagtac gttagccatg agggtttagt tcgttaaaca tgagagctta gtacgttaaa    11160
catgagagct tagtacgtga acatgagag cttagtacgt actatcaaca ggttgaactg    11220
ctgatcttca gatcctctac gccgacgca tcgtggccgg atcttgcggc cgcaaaaatt    11280
aaaaatgaag ttttaaatca atctaaagta tatgagta aacttggtct gacagttacc    11340
aatgcttaat cagtgaggca ccaataactg cctttgatct tttctacggg gtctgacgct    11400
cagtggaacg aaaactcacg ttaagggatt ttggtcatga gattatcaaa aaggatcttc    11460
acctagatcc tttaaa                                                   11477

<210> SEQ ID NO 3
<211> LENGTH: 12840
<212> TYPE: DNA
<213> ORGANISM: Artificial sequence
<220> FEATURE:
<223> OTHER INFORMATION: Synthetic construct

<400> SEQUENCE: 3
ttaaaaatga agttttaaat caatctaaag tatatatgag taaacttggt ctgacagtta      60
ccaatgctta atcagtgagg cacctatctc agcgatctgt ctatttcgtt catccatagt     120
tgcctgactc cccgtcgtgt agataactac gatacgggag ggcttaccat ctggccccag     180
tgctgcaatg ataccgcggg acccacgctc accggctcca gatttatcag caataaacca     240
gccagccgga agggccgagc gcagaagtgg tcctgcaact ttatccgcct ccatccagtc     300
tattaattgt tgccgggaag ctagagtaag tagttcgcca gttaatagtt tgcgcaacgt     360
tgttgccatt gctacaggca tcgtggtgtc acgctcgtcg tttggtatgg cttcattcag     420
ctccggttcc caacgatcaa ggcgagttac atgatccccc atgttgtgca aaaaagcggt     480
tagctccttc ggtcctccga tcgttgtcag aagtaagttg gccgcagtgt tatcactcat     540
ggttatggca gcactgcata attctcttac tgtcatgcca tccgtaagat gcttttctgt     600
gactggtgag tactcaacca agtcattctg agaatagtgt atgcggcgac cgagttgctc     660
ttgcccggcg tcaatacggg ataataccgc gccacatagc agaactttaa aagtgctcat     720
cattggaaaa cgttcttcgg ggcgaaaact ctcaaggatc ttaccgctgt tgagatccag     780
ttcgatgtaa cccactcgtg cacccaactg atcttcagca tcttttactt tcaccagcgt     840
ttctgggtga gcaaaaacag gaaggcaaaa tgccgcaaaa aagggaataa gggcgacacg     900
gaaatgttga atactcatac tcttcctttt tcaatattat tgaagcattt atcagggtta     960
ttgtctcatg agcggataca tatttgaatg tatttagaaa aataaacaaa tagggggttcc    1020 gcgcacattt ccccgaaaag tgccacctga cgtctaagaa accattatta tcatgacatt    1080
aacctataaa aataggcgta tcacgaggcc ctttcgtctc gcgcgtttcg gtgatgacgg    1140
tgaaaacctc tgacacatgc agctcccgga gacggtcaca gcttgtctgt aagcggatgc    1200
```

```
cgggagcaga caagcccgtc agggcgcgtc agcgggtgtt ggcgggtgtc ggggctggct    1260
taactatgcg gcatcagagc agattgtact gagagtgcac catatgcggt gtgaaatacc    1320
gcacagatgc gtaaggagaa ataccgcat caggcgccat tcgccattca ggctgcgcaa     1380
ctgttgggaa gggcgatcgg tgcgggcctc ttcgctatta cgccagctag aggaccagcc    1440
gcgtaacctg gcaaaatcgg ttacggttga gtaataaatg gatgccctgc gtaagcgggt    1500
gtgggcggac aataaagtct taaactgaac aaaatagatc taaactatga caataaagtc    1560
ttaaactaga cagaatagtt gtaaactgaa atcagtccag ttatgctgtg aaaaagcata    1620
ctggactttt gttatggcta aagcaaactc ttcattttct gaagtgcaaa ttgcccgtcg    1680
tattaaagag gggcgtgggg ttcgaggtcg acggtatcga taagctagct taattagctg    1740
agcttggact cctgttgata gatccagtaa tgacctcaga actccatctg gatttgttca    1800
gaacgctcgg ttgccgccgg gcgttttta ttggtgagaa tccaagctag actgcgatga     1860
gtggcagggc ggggcgtaat ttttttaagg cagttattgg tgcccttaaa cgcctggggt    1920
aatgactctc tagcttgagg catcaaataa acgaaaggc tcagtcgaaa gactgggcct     1980
ttcgttttat ctgttgtttg tcggtgaacg ctctcctgag taggacaaat ccgccgctag    2040
gagcttgcgg cccggacgat gagctcgaat tggggatctt gaagtaccta ttccgaagtt    2100
cctattctct agaaagtata ggaacttcag agcgcttttg aagctgatgc tcgagtgctt    2160
aaaaacttac tcaatggaat aattctagat aattcttagg ccacacgttc aagtgcagcc    2220
acaggataaa tttgcactga gcctgggtgg gattcggact cgaccgcata gccttcagga    2280
gtgagttttg tgcaatacca accgacgact tgacctgcc aagcggcacc agattcttg      2340
cgtacgcgat cccctaagcc aaaggtggca ctcagggaa gcgcaaactg ccctgcaacg     2400
ggagcgttgg cttcatcgct actttgaccc atgtcgaatc cttcttgtga atctattatg    2460
gcgacaagca aatcgagctc tgactgccta ccccacaaca actatcagaa agcaccagca    2520
caacggctgc ctaactttgt tttagggcga ctgccctgct gcgtaacatc gttgctgctc    2580
cataacatca aacatcgacc cacggcgtaa cgcgcttgct gcttggatgc ccgaggctag    2640
actgtacaaa aaaacagtca taacaagcca tgaaaaccgc cactgcgccg ttaccaccgc    2700
tgcgttcggt caaggttctg gaccagttgc gtgagcgcat acgctacttg cattacagtt    2760
tacgaaccga acaggcttat gtcaactggg ttcgtgaatt atccattgct gttgacaaag    2820
ggaatcaggc tcgagagttc aacagacagc cttcgttctt atggccgttc aggaggaagt    2880
tcctattccg aagttcctat tctctagaaa gtataggaac ttcttgagaa gagaaaagaa    2940
aaccgccgat cctgtccacc gcattactgc aaggtagtgg acaagaccgg cggtcttaag    3000
tttttttggct gaaacgaatg acgaaaaggc tgtctgagca aatccaggag gtcgttttta    3060
ttaagcaccg gtggagtgac gaccttcagc acgttcgtac tgttcaacga tggtgtagtc    3120
ttcgttgtgg gaggtgatgt ccagtttgat gtcggttttg taagcacccg gcagctgaac    3180
cggttttta gccatgtagg tggttttaac ttcagcgtcg tagtgaccac cgtctttcag    3240
tttcagacgc attttgattt caccttcag agcaccgtct tccgggtaca tacgttcggt    3300
ggaagcttcc caacccatgg tttttttctg cataaccgga ccgtcggacg ggaagttggt    3360
accacgcagt ttaactttgt agatgaactc accgtcttgc agggaggagt cctgggtaac    3420
ggtaacaaca ccaccgtctt cgaagttcat aacacgttcc catttgaaac cttccgggaa    3480
ggacagtttc agtagtccg gatgtcagc cgggtgttta acgtaagctt tggaaccgta      3540
ctggaactgc ggggacagga tgtcccaagc gaacggcagc ggaccaccct tggtaacttt    3600
```

```
cagtttagcg gtctgggtac cttcgtacgg acgaccttca ccttcacctt cgatttcgaa   3660
ctcgtgaccg ttaacggaac cttccatacg aactttgaaa cgcatgaact ctttgataac   3720
gtcttcgcta ctcgccatgg tacctttctc ctctttaatg aattcagatc tattatacct   3780
aggactgagc tagctgtcaa attcaccacc ctgaattgac tctcaaaccg tattagcccg   3840
gtattttgga aatagcggaa gcactgactt ttgttatcaa taaaaaaggc cccccgttag   3900
ggaggcctta ttgttcgtct actcggaaga gcgagagaca acagaacggt cagccacatg   3960
aattcaaaaa aaaagcaccg actcggtgcc acttttttcaa gttgataacg gactagcctt   4020
atttaaactt gctatgctgt ttccagcata gctcttaaac agaccgctaa actgaaagtt   4080
ccacacatta tacgagccgg atgattaatt gtcaacagct catttcagaa tatttgccag   4140
aaccggaatt ctttcagctc agtcgatagg tagtaggcaa gagtagtcgc acctttggtc   4200
gaaaaaaaaa gcccgcactg tcaggtgcgg gctttttctc tgtttccccc aaaagtaaaa   4260
acccgccgaa gcgggttttt acgtaaaaca ggtgaaactg accagacgag aaggctttgg   4320
aggtgataat ggggctcaag gaccctgggg tgcctaatga gtgagctaac tcacattaat   4380
tgcgttgcgc tcactgcccg ctttccagtc gggaaacctg tcgtgccagc tgcattaatg   4440
aatcggccaa cgcgcgggga gaggcggttt gcgtattggg cgccagggtg ttttttcttt   4500
tcaccagtga cgggcaac agctgattgc ccttcaccgc ctggccctga gagagttgca   4560
gcaagcggtc cacgctggtt tgccccagca ggcgaaaatc ctgtttgatg gtggttaacg   4620 gcggatata acatgagctg tcttcggtat cgtcgtatcc cactaccgag atatccgcac   4680
caacgcgcag cccggactcg gtaatggcgc gcattgcgcc cagcgccatc tgatcgttgg   4740
caaccagcat cgcagtggga acgatgccct cattcagcat ttgcatggtt tgttgaaaac   4800
cggacatggc actccagtcg ccttcccgtt ccgctatcgg ctgaatttga ttgcgagtga   4860
gatatttatg ccagccagcc agacgcagac gcgccgagac agaacttaat gggcccgcta   4920
acagcgcgat ttgctggtga cccaatgcga ccagatgctc cacgcccagt cgcgtaccgt   4980
cttcatggga aaaataata ctgttgatgg gtgtctggtc agagacatca agaaataacg   5040
ccggaacatt agtgcaggca gcttccacag caatggcatc ctggtcatcc agcggatagt   5100
taatgatcag cccactgacg cgttgcgcga agattgtg caccgccgct ttacaggctt   5160
cgacgccgct tcgttctacc atcgacacca ccacgctggc acccagttga tcggcgcgag   5220
atttaatcgc cgcgacaatt tgcgacggcg cgtgcagggc cagactggag gtggcaacgc   5280
caatcagcaa cgactgtttg cccgccagtt gttgtgccac gcggttggga atgtaattca   5340
gctccgccat cgccgcttcc acttttttccc gcgttttcgc agaaacgtgg ctggcctggt   5400
tcaccacgcg ggaaacggtc tgataagaga caccggcata ctctgcgaca tcgtataacg   5460
ttactggttt cacattcacc accctgaatt gactctcttc cgggcgctat catgccatac   5520
cgcgaaaggt tttgcaccat tcgatggtgt caacgtaaat gcatgccgct tcgaggcag   5580 ataggtaggc atggccccca ttttcaatac aagcaacgca tgagaaagcc cccggaagat   5640
caccttccgg gggctttttt attgcgctcc ggcaattaaa aaagcggcta accacgccgc   5700 ttttttttacg tctgcagagc tcataggcaa gcgaatcgtg atgcctctta gccagtacta   5760
gtttatgaca acttgacggc tacatcattc acttttcctt cacaaccggc acggaactcg   5820
ctggtcccac agaatgagca tcatggcact agtttatgac aacttgacgg ctacacagaa   5880
tgagcatcat ggcactagtt tatgacaact tgacggctac atcattcact ttttcttcac   5940
```

```
aaccggcacg gaactcgctc gggctggccc cggtgcattt tttaaatacc cgcgagaaat    6000
agagttgatc gtcaaaacca acattgcgac cgacggtggc gataggcatc cgggtggtgc    6060
tcaaaagcag cttcgcctgg ctgatacgtt ggtcctcgcg ccagcttaag acgctaatcc    6120
ctaactgctg gcggaaaaga tgtgacagac gcgacggcga caagcaaaca tgctgtgcga    6180
cgctggcgat atcaaaattg ctgtctgcca ggtgatcgct gatgtactga caagcctcgc    6240
gtacccgatt atccatcggt ggatggagcg actcgttaat cgcttccatg cgccgcagta    6300
acaattgctc aagcagattt atcgccagca gctccgaata gcgcccttcc ccttgcccgg    6360
cgttaatgat ttgcccaaac aggtcgctga atgcggctg gtgcgcttca tccgggcgaa     6420
agaaccccgt attggcaaat attgacggcc agttaagcca ttcatgccag taggcgcgcg    6480
gacgaaagta aacccactgg tgataccatt cgcgagcctc cggatgacga ccgtagtgat    6540
gaatctctcc tggcgggaac agcaaaatat caccccggtcg gcaaacaaat tctcgtccct    6600 gattttcac cacccctga ccgcgaatgg tgagattgag aatataaccT ttcattccca      6660
gcggtcggtc gataaaaaaa tcgagataac cgttggcctc aatcggcgtt aaacccgcca    6720
ccagatgggc attaaacgag tatcccggca gcagggaTC attttgcgct tcagccatac    6780
ttttcatact cccgccattc agagaagaaa ccaattgtcc atattgcatc agacattgcc    6840
gtcactgcgt cttttactgg ctcttctcgc taaccaaacc ggtaaccccg cttattaaaa    6900
gcattctgta acaaagcggg accaaagcca tgacaaaaac gcgtaacaaa agtgtctata    6960
atcacggcag aaaagtccac attgattatt tgcacggcgt cacactttgc tatgccatag    7020 cattttatc cataagatta gcggatccta cctgacgctt tttatcgcaa ctctctactg     7080
tttctccata cccgtttttt tgggctagaa ataattttgt ttaactttaa gaaggagata    7140
tacataccca tggacaagaa gtacagcatc ggcctggcca tcggcaccaa ctctgtgggc    7200
tgggccgtga tcaccgacga gtacaaggtg cccagcaaga aattcaaggt gctgggcaac    7260
accgaccggc acagcatcaa gaagaacctg atcggcgccc tgctgttcga cagcggagaa    7320
acagccgagg ccacccggct gaagagaacc gccagaagaa gatacaccag acggaagaac    7380
cggatctgct atctgcaaga gatcttcagc aacgagatgg ccaaggtgga cgacagcttc    7440
ttccacagac tggaagagtc cttcctggtg gaagaggata agaagcacga gcggcacccc    7500
atcttcggca catcgtgga cgaggtggcc taccacgaga gtaccccac catctaccac     7560 ctgagaaaga aactggtgga cagcaccgac aaggccgacc tgcggctgat ctatctggcc    7620
ctggcccaca tgatcaagtt ccggggccac ttcctgatcg agggcgacct gaaccccgac    7680
aacagcgacg tggacaagct gttcatccag ctggtgcaga cctacaacca gctgttcgag    7740
gaaaccccca tcaacgccag cggcgtggac gccaaggcca tcctgtctgc cagactgagc    7800
aagagcagac ggctggaaaa tctgatcgcc cagctgcccg gcgagaagaa gaatggcctg    7860
ttcggcaacc tgattgccct gagcctgggc ctgaccccca acttcaagag caacttcgac    7920
ctggccgagg atgccaaact gcagctgagc aaggacacct acgacgacga cctggacaac    7980
ctgctggccc agatcggcga ccagtacgcc gacctgtttc tggccgccaa gaacctgtcc    8040
gacgccatcc tgctgagcga catcctgaga gtgaacaccg agatcaccaa ggccccctg    8100 agcgcctcta tgatcaagag atacgacgag caccaccagg acctgaccct gctgaaagct    8160
ctcgtgcggc agcagctgcc tgagaagtac aaagagattt tcttcgacca gagcaagaac    8220
ggctacgccg gctacatcga tggcggagcc agccaggaag agttctacaa gttcatcaag    8280
cccatcctgg aaaagatgga cggcaccgag gaactgctcg tgaagctgaa cagagaggac    8340
```

```
ctgctgcgga agcagcggac cttcgacaac ggcagcatcc cccaccagat ccacctggga   8400
gagctgcacg ccattctgcg gcggcaggaa gatttttacc cattcctgaa ggacaaccgg   8460
gaaaagatcg agaagatcct gaccttccgc atcccctact acgtgggccc tctggccagg   8520
ggaaacagca gattcgcctg gatgaccaga agagcgagg aaaccatcac ccctggaac     8580 ttcgaggaag tggtggacaa gggcgccagc gcccagagct tcatcgagcg atgaccaac    8640 ttcgataaga acctgcccaa cgagaaggtg ctgcccaagc acagcctgct gtacgagtac   8700
ttcaccgtgt acaacgagct gaccaaagtg aaatacgtga ccgagggaat gagaaagccc   8760
gccttcctga cgcgcgagca aaaaaagcc atcgtggacc tgctgttcaa gaccaaccgg   8820
aaagtgaccg tgaagcagct gaaagaggac tacttcaaga aaatcgagtg cttcgactcc   8880
gtggaaatct ccggcgtgga agatcggttc aacgcctccc tgggcacata ccacgatctg   8940
ctgaaaatta tcaaggacaa ggacttcctg gacaatgagg aaaacgagga cattctggaa   9000
gatatcgtgc tgaccctgac actgtttgag gacagagaga tgatcgagga acggctgaaa   9060
acctatgccc acctgttcga cgacaaagtg atgaagcagc tgaagcggcg agatacacc    9120 ggctggggca ggctgagccg gaagctgatc aacggcatcc gggacaagca gtccggcaag   9180
acaatcctgg atttcctgaa gtccgacggc ttcgccaaca gaaacttcat gcagctgatc   9240
cacgacgaca gcctgacctt taaagaggac atccagaaag cccaggtgtc cggccagggc   9300
gatagcctgc acgagcacat tgccaatctg gccggcagcc ccgccattaa gaagggcatc   9360
ctgcagacag tgaaggtggt ggacgagctc gtgaaagtga tgggccggca caagcccgag   9420
aacatcgtga tcgaaatggc cagagagaac cagaccaccc agaagggaca gaagaacagc   9480
cgcgagagaa tgaagcggat cgaagagggc atcaaagagc tgggcagcca gatcctgaaa   9540
gaacaccccg tggaaaacac ccagctgcag aacgagaagc tgtacctgta ctacctgcag   9600
aatgggcggg atatgtacgt ggaccaggaa ctggacatca accggctgtc cgactacgat   9660
gtggacgcta tcgtgcctca gagctttctg aaggacgact ccatcgataa caaagtgctg   9720
actcggagcg acaagaaccg gggcaagagc gacaacgtgc cctccgaaga ggtcgtgaag   9780
aagatgaaga actactggcg ccagctgctg aatgccaagc tgattaccca gaggaagttc   9840
gacaatctga ccaaggccga gagaggcggc ctgagcgaac tggataaggc cggcttcatc   9900
aagagacagc tggtggaaac ccggcagatc acaaagcacg tggcacagat cctggactcc   9960
cggatgaaca ctaagtacga cgagaacgac aaactgatcc gggaagtgaa agtgatcacc  10020
ctgaagtcca gctggtgtc cgatttccgg aaggatttcc agtttacaa agtgcgcgag  10080 atcaacaact accaccacgc ccacgacgcc tacctgaacg ccgtcgtggg aaccgccctg  10140
atcaaaaagt accctaagct ggaaagcgag ttcgtgtacg gcgactacaa ggtgtacgac  10200
gtgcggaaga tgatcgccaa gagcgagcag gaaatcggca aggctaccgc caagtacttc  10260
ttctacagca acatcatgaa cttttttcaag accgagatta ccctggccaa cggcgagatc  10320
cggaagcggc ctctgatcga gacaaacggc gaaacaggcg agatcgtgtg ggataagggc  10380
cgggactttg ccaccgtgcg gaaagtgctg tctatgcccc aagtgaatat cgtgaaaaag  10440
accgaggtgc agacaggcgg cttcagcaaa gagtctatcc tgcccaagag gaacagcgac  10500
aagctgatcg ccagaaagaa ggactgggac cctaagaagt acggcggctt cgacagcccc  10560
accgtggcct attctgtgct ggtggtggcc aaagtggaaa agggcaagtc caagaaactg  10620
aagagtgtga aagagctgct ggggatcacc atcatggaaa gaagcagctt cgagaagaat  10680
```

```
cccatcgact ttctggaagc caagggctac aaagaagtga aaaaggacct gatcatcaag    10740
ctgcctaagt actccctgtt cgagctggaa acggccgga agagaatgct ggcctctgcc    10800
ggcgaactgc agaagggaaa cgaactggcc ctgccctcca aatatgtgaa cttcctgtac    10860
ctggccagcc actatgagaa gctgaagggc tcccccgagg ataatgagca gaaacagctg    10920
tttgtggaac agcacaaaca ctacctggac gagatcatcg agcagatcag cgagttctcc    10980
aagagagtga tcctggccga cgctaatctg gacaaggtgc tgagcgccta caacaagcac    11040
agagacaagc ctatcagaga gcaggccgag aatatcatcc acctgtttac cctgaccaat    11100
ctgggagccc ctgccgcctt caagtacttt gacaccacca tcgaccggaa gaggtacacc    11160
agcaccaaag aggtgctgga cgccaccctg atccaccaga gcatcaccgg cctgtacgag    11220
acacggatcg acctgtctca gctgggaggc gacgcggccg cggagcagaa actcatctct    11280
gaagaagatc tggaacaaaa gttgatttca gaagaagatc tggaacagaa gctcatctct    11340
gaggaagatc tgtaataagg cgcgcctcct taatgggact tgcagcctcg gtaccaaatt    11400
ccagaaaaga caccgaaag ggtgttttt cgttttggtc ccacagaatg agcatcatgg    11460
cactagtcga catcggagaa gagtacggct cttttaaccg cctcaagaac cagataagtg    11520
aaatctagtt ccaaactatt ttgtcatttt taattttcgt attagcttac gacgctacac    11580
ccagttccca tctatttgt cactcttccc taaataatcc ttaaaaactc catttccacc    11640
cctcccagtt cccaactatt ttgtccgccc acagcggggc attttcttc ctgttatgtt    11700
tgggcgctgc attaatgaat cggccaacgc gcggggagag cggtttgcg tattgggcgc    11760
tcttccgctt cctcgctcac tgaccgctg cgctcggtcg ttcggctgcg gcgagcggta    11820
tcagagctta tcggccagcc tcgcagagca ggattcccgt tgagcaccgc caggtgcgaa    11880
taagggacag tgaagaagga acaccgctc gcgggtgggc ctacttcacc tatcctgccc    11940
ggctgacgcc gttggataca ccaaggaaag tctacacgaa cccctttggca aaatcctgta    12000
tatcgtgcga aaaaggatgg atataccgaa aaaatcgcta taatgacccc gaagcagggt    12060
tatgcagcgg aaagtatacc ttaaggaatc ccctgataac gcaggaaaga acatgtgagc    12120
aaaaggccag caaaaggcca ggaaccgtaa aaaggccgca ctccctgcct ctgtcatcac    12180
gatactgtga tgccatggct aattcccatg tcagccgtta agtgttcctg tgtcactcaa    12240
aattgctttg agaggctcta agggcttctc agtgcgttac atccctggct tgttgtccac    12300
aaccgttaaa ccttaaaagc tttaaaagcc ttatatattc tttttttct tataaaactt    12360
aaaaccttag aggctattta agttgctgat ttatattaat tttattgttc aaacatgaga    12420
gcttagtacg tgaaacatga gagcttagta cgttagccat gagagcttag tacgttagcc    12480
atgagggttt agttcgttaa acatgagagc ttagtacgtt aaacatgaga gcttagtacg    12540
tgaaacatga gagcttagta cgtactatca acaggttgaa ctgctgatct tcagatcctc    12600
tacgccggac gcatcgtggc cggatcttgc ggccgcaaaa attaaaaatg aagttttaaa    12660
tcaatctaaa gtatatatga gtaaacttgg tctgacagtt accaatgctt aatcagtgag    12720
gcaccaataa ctgcctttga tcttttctac ggggtctgac gctcagtgga acgaaaactc    12780
acgttaaggg attttggtca tgagattatc aaaaaggatc ttcacctaga tccttttaaa    12840
```

<210> SEQ ID NO 4
<211> LENGTH: 10671
<212> TYPE: DNA
<213> ORGANISM: Artificial sequence
<220> FEATURE:
<223> OTHER INFORMATION: Synthetic construct

<400> SEQUENCE: 4

```
ctgataccgc tcgccgcagc cgaacgaccg agcgcagcgg gtcagtgagc gaggaagcgg      60
aagagcgccc aatacgcaaa ccgcctctcc ccgcgcgttg gccgattcat taatgcagcg     120
cccaaacata acaggaagaa aaatgccccg ctgtgggcgg acaaaatagt tgggaactgg     180
gaggggtgga aatggagttt ttaaggatta tttagggaag agtgacaaaa tagatgggaa     240
ctgggtgtag cgtcgtaagc taatacgaaa attaaaaatg acaaaatagt ttggaactag     300
atttcactta tctggttctt gaggcggtta aaagagccgt actcttctcc gatgtcgact     360
aggccatgat gctcattctg tgggaccaaa acgaaaaaac acccttttcgg gtgtcttttc    420
tggaatttgg taccgaggct gcaagtccca ttaaggaggc gcgccttatt acagatcttc     480
ctcagagatg agcttctgtt ccagatcttc ttctgaaatc aacttttgtt ccagatcttc     540
ttcagagatg agtttctgct ccgcggccgc gtcgcctccc agctgagaca ggtcgatccg     600
tgtctcgtac aggccggtga tgctctggtg gatcagggtg gcgtccagca cctctttggt     660
gctggtgtac ctcttccggt cgatggtggt gtcaaagtac ttgaaggcgg caggggctcc     720
cagattggtc agggtaaaca ggtggatgat attctcggcc tgctctctga taggcttgtc     780
tctgtgcttg ttgtaggcgc tcagcacctt gtccagatta gcgtcggcca ggatcactct     840
cttggagaac tcgctgatct gctcgatgat ctcgtccagg tagtgtttgt gctgttccac     900
aaacagctgt ttctgctcat tatcctcggg ggagcccttc agcttctcat agtggctggc     960
caggtacagg aagttcacat atttggaggg caggggccagt tcgtttccct tctgcagttc    1020
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttcttttccat gatggtgatc cccagcagct ctttcacact    1200
cttcagtttc ttggacttgc ccttttccac tttggccacc accagcacag aataggccac    1260
ggtggggctg tcgaagccgc cgtacttctt agggtcccag tccttctttc tggcgatcag    1320
cttgtcgctg ttcctcttgg gcaggataga ctctttgctg aagccgcctg tctgcacctc    1380
ggtcttttc acgatattca cttggggcat agacagcact ttccgcacgg tggcaaagtc     1440
ccggccctta tcccacacga tctcgcctgt ttcgccgttt gtctcgatca gaggccgctt    1500
ccggatctcg ccgttggcca gggtaatctc ggtcttgaaa aagttcatga tgttgctgta    1560
gaagaagtac ttggcggtag ccttgccgat ttcctgctcg ctcttggcga tcatcttccg    1620
cacgtcgtac accttgtagt cgccgtacac gaactcgctt tccagcttag ggtacttttt    1680
gatcagggcg gttcccacga cggcgttcag gtaggcgtcg tgggcgtggt ggtagttgtt    1740
gatctcgcgc actttgtaaa actggaaatc cttccggaaa tcggacacca gcttggactt    1800
cagggtgatc actttcactt cccggatcag tttgtcgttc tcgtcgtact agtgttcat     1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcgacagcc ggttgatgtc cagttcctgg tccacgtaca tatcccgccc     2220
attctgcagg tagtacaggt acagcttctc gttctgcagc tgggtgtttt ccacggggtg    2280
```

-continued

```
ttctttcagg atctggctgc ccagctcttt gatgccctct tcgatccgct tcattctctc      2340
gcggctgttc ttctgtccct tctgggtggt ctggttctct ctggccattt cgatcacgat      2400
gttctcgggc ttgtgccggc ccatcacttt cacgagctcg tccaccacct tcactgtctg      2460
caggatgccc ttcttaatgg cggggctgcc ggccagattg caatgtgct cgtgcaggct      2520 atcgccctgg ccggacacct gggctttctg gatgtcctct ttaaaggtca ggctgtcgtc      2580
gtggatcagc tgcatgaagt ttctgttggc gaagccgtcg acttcagga aatccaggat      2640 tgtcttgccg gactgcttgt cccggatgcc gttgatcagc ttccggctca gcctgcccca      2700
gccggtgtat ctccgccgct tcagctgctt catcactttg tcgtcgaaca ggtgggcata      2760
ggttttcagc cgttcctcga tcatctctct gtcctcaaac agtgtcaggg tcagcacgat      2820
atcttccaga atgtcctcgt tttcctcatt gtccaggaag tccttgtcct tgataatttt      2880
cagcagatcg tggtatgtgc ccaggaggc gttgaaccga tcttccacgc cggagatttc      2940
cacggagtcg aagcactcga ttttcttgaa gtagtcctct ttcagctgct tcacggtcac      3000
tttccggttg gtcttgaaca gcaggtccac gatggctttt ttctgctcgc cgctcaggaa      3060
ggcgggcttt ctcattccct cggtcacgta tttcactttg gtcagctcgt tgtacacggt      3120
gaagtactcg tacagcaggc tgtgcttggg cagcaccttc tcgttgggca ggttcttatc      3180
gaagttggtc atccgctcga tgaagctctg ggcgctggcg cccttgtcca ccacttcctc      3240
gaagttccag ggggtgatgg tttcctcgct ctttctggtc atccaggcga atctgctgtt      3300 tccctggcc agagggccca cgtagtaggg gatgcggaag gtcaggatct tctcgatctt      3360 ttccggttg tccttcagga atgggtaaaa atcttcctgc cgccgcagaa tggcgtgcag      3420
ctctcccagg tggatctggt gggggatgct gccgttgtcg aaggtccgct gcttccgcag      3480
caggtcctct ctgttcagct tcacgagcag ttcctcggtg ccgtccatct tttccaggat      3540
gggcttgatg aacttgtaga actcttcctg gctggctccg ccatcgatgt agccggcgta      3600
gccgttcttg ctctggtcga agaaaatctc tttgtacttc tcaggcagct gctgccgcac      3660
gagagctttc agcagggtca ggtcctggtg gtgctcgtcg tatctcttga tcatagaggc      3720 gctcagggg gccttggtga tctcggtgtt cactctcagg atgtcgctca gcaggatggc      3780
gtcggacagg ttcttggcgg ccagaaacag gtcggcgtac tggtcgccga tctgggccag      3840
caggttgtcc aggtcgtcgt cgtaggtgtc cttgctcagc tgcagtttgg catcctcggc      3900
caggtcgaag ttgctcttga agttgggggt caggcccagg ctcagggcaa tcaggttgcc      3960
gaacaggcca ttcttcttct cgccgggcag ctgggcgatc agattttcca gccgtctgct      4020
cttgctcagt ctggcagaca ggatggcctt ggcgtccacg ccgctggcgt tgatgggtt      4080 ttcctcgaac agctggttgt aggtctgcac cagctggatg aacagcttgt ccacgtcgct      4140
gttgtcgggg ttcaggtcgc cctcgatcag gaagtggccc cggaacttga tcatgtgggc      4200
cagggccaga tagatcagcc gcaggtcggc cttgtcggtg ctgtccacca gtttctttct      4260
caggtggtag atggtggggt acttctcgtg gtaggccacc tcgtccacga tgttgccgaa      4320
gatggggtgc cgctcgtgct tcttatcctc ttccaccagg aaggactctt ccagtctgtg      4380
gaagaagctg tcgtccacct tggccatctc gttgctgaag atctcttgca gatagcagat      4440
ccggttcttc cgtctggtgt atcttcttct ggcggttctc ttcagccggg tggcctcggc      4500
tgtttctccg ctgtcgaaca gcagggcgcc gatcaggttc ttcttgatgc gtgccggtc      4560 ggtgttgccc agcaccttga atttcttgct gggcaccttg tactcgtcgg tgatcacggc      4620
ccagcccaca gagttggtgc cgatggccag gccgatgctg tacttcttgt ccatgggtat      4680
```

```
gtatatctcc ttcttaaagt taaacaaaat tatttctagc ccaaaaaaac gggtatggag    4740
aaacagtaga gagttgcgat aaaaagcgtc aggtaggatc cgctaatctt atggataaaa    4800
atgctatggc atagcaaagt gtgacgccgt gcaaataatc aatgtggact tttctgccgt    4860
gattatagac acttttgtta cgcgttttig tcatggcttt ggtcccgctt tgttacagaa    4920
tgcttttaat aagcggggtt accggtttgg ttagcgagaa gagccagtaa aagacgcagt    4980
gacggcaatg tctgatgcaa tatggacaat tggtttcttc tctgaatggc gggagtatga    5040
aaagtatggc tgaagcgcaa aatgatcccc tgctgccggg atactcgttt aatgcccatc    5100
tggtggcggg tttaacgccg attgaggcca acggttatct cgattttttt atcgaccgac    5160
cgctgggaat gaaaggttat attctcaatc tcaccattcg cggtcagggg gtggtgaaaa    5220
atcagggacg agaatttgtt tgccgaccgg gtgatatttt gctgttcccg ccaggagaga    5280
ttcatcacta cggtcgtcat ccggaggctc gcgaatggta tcaccagtgg gtttactttc    5340
gtccgcgcgc ctactggcat gaatggctta actggccgtc aatatttgcc aatacggggt    5400
tctttcgccc ggatgaagcg caccagccgc atttcagcga cctgtttggg caaatcatta    5460
acgccgggca aggggaaggg cgctattcgg agctgctggc gataaatctg cttgagcaat    5520
tgttactgcg gcgcatggaa gcgattaacg agtcgctcca tccaccgatg gataatcggg    5580
tacgcgaggc ttgtcagtac atcagcgatc acctggcaga cagcaatttt gatatcgcca    5640
gcgtcgcaca gcatgtttgc ttgtcgccgt cgcgtctgtc acatcttttc cgccagcagt    5700
tagggattag cgtcttaagc tggcgcgagg accaacgtat cagccaggcg aagctgcttt    5760
tgagcaccac ccggatgcct atcgccaccg tcggtcgcaa tgttggtttt gacgatcaac    5820
tctatttctc gcgggtattt aaaaaatgca ccggggccag cccgagcgag ttccgtgccg    5880
gttgtgaaga aaaagtgaat gatgtagccg tcaagttgtc ataaactagt ctgcagacgt    5940
aaaaaaagcg gcgtggttag ccgctttttt aattgccgga gcgcaataaa aaagcccccg    6000
gaaggtgatc ttccggggc tttctcatgc gttgcttgta ttgaaaatgg gggccatgcc    6060
tacctatctg cctcccgggt ccttgagccc cattatcacc tccaaagcct tctcgtctgg    6120
tcagtttcac ctgttttacg taaaaacccg cttcggcggg tttttacttt tggggaaaca    6180
cagaaaaaag cccgcacctg acagtgcggg ctttttttttt cgaccaaagg tgcgactact    6240
cttgcctact acctatcgac tgagctgaaa gaattccggt tctggcaaat attctgaaat    6300
gagctgttga caattaatca tccggctcgt ataattctag tcgcagacgc tcgatgtcga    6360
ggtttaagag ctatgctgga aacagcatag caagtttaaa taaggctagt ccgttatcaa    6420
cttgaaaaag tggcaccgag tcggtgcttt tttttgaat tcatgtggct gaccgttctg    6480
ttgtctctcg ctcttccgag tagacgaaca ataaggcctc cctaacgggg ggccttttt    6540 attgataaca aaagtcagtg cttccgctat ttccaaaata ccgggctaat acggtttaaa    6600
cgacctcctg gatttgctca gacagccttt tcgtcattcg tttcagccaa aaaacttaag    6660
accgccggtc ttgtccacta ccttgcagta atgcggtgga caggatcggc ggttttcttt    6720
tctcttctca agaagttcct atactttcta gagaatagga acttcggaat aggaacttcc    6780
tcctgaacgg ccataagaac gaaggctgtc tgttgaactc tcgagcctga ttcccttgt    6840 caacagcaat ggataattca cgaacccagt tgacataagc ctgttcggtt cgtaaactgt    6900
aatgcaagta gcgtatgcgc tcacgcaact ggtccgagaac cttgaccgaa cgcagcggtg    6960
gtaacggcgc agtggcggtt ttcatggctt gttatgactg tttttttgta cagtctatgc    7020
```

```
ctcgggcatc caagcagcaa gcgcgttacg ccgtgggtcg atgtttgatg ttatggagca    7080
gcaacgatgt tacgcagcag ggcagtcgcc ctaaaacaaa gttaggcagc cgttgtgctg    7140
gtgctttctg atagttgttg tggggtaggc agtcagagct cgatttgctt gtcgccataa    7200
tagattcaca agaaggattc gacatgggtc aaagtagcga tgaagccaac gctcccgttg    7260 caggcagtt tgcgcttccc ctgagtgcca cctttggctt aggggatcgc gtacgcaaga    7320
aatctggtgc cgcttggcag ggtcaagtcg tcggttggta ttgcacaaaa ctcactcctg    7380
aaggctatgc ggtcgagtcc gaatcccacc caggctcagt gcaaatttat cctgtggctg    7440
cacttgaacg tgtggcctaa gaattatcta gaattattcc attgagtaag ttttaagca    7500 ctcgagcatc agcttcaaaa gcgctctgaa gttcctatac tttctagaga ataggaactt    7560
cggaataggt acttcaagat ccccaattcg agctcatcgt ccgggccgca agctcctagc    7620
ggcggatttg tcctactcag gagagcgttc accgacaaac aacagataaa acgaaaggcc    7680
cagtctttcg actgagcctt tcgtttatt tgatgcctca agctagagag tcattacccc    7740
aggcgtttaa gggcaccaat aactgcctta aaaaattac gccccgccct gccactcatc    7800
gcagtctagc ttggattctc accaataaaa aacgcccggc ggcaaccgag cgttctgaac    7860
aaatccagat ggagttctga ggtcattact ggatctatca acaggagtcc aagctcagct    7920
aattaagcta gcttatcgat accgtcgacc tcgaacccca cgcccctctt taatacgacg    7980
ggcaatttgc acttcagaaa atgaagagtt tgctttagcc ataacaaaag tccagtatgc    8040 ttttcacag cataactgga ctgatttcag tttacaacta ttctgtctag tttaagactt    8100
tattgtcata gtttagatct atttgttca gtttaagact ttattgtccg cccacacccg    8160
cttacgcagg gcatccattt attactcaac cgtaaccgat tttgccaggt tacgcggctg    8220
gtcctctagc tggcgtaata gcgaagaggc ccgcaccgat cgcccttccc aacagttgcg    8280
cagcctgaat ggcgaatggc gcctgatgcg gtattttctc cttacgcatc tgtgcggtat    8340
ttcacaccgc atatggtgca ctctcagtac aatctgctct gatgccgcat agttaagcca    8400
gccccgacac ccgccaacac ccgctgacgc gccctgacgg gcttgtctgc tcccggcatc    8460
cgcttacaga caagctgtga ccgtctccgg gagctgcatg tgtcagaggt tttcaccgtc    8520
atcaccgaaa cgcgcgagac gaaagggcct cgtgatacgc ctatttttat aggttaatgt    8580
catgataata atggtttctt agacgtcagg tggcacttt cggggaaatg tgcgcggaac    8640
ccctatttgt ttatttttct aaatacattc aaatatgtat ccgctcatga caataaacc    8700 ctgataaatg cttcaataat attgaaaaag gaagagtatg agtattcaac atttccgtgt    8760
cgcccttatt cccttttttg cggcattttg ccttcctgtt tttgctcacc cagaaacgct    8820
ggtgaaagta aaagatgctg aagatcagtt gggtgcacga gtgggttaca tcgaactgga    8880
tctcaacagc ggtaagatcc ttgagagttt tcgccccgaa gaacgttttc caatgatgag    8940
cacttttaaa gttctgctat gtggcgcggt attatcccgt attgacgccg ggcaagagca    9000
actcggtcgc cgcatacact attctcagaa tgacttggtt gagtactcac cagtcacaga    9060
aaagcatctt acggatggca tgacagtaag agaattatgc agtgctgcca taaccatgag    9120
tgataacact gcggccaact tacttctgac aacgatcgga ggaccgaagg agctaaccgc    9180
ttttttgcac aacatggggg atcatgtaac tcgccttgat cgttgggaac cggagctgaa    9240
tgaagccata ccaaacgacg agcgtgacac cacgatgcct gtagcaatgg caacaacgtt    9300
gcgcaaacta ttaactggcg aactacttac tctagcttcc cggcaacaat taatagactg    9360
gatggaggcg gataaagttg caggaccact tctgcgctcg gcccttccgg ctggctggtt    9420
```

```
tattgctgat aaatctggag ccggtgagcg tgggtcccgc ggtatcattg cagcactggg    9480
gccagatggt aagccctccc gtatcgtagt tatctacacg acggggagtc aggcaactat    9540
ggatgaacga aatagacaga tcgctgagat aggtgcctca ctgattaagc attggtaact    9600
gtcagaccaa gtttactcat atatacttta gattgattta aaacttcatt tttaatttaa    9660
aaggatctag gtgaagatcc ttttgataa tctcatgacc aaaatcccctt aacgtgagtt    9720 ttcgttccac tgagcgtcag accccgtaga aaagatcaaa ggcagttatt ggtgcctcac    9780
tgattaagca ttggtaactg tcagaccaag tttactcata tactttag attgatttaa    9840 aacttcattt ttaattttg cggccgcaag atccggccac gatgcgtccg cgtagagga    9900 tctgaagatc agcagttcaa cctgttgata gtacgtacta agctctcatg tttcacgtac    9960
taagctctca tgtttaacgt actaagctct catgtttaac gaactaaacc ctcatggcta  10020
acgtactaag ctctcatggc taacgtacta agctctcatg tttcacgtac taagctctca  10080
tgtttgaaca ataaaattaa tataaatcag caacttaaat agcctctaag gttttaagtt  10140
ttataagaaa aaaagaata tataaggctt ttaaagcttt taaggtttaa cggttgtgga  10200
caacaagcca gggatgtaac gcactgagaa gcccttagag cctctcaaag caattttgag  10260
tgacacagga acacttaacg gctgacatgg gaattagcca tggcatcaca gtatcgtgat  10320
gacagaggca gggagtgcgg cctttttacg gttcctggcc ttttgctggc cttttgctca  10380
catgttcttt cctgcgttat cagggggattc cttaaggtat actttccgct gcataaccct  10440
gcttcggggt cattatagcg atttttttcgg tatatccatc ctttttcgca cgatatacag  10500
gattttgcca aagggttcgt gtagactttc cttggtgtat ccaacggcgt cagccgggca  10560
ggataggtga gtaggcccaa cccgcgagcg ggtgttcctt cttcactgtc ccttattcgc  10620
acctggcggt gctcaacggg aatcctgctc tgcgaggctg ccgataagc t              10671

<210> SEQ ID NO 5
<211> LENGTH: 10671
<212> TYPE: DNA
<213> ORGANISM: Artificial sequence
<220> FEATURE:
<223> OTHER INFORMATION: Synthetic construct

<400> SEQUENCE: 5
ctgataccgc tcgccgcagc cgaacgaccg agcgcagcgg gtcagtgagc gaggaagcgg     60
aagagcgccc aatacgcaaa ccgcctctcc ccgcgcgttg gccgattcat taatgcagcg    120
cccaaacata acaggaagaa aaatgccccg ctgtgggcgg acaaaatagt tgggaactgg    180
gaggggtgga aatggagttt ttaaggatta tttaggaag agtgacaaaa tagatgggaa    240
ctgggtgtag cgtcgtaagc taatacgaaa attaaaaatg acaaaatagt ttggaactag    300
atttcactta tctggttctt gaggcggtta aaagagccgt actcttctcc gatgtcgact    360
aggccatgat gctcattctg tgggaccaaa acgaaaaaac accctttcgg gtgtctttc    420 tggaatttgg taccgaggct gcaagtccca ttaaggaggc gcgccttatt acagatcttc    480
ctcagagatg agcttctgtt ccagatcttc ttctgaaatc aacttttgtt ccagatcttc    540
ttcagagatg agtttctgct ccgcggccgc gtcgcctccc agctgagaca ggtcgatccg    600
tgtctcgtac aggccggtga tgctctggtg gatcagggtg gcgtccagca cctctttggt    660
gctggtgtac ctcttccggt cgatggtggt gtcaaagtac ttgaaggcgg caggggctcc    720
cagattggtc agggtaaaca ggtggatgat attctcggcc tgctctctga taggcttgtc    780
```

| | |
|---|---|
| tctgtgcttg ttgtaggcgc tcagcacctt gtccagatta gcgtcggcca ggatcactct | 840 |
| cttggagaac tcgctgatct gctcgatgat ctcgtccagg tagtgtttgt gctgttccac | 900 |
| aaacagctgt ttctgctcat tatcctcggg ggagcccttc agcttctcat agtggctggc | 960 |
| caggtacagg aagttcacat atttggaggg cagggccagt tcgtttccct tctgcagttc | 1020 |
| gccggcagag gccagcattc tcttccggcc gttttccagc tcgaacaggg agtacttagg | 1080 |
| cagcttgatg atcaggtcct tttcacttc tttgtagccc ttggcttcca gaaagtcgat | 1140 |
| gggattcttc tcgaagctgc ttcttccat gatggtgatc cccagcagct ctttcacact | 1200 |
| cttcagtttc ttggacttgc ccttttccac tttggccacc accagcacag aataggccac | 1260 |
| ggtggggctg tcgaagccgc cgtacttctt agggtcccag tccttctttc tggcgatcag | 1320 |
| cttgtcgctg ttcctcttgg gcaggataga ctctttgctg aagccgcctg tctgcacctc | 1380 |
| ggtcttttc acgatattca cttggggcat agacagcact ttccgcacgg tggcaaagtc | 1440 |
| ccggccctta tcccacacga tctcgcctgt ttcgccgttt gtctcgatca gaggccgctt | 1500 |
| ccggatctcg ccgttggcca gggtaatctc ggtcttgaaa aagttcatga tgttgctgta | 1560 |
| gaagaagtac ttggcggtag ccttgccgat ttcctgctcg ctcttggcga tcatcttccg | 1620 |
| cacgtcgtac accttgtagt cgccgtacac gaactcgctt ccagcttag ggtactttt | 1680 |
| gatcagggcg gttcccacga cggcgttcag gtaggcgtcg tgggcgtggt ggtagttgtt | 1740 |
| gatctcgcgc actttgtaaa actggaaatc cttccggaaa tcggacacca gcttggactt | 1800 |
| cagggtgatc actttcactt cccggatcag tttgtcgttc tcgtcgtact tagtgttcat | 1860 |
| ccgggagtcc aggatctgtg ccacgtgctt tgtgatctgc cgggtttcca ccagctgtct | 1920 |
| cttgatgaag ccggccttat ccagttcgct caggccgcct ctctcggcct tggtcagatt | 1980 |
| gtcgaacttc ctctgggtaa tcagcttggc attcagcagc tggcgccagt agttcttcat | 2040 |
| cttcttcacg acctcttcgg agggcacgtt gtcgctcttg ccccggttct tgtcgctccg | 2100 |
| agtcagcact ttgttatcga tggagtcgtc cttcagaaag ctctgaggca cgatagcgtc | 2160 |
| cacatcgtag tcggacagcc ggttgatgtc cagttcctgg tccacgtaca tatcccgccc | 2220 |
| attctgcagg tagtacaggt acagcttctc gttctgcagc tgggtgtttt ccacggggtg | 2280 |
| ttctttcagg atctggctgc ccagctcttt gatgccctct tcgatccgct tcattctctc | 2340 |
| gcggctgttc ttctgtccct tctgggtggt ctggttctct ctggccattt cgatcacgat | 2400 |
| gttctcgggc ttgtgccggc ccatcacttt cacgagctcg tccaccacct tcactgtctg | 2460 |
| caggatgccc ttcttaatgg cggggctgcc ggccagattg gcaatgtgct cgtgcaggct | 2520 |
| atcgccctgg ccggacacct gggctttctg gatgtcctct ttaaaggtca ggctgtcgtc | 2580 |
| gtggatcagc tgcatgaagt ttctgttggc gaagccgtcg gacttcagga aatccaggat | 2640 |
| tgtcttgccg gactgcttgt cccggatgcc gttgatcagc ttccggctca gcctgcccca | 2700 |
| gccggtgtat ctccgccgct tcagctgctt catcactttg tcgtcgaaca ggtgggcata | 2760 |
| ggttttcagc cgttcctcga tcatctctct gtcctcaaac agtgtcaggg tcagcacgat | 2820 |
| atcttccaga atgtcctcgt tttcctcatt gtccaggaag tccttgtcct tgataatttt | 2880 |
| cagcagatcg tggtatgtgc ccagggaggc gttgaaccga tcttccacgc cggagatttc | 2940 |
| cacggagtcg aagcactcga ttttcttgaa gtagtcctct ttcagctgct tcacggtcac | 3000 |
| tttccggttg gtcttgaaca gcaggtccac gatggctttt ttctgctcgc cgctcaggaa | 3060 |
| ggcgggcttt ctcattccct cggtcacgta tttcactttg gtcagctcgt tgtacacggt | 3120 |
| gaagtactcg tacagcaggc tgtgcttggg cagcaccttc tcgttgggca ggttcttatc | 3180 |

```
gaagttggtc atccgctcga tgaagctctg ggcgctggcg cccttgtcca ccacttcctc   3240
gaagttccag ggggtgatgg tttcctcgct ctttctggtc atccaggcga atctgctgtt   3300
tccnctggcc agagggccca cgtagtaggg gatgcggaag gtcaggatct tctcgatctt   3360
ttcccggttg tccttcagga atgggtaaaa atcttcctgc cgccgcagaa tggcgtgcag   3420
ctctcccagg tggatctggt gggggatgct gccgttgtcg aaggtccgct gcttccgcag   3480
caggtcctct ctgttcagct tcacgagcag ttcctcggtg ccgtccatct tttccaggat   3540
gggcttgatg aacttgtaga actcttcctg gctggctccg ccatcgatgt agccggcgta   3600
gccgttcttg ctctggtcga agaaaatctc tttgtacttc tcaggcagct gctgccgcac   3660
gagagctttc agcagggtca ggtcctggtg gtgctcgtcg tatctcttga tcatagaggc   3720
gctcaggggg gccttggtga tctcggtgtt cactctcagg atgtcgctca gcaggatggc   3780
gtcggacagg ttcttggcgg ccagaaacag gtcggcgtac tggtcgccga tctgggccag   3840
caggttgtcc aggtcgtcgt cgtaggtgtc cttgctcagc tgcagtttgg catcctcggc   3900
caggtcgaag ttgctcttga agttgggggt caggcccagg ctcagggcaa tcaggttgcc   3960
gaacaggcca ttcttcttct cgccgggcag ctgggcgatc agattttcca gccgtctgct   4020
cttgctcagt ctggcagaca ggatggcctt ggcgtccacg ccgctggcgt tgatgggtt    4080 ttcctcgaac agctggttgt aggtctgcac cagctggatg aacagcttgt ccacgtcgct   4140
gttgtcgggg ttcaggtcgc cctcgatcag gaagtggccc cggaacttga tcatgtgggc   4200
cagggccaga tagatcagcc gcaggtcggc cttgtcggtg ctgtccacca gtttcttttct  4260 caggtggtag atggtggggt acttctcgtg gtaggccacc tcgtccacga tgttgccgaa   4320
gatggggtgc cgctcgtgct tcttatcctc ttccaccagg aaggactctt ccagtctgtg   4380
gaagaagctg tcgtccacct tggccatctc gttgctgaag atctcttgca gatagcagat   4440
ccggttcttc cgtctggtgt atcttcttct ggcggttctc ttcagccggg tggcctcggc   4500
tgtttctccg ctgtcgaaca gcagggcgcc gatcaggttc ttcttgatgc tgtgccggtc   4560
ggtgttgccc agcaccttga atttcttgct gggcaccttg tactcgtcgg tgatcacggc   4620
ccagcccaca gagttggtgc cgatggccag gccgatgctg tacttcttgt ccatgggtat   4680
gtatatctcc ttcttaaagt taaacaaaat tatttctagc ccaaaaaaac gggtatggag   4740
aaacagtaga gagttgcgat aaaaagcgtc aggtaggatc cgctaatctt atggataaaa   4800
atgctatggc atagcaaagt gtgacgccgt gcaaataatc aatgtggact tttctgccgt   4860
gattatagac acttttgtta cgcgttttg tcatggcttt ggtcccgctt tgttacagaa    4920
tgcttttaat aagcggggtt accggtttgg ttagcgagaa gagccagtaa aagacgcagt   4980
gacggcaatg tctgatgcaa tatggacaat tggtttcttc tctgaatggc gggagtatga   5040
aaagtatggc tgaagcgcaa aatgatcccc tgctgccggg atactcgttt aatgcccatc   5100
tggtggcggg tttaacgccg attgaggcca acgttatct cgattttttt atcgaccgac     5160
cgctgggaat gaaaggttat attctcaatc tcaccattcg cggtcagggg gtggtgaaaa   5220
atcagggacg agaatttgtt tgccgaccgg gtgatatttt gctgttccg ccaggagaga    5280 ttcatcacta cggtcgtcat ccggaggctc gcgaatggta tcaccagtgg gtttactttc   5340
gtccgcgcgc ctactggcat gaatggctta actggccgtc aatatttgcc aatacggggt   5400
tctttcgccc ggatgaagcg caccagccgc atttcagcga cctgtttggg caaatcatta   5460
acgccgggca aggggaaggg cgctattcgg agctgctggc gataaatctg cttgagcaat   5520
```

```
tgttactgcg gcgcatggaa gcgattaacg agtcgctcca tccaccgatg gataatcggg    5580
tacgcgaggc ttgtcagtac atcagcgatc acctggcaga cagcaatttt gatatcgcca    5640
gcgtcgcaca gcatgtttgc ttgtcgccgt cgcgtctgtc acatcttttc cgccagcagt    5700
tagggattag cgtcttaagc tggcgcgagg accaacgtat cagccaggcg aagctgcttt    5760
tgagcaccac ccggatgcct atcgccaccg tcggtcgcaa tgttggtttt gacgatcaac    5820
tctatttctc gcgggtattt aaaaaatgca cggggccag cccgagcgag ttccgtgccg    5880
gttgtgaaga aaagtgaat gatgtagccg tcaagttgtc ataaactagt ctgcagacgt    5940 aaaaaagcg gcgtggttag ccgcttttt aattgccgga gcgcaataaa aaagcccccg    6000
gaaggtgatc ttccggggc tttctcatgc gttgcttgta ttgaaaatgg gggccatgcc    6060
tacctatctg cctcccggt ccttgagccc cattatcacc tccaaagcct tctcgtctgg    6120
tcagtttcac ctgttttacg taaaaacccg cttcggcggg tttttacttt tggggaaaca    6180
cagaaaaaag cccgcacctg acagtgcggg ctttttttt cgaccaaagg tgcgactact    6240
cttgcctact acctatcgac tgagctgaaa gaattccggt tctggcaaat attctgaaat    6300
gagctgttga caattaatca tccggctcgt ataattctag tgcaacggga cttccattcc    6360
cgtttaagag ctatgctgga aacagcatag caagtttaaa taaggctagt ccgttatcaa    6420
cttgaaaaag tggcaccgag tcggtgcttt tttttgaat tcatgtggct gaccgttctg    6480
ttgtctctcg ctcttccgag tagacgaaca ataaggcctc cctaacgggg ggcctttttt    6540
attgataaca aaagtcagtg cttccgctat ttccaaaata ccgggctaat acggtttaaa    6600
cgacctcctg gatttgctca gacagccttt tcgtcattcg tttcagccaa aaaacttaag    6660
accgccggtc ttgtccacta ccttgcagta atgcggtgga caggatcggc ggttttcttt    6720
tctcttctca agaagttcct atactttcta gagaatagga acttcggaat aggaacttcc    6780
tcctgaacgg ccataagaac gaaggctgtc tgttgaactc tcgagcctga ttccctttgt    6840
caacagcaat ggataattca cgaacccagt tgacataagc ctgttcggtt cgtaaactgt    6900
aatgcaagta gcgtatgcgc tcacgcaact ggtccagaac cttgaccgaa cgcagcggtg    6960
gtaacggcgc agtggcggtt ttcatggctt gttatgactg ttttttttgta cagtctatgc    7020 ctcgggcatc caagcagcaa gcgcgttacg ccgtgggtcg atgtttgatg ttatggagca    7080
gcaacgatgt tacgcagcag ggcagtcgcc ctaaaacaaa gttaggcagc cgttgtgctg    7140
gtgctttctg atagttgttg tggggtaggc agtcagagct cgatttgctt gtcgccataa    7200
tagattcaca agaaggattc gacatgggtc aaagtagcga tgaagccaac gctcccgttg    7260
cagggcagtt tgcgcttccc ctgagtgcca cctttggctt aggggatcgc gtacgcaaga    7320
aatctggtgc cgcttggcag ggtcaagtcg tcggttggta ttgcacaaaa ctcactcctg    7380
aaggctatgc ggtcgagtcc gaatcccacc caggctcagt gcaaatttat cctgtggctg    7440
cacttgaacg tgtggcctaa gaattatcta gaattattcc attgagtaag ttttttaagca    7500 ctcgagcatc agcttcaaaa gcgctctgaa gttcctatac tttctagaga ataggaactt    7560
cggaataggt acttcaagat ccccaattcg agctcatcgt ccgggccgca agctcctagc    7620
ggcggatttg tcctactcag gagagcgttc accgacaaac aacagataaa acgaaaggcc    7680
cagtctttcg actgagcctt tcgttttatt tgatgcctca agctagagag tcattacccc    7740
aggcgtttaa gggcaccaat aactgcctta aaaaattac gccccgccct gccactcatc    7800
gcagtctagc ttggattctc accaataaaa acgcccggc ggcaaccgag cgttctgaac    7860
aaatccagat ggagttctga ggtcattact ggatctatca acaggagtcc aagctcagct    7920
```

-continued

```
aattaagcta gcttatcgat accgtcgacc tcgaacccca cgcccctctt taatacgacg   7980
ggcaatttgc acttcagaaa atgaagagtt tgctttagcc ataacaaaag tccagtatgc   8040
tttttcacag cataactgga ctgatttcag tttacaacta ttctgtctag tttaagactt   8100
tattgtcata gtttagatct atttttgttca gtttaagact ttattgtccg cccacacccg   8160
cttacgcagg gcatccattt attactcaac cgtaaccgat tttgccaggt tacgcggctg   8220
gtcctctagc tggcgtaata gcgaagaggc ccgcaccgat cgcccttccc aacagttgcg   8280
cagcctgaat ggcgaatggc gcctgatgcg gtattttctc cttacgcatc tgtgcggtat   8340
ttcacaccgc atatggtgca ctctcagtac aatctgctct gatgccgcat agttaagcca   8400
gccccgacac ccgccaacac ccgctgacgc gccctgacgg gcttgtctgc tcccggcatc   8460
cgcttacaga caagctgtga ccgtctccgg gagctgcatg tgtcagaggt tttcaccgtc   8520
atcaccgaaa cgcgcgagac gaaagggcct cgtgatacgc ctatttttat aggttaatgt   8580
catgataata atggtttctt agacgtcagg tggcacttt cggggaaatg tgcgcggaac   8640
ccctatttgt ttatttttct aaatacattc aaatatgtat ccgctcatga caataacc    8700 ctgataaatg cttcaataat attgaaaaag gaagagtatg agtattcaac atttccgtgt   8760
cgcccttatt ccctttttg cggcattttg ccttcctgtt tttgctcacc cagaaacgct   8820
ggtgaaagta aaagatgctg aagatcagtt gggtgcacga gtgggttaca tcgaactgga   8880
tctcaacagc ggtaagatcc ttgagagttt tcgccccgaa gaacgttttc caatgatgag   8940
cacttttaaa gttctgctat gtggcgcggt attatcccgt attgacgccg ggcaagagca   9000
actcggtcgc cgcatacact attctcagaa tgacttggtt gagtactcac cagtcacaga   9060
aaagcatctt acggatggca tgacagtaag agaattatgc agtgctgcca taaccatgag   9120
tgataacact gcggccaact tacttctgac aacgatcgga ggaccgaagg agctaaccgc   9180 tttttttgcac aacatggggg atcatgtaac tcgccttgat cgttgggaac cggagctgaa   9240
tgaagccata ccaaacgacg agcgtgacac cacgatgcct gtagcaatgg caacaacgtt   9300
gcgcaaacta ttaactggcg aactacttac tctagcttcc cggcaacaat taatagactg   9360
gatggaggcg gataaagttg caggaccact tctgcgctcg gcccttccgg ctggctggtt   9420
tattgctgat aaatctggag ccggtgagcg tgggtcccgc ggtatcattg cagcactggg   9480
gccagatggt aagccctccc gtatcgtagt tatctacacg acggggagtc aggcaactat   9540
ggatgaacga aatagacaga tcgctgagat aggtgcctca ctgattaagc attggtaact   9600
gtcagaccaa gtttactcat atatacttta gattgattta aaacttcatt tttaatttaa   9660
aaggatctag gtgaagatcc ttttgataa tctcatgacc aaaatccctt aacgtgagtt   9720
ttcgttccac tgagcgtcag accccgtaga aaagatcaaa ggcagttatt ggtgcctcac   9780
tgattaagca ttggtaactg tcagaccaag tttactcata tactttag attgatttaa   9840 aacttcattt ttaatttttg cggccgcaag atccggccac gatgcgtccg gcgtagagga   9900
tctgaagatc agcagttcaa cctgttgata gtacgtacta agctctcatg tttcacgtac   9960
taagctctca tgtttaacgt actaagctct catgtttaac gaactaaacc ctcatggcta  10020
acgtactaag ctctcatggc taacgtacta agctctcatg tttcacgtac taagctctca  10080
tgtttgaaca ataaaattaa tataaatcag caacttaaat agcctctaag gtttaagtt   10140 ttataagaaa aaaagaata tataaggctt ttaaagcttt taaggtttaa cggttgtgga  10200
caacaagcca gggatgtaac gcactgagaa gcccttagag cctctcaaag caattttgag  10260
```

| | |
|---|---|
| tgacacagga acacttaacg gctgacatgg gaattagcca tggcatcaca gtatcgtgat | 10320 |
| gacagaggca gggagtgcgg cctttttacg gttcctggcc ttttgctggc cttttgctca | 10380 |
| catgttcttt cctgcgttat caggggattc cttaaggtat actttccgct gcataaccct | 10440 |
| gcttcggggt cattatagcg attttttcgg tatatccatc cttttcgca cgatatacag | 10500 |
| gattttgcca aagggttcgt gtagactttc cttggtgtat ccaacggcgt cagccgggca | 10560 |
| ggataggtga agtaggccca cccgcgagcg ggtgttcctt cttcactgtc ccttattcgc | 10620 |
| acctggcggt gctcaacggg aatcctgctc tgcgaggctg ccgataagc t | 10671 |

<210> SEQ ID NO 6
<211> LENGTH: 10671
<212> TYPE: DNA
<213> ORGANISM: Artificial sequence
<220> FEATURE:
<223> OTHER INFORMATION: Synthetic construct

<400> SEQUENCE: 6

| | |
|---|---|
| ctgataccgc tcgccgcagc cgaacgaccg agcgcagcgg gtcagtgagc gaggaagcgg | 60 |
| aagagcgccc aatacgcaaa ccgcctctcc ccgcgcgttg gccgattcat taatgcagcg | 120 |
| cccaaacata acaggaagaa aaatgccccg ctgtgggcgg acaaaatagt tgggaactgg | 180 |
| gaggggtgga aatggagttt ttaaggatta tttaggaag agtgacaaaa tagatgggaa | 240 |
| ctgggtgtag cgtcgtaagc taatacgaaa attaaaaatg acaaaatagt ttggaactag | 300 |
| atttcactta tctggttctt gaggcggtta aaagagccgt actcttctcc gatgtcgact | 360 |
| aggccatgat gctcattctg tgggaccaaa acgaaaaaac cccctttcgg gtgtcttttc | 420 |
| tggaatttgg taccgaggct gcaagtccca ttaaggaggc gcgccttatt acagatcttc | 480 |
| ctcagagatg agcttctgtt ccagatcttc ttctgaaatc aacttttgtt ccagatcttc | 540 |
| ttcagagatg agtttctgct ccgcggccgc gtcgcctccc agctgagaca ggtcgatccg | 600 |
| tgtctcgtac aggccggtga tgctctggtg gatcagggtg gcgtccagca cctctttggt | 660 |
| gctggtgtac ctcttccggt cgatggtggt gtcaaagtac ttgaaggcgg caggggctcc | 720 |
| cagattggtc agggtaaaca ggtggatgat attctcggcc tgctctctga taggcttgtc | 780 |
| tctgtgcttg ttgtaggcgc tcagcacctt gtccagatta gcgtcggcca ggatcactct | 840 |
| cttggagaac tcgctgatct gctcgatgat ctcgtccagg tagtgtttgt gctgttccac | 900 |
| aaacagctgt ttctgctcat tatcctcggg ggagcccttc agcttctcat agtggctggc | 960 |
| caggtacagg aagttcacat atttggaggg cagggccagt tcgtttccct tctgcagttc | 1020 |
| gccggcagag gccagcattc tcttccggcc gttttccagc tcgaacaggg agtacttagg | 1080 |
| cagcttgatg atcaggtcct tttcacttc tttgtagccc ttggcttcca gaaagtcgat | 1140 |
| gggattcttc tcgaagctgc ttcttccat gatggtgatc cccagcagct cttcacact | 1200 |
| cttcagtttc ttggacttgc ccttttccac tttggccacc accagcacag aataggccac | 1260 |
| ggtgggctg tcgaagccgc cgtacttctt agggtcccag tccttcttc tggcgatcag | 1320 |
| cttgtcgctg ttcctcttgg gcaggataga ctctttgctg aagccgcctg tctgcacctc | 1380 |
| ggtcttttc acgatattca cttggggcat agacagcact ttccgcacgg tggcaaagtc | 1440 |
| ccggccctta tcccacacga tctcgcctgt ttcgccgttt gtctcgatca gaggccgctt | 1500 |
| ccggatctcg ccgttggcca gggtaatctc ggtcttgaaa aagttcatga tgttgctgta | 1560 |
| gaagaagtac ttggcggtag ccttgccgat ttcctgctcg ctcttggcga tcatcttccg | 1620 |
| cacgtcgtac accttgtagt cgccgtacac gaactcgctt tccagcttag ggtactttt | 1680 |

```
gatcagggcg gttcccacga cggcgttcag gtaggcgtcg tgggcgtggt ggtagttgtt    1740
gatctcgcgc actttgtaaa actggaaatc cttccggaaa tcggacacca gcttggactt    1800
cagggtgatc actttcactt cccggatcag tttgtcgttc tcgtcgtact tagtgttcat    1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctggtggt ctggttctct ctggccattt cgatcacgat     2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccggacacct gggctttctg gatgtcctct ttaaaggtca ggctgtcgtc    2580
gtggatcagc tgcatgaagt ttctgttggc gaagccgtcg gacttcagga atccaggat    2640
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccaggaggc gttgaaccga tcttccacgc cggagatttc     2940
cacgagtcg aagcactcga ttttcttgaa gtagtcctct ttcagctgct tcacggtcac     3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tcccctggcc agagggccca cgtagtaggg gatgcggaag gtcaggatct tctcgatctt    3360
ttccggttg tccttcagga atgggtaaaa atcttcctgc cgccgcagaa tggcgtgcag     3420
ctctcccagg tggatctggt gggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720
gctcaggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
```

```
cttgctcagt ctggcagaca ggatggcctt ggcgtccacg ccgctggcgt tgatggggtt    4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatgggtat    4680
gtatatctcc ttcttaaagt taaacaaaat tatttctagc ccaaaaaaac gggtatggag    4740
aaacagtaga gagttgcgat aaaaagcgtc aggtaggatc cgctaatctt atggataaaa    4800
atgctatggc atagcaaagt gtgacgccgt gcaaataatc aatgtggact tttctgccgt    4860
gattatagac acttttgtta cgcgttttg tcatggcttt ggtcccgctt tgttacagaa    4920
tgcttttaat aagcggggtt accggtttgg ttagcgagaa gagccagtaa aagacgcagt    4980
gacggcaatg tctgatgcaa tatggacaat tggtttcttc tctgaatggc gggagtatga    5040
aaagtatggc tgaagcgcaa aatgatcccc tgctgccggg atactcgttt aatgcccatc    5100
tggtggcggg tttaacgccg attgaggcca acgttatct cgattttttt atcgaccgac    5160
cgctgggaat gaaaggttat attctcaatc tcaccattcg cggtcagggg gtggtgaaaa    5220
atcagggacg agaatttgtt tgccgaccgg gtgatatttt gctgttcccg ccaggagaga    5280
ttcatcacta cggtcgtcat ccggaggctc gcgaatggta tcaccagtgg gtttactttc    5340
gtccgcgcgc ctactggcat gaatggctta actggccgtc aatatttgcc aatacggggt    5400
tctttcgccc ggatgaagcg caccagccgc atttcagcga cctgtttggg caaatcatta    5460
acgccgggca aggggaaggg cgctattcgg agctgctggc gataaatctg cttgagcaat    5520
tgttactgcg gcgcatggaa gcgattaacg agtcgctcca tccaccgatg gataatcggg    5580
tacgcgaggc ttgtcagtac atcagcgatc acctggcaga cagcaatttt gatatcgcca    5640
gcgtcgcaca gcatgtttgc ttgtcgccgt cgcgtctgtc acatcttttc cgccagcagt    5700
tagggattag cgtcttaagc tggcgcgagg accaacgtat cagccaggcg aagctgcttt    5760
tgagcaccac ccggatgcct atcgccaccg tcggtcgcaa tgttggtttt gacgatcaac    5820
tctatttctc gcgggtattt aaaaaatgca ccggggccag cccgagcgag ttccgtgccg    5880
gttgtgaaga aaaagtgaat gatgtagccg tcaagttgtc ataaactagt ctgcagacgt    5940
aaaaaaagcg gcgtggttag ccgcttttt aattgccgga gcgcaataaa aaagcccccg    6000
gaaggtgatc ttccgggggc tttctcatgc gttgcttgta ttgaaaatgg gggccatgcc    6060
tacctatctg cctcccgggt ccttgagccc cattatcacc tccaaagcct tctcgtctgg    6120
tcagtttcac ctgttttacg taaaaacccg cttcggcggg tttttacttt tggggaaaca    6180
cagaaaaaag cccgcacctg acagtgcggg cttttttttt cgaccaaagg tgcgactact    6240
cttgcctact acctatcgac tgagctgaaa gaattccggt tctggcaaat attctgaaat    6300
gagctgttga caattaatca tccgctcgt ataattctag tgctgcgagc cggaagttca    6360
cgtttaagag ctatgctgga aacagcatag caagtttaaa taaggctagt ccgttatcaa    6420
```

```
cttgaaaaag tggcaccgag tcggtgcttt ttttttgaat tcatgtggct gaccgttctg    6480
ttgtctctcg ctcttccgag tagacgaaca ataaggcctc cctaacgggg ggcctttttt    6540
attgataaca aaagtcagtg cttccgctat ttccaaaata ccgggctaat acggtttaaa    6600
cgacctcctg gatttgctca gacagccttt tcgtcattcg tttcagccaa aaaacttaag    6660
accgccggtc ttgtccacta ccttgcagta atgcggtgga caggatcggc ggttttcttt    6720
tctcttctca agaagttcct atactttcta gagaatagga acttcggaat aggaacttcc    6780
tcctgaacgg ccataagaac gaaggctgtc tgttgaactc tcgagcctga ttcccttttgt   6840 caacagcaat ggataattca cgaacccagt tgacataagc ctgttcggtt cgtaaactgt    6900
aatgcaagta gcgtatgcgc tcacgcaact ggtccagaac cttgaccgaa cgcagcggtg    6960
gtaacggcgc agtggcggtt ttcatggctt gttatgactg ttttttttgta cagtctatgc   7020 ctcgggcatc caagcagcaa gcgcgttacg ccgtgggtcg atgtttgatg ttatggagca    7080
gcaacgatgt tacgcagcag ggcagtcgcc ctaaaacaaa gttaggcagc cgttgtgctg    7140
gtgctttctg atagttgttg tggggtaggc agtcagagct cgatttgctt gtcgccataa    7200
tagattcaca agaaggattc gacatgggtc aaagtagcga tgaagccaac gctcccgttg    7260
cagggcagtt tgcgcttccc ctgagtgcca cctttggctt aggggatcgc gtacgcaaga    7320
aatctggtgc cgcttggcag ggtcaagtcg tcggttggta ttgcacaaaa ctcactcctg    7380
aaggctatgc ggtcgagtcc gaatcccacc caggctcagt gcaaatttat cctgtggctg    7440
cacttgaacg tgtggcctaa gaattatcta gaattattcc attgagtaag ttttttaagca   7500 ctcgagcatc agcttcaaaa gcgctctgaa gttcctatac tttctagaga ataggaactt    7560
cggaataggt acttcaagat ccccaattcg agctcatcgt ccgggccgca agctcctagc    7620
ggcggatttg tcctactcag gagagcgttc accgacaaac aacagataaa acgaaaggcc    7680
cagtctttcg actgagcctt tcgttttatt tgatgcctca agctagagag tcattacccc    7740
aggcgtttaa gggcaccaat aactgcctta aaaaaattac gccccgccct gccactcatc    7800
gcagtctagc ttggattctc accaataaaa aacgcccggc ggcaaccgag cgttctgaac    7860
aaatccagat ggagttctga ggtcattact ggatctatca acaggagtcc aagctcagct    7920
aattaagcta gcttatcgat accgtcgacc tcgaacccca cgcccctctt taatacgacg    7980
ggcaatttgc acttcagaaa atgaagagtt tgctttagcc ataacaaaag tccagtatgc    8040
tttttcacag cataactgga ctgatttcag tttacaacta ttctgtctag tttaagactt    8100
tattgtcata gtttagatct attttgttca gtttaagact ttattgtccg cccacacccg    8160
cttacgcagg gcatccattt attactcaac cgtaaccgat tttgccaggt tacgcggctg    8220
gtcctctagc tggcgtaata gcgaagaggc ccgcaccgat cgcccttccc aacagttgcg    8280
cagcctgaat ggcgaatggc gcctgatgcg gtattttctc cttacgcatc tgtgcggtat    8340
ttcacaccgc atatggtgca ctctcagtac aatctgctct gatgccgcat agttaagcca    8400
gccccgacac ccgccaacac ccgctgacgc gccctgacgg gcttgtctgc tcccggcatc    8460
cgcttacaga caagctgtga ccgtctccgg gagctgcatg tgtcagaggt tttcaccgtc    8520
atcaccgaaa cgcgcgagac gaaagggcct cgtgatacgc ctatttttat aggttaatgt    8580
catgataata atggtttctt agacgtcagg tggcactttt cggggaaatg tgcgcggaac    8640
ccctatttgt ttatttttct aaatacattc aaatatgtat ccgctcatga acaataaccc   8700
ctgataaatg cttcaataat attgaaaaag gaagagtatg agtattcaac atttccgtgt    8760
```

| | |
|---|---|
| cgcccttatt cccttttttg cggcattttg ccttcctgtt tttgctcacc cagaaacgct | 8820 |
| ggtgaaagta aaagatgctg aagatcagtt gggtgcacga gtgggttaca tcgaactgga | 8880 |
| tctcaacagc ggtaagatcc ttgagagttt tcgccccgaa gaacgttttc caatgatgag | 8940 |
| cactttaaa gttctgctat gtggcgcggt attatcccgt attgacgccg gcaagagca | 9000 |
| actcggtcgc cgcatacact attctcagaa tgacttggtt gagtactcac cagtcacaga | 9060 |
| aaagcatctt acggatggca tgacagtaag agaattatgc agtgctgcca taaccatgag | 9120 |
| tgataacact gcggccaact tacttctgac aacgatcgga ggaccgaagg agctaaccgc | 9180 |
| ttttttgcac aacatggggg atcatgtaac tcgccttgat cgttgggaac cggagctgaa | 9240 |
| tgaagccata ccaaacgacg agcgtgacac cacgatgcct gtagcaatgg caacaacgtt | 9300 |
| gcgcaaacta ttaactggcg aactacttac tctagcttcc cggcaacaat taatagactg | 9360 |
| gatggaggcg gataaagttg caggaccact tctgcgctcg gcccttccgg ctggctggtt | 9420 |
| tattgctgat aaatctggag ccggtgagcg tgggtcccgc ggtatcattg cagcactggg | 9480 |
| gccagatggt aagccctccc gtatcgtagt tatctacacg acggggagtc aggcaactat | 9540 |
| ggatgaacga aatagacaga tcgctgagat aggtgcctca ctgattaagc attggtaact | 9600 |
| gtcagaccaa gtttactcat atatacttta gattgattta aaacttcatt tttaatttaa | 9660 |
| aaggatctag gtgaagatcc tttttgataa tctcatgacc aaaatccctt aacgtgagtt | 9720 |
| ttcgttccac tgagcgtcag accccgtaga aaagatcaaa ggcagttatt ggtgcctcac | 9780 |
| tgattaagca ttggtaactg tcagaccaag tttactcata tactttag attgatttaa | 9840 |
| aacttcattt ttaattttg cggccgcaag atccggccac gatgcgtccg gcgtagagga | 9900 |
| tctgaagatc agcagttcaa cctgttgata gtacgtacta agctctcatg tttcacgtac | 9960 |
| taagctctca tgtttaacgt actaagctct catgtttaac gaactaaacc ctcatggcta | 10020 |
| acgtactaag ctctcatggc taacgtacta agctctcatg tttcacgtac taagctctca | 10080 |
| tgtttgaaca ataaaattaa tataaatcag caacttaaat agcctctaag gttttaagtt | 10140 |
| ttataagaaa aaaagaata tataaggctt ttaaagcttt aaggtttaa cggttgtgga | 10200 |
| caacaagcca gggatgtaac gcactgagaa gcccttagag cctctcaaag caattttgag | 10260 |
| tgacacagga acacttaacg gctgacatgg gaattagcca tggcatcaca gtatcgtgat | 10320 |
| gacagaggca gggagtgcgg cctttttacg gttcctggcc ttttgctggc cttttgctca | 10380 |
| catgttcttt cctgcgttat caggggattc cttaaggtat actttccgct gcataaccct | 10440 |
| gcttcgggt cattatagcg attttttcgg tatatccatc cttttttcgca cgatatacag | 10500 |
| gattttgcca aagggttcgt gtagactttc cttggtgtat ccaacggcgt cagccgggca | 10560 |
| ggataggtga gtaggccca cccgcgagcg ggtgttcctt cttcactgtc ccttattcgc | 10620 |
| acctggcggt gctcaacggg aatcctgctc tgcgaggctg ccgataagc t | 10671 |

<210> SEQ ID NO 7
<211> LENGTH: 9461
<212> TYPE: DNA
<213> ORGANISM: Artificial sequence
<220> FEATURE:
<223> OTHER INFORMATION: Synthetic construct

<400> SEQUENCE: 7

| | |
|---|---|
| agcttatcgg ccagcctcgc agagcaggat tcccgttgag caccgccagg tgcgaataag | 60 |
| ggacagtgaa gaaggaacac ccgctcgcgg gtgggcctac ttcacctatc ctgcccggct | 120 |
| gacgccgttg gatacaccaa ggaaagtcta cacgaaccct ttggcaaaat cctgtatatc | 180 |

```
gtgcgaaaaa ggatggatat accgaaaaaa tcgctataat gaccccgaag cagggttatg    240
cagcggaaag tataccttaa ggaatcccct gataacgcag gaaagaacat gtgagcaaaa    300
ggccagcaaa aggccaggaa ccgtaaaaag gccgcactcc ctgcctctgt catcacgata    360
ctgtgatgcc atggctaatt cccatgtcag ccgttaagtg ttcctgtgtc actcaaaatt    420
gctttgagag gctctaaggg cttctcagtg cgttacatcc ctggcttgtt gtccacaacc    480
gttaaacctt aaaagcttta aaagccttat atattctttt ttttcttata aaacttaaaa    540
ccttagaggc tatttaagtt gctgatttat attaattta ttgttcaaac atgagagctt    600
agtacgtgaa acatgagagc ttagtacgtt agccatgaga gcttagtacg ttagccatga    660
gggtttagtt cgttaaacat gagagcttag tacgttaaac atgagagctt agtacgtgaa    720
acatgagagc ttagtacgta ctatcaacag gttgaactgc tgatcttcag atcctctacg    780
ccggacgcat cgtggccgga tcttgcggcc gcaaaaatta aaaatgaagt tttaaatcaa    840
tctaaagtat atatgagtaa acttggtctg acagttacca atgcttaatc agtgaggcac    900
caataactgc ctttgatctt ttctacgggg tctgacgctc agtggaacga aaactcacgt    960
taagggattt tggtcatgag attatcaaaa aggatcttca cctagatcct tttaaattaa   1020
aaatgaagtt ttaaatcaat ctaaagtata tatgagtaaa cttggtctga cagttaccaa   1080
tgcttaatca gtgaggcacc tatctcagcg atctgtctat ttcgttcatc catagttgcc   1140
tgactccccg tcgtgtagat aactacgata cgggagggct taccatctgg ccccagtgct   1200
gcaatgatac cgcgagaccc acgctcaccg gctccagatt tatcagcaat aaaccagcca   1260
gccggaaggg ccgagcgcag aagtggtcct gcaactttat ccgcctccat ccagtctatt   1320
aattgttgcc gggaagctag agtaagtagt tcgccagtta atagtttgcg caacgttgtt   1380
gccattgcta caggcatcgt ggtgtcacgc tcgtcgtttg gtatggcttc attcagctcc   1440
ggttcccaac gatcaaggcg agttacatga tcccccatgt tgtgcaaaaa agcggttagc   1500
tccttcggtc ctccgatcgt tgtcagaagt aagttggccg cagtgttatc actcatggtt   1560
atggcagcac tgcataattc tcttactgtc atgccatccg taagatgctt ttctgtgact   1620
ggtgagtact caaccaagtc attctgagaa tagtgtatgc ggcgaccgag ttgctcttgc   1680
ccggcgtcaa tacgggataa taccgcgcca catagcagaa ctttaaaagt gctcatcatt   1740
ggaaaacgtt cttcggggcg aaaactctca aggatcttac cgctgttgag atccagttcg   1800
atgtaaccca ctcgtgcacc caactgatct tcagcatctt ttactttcac cagcgtttct   1860
gggtgagcaa aaacaggaag gcaaaatgcc gcaaaaaagg gaataagggc gacacggaaa   1920
tgttgaatac tcatactctt cctttttcaa tattattgaa gcatttatca gggttattgt   1980
ctcatgagcg gatacatatt tgaatgtatt tagaaaaata aacaaatagg ggttccgcgc   2040
acatttcccc gaaaagtgcc acctgacgtc taagaaacca ttattatcat gacattaacc   2100
tataaaaata ggcgtatcac gaggcccttt cgtctcgcgc gtttcggtga tgacggtgaa   2160
aacctctgac acatgcagct cccggagacg gtcacagctt gtctgtaagc ggatgccggg   2220
agcagacaag cccgtcaggg cgcgtcagcg ggtgttggcg ggtgtcgggg ctggcttaac   2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt   2400
tgggaagggc gatcggtgcg ggcctcttcg ctattacgcc agctagagga ccagccgcgt   2460
aacctggcaa aatcggttac ggttgagtaa taaatggatg ccctgcgtaa gcgggtgtgg   2520
```

```
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700
aaagaggggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gtgcttaaaa    3180
acttactcaa tggaataatt ctagataatt cttaggccac acgttcaagt gcagccacag    3240
gataaatttg cactgagcct gggtgggatt cggactcgac cgcatagcct tcaggagtga    3300
gttttgtgca ataccaaccg acgacttgac cctgccaagc ggcaccagat ttcttgcgta    3360
cgcgatcccc taagccaaag gtggcactca ggggaagcgc aaactgccct gcaacgggag    3420
cgttggcttc atcgctactt tgacccatgt cgaatccttc ttgtgaatct attatggcga    3480
caagcaaatc gagctctgac tgcctacccc acaacaacta tcagaaagca ccagcacaac    3540
ggctgcctaa ctttgtttta gggcgactgc cctgctgcgt aacatcgttg ctgctccata    3600
acatcaaaca tcgacccacg gcgtaacgcg cttgctgctt ggatgcccga ggcatagact    3660
gtacaaaaaa acagtcataa caagccatga aaaccgccac tgcgccgtta ccaccgctgc    3720
gttcggtcaa ggttctggac cagttgcgtg agcgcatacg ctacttgcat tacagtttac    3780
gaaccgaaca ggcttatgtc aactgggttc gtgaattatc cattgctgtt gacaagggga    3840
atcaggctcg agagttcaac agacagcctt cgttcttatg gccgttcagg aggaagttcc    3900
tattccgaag ttcctattct ctagaaagta taggaacttc ttgagaagag aaaagaaaac    3960
cgccgatcct gtccaccgca ttactgcaag gtagtggaca agaccggcgg tcttaagttt    4020
tttggctgaa acgaatgacg aaaaggctgt ctgagcaaat ccaggaggtc gtttaaaccg    4080
tattagcccg gtattttgga aatagcggaa gcactgactt ttgttatcaa taaaaaaggc    4140
cccccgttag ggaggcctta ttgttcgtct actcggaaga gcgagagaca acagaacggt    4200
cagccacatg aattcaaaaa aaaagcaccg actcggtgcc acttttttcaa gttgataacg    4260 gactagcctt attaaacttt gctatgctgt ttccagcata gctcttaaac agaccgctaa    4320
actgaaagtt ccacacatta tacgagccgg atgattaatt gtcaacagct catttcagaa    4380
tatttgccag aaccggaatt ctttcagctc agtcgatagg tagtaggcaa gagtagtcgc    4440
acctttggtc gaaaaaaaaa gcccgcactg tcaggtgcgg gcttttttct gtgtttcccc    4500
aaaagtaaaa acccgccgaa gcgggttttt acgtaaaaca ggtgaaactg accagacgag    4560
aaggctttgg aggtgataat ggggctcaag gacccgggag gcagataggt aggcatggcc    4620 cccatttttca atacaagcaa cgcatgagaa agccccggga agatcacctt ccgggggctt    4680
ttttattgcg ctccggcaat taaaaaagcg gctaaccacg ccgctttttt tacgtctgca    4740
gagctcatag gcaagcgaat cgtgatgcct cttagccagt actagtatgg ataagaaata    4800
ctcaataggc ttagctatcg gcacaaatag cgtcggatgg gcggtgatca ctgatgaata    4860
taaggttccg tctaaaaagt tcaaggttct gggaaataca gaccgccaca gtatcaaaaa    4920
```

```
aaatcttata ggggctcttt tatttgacag tggagagaca gcggaagcga ctcgtctcaa    4980
acggacagct cgtagaaggt atacacgtcg gaagaatcgt atttgttatc tacaggagat    5040
tttttcaaat gagatggcga aagtagatga tagtttcttt catcgacttg aagagtcttt    5100
tttggtggaa aagacaaga agcatgaacg tcatcctatt tttggaaata tagtagatga    5160
agttgcttat catgagaaat atccaactat ctatcatctg cgaaaaaaat tggtagattc    5220
tactgataaa gcggatttgc gcttaatcta tttggcctta gcgcatatga ttaagtttcg    5280
tggtcatttt ttgattgagg gagatttaaa tcctgataat agtgatgtgg acaaactatt    5340
tatccagttg gtacaaacct acaatcaatt atttgaagaa aaccctatta acgcaagtgg    5400
agtagatgct aaagcgattc tttctgcacg attgagtaaa tcaagacgat tagaaaatct    5460
cattgctcag ctccccggtg agaagaaaaa tggcttattt gggaatctca ttgctttgtc    5520
attgggtttg acccctaatt ttaaatcaaa ttttgatttg gcagaagatg ctaaattaca    5580
gctttcaaaa gatacttacg atgatgattt agataattta ttggcgcaaa ttggagatca    5640
atatgctgat ttgttttttgg cagctaagaa tttatcagat gctattttac tttcagatat    5700
cctaagagta aatactgaaa taactaaggc tcccctatca gcttcaatga ttaaacgcta    5760
cgatgaacat catcaagact tgactctttt aaaagcttta gttcgacaac aacttccaga    5820
aaagtataaa gaaatctttt ttgatcaatc aaaaaacgga tatgcaggtt atattgatgg    5880
gggagctagc caagaagaat tttataaatt tatcaaacca attttagaaa aatggatgg    5940 tactgaggaa ttattggtga aactaaatcg tgaagatttg ctgcgcaagc aacggaccct    6000
tgacaacggc tctattcccc atcaaattca cttgggtgag ctgcatgcta ttttgagaag    6060
acaagaagac ttttatccat tttaaaagaa caatcgtgag aagattgaaa aaatcttgac    6120
ttttcgaatc ccttattatg ttggtccatt ggcgcgtggc aatagtcgtt ttgcatggat    6180
gactcggaag tctgaagaaa caattacccc atggaatttt gaagaagttg tcgataaagg    6240
tgcttcagct caatcattta ttgaacgcat gacaaacttt gataaaaatc ttccaaatga    6300 aaagtactc caaacata gtttgctta tgagtatttt acggtttata acgaattgac    6360
aaaggtcaaa tatgttactg aaggaatgcg aaaaccagca tttctttcag gtgaacagaa    6420
gaaagccatt gttgatttac tcttcaaaac aaatcgaaaa gtaaccgtta agcaattaaa    6480
agaagattat ttcaaaaaaa tagaatgttt tgatagtgtt gaaatttcag gagttgaaga    6540
tagatttaat gcttcattag gtacctacca tgatttgcta aaaattatta agataaaga    6600 ttttttggat aatgaagaaa atgaagatat cttagaggat attgttttaa cattgaccttt    6660 atttgaagat agggagatga ttgaggaaag acttaaaaca tatgctcacc tctttgatga    6720
taaggtgatg aaacagctta acgtcgccg ttatactggt tggggacgtt tgtctcgaaa    6780
attgattaat ggtattaggg ataagcaatc tggcaaaaca atattagatt ttttgaaatc    6840
agatggtttc gccaatcgca attttatgca gctgatccat gatgatagtt tgacattaa    6900 agaagacatt caaaaagcac aagtgtctgg acaaggcgat agtttacatg aacatattgc    6960
aaatttagct ggtagccctg ctattaaaaa aggtatttta cagactgtaa aagttgttga    7020
tgaattggtc aaagtaatgg ggcggcataa gccagaaaat atcgttattg aaatggcacg    7080
tgaaaatcag acaactcaaa agggccagaa aaattcgcga gagcgtatga acgaatcga    7140 agaaggtatc aaagaattag gaagtcagat tcttaaagag catcctgttg aaaatactca    7200
attgcaaaat gaaaagctct atctctatta tctccaaaat ggaagagaca tgtatgtgga    7260
```

```
ccaagaatta gatattaatc gtttaagtga ttatgatgtc gatgccattg ttccacaaag    7320
tttccttaaa gacgattcaa tagacaataa ggtcttaacg cgttctgata aaaatcgtgg    7380
taaatcggat aacgttccaa gtgaagaagt agtcaaaaag atgaaaaact attggagaca    7440
acttctaaac gccaagttaa tcactcaacg taagtttgat aatttaacga aagctgaacg    7500
tggaggtttg agtgaacttg ataaagctgg ttttatcaaa cgccaattgg ttgaaactcg    7560
ccaaatcact aagcatgtgg cacaaatttt ggatagtcgc atgaatacta atacgatga    7620 aaatgataaa cttattcgag aggttaaagt gattacctta aaatctaaat tagtttctga    7680
cttccgaaaa gatttccaat tctataaagt acgtgagatt aacaattacc atcatgccca    7740
tgatgcgtat ctaaatgccg tcgttggaac tgctttgatt aagaaatatc caaaacttga    7800
atcggagttt gtctatggtg attataaagt ttatgatgtt cgtaaaatga ttgctaagtc    7860
tgagcaagaa ataggcaaag caaccgcaaa atatttcttt tactctaata tcatgaactt    7920
cttcaaaaca gaaattacac ttgcaaatgg agagattcgc aaacgccctc taatcgaaac    7980
taatggggaa actggagaaa ttgtctggga taaagggcga gattttgcca cagtgcgcaa    8040
agtattgtcc atgccccaag tcaatattgt caagaaaaca gaagtacaga caggcggatt    8100
ctccaaggag tcaattttac caaaaagaaa ttcggacaag cttattgctc gtaaaaaaga    8160
ctgggatcca aaaaaatatg gtggttttga tagtccaacg gtagcttatt cagtcctagt    8220
ggttgctaag gtggaaaaag ggaaatcgaa gaagttaaaa tccgttaaag agttactagg    8280
gatcacaatt atggaaagaa gttcctttga aaaaaatccg attgactttt tagaagctaa    8340
aggatataag gaagttaaaa aagacttaat cattaaacta cctaaatata gtcttttga    8400 gttagaaaac ggtcgtaaac ggatgctggc tagtgccgga gaattacaaa aggaaatga    8460 gctggctctg ccaagcaaat atgtgaattt tttatattta gctagtcatt atgaaaagtt    8520
gaagggtagt ccagaagata acgaacaaaa acaattgttt gtggagcagc ataagcatta    8580
tttagatgag attattgagc aaatcagtga attttctaag cgtgttattt tagcagatgc    8640
caatttagat aaagttctta gtgcatataa caaacataga gacaaaccaa tacgtgaaca    8700
agcagaaaat attattcatt tatttacgtt gacgaatctt ggagctcccg ctgcttttaa    8760
atattttgat acaacaattg atcgtaaacg atatacgtct acaaaagaag ttttagatgc    8820
cactcttatc catcaatcca tcactggtct ttatgaaaca cgcattgatt tgagtcagct    8880
aggaggtgac gcggccgcgg agcagaaact catctctgaa gaagatctgg aacaaaagtt    8940
gatttcagaa gaagatctgg aacagaagct catctctgag gaagatctgt aataaggcgc    9000
gcctccttaa tgggacttgc agcctcggta ccaaattcca gaaagacac ccgaaagggt    9060 gtttttttcgt tttggtccca cagaatgagc atcatggctc tagtcgacat cggagaagag    9120
tacggctctt ttaaccgcct caagaaccag ataagtgaaa tctagttcca aactattttg    9180 tcattttaa ttttcgtatt agcttacgac gctacaccca gttccatct attttgtcac    9240 tcttccctaa ataatccta aaaactccat ttccaccct cccagttccc aactattttg    9300
tccgcccaca gcggggcatt tttcttcctg ttatgtttgg gcgctgcatt aatgaatcgg    9360
ccaacgcgcg gggagaggcg gtttgcgtat gggcgctct tccgcttcct cgctcactga    9420
cccgctgcgc tcggtcgttc ggctgcggcg agcggtatca g                        9461
```

<210> SEQ ID NO 8
<211> LENGTH: 11839
<212> TYPE: DNA
<213> ORGANISM: Artificial sequence
<220> FEATURE:
<223> OTHER INFORMATION: Synthetic construct

<400> SEQUENCE: 8

```
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc     180
gtgcgaaaaa ggatggatat accgaaaaaa tcgctataat gaccccgaag cagggttatg     240
cagcggaaag tataccttaa ggaatcccct gataacgcag gaaagaacat gtgagcaaaa     300
ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagccttat atattctttt ttttcttata aacttaaaa     540
ccttagaggc tatttaagtt gctgatttat attaatttta ttgttcaaac atgagagctt     600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaatgaagt tttaaatcaa     840
tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140
tgactcccg tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaataggg gttccgcgc     2040
acatttcccc gaaaagtgcc acctgacgtc taagaaacca ttattatcat gacattaacc    2100
tataaaaata ggcgtatcac gaggcccttt cgtctcgcgc gtttcggtga tgacggtgaa    2160
aacctctgac acatgcagct cccggagacg gtcacagctt gtctgtaagc ggatgccggg    2220
```

```
agcagacaag cccgtcaggg cgcgtcagcg ggtgttggcg ggtgtcgggg ctggcttaac    2280
tatgcggcat cagagcagat tgtactgaga gtgcaccata tgcggtgtga aataccgcac    2340
agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa aatcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gatctcggct    3180
tgaacgaatt gttaggtggc ggtacttggg tcgatatcaa agtgcatcac ttcttcccgt    3240
atgcccaact ttgtatagag agccactgcg ggatcgtcac cgtaatctgc ttgcacgtag    3300
atcacataag caccaagcgc gttggcctca tgcttgagga gattgatgag cgcggtggca    3360
atgccctgcc tccggtgctc gccggagact gcgagatcat agatatagat ctcactacgc    3420
ggctgctcaa acctgggcag aacgtaagcc gcgagagcgc caacaaccgc ttcttggtcg    3480
aaggcagcaa gcgcgatgaa tgtcttacta cggagcaagt tcccgaggta atcggagtcc    3540
ggctgatgtt gggagtaggt ggctacgtct ccgaactcac gaccgaaaag atcaagagca    3600
gcccgcatgg atttgacttg gtcagggccg agcctacatg tgcgaatgat gcccatactt    3660
gagccaccta actttgtttt agggcgactg ccctgctgcg taacatcgtt gctgctgcgt    3720
aacatcgttg ctgctccata acatcaaaca tcgacccacg gcgtaacgcg cttgctgctt    3780
ggatgcccga ggcatagact gtacaaaaaa acagtcataa caagccatga aaaccgccac    3840
tgcgccgtta ccaccgctgc gttcggtcaa ggttctggac cagttgcgtg agcgcatacg    3900
ctacttgcat tacagtttac gaaccgaaca ggcttatgtc aactgggttc gtgccttcat    3960
ccgtttccac ggtgtgcgtc catgggcaaa tattatacgc aaggcgacaa ggctcgagag    4020
ttcaacagac agccttcgtt cttatggccg ttcaggagga agttcctatt ccgaagttcc    4080
tattctctag aaagtatagg aacttcttga gaagagaaaa gaaaaccgcc gatcctgtcc    4140
accgcattac tgcaaggtag tggacaagac cggcggtctt aagttttttg gctgaaacga    4200
atgacgaaaa ggctgtctga gcaaatccag gaggtcgttt ttattaagca ccggtggagt    4260
gacgaccttc agcacgttcg tactgttcaa cgatggtgta gtcttcgttg tgggaggtga    4320
tgtccagttt gatgtcggtt ttgtaagcac ccggcagctg aaccggtttt ttagccatgt    4380
aggtggtttt aacttcagcg tcgtagtgac caccgtcttt cagtttcaga cgcatttttga    4440 tttcaccttt cagagcaccg tcttccgggt acatacgttc ggtggaagct tcccaaccca    4500
tggttttttt ctgcataacc ggaccgtcgg acgggaagtt ggtaccacgc agtttaactt    4560
tgtagatgaa ctcaccgtct tgcagggagg agtcctgggt aacggtaaca acaccaccgt    4620
```

```
cttcgaagtt cataacacgt tcccatttga aaccttccgg gaaggacagt ttcaggtagt    4680
ccgggatgtc agccgggtgt ttaacgtaag ctttggaacc gtactggaac tgcggggaca    4740
ggatgtccca agcgaacggc agcggaccac ctttggtaac tttcagttta gcggtctggg    4800
taccttcgta cggacgacct tcaccttcac cttcgatttc gaactcgtga ccgttaacgg    4860
aaccttccat acgaactttg aaacgcatga actctttgat aacgtcttcg ctactcgcca    4920
tggtaccttt ctcctcttta attaattcag atctattata cctaggactg agctagctgt    4980
caaattcacc accctgaatt gactctcaaa ccgtattagc ccggtatttt ggaaatagcg    5040
gaagcactga cttttgttat caataaaaaa ggccccccgt tagggaggcc ttattgttcg    5100
tctactcgga agagcgagag acaacagaac ggtcagccac atgaattcaa aaaaaagca    5160 ccgactcggt gccacttttt caagttgata acggactagc cttatttaaa cttgctatgc    5220
tgtttccagc atagctctta aacagaccgc taaactgaaa gttactagaa gtatcttgtt    5280
atccgctcac aatgtcaatg ttatccgctc acatttatag atctttagga attctttcag    5340
ctcagtcgat aggtagtagg caagagtagt cgcacctttg gtcgaaaaaa aaagcccgca    5400
ctgtcaggtg cgggcttttt tctgtgtttc cccaaaagta aaacccgcc gaagcgggtt    5460 tttacgtaaa acaggtgaaa ctgaccagac gagaaggctt tggaggtgat aatggggctc    5520
aaggaccctg gggtgcctaa tgagtgagct aactcacatt aattgcgttg cgctcactgc    5580
ccgctttcca gtcgggaaac ctgtcgtgcc agctgcatta atgaatcggc caacgcgcgg    5640
ggagaggcgg tttgcgtatt gggcgccagg gtggtttttc ttttcaccag tgagacgggc    5700
aacagctgat tgcccttcac cgcctggccc tgagagagtt gcagcaagcg gtccacgctg    5760
gtttgcccca gcaggcgaaa atcctgtttg atggtggtta acggcgggat ataacatgag    5820
ctgtcttcgg tatcgtcgta tcccactacc gagatatccg caccaacgcg cagcccggac    5880
tcggtaatgg cgcgcattgc gcccagcgcc atctgatcgt tggcaaccag catcgcagtg    5940
ggaacgatgc cctcattcag catttgcatg gtttgttgaa aaccggacat ggcactccag    6000
tcgccttccc gttccgctat cggctgaatt tgattgcgag tgagatattt atgccagcca    6060
gccagacgca gacgcgccga cagaacctt aatgggcccg ctaacagcgc gatttgctgg    6120
tgacccaatg cgaccagatg ctccacgccc agtcgcgtac cgtcttcatg ggagaaaata    6180
atactgttga tgggtgtctg gtcagagaca tcaagaaata cgccggaac attagtgcag    6240 gcagcttcca cagcaatggc atcctggtca tccagcggat agttaatgat cagcccactg    6300
acgcgttgcg cgagaagatt gtgcaccgcc gctttacagg cttcgacgcc gcttcgttct    6360
accatcgaca ccaccacgct ggcacccagt tgatcggcgc gagatttaat cgccgcgaca    6420
atttgcgacg cgcgtgcag gccagactg gaggtggcaa cgccaatcag caacgactgt    6480
ttgcccgcca gttgttgtgc cacgcggttg ggaatgtaat tcagctccgc catcgccgct    6540
tccacttttt cccgcgtttt cgcagaaacg tggctggcct ggttcaccac gcgggaaacg    6600
gtctgataag agacaccggc atactctgcg acatcgtata acgttactgg tttcacattc    6660
accaccctga attgactctc ttccgggcgc tatcatgcca taccgcgaaa ggttttgcac    6720
cattcgatgg tgtcaacgta aatgcatgcc gcttgggagg cagataggta ggcatggccc    6780
ccattttcaa tacaagcaac gcatgagaaa gccccggaa gatcaccttc cgggggcttt    6840
tttattgcgc tccggcaatt aaaaaagcgg ctaaccacgc cgcttttttt acgtctgcag    6900
gcgaattgat ctggtttgac agcttatcac caagccagtt acctcggttc aaagagttgg    6960
```

```
tagctcagag aaccttcgaa aaaccgccct gcaaggcggt ttttcgttt tcagagcaag    7020 agattacgcg cagaccaaaa cgatctcaag aagatcatct tattaatcag ataaaatatt    7080
ataaatgtga gcggataaca ttgacattgt gagcggataa caagatactg agcacatcag    7140
caggtttcac acaggaaaac tagtatggat aagaaatact caataggctt agctatcggc    7200
acaaatagcg tcggatgggc ggtgatcact gatgaatata aggttccgtc taaaaagttc    7260
aaggttctgg gaaatacaga ccgccacagt atcaaaaaaa atcttatagg ggctctttta    7320
tttgacagtg gagagacagc ggaagcgact cgtctcaaac ggacagctcg tagaaggtat    7380
acacgtcgga agaatcgtat ttgttatcta caggagattt tttcaaatga gatggcgaaa    7440
gtagatgata gtttctttca tcgacttgaa gagtctttt tggtggaaga agacaagaag    7500
catgaacgtc atcctatttt tggaaatata gtagatgaag ttgcttatca tgagaaatat    7560
ccaactatct atcatctgcg aaaaaaattg gtagattcta ctgataaagc ggatttgcgc    7620
ttaatctatt tggccttagc gcatatgatt aagtttcgtg gtcatttttt gattgaggga    7680
gatttaaatc ctgataatag tgatgtggac aaactatta tccagttggt acaaacctac    7740
aatcaattat ttgaagaaaa ccctattaac gcaagtggag tagatgctaa agcgattctt    7800
tctgcacgat tgagtaaatc aagacgatta gaaaatctca ttgctcagct ccccggtgag    7860
aagaaaaatg gcttatttgg gaatctcatt gctttgtcat tgggtttgac ccctaattt    7920 aaatcaaatt ttgatttggc agaagatgct aaattacagc tttcaaaaga tacttacgat    7980
gatgatttag ataatttatt ggcgcaaatt ggagatcaat atgctgattt gttttttggca    8040 gctaagaatt tatcagatgc tattttactt tcagatatcc taagagtaaa tactgaaata    8100
actaaggctc ccctatcagc ttcaatgatt aaacgctacg atgaacatca tcaagacttg    8160
actcttttaa aagctttagt tcgacaacaa cttccagaaa agtataaaga aatcttttt    8220 gatcaatcaa aaaacggata tgcaggttat attgatgggg gagctagcca agaagaattt    8280
tataaattta tcaaaccaat tttagaaaaa atggatggta ctgaggaatt attggtgaaa    8340
ctaaatcgtg aagatttgct gcgcaagcaa cggacctttg acaacggctc tattccccat    8400
caaattcact gggtgagct gcatgctatt ttgagaagac aagaagactt ttatccattt    8460
ttaaaagaca atcgtgagaa gattgaaaaa atcttgactt ttcgaatccc ttattatgtt    8520
ggtccattgg cgcgtggcaa tagtcgtttt gcatggatga ctcggaagtc tgaagaaaca    8580
attaccccat ggaattttga agaagttgtc gataaaggtg cttcagctca atcatttatt    8640
gaacgcatga caaactttga taaaaatctt ccaaatgaaa agtactacc aaaacatagt    8700 ttgctttatg agtattttac ggtttataac gaattgacaa aggtcaaata tgttactgaa    8760
ggaatgcgaa aaccagcatt tcttcaggt gaacagaaga aagccattgt tgatttactc    8820
ttcaaaacaa atcgaaaagt aaccgttaag caattaaaag aagattattt caaaaaaata    8880
gaatgttttg atagtgttga aatttcagga gttgaagata gatttaatgc ttcattaggt    8940
acctaccatg atttgctaaa aattattaaa gataaagatt ttttggataa tgaagaaaat    9000
gaagatatct tagaggatat tgttttaaca ttgaccttat ttgaagatag ggagatgatt    9060
gaggaaagac ttaaaacata tgctcacctc tttgatgata aggtgatgaa acagcttaaa    9120
cgtcgccgtt atactggttg gggacgtttg tctcgaaaat tgattaatgg tattagggat    9180
aagcaatctg gcaaaacaat attagatttt ttgaaatcag atggttttgc caatcgcaat    9240
tttatgcagc tgatccatga tgatagtttg acatttaaag aagacattca aaaagcacaa    9300
gtgtctggac aaggcgatag tttacatgaa catattgcaa atttagctgg tagccctgct    9360
```

```
attaaaaaag gtattttaca gactgtaaaa gttgttgatg aattggtcaa agtaatgggg    9420
cggcataagc cagaaaatat cgttattgaa atggcacgtg aaaatcagac aactcaaaag    9480
ggccagaaaa attcgcgaga gcgtatgaaa cgaatcgaag aaggtatcaa agaattagga    9540
agtcagattc ttaaagagca tcctgttgaa aatactcaat tgcaaaatga aaagctctat    9600
ctctattatc tccaaaatgg aagagacatg tatgtggacc aagaattaga tattaatcgt    9660
ttaagtgatt atgatgtcga tgccattgtt ccacaaagtt tccttaaaga cgattcaata    9720
gacaataagg tcttaacgcg ttctgataaa aatcgtggta atcggataa cgttccaagt     9780
gaagaagtag tcaaaaagat gaaaaactat tggagacaac ttctaaacgc caagttaatc    9840
actcaacgta agtttgataa tttaacgaaa gctgaacgtg gaggtttgag tgaacttgat    9900
aaagctggtt ttatcaaacg ccaattggtt gaaactcgcc aaatcactaa gcatgtggca    9960
caaattttgg atagtcgcat gaatactaaa tacgatgaaa atgataaact tattcgagag   10020
gttaaagtga ttccttaaa atctaaatta gtttctgact tccgaaaaga tttccaattc    10080
tataaagtac gtgagattaa caattaccat catgcccatg atgcgtatct aaatgccgtc   10140
gttggaactg ctttgattaa gaaatatcca aaacttgaat cggagtttgt ctatggtgat   10200
tataaagttt atgatgttcg taaaatgatt gctaagtctg agcaagaaat aggcaaagca   10260
accgcaaaat atttctttta ctctaatatc atgaacttct tcaaaacaga aattacactt   10320
gcaaatggag agattcgcaa acgccctcta atcgaaacta tggggaaac tggagaaatt    10380
gtctgggata aagggcgaga ttttgccaca gtgcgcaaag tattgtccat gccccaagtc   10440
aatattgtca agaaaacaga agtacagaca ggcggattct ccaaggagtc aattttacca   10500
aaaagaaatt cggacaagct tattgctcgt aaaaagact gggatccaaa aaatatggt    10560
ggttttgata gtccaacggt agcttattca gtcctagtgg ttgctaaggt ggaaaagg    10620
aaatcgaaga agtaaaatc cgttaaagag ttactagga tcacaattat ggaagaagt     10680
tcctttgaaa aaaatccgat tgacttttta gaagctaaag gatataagga agttaaaaaa   10740
gacttaatca ttaaactacc taaatatagt ctttttgagt tagaaaacgg tcgtaaacgg   10800
atgctggcta gtgccggaga attacaaaaa ggaaatgagc tggctctgcc aagcaaatat   10860
gtgaatttt tatatttagc tagtcattat gaaaagttga agggtagtcc agaagataac    10920
gaacaaaaac aattgtttgt ggagcagcat aagcattatt tagatgagat tattgagcaa   10980
atcagtgaat tttctaagcg tgttatttta gcagatgcca atttagataa agttcttagt   11040
gcatataaca acatagaga caaaccaata cgtgaacaag cagaaaatat tattcattta    11100
tttacgttga cgaatcttgg agctcccgct gcttttaaat attttgatac aacaattgat   11160
cgtaaacgat atacgtctac aaaagaagtt ttagatgcca ctcttatcca tcaatccatc   11220
actggtcttt atgaaacacg cattgatttg agtcagctag gaggtgacgc ggccgcggag   11280
cagaaactca tctctgaaga agatctggaa caaaagttga tttcagaaga agatctggaa   11340
cagaagctca tctctgagga agatctgtaa taaggcgcgc ctccttaatg ggacttgcag   11400
cctcggtacc aaattccaga aaagacaccc gaaagggtgt ttttcgtttt tggtcccaca   11460
gaatgagcat catggctcta gtcgacatcg gagaagagta cggctctttt aaccgcctca   11520
agaaccagat aagtgaaatc tagttccaaa ctattttgtc attttaatt ttcgtattag    11580
cttacgacgc tacacccagt tcccatctat tttgtcactc ttccctaaat aatccttaaa   11640
aactccattt ccacccctcc cagttcccaa ctattttgtc cgcccacagc ggggcatttt   11700
```

```
tcttcctgtt atgtttgggc gctgcattaa tgaatcggcc aacgcgcggg gagaggcggt    11760
ttgcgtattg ggcgctcttc cgcttcctcg ctcactgacc cgctgcgctc ggtcgttcgg    11820
ctgcggcgag cggtatcag                                                 11839

<210> SEQ ID NO 9
<211> LENGTH: 11839
<212> TYPE: DNA
<213> ORGANISM: Artificial sequence
<220> FEATURE:
<223> OTHER INFORMATION: Synthetic construct

<400> SEQUENCE: 9
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc     180
gtgcgaaaaa ggatggatat accgaaaaaa tcgctataat gaccccgaag cagggttatg     240
cagcggaaag tataccttaa ggaatcccct gataacgcag gaaagaacat gtgagcaaaa     300
ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagccttat atattctttt ttttcttata aaacttaaaa     540
ccttagaggc tatttaagtt gctgatttat attaatttta ttgttcaaac atgagagctt     600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaaatgaagt tttaaatcaa     840
tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct ttaaattaa    1020 aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140 tgactcccg tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
```

```
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggccctt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa atcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gatctcggct    3180
tgaacgaatt gttaggtggc ggtacttggg tcgatatcaa agtgcatcac ttcttcccgt    3240
atgcccaact ttgtatagag agccactgcg ggatcgtcac cgtaatctgc ttgcacgtag    3300
atcacataag caccaagcgc gttggcctca tgcttgagga gattgatgag cgcggtggca    3360
atgccctgcc tccggtgctc gccggagact gcgagatcat agatatagat ctcactacgc    3420
ggctgctcaa acctgggcag aacgtaagcc gcgagagcgc caacaaccgc ttcttggtcg    3480
aaggcagcaa gcgcgatgaa tgtcttacta cggagcaagt tcccgaggta atcggagtcc    3540
ggctgatgtt gggagtaggt ggctacgtct ccgaactcac gaccgaaaag atcaagagca    3600
gcccgcatgg atttgacttg gtcagggccg agcctacatg tgcgaatgat gcccatactt    3660
gagccaccta actttgtttt agggcgactg ccctgctgcg taacatcgtt gctgctgcgt    3720
aacatcgttg ctgctccata acatcaaaca tcgacccacg cgtaacgcg cttgctgctt    3780 ggatgcccga ggcatagact gtacaaaaaa acagtcataa caagccatga aaaccgccac    3840
tgcgccgtta ccaccgctgc gttcggtcaa ggttctggac cagttgcgtg agcgcatacg    3900
ctacttgcat tacagtttac gaaccgaaca ggcttatgtc aactgggttc gtgccttcat    3960
ccgtttccac ggtgtgcgtc catgggcaaa tattatacgc aaggcgacaa ggctcgagag    4020
ttcaacagac agccttcgtt cttatggccg ttcaggagga agttcctatt ccgaagttcc    4080
tattctctag aaagtatagg aacttcttga gaagagaaaa gaaaccgcc gatcctgtcc    4140 accgcattac tgcaaggtag tggacaagac cggcggtctt aagttttttg gctgaaacga    4200
atgacgaaaa ggctgtctga gcaaatccag gaggtcgttt ttattaagca ccggtggagt    4260
```

```
gacgaccttc agcacgttcg tactgttcaa cgatggtgta gtcttcgttg tgggaggtga    4320
tgtccagttt gatgtcggtt ttgtaagcac ccggcagctg aaccggtttt ttagccatgt    4380
aggtggtttt aacttcagcg tcgtagtgac caccgtcttt cagtttcaga cgcattttga    4440
tttcaccttt cagagcaccg tcttccgggt acatacgttc ggtggaagct tcccaaccca    4500
tggttttttt ctgcataacc ggaccgtcgg acgggaagtt ggtaccacgc agtttaactt    4560
tgtagatgaa ctcaccgtct tgcagggagg agtcctgggt aacggtaaca acaccaccgt    4620
cttcgaagtt cataacacgt tcccatttga aaccttccgg aaggacagtt tcaggtagt    4680 ccgggatgtc agccggtgt ttaacgtaag ctttggaacc gtactggaac tgcggggaca    4740
ggatgtccca agcgaacggc agcggaccac ctttggtaac tttcagttta gcggtctggg    4800
taccttcgta cggacgacct tcaccttcac cttcgatttc gaactcgtga ccgttaacgg    4860
aaccttccat acgaactttg aaacgcatga actctttgat aacgtcttcg ctactcgcca    4920
tggtaccttt ctcctcttta attaattcag atctattata cctaggactg agctagctgt    4980
caaattcacc accctgaatt gactctcaaa ccgtattagc ccggtatttt ggaaatagcg    5040
gaagcactga cttttgttat caataaaaaa ggccccccgt tagggaggcc ttattgttcg    5100
tctactcgga agagcgagag acaacagaac ggtcagccac atgaattcaa aaaaaaagca    5160
ccgactcggt gccactttt caagttgata acggactagc cttatttaaa cttgctatgc    5220
tgtttccagc atagctctta aacagaccgc taaactgaaa gttactagaa gtatcttgtt    5280
atccgctcac aatgtcaatg ttatccgctc acatttatag atctttagga attctttcag    5340
ctcagtcgat aggtagtagg caagagtagt cgcacctttg gtcgaaaaaa aaagcccgca    5400
ctgtcaggtg cgggcttttt tctgtgtttc cccaaaagta aaacccgcc gaagcgggtt    5460 tttacgtaaa acaggtgaaa ctgaccagac gagaaggctt tggaggtgat aatgggctc    5520 aaggaccctg gggtgcctaa tgagtgagct aactcacatt aattgcgttg cgctcactgc    5580
ccgctttcca gtcgggaaac ctgtcgtgcc agctgcatta atgaatcggc caacgcgcgg    5640
ggagaggcgg tttgcgtatt gggcgccagg gtggtttttc ttttcaccag tgagacgggc    5700
aacagctgat tgcccttcac cgcctggccc tgagagagtt gcagcaagcg gtccacgctg    5760
gtttgcccca gcaggcgaaa atcctgtttg atggtggtta acggcgggat ataacatgag    5820
ctgtcttcgg tatcgtcgta tcccactacc gagatatccg caccaacgcg cagcccggac    5880
tcggtaatgg cgcgcattgc gcccagcgcc atctgatcgt tggcaaccag catcgcagtg    5940
ggaacgatgc cctcattcag catttgcatg gtttgttgaa aaccgacat ggcactccag    6000 tcgccttccc gttccgctat cggctgaatt tgattgcgag tgagatattt atgccagcca    6060
gccagacgca gacgcgccga gacagaactt aatgggcccg ctaacagcgc gatttgctgg    6120
tgacccaatg cgaccagatg ctccacgccc agtcgcgtac cgtcttcatg ggagaaaata    6180
atactgttga tgggtgtctg gtcagagaca tcaagaaata cgccggaac attagtgcag    6240 gcagcttcca cagcaatggc atcctggtca tccagcggat agttaatgat cagcccactg    6300
acgcgttgcg cgagaagatt gtgcaccgcc gctttacagg cttcgacgcc gcttcgttct    6360
accatcgaca ccaccacgct ggcacccagt tgatcggcgc gagatttaat cgccgcgaca    6420
atttgcgacg gcgcgtgcag ggccagactg gaggtggcaa cgccaatcag caacgactgt    6480
ttgcccgcca gttgttgtgc cacgcggttg ggaatgtaat tcagctccgc catcgccgct    6540
tccacttttt cccgcgtttt cgcagaaacg tggctggcct ggttcaccac gcgggaaacg    6600
gtctgataag agacaccggc atactctgcg acatcgtata acgttactgg tttcacattc    6660
```

```
accaccctga attgactctc ttccgggcgc tatcatgcca taccgcgaaa ggttttgcac    6720
cattcgatgg tgtcaacgta aatgcatgcc gcttgggagg cagataggta ggcatggccc    6780 ccatttcaa  tacaagcaac gcatgagaaa gcccccggaa gatcaccttc cgggggcttt    6840
tttattgcgc tccggcaatt aaaaaagcgg ctaaccacgc cgctttttt  acgtctgcag    6900 gcgaattgat ctggtttgac agcttatcac caagccagtt acctcggttc aaagagttgg    6960
tagctcagag aaccttcgaa aaaccgccct gcaaggcggt ttttcgttt  tcagagcaag    7020 agattacgcg cagaccaaaa cgatctcaag aagatcatct tattaatcag ataaaatatt    7080
ataaatgtga gcggataaca ttgacattgt gagcggataa caagatactg agcacatcag    7140
caggtttcac acaggaaaac tagtatggac aagaagtaca gcatcggcct ggccatcggc    7200
accaactctg tgggctgggc cgtgatcacc gacgagtaca aggtgcccag caagaaattc    7260
aaggtgctgg gcaacaccga ccggcacagc atcaagaaga acctgatcgg cgccctgctg    7320
ttcgacagcg gagaaacagc cgaggccacc cggctgaaga gaaccgccag aagaagatac    7380
accagacgga agaaccggat ctgctatctg caagagatct tcagcaacga gatggccaag    7440
gtggacgaca gcttcttcca cagactggaa gagtccttcc tggtggaaga ggataagaag    7500
cacgagcggc accccatctt cggcaacatc gtggacgagg tggcctacca cgagaagtac    7560
cccaccatct accacctgag aaagaaactg gtggacagca ccgacaaggc cgacctgcgg    7620
ctgatctatc tggccctggc ccacatgatc aagttccggg gccacttcct gatcgagggc    7680
gacctgaacc ccgacaacag cgacgtggac aagctgttca tccagctggt gcagacctac    7740
aaccagctgt tcgaggaaaa ccccatcaac gccagcggcg tggacgccaa ggccatcctg    7800
tctgccagac tgagcaagag cagacggctg gaaaatctga tcgcccagct gcccggcgag    7860
aagaagaatg gcctgttcgg caacctgatt gccctgagcc tgggcctgac ccccaacttc    7920
aagagcaact tcgacctggc cgaggatgcc aaactgcagc tgagcaagga cacctacgac    7980
gacgacctgg acaacctgct ggcccagatc ggcgaccagt acgccgacct gtttctggcc    8040
gccaagaacc tgtccgacgc catcctgctg agcgacatcc tgagagtgaa caccgagatc    8100
accaaggccc ccctgagcgc ctctatgatc aagagatacg acgagcacca ccaggacctg    8160
accctgctga aagctctcgt gcggcagcag ctgcctgaga agtacaaaga gatttcttc    8220 gaccagagca agaacggcta cgccggctac atcgatggcg gagccagcca ggaagagttc    8280
tacaagttca tcaagcccat cctggaaaag atggacggca ccgaggaact gctcgtgaag    8340
ctgaacagag gacctgctt gcggaagcag cggaccttcg acaacggcag catcccccac    8400
cagatccacc tgggagagct gcacgccatt ctgcggcggc aggaagattt ttacccattc    8460
ctgaaggaca accgggaaaa gatcgagaag atcctgacct tccgcatccc ctactacgtg    8520
ggccctctgg ccaggggaaa cagcagattc gcctggatga ccagaaagag cgaggaaacc    8580
atcaccccct ggaacttcga ggaagtggtg gacaagggcg ccagcgccca gagcttcatc    8640
gagcggatga ccaacttcga taagaacctg cccaacgaga aggtgctgcc caagcacagc    8700
ctgctgtacg agtacttcac cgtgtacaac gagctgacca agtgaaaata cgtgaccgag    8760
ggaatgagaa agcccgcctt cctgagcggc gagcagaaaa agccatcgt  ggacctgctg    8820 ttcaagacca accggaaagt gaccgtgaag cagctgaaag aggactactt caagaaaatc    8880
gagtgcttcg actccgtgga aatctccggc gtgaagatc  ggttcaacgc ctccctgggc    8940
acataccacg atctgctgaa aattatcaag gacaaggact cctggacaa  tgaggaaaac    9000
```

```
gaggacattc tggaagatat cgtgctgacc ctgacactgt ttgaggacag agagatgatc    9060
gaggaacggc tgaaaaccta tgcccacctg ttcgacgaca aagtgatgaa gcagctgaag    9120
cggcggagat acaccggctg gggcaggctg agccggaagc tgatcaacgg catccgggac    9180
aagcagtccg gcaagacaat cctggatttc ctgaagtccg acggcttcgc caacagaaac    9240
ttcatgcagc tgatccacga cgacagcctg acctttaaag aggacatcca gaaagcccag    9300
gtgtccggcc agggcgatag cctgcacgag cacattgcca atctggccgg cagccccgcc    9360
attaagaagg gcatcctgca gacagtgaag gtggtggacg agctcgtgaa agtgatgggc    9420
cggcacaagc ccgagaacat cgtgatcgaa atggccagag agaaccagac cacccagaag    9480
ggacagaaga acagccgcga gagaatgaag cggatcgaag agggcatcaa agagctgggc    9540
agccagatcc tgaaagaaca ccccgtggaa acacccagc tgcagaacga gaagctgtac    9600
ctgtactacc tgcagaatgg gcgggatatg tacgtggacc aggaactgga catcaaccgg    9660
ctgtccgact acgatgtgga cgctatcgtg cctcagagct ttctgaagga cgactccatc    9720
gataacaaag tgctgactcg gagcgacaag aaccggggca gagcgacaa cgtgccctcc    9780 gaagaggtcg tgaagaagat gaagaactac tggcgccagc tgctgaatgc caagctgatt    9840
acccagagga agttcgacaa tctgaccaag gccgagagag cggcctgag cgaactggat    9900 aaggccggct tcatcaagag acagctggtg gaaacccggc agatcacaaa gcacgtggca    9960
cagatcctgg actcccggat gaacactaag tacgacgaga cgacaaact gatccgggaa    10020 gtgaaagtga tcaccctgaa gtccaagctg gtgtccgatt tccggaagga tttccagttt    10080
tacaaagtgc gcgagatcaa caactaccac cacgcccacg acgcctacct gaacgccgtc    10140
gtgggaaccg ccctgatcaa aaagtaccct aagctggaaa gcgagttcgt gtacggcgac    10200
tacaaggtgt acgacgtgcg gaagatgatc gccaagagcg agcaggaaat cggcaaggct    10260
accgccaagt acttcttcta cagcaacatc atgaactttt tcaagaccga gattaccctg    10320
gccaacggcg agatccggaa gcggcctctg atcgagacaa acggcgaaac aggcgagatc    10380
gtgtgggata agggccggga ctttgccacc gtgcggaaag tgctgtctat gccccaagtg    10440
aatatcgtga aaaagaccga ggtgcagaca ggcggcttca gcaaagagtc tatcctgccc    10500
aagaggaaca gcgacaagct gatcgccaga aagaaggact gggaccctaa gaagtacggc    10560
ggcttcgaca cccccaccgt ggcctattct gtgctggtgg tggccaaagt ggaaaagggc    10620
aagtccaaga aactgaagag tgtgaaagag ctgctgggga tcaccatcat ggaaagaagc    10680
agcttcgaga gaatcccat cgactttctg gaagccaagg ctacaaaga agtgaaaaag    10740 gacctgatca tcaagctgcc taagtactcc ctgttcgagc tggaaaacgg ccggaagaga    10800
atgctggcct ctgccggcga actgcagaag ggaaacgaac tggccctgcc ctccaaatat    10860
gtgaacttcc tgtacctggc cagccactat gagaagctga agggctcccc cgaggataat    10920
gagcagaaac agctgtttgt ggaacagcac aaacactacc tggacgagat catcgagcag    10980
atcagcgagt tctccaagag agtgatcctg gccgacgcta tctggacaa ggtgctgagc    11040 gcctacaaca gcacagaga caagcctatc agagagcagg ccgagaatat catccacctg    11100 tttacccctga ccaatctggg agccctgcc gccttcaagt actttgacac caccatcgac    11160
cggaagaggt acaccagcac caaagaggtg ctggacgcca cctgatcca ccagagcatc    11220 accggcctgt acgagacacg gatcgacctg tctcagctgg aggcgacgc ggccgcggag    11280 cagaaactca tctctgaaga agatctggaa caaaagttga tttcagaaga agatctggaa    11340
cagaagctca tctctgagga agatctgtaa taaggcgcgc ctccttaatg ggacttgcag    11400
```

```
cctcggtacc aaattccaga aaagacaccc gaaagggtgt tttttcgttt tggtcccaca    11460
gaatgagcat catggctcta gtcgacatcg gagaagagta cggctctttt aaccgcctca    11520
agaaccagat aagtgaaatc tagttccaaa ctattttgtc attttttaatt ttcgtattag   11580 cttacgacgc tacacccagt tcccatctat tttgtcactc ttccctaaat aatccttaaa    11640
aactccattt ccacccctcc cagttcccaa ctattttgtc cgcccacagc ggggcatttt    11700
tcttcctgtt atgtttgggc gctgcattaa tgaatcggcc aacgcgcggg gagaggcggt    11760
ttgcgtattg ggcgctcttc cgcttcctcg ctcactgacc cgctgcgctc ggtcgttcgg    11820
ctgcggcgag cggtatcag                                                 11839

<210> SEQ ID NO 10
<211> LENGTH: 11987
<212> TYPE: DNA
<213> ORGANISM: Artificial sequence
<220> FEATURE:
<223> OTHER INFORMATION: Synthetic construct

<400> SEQUENCE: 10
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg atacaccaa ggaaagtcta cacgaaccct ttggcaaaat cctgtatatc      180
gtgcgaaaaa ggatggatat accgaaaaaa tcgctataat gaccccgaag cagggttatg     240
cagcggaaag tataccttaa ggaatcccct gataacgcag gaaagaacat gtgagcaaaa     300
ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagcttat atattctttt ttttcttata aacttaaaa      540 ccttagaggc tatttaagtt gctgatttat attaatttta ttgttcaaac atgagagctt     600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaaatgaagt tttaaatcaa     840
tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140
tgactccccg tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
```

-continued

```
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggccctt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa aatcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagcgc cttttgaagc tgatgctcga gtcatttcga    3180
accccagagt cccgctcaga agaactcgtc aagaaggcga tagaaggcga tgcgctgcga    3240
atcgggagcg gcgataccgt aaagcacgag gaagcggtca gcccattcgc cgccaagctc    3300
ttcagcaata tcacgggtag ccaacgctat gtcctgatag cggtccgcca cacccagccg    3360
gccacagtcg atgaatccag aaaagcggcc attttccacc atgatattcg gcaagcaggc    3420
atcgccatgg gtcacgacga gatcctcgcc gtcgggcatg cgcgccttga gcctggcgaa    3480
cagttcggct ggcgcgagcc cctgatgctc ttcgtccaga tcatcctgat cgacaagacc    3540
ggcttccatc cgagtacgtg ctcgctcgat gcgatgtttc gcttggtggt cgaatgggca    3600
ggtagccgga tcaagcgtat gcagccgccg cattgcatca gccatgatgg atactttctc    3660
ggcaggagca aggtgagatg acaggagatc ctgccccggc acttcgccca atagcagcca    3720
gtcccttccc gcttcagtga caacgtcgag cacagctgcg caaggaacgc ccgtcgtggc    3780
cagccacgat agccgcgctg cctcgtcctg cagttcattc agggcaccgg acaggtcggt    3840
cttgacaaaa agaaccgggc gcccctgcgc tgacagccgg aacacggcgg catcagagca    3900
gccgattgtc tgttgtgccc agtcatagcc gaatagcctc tccacccaag cggccggaga    3960
```

-continued

```
acctgcgtgc aatccatctt gttcaatcat gcgaaacgat cctcatcctg tctcttgatc    4020
agatcttgat cccctgcgcc atcagatcct tggcggcaag aaagccatcc agttttgagc    4080
gcatacgcta cttgcattac agtttacgaa ccgaacaggc ttatgtcaac tgggttcgtg    4140
ccttcatccg tttccacggt ctcgagagtt caacagacag ccttcgttct tatggccgtt    4200
caggaggaag ttcctattcc gaagttccta ttctctagaa agtataggaa cttcttgaga    4260
agagaaaaga aaaccgccga tcctgtccac cgcattactg caaggtagtg acaagaccg     4320 gcggtcttaa gttttttggc tgaaacgaat gacgaaaagg ctgtctgagc aaatccagga    4380
ggtcgttttt attaagcacc ggtggagtga cgaccttcag cacgttcgta ctgttcaacg    4440
atggtgtagt cttcgttgtg ggaggtgatg tccagtttga tgtcggtttt gtaagcaccc    4500
ggcagctgaa ccggtttttt agccatgtag gtggttttaa cttcagcgtc gtagtgacca    4560
ccgtctttca gtttcagacg cattttgatt tcacctttca gagcaccgtc ttccgggtac    4620
atacgttcgg tggaagcttc ccaacccatg gttttttct gcataaccgg accgtcggac     4680
gggaagttgg taccacgcag tttaactttg tagatgaact caccgtcttg cagggaggag    4740
tcctgggtaa cggtaacaac accaccgtct tcgaagttca taacacgttc ccatttgaaa    4800
ccttccggga aggacagttt caggtagtcc gggatgtcag ccgggtgttt aacgtaagct    4860
ttggaaccgt actggaactg cggggacagg atgtcccaag cgaacggcag cggaccacct    4920
ttggtaactt tcagtttagc ggtctgggta ccttcgtacg gacgaccttc accttcacct    4980
tcgatttcga actcgtgacc gttaacggaa ccttccatac gaactttgaa acgcatgaac    5040
tctttgataa cgtcttcgct actcgccatg gtacctttct cctctttaat taattcagat    5100
ctattatacc taggactgag ctagctgtca aattcaccac cctgaattga ctctcaaacc    5160
gtattagccc ggtattttgg aaatagcgga agcactgact tttgttatca ataaaaaagg    5220
ccccccgtta gggaggcctt attgttcgtc tactcggaag agcgagagac aacagaacgg    5280
tcagccacat gaattcaaaa aaaaagcacc gactcggtgc cacttttca agttgataac     5340 ggactagcct tatttaaact tgctatgctg tttccagcat agctcttaaa cagaccgcta    5400
aactgaaagt tactagaagt atcttgttat ccgctcacaa tgtcaatgtt atccgctcac    5460
atttatagat cttttaggaat tctttcagct cagtcgatag gtagtaggca agagtagtcg    5520
cacctttggt cgaaaaaaaa agcccgcact gtcaggtgcg ggcttttttc tgtgtttccc    5580
caaaagtaaa aacccgccga agcgggtttt tacgtaaaac aggtgaaact gaccagacga    5640
gaaggctttg gaggtgataa tggggctcaa ggacccatggg gtgcctaatg agtgagctaa    5700
ctcacattaa ttgcgttgcg ctcactgccc gctttccagt cgggaaacct gtcgtgccag    5760
ctgcattaat gaatcggcca acgcgcgggg agaggcggtt tgcgtattgg cgccagggt     5820 ggttttttctt ttcaccagtg agacgggcaa cagctgattg cccttcaccg cctggccctg    5880
agagagttgc agcaagcggt ccacgctggt ttgccccagc aggcgaaaat cctgtttgat    5940
ggtggttaac ggcgggatat aacatgagct gtcttcggta tcgtcgtatc ccactaccga    6000
gatatccgca ccaacgcgca gcccggactc ggtaatggcg cgcattgcgc ccagcgccat    6060
ctgatcgttg gcaaccagca tcgcagtggg aacgatgccc tcattcagca tttgcatggt    6120
ttgttgaaaa ccggacatgg cactccagtc gccttcccgt tccgctatcg gctgaatttg    6180
attgcgagtg agatatttat gccagccagc cagacgcaga cgcgccgaga cagaacttaa    6240
tgggcccgct aacagcgcga tttgctggtg acccaatgcg accagatgct ccacgcccag    6300
```

```
tcgcgtaccg tcttcatggg agaaaataat actgttgatg ggtgtctggt cagagacatc    6360
aagaaataac gccggaacat tagtgcaggc agcttccaca gcaatggcat cctggtcatc    6420
cagcggatag ttaatgatca gcccactgac gcgttgcgcg agaagattgt gcaccgccgc    6480
tttacaggct tcgacgccgc ttcgttctac catcgacacc accacgctgg cacccagttg    6540
atcggcgcga gatttaatcg ccgcgacaat ttgcgacggc gcgtgcaggg ccagactgga    6600
ggtggcaacg ccaatcagca acgactgttt gcccgccagt tgttgtgcca cgcggttggg    6660
aatgtaattc agctccgcca tcgccgcttc cacttttttcc cgcgttttcg cagaaacgtg    6720
gctggcctgg ttcaccacgc gggaaacggt ctgataagag acaccggcat actctgcgac    6780
atcgtataac gttactggtt tcacattcac caccctgaat tgactctctt ccgggcgcta    6840
tcatgccata ccgcgaaagg ttttgcacca ttcgatggtg tcaacgtaaa tgcatgccgc    6900
ttgggaggca gataggtagg catggccccc attttcaata caagcaacgc atgagaaagc    6960
ccccggaaga tcaccttccg ggggcttttt tattgcgctc cggcaattaa aaaagcggct    7020
aaccacgccg cttttttttac gtctgcaggc gaattgatct ggtttgacag cttatcacca    7080
agccagttac ctcggttcaa agagttggta gctcagagaa ccttcgaaaa accgccctgc    7140
aaggcggttt tttcgttttc agagcaagag attacgcgca gaccaaaacg atctcaagaa    7200
gatcatctta ttaatcagat aaaatattat aaatgtgagc ggataacatt gacattgtga    7260
gcggataaca agatactgag cacatcagca ggtttcacac aggaaaacta gtatggataa    7320
gaaatactca ataggcttag ctatcggcac aaatagcgtc ggatgggcgg tgatcactga    7380
tgaatataag gttccgtcta aaaagttcaa ggttctggga aatacagacc gccacagtat    7440
caaaaaaaat cttatagggg ctcttttatt tgacagtgga gagacagcgg aagcgactcg    7500
tctcaaacgg acagctcgta gaaggtatac acgtcggaag aatcgtattt gttatctaca    7560
ggagattttt tcaaatgaga tggcgaaagt agatgatagt ttctttcatc gacttgaaga    7620 gtctttttg gtggaagaag acaagaagca tgaacgtcat cctatttttg gaaatatagt    7680
agatgaagtt gcttatcatg agaaatatcc aactatctat catctgcgaa aaaaattggt    7740
agattctact gataaagcgg attttgcgctt aatctatttg gccttagcgc atatgattaa    7800
gtttcgtggt cattttttga ttgagggaga tttaaatcct gataatagtg atgtggacaa    7860
actatttatc cagttggtac aaacctacaa tcaattattt gaagaaaacc ctattaacgc    7920
aagtggagta gatgctaaag cgattctttc tgcacgattg agtaaatcaa gacgattaga    7980
aaatctcatt gctcagctcc ccggtgagaa gaaaaatggc ttatttggga atctcattgc    8040
tttgtcattg ggtttgaccc ctaatttttaa atcaaatttt gatttggcag aagatgctaa    8100
attacagctt tcaaaagata cttacgatga tgatttagat aatttattgg cgcaaattgg    8160
agatcaatat gctgatttgt ttttggcagc taagaattta tcagatgcta ttttactttc    8220
agatatccta agagtaaata ctgaaataac taaggctccc ctatcagctt caatgattaa    8280
acgctacgat gaacatcatc aagacttgac tcttttaaaa gctttagttc gacaacaact    8340
tccagaaaag tataaagaaa tcttttttga tcaatcaaaa aacggatatg caggttatat    8400
tgatggggga gctagccaag aagaatttta taaatttatc aaaccaattt tagaaaaaat    8460
ggatggtact gaggaattat tggtgaaact aaatcgtgaa gatttgctgc gcaagcaacg    8520
gacctttgac aacggctcta ttccccatca aattcacttg ggtgagctgc atgctatttt    8580
gagaagacaa aagactttt atccattttt aaaagacaat cgtgagaaga ttgaaaaaat    8640
cttgactttt cgaatcccct tattatgttgg tccattggcg cgtggcaata gtcgttttgc    8700
```

```
atggatgact cggaagtctg aagaaacaat tacccatgg aattttgaag aagttgtcga    8760
taaaggtgct tcagctcaat catttattga acgcatgaca aactttgata aaaatcttcc    8820
aaatgaaaaa gtactaccaa aacatagttt gctttatgag tattttacgg tttataacga    8880
attgacaaag gtcaaatatg ttactgaagg aatgcgaaaa ccagcatttc tttcaggtga    8940
acagaagaaa gccattgttg atttactctt caaaacaaat cgaaaagtaa ccgttaagca    9000
attaaaagaa gattatttca aaaaaataga atgttttgat agtgttgaaa tttcaggagt    9060
tgaagataga tttaatgctt cattaggtac ctaccatgat ttgctaaaaa ttattaaaga    9120
taaagatttt ttggataatg aagaaaatga agatatctta gaggatattg ttttaacatt    9180
gaccttattt gaagataggg agatgattga ggaaagactt aaaacatatg ctcacctctt    9240
tgatgataag gtgatgaaac agcttaaacg tcgccgttat actggttggg gacgtttgtc    9300
tcgaaaattg attaatggta ttagggataa gcaatctggc aaaacaatat tagatttttt    9360
gaaatcagat ggttttgcca atcgcaattt tatgcagctg atccatgatg atagtttgac    9420
atttaaagaa gacattcaaa aagcacaagt gtctggacaa ggcgatagtt tacatgaaca    9480
tattgcaaat ttagctggta gccctgctat taaaaaggt attttacaga ctgtaaaagt    9540
tgttgatgaa ttggtcaaag taatggggcg gcataagcca gaaaatatcg ttattgaaat    9600
ggcacgtgaa aatcagacaa ctcaaaaggg ccagaaaaat tcgcgagagc gtatgaaacg    9660
aatcgaagaa ggtatcaaag aattaggaag tcagattctt aaagagcatc ctgttgaaaa    9720
tactcaattg caaaatgaaa agctctatct ctattatctc caaaatggaa gagacatgta    9780
tgtggaccaa gaattagata ttaatcgttt aagtgattat gatgtcgatg ccattgttcc    9840
acaaagtttc cttaaagacg attcaataga caataaggtc ttaacgcgtt ctgataaaaa    9900
tcgtggtaaa tcggataacg ttccaagtga agaagtagtc aaaaagatga aaaactattg    9960
gagacaactt ctaaacgcca agttaatcac tcaacgtaag tttgataatt taacgaaagc    10020
tgaacgtgga ggtttgagtg aacttgataa agctggtttt atcaaacgcc aattggttga    10080
aactcgccaa atcactaagc atgtggcaca aattttggat agtcgcatga atactaaata    10140
cgatgaaaat gataaactta ttcgagaggt taaagtgatt accttaaaat ctaaattagt    10200
ttctgacttc cgaaaagatt tccaattcta taaagtacgt gagattaaca attaccatca    10260
tgcccatgat gcgtatctaa atgccgtcgt tggaactgct ttgattaaga atatccaaa    10320 acttgaatcg gagtttgtct atggtgatta taaagtttat gatgttcgta aaatgattgc    10380
taagtctgag caagaaatag gcaaagcaac cgcaaaatat ttcttttact ctaatatcat    10440
gaacttcttc aaaacagaaa ttacacttgc aaatggagag attcgcaaac gccctctaat    10500
cgaaactaat gggaaactg gagaaattgt ctgggataaa gggcgagatt ttgccacagt    10560
gcgcaaagta ttgtccatgc cccaagtcaa tattgtcaag aaaacagaag tacagacagg    10620
cggattctcc aaggagtcaa ttttaccaaa agaaattcg acaagctta ttgctcgtaa    10680 aaaagactgg gatccaaaaa aatatggtgg ttttgatagt ccaacggtag cttattcagt    10740
cctagtggtt gctaaggtgg aaaaagggaa atcgaagaag ttaaaatccg ttaaagagtt    10800
actagggatc acaattatgg aaagaagttc ctttgaaaaa atccgattg acttttaga    10860 agctaaagga tataaggaag ttaaaaaaga cttaatcatt aaactaccta aatatagtct    10920
ttttgagtta gaaaacggtc gtaaacggat gctggctagt gccggagaat acaaaaagg    10980 aaatgagctg gctctgccaa gcaaatatgt gaattttta tatttagcta gtcattatga    11040
```

| | | | | | |
|---|---|---|---|---|---|
| aaagttgaag | ggtagtccag | aagataacga | acaaaaacaa | ttgtttgtgg | agcagcataa | 11100 |
| gcattattta | gatgagatta | ttgagcaaat | cagtgaattt | tctaagcgtg | ttattttagc | 11160 |
| agatgccaat | ttagataaag | ttcttagtgc | atataacaaa | catagagaca | aaccaatacg | 11220 |
| tgaacaagca | gaaatatta | ttcatttatt | tacgttgacg | aatcttggag | ctcccgctgc | 11280 |
| ttttaaatat | tttgatacaa | caattgatcg | taaacgatat | acgtctacaa | aagaagtttt | 11340 |
| agatgccact | cttatccatc | aatccatcac | tggtctttat | gaaacacgca | ttgatttgag | 11400 |
| tcagctagga | ggtgacgcgg | ccgcggagca | gaaactcatc | tctgaagaag | atctggaaca | 11460 |
| aaagttgatt | tcagaagaag | atctggaaca | gaagctcatc | tctgaggaag | atctgtaata | 11520 |
| aggcgcgcct | ccttaatggg | acttgcagcc | tcggtaccaa | attccagaaa | agacacccga | 11580 |
| aagggtgttt | tttcgttttg | gtcccacaga | atgagcatca | tggctctagt | cgacatcgga | 11640 |
| gaagagtacg | gctcttttaa | ccgcctcaag | aaccagataa | gtgaaatcta | gttccaaact | 11700 |
| attttgtcat | ttttaattt | cgtattagct | tacgacgcta | cacccagttc | ccatctattt | 11760 |
| tgtcactctt | ccctaaataa | tccttaaaaa | ctccatttcc | acccctccca | gttcccaact | 11820 |
| attttgtccg | cccacagcgg | ggcattttc | ttcctgttat | gtttgggcgc | tgcattaatg | 11880 |
| aatcggccaa | cgcgcgggga | gaggcggttt | gcgtattggg | cgctcttccg | cttcctcgct | 11940 |
| cactgacccg | ctgcgctcgg | tcgttcggct | gcggcgagcg | gtatcag | | 11987 |

<210> SEQ ID NO 11
<211> LENGTH: 11987
<212> TYPE: DNA
<213> ORGANISM: Artificial sequence
<220> FEATURE:
<223> OTHER INFORMATION: Synthetic construct

<400> SEQUENCE: 11

| | | | | | |
|---|---|---|---|---|---|
| agcttatcgg | ccagcctcgc | agagcaggat | tcccgttgag | caccgccagg | tgcgaataag | 60 |
| ggacagtgaa | gaaggaacac | ccgctcgcgg | gtgggcctac | ttcacctatc | ctgcccggct | 120 |
| gacgccgttg | gatacaccaa | ggaaagtcta | cacgaaccct | ttggcaaaat | cctgtatatc | 180 |
| gtgcgaaaaa | ggatggatat | accgaaaaaa | tcgctataat | gaccccgaag | cagggttatg | 240 |
| cagcggaaag | tataccttaa | ggaatcccct | gataacgcag | gaaagaacat | gtgagcaaaa | 300 |
| ggccagcaaa | aggccaggaa | ccgtaaaaag | gccgcactcc | ctgcctctgt | catcacgata | 360 |
| ctgtgatgcc | atggctaatt | cccatgtcag | ccgttaagtg | ttcctgtgtc | actcaaaatt | 420 |
| gctttgagag | gctctaaggg | cttctcagtg | cgttacatcc | ctggcttgtt | gtccacaacc | 480 |
| gttaaacctt | aaaagcttta | aaagccttat | atattctttt | ttttcttata | aaacttaaaa | 540 |
| ccttagaggc | tatttaagtt | gctgatttat | attaatttta | ttgttcaaac | atgagagctt | 600 |
| agtacgtgaa | acatgagagc | ttagtacgtt | agccatgaga | gcttagtacg | ttagccatga | 660 |
| gggtttagtt | cgttaaacat | gagagcttag | tacgttaaac | atgagagctt | agtacgtgaa | 720 |
| acatgagagc | ttagtacgta | ctatcaacag | gttgaactgc | tgatcttcag | atcctctacg | 780 |
| ccggacgcat | cgtggccgga | tcttgcggcc | gcaaaaatta | aaaatgaagt | tttaaatcaa | 840 |
| tctaaagtat | atatgagtaa | acttggtctg | acagttacca | atgcttaatc | agtgaggcac | 900 |
| caataactgc | ctttgatctt | ttctacgggg | tctgacgctc | agtggaacga | aaactcacgt | 960 |
| taagggattt | tggtcatgag | attatcaaaa | aggatcttca | cctagatcct | tttaaattaa | 1020 |
| aaatgaagtt | ttaaatcaat | ctaaagtata | tatgagtaaa | cttggtctga | cagttaccaa | 1080 |
| tgcttaatca | gtgaggcacc | tatctcagcg | atctgtctat | ttcgttcatc | catagttgcc | 1140 |

```
tgactcccct tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg aataagggc gacacggaaa    1920 tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggccctt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa aatcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700
aaagaggggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt ttttattgg tgagaatcca agctagactg cgatgagtgg    2880
cagggcgggg cgtaatttt taaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gtcatttcga    3180
accccagagt cccgctcaga agaactcgtc aagaaggcga tagaaggcga tgcgctgcga    3240
atcgggagcg gcgataccgt aaagcacgag gaagcggtca gcccattcgc cgccaagctc    3300
ttcagcaata tcacgggtag ccaacgctat gtcctgatag cggtccgcca cacccagccg    3360
gccacagtcg atgaatccag aaaagcggcc attttccacc atgatattcg gcaagcaggc    3420
atcgccatgg gtcacgacga gatcctcgcc gtcgggcatg cgcgccttga gcctggcgaa    3480
```

```
cagttcggct ggcgcgagcc cctgatgctc ttcgtccaga tcatcctgat cgacaagacc   3540
ggcttccatc cgagtacgtg ctcgctcgat gcgatgtttc gcttggtggt cgaatgggca   3600
ggtagccgga tcaagcgtat gcagccgccg cattgcatca gccatgatgg atactttctc   3660
ggcaggagca aggtgagatg acaggagatc ctgccccggc acttcgccca atagcagcca   3720
gtcccttccc gcttcagtga acgtcgag cacagctgcg caaggaacgc ccgtcgtggc   3780
cagccacgat agccgcgctg cctcgtcctg cagttcattc agggcaccgg acaggtcggt   3840
cttgacaaaa agaaccgggc gccctgcgc tgacagccgg aacacggcgg catcagagca   3900
gccgattgtc tgttgtgccc agtcatagcc gaatagcctc tccacccaag cggcggaga   3960 acctgcgtgc aatccatctt gttcaatcat gcgaaacgat cctcatcctg tctcttgatc   4020
agatcttgat ccctgcgcc atcagatcct tggcggcaag aaagccatcc agttttgagc   4080
gcatacgcta cttgcattac agtttacgaa ccgaacaggc ttatgtcaac tgggttcgtg   4140
ccttcatccg tttccacggt ctcgagagtt caacagacag ccttcgttct tatggccgtt   4200
caggaggaag ttcctattcc gaagttccta ttctctagaa agtataggaa cttcttgaga   4260
agagaaaaga aaaccgccga tcctgtccac cgcattactg caaggtagtg dacaagaccg   4320
gcggtcttaa gttttttggc tgaaacgaat gacgaaaagg ctgtctgagc aaatccagga   4380
ggtcgttttt attaagcacc ggtggagtga cgaccttcag cacgttcgta ctgttcaacg   4440
atggtgtagt cttcgttgtg ggaggtgatg tccagtttga tgtcggtttt gtaagcaccc   4500
ggcagctgaa ccggtttttt agccatgtag gtggttttaa cttcagcgtc gtagtgacca   4560
ccgtctttca gttcagacg catttgatt tcacctttca gagcaccgtc ttccgggtac   4620
atacgttcgg tggaagcttc ccaacccatg gttttttct gcataaccgg accgtcggac   4680
gggaagttgg taccacgcag tttaactttg tagatgaact caccgtcttg cagggaggag   4740
tcctgggtaa cggtaacaac accaccgtct tcgaagttca taacacgttc ccatttgaaa   4800
ccttccggga aggacagttt caggtagtcc gggatgtcag ccgggtgttt aacgtaagct   4860
ttggaaccgt actggaactg cggggacagg atgtcccaag cgaacggcag cggaccacct   4920
ttggtaactt tcagtttagc ggtctgggta ccttcgtacg gacgaccttc accttcacct   4980
tcgatttcga actcgtgacc gttaacggaa ccttccatac gaactttgaa acgcatgaac   5040
tctttgataa cgtcttcgct actcgccatg gtacctttct cctctttaat taattcagat   5100
ctattatacc taggactgag ctagctgtca aattcaccac cctgaattga ctctcaaacc   5160
gtattagccc ggtattttgg aaatagcgga agcactgact tttgttatca ataaaaaagg   5220 cccccgtta gggaggcctt attgttcgtc tactcggaag agcgagagac aacagaacgg   5280
tcagccacat gaattcaaaa aaaaagcacc gactcggtgc cacttttca agttgataac   5340 ggactagcct tatttaaact tgctatgctg tttccagcat agctcttaaa cagaccgcta   5400
aactgaaagt tactagaagt atcttgttat ccgctcacaa tgtcaatgtt atccgctcac   5460
atttatagat ctttaggaat tctttcagct cagtcgtag gtagtaggca agagtagtcg   5520
cacctttggt cgaaaaaaa agcccgcact gtcaggtgcg gcttttttc tgtgtttccc   5580 caaaagtaaa aacccgccga agcgggtttt tacgtaaaac aggtgaaact gaccagacga   5640
gaaggctttg gaggtgataa tggggctcaa ggaccctggg gtgcctaatg agtgagctaa   5700
ctcacattaa ttgcgttgcg ctcactgccc gctttccagt cgggaaacct gtcgtgccag   5760
ctgcattaat gaatcggcca acgcgcgggg agaggcggtt tgcgtattgg gcgccagggt   5820
ggttttcctt ttcaccagtg agacgggcaa cagctgattg cccttcaccg cctggccctg   5880
```

```
agagagttgc agcaagcggt ccacgctggt ttgccccagc aggcgaaaat cctgtttgat    5940
ggtggttaac ggcgggatat aacatgagct gtcttcggta tcgtcgtatc ccactaccga    6000
gatatccgca ccaacgcgca gcccggactc ggtaatggcg cgcattgcgc ccagcgccat    6060
ctgatcgttg gcaaccagca tcgcagtggg aacgatgccc tcattcagca tttgcatggt    6120
ttgttgaaaa ccggacatgg cactccagtc gccttcccgt tccgctatcg gctgaatttg    6180
attgcgagtg agatatttat gccagccagc cagacgcaga cgcgccgaga cagaacttaa    6240
tgggcccgct aacagcgcga tttgctggtg acccaatgcg accagatgct ccacgcccag    6300
tcgcgtaccg tcttcatggg agaaaataat actgttgatg ggtgtctggt cagagacatc    6360
aagaaataac gccggaacat tagtgcaggc agcttccaca gcaatggcat cctggtcatc    6420
cagcggatag ttaatgatca gcccactgac gcgttgcgcg agaagattgt gcaccgccgc    6480
tttacaggct tcgacgccgc ttcgttctac catcgacacc accacgctgg cacccagttg    6540
atcggcgcga gatttaatcg ccgcgacaat ttgcgacggc gcgtgcaggg ccagactgga    6600
ggtggcaacg ccaatcagca acgactgttt gcccgccagt tgttgtgcca cgcggttggg    6660
aatgtaattc agctccgcca tcgccgcttc cacttttttcc cgcgttttcg cagaaacgtg    6720
gctggcctgg ttcaccacgc gggaaacggt ctgataagag acaccggcat actctgcgac    6780
atcgtataac gttactggtt tcacattcac caccctgaat tgactctctt ccgggcgcta    6840
tcatgccata ccgcgaaagg ttttgcacca ttcgatggtg tcaacgtaaa tgcatgccgc    6900
ttgggaggca gataggtagg catggccccc attttcaata caagcaacgc atgagaaagc    6960
ccccggaaga tcaccttccg ggggcttttt tattgcgctc cggcaattaa aaaagcggct    7020
aaccacgccg ctttttttac gtctgcaggc gaattgatct ggtttgacag cttatcacca    7080
agccagttac ctcggttcaa agagttggta gctcagagaa ccttcgaaaa accgccctgc    7140
aaggcggttt tttcgttttc agagcaagag attacgcgca gaccaaaacg atctcaagaa    7200
gatcatctta ttaatcagat aaaatattat aaatgtgagc ggataacatt gacattgtga    7260
gcggataaca agatactgag cacatcagca ggtttcacac aggaaaacta gtatggacaa    7320
gaagtacagc atcggcctgg ccatcggcac caactctgtg ggctgggccg tgatcaccga    7380
cgagtacaag gtgcccagca agaaattcaa ggtgctgggc aacaccgacc ggcacagcat    7440
caagaagaac ctgatcggcg ccctgctgtt cgacagcgga gaaacagccg aggccacccg    7500
gctgaagaga accgccagaa gaagatacac cagacggaag aaccggatct gctatctgca    7560
agagatcttc agcaacgaga tggccaaggt ggacgacagc ttcttccaca ctggaagaa    7620
gtccttcctg gtggaagagg ataagaagca cgagcggcac cccatcttcg gcaacatcgt    7680
ggacgaggtg gcctaccacg agaagtaccc caccatctac cacctgagaa agaaactggt    7740
ggacagcacc gacaaggccg acctgcggct gatctatctg gccctggccc acatgatcaa    7800
gttccggggc cacttcctga tcgagggcga cctgaacccc gacaacagcg acgtggacaa    7860
gctgttcatc cagctggtgc agacctacaa ccagctgttc gaggaaaacc ccatcaacgc    7920
cagcggcgtg gacgccaagg ccatcctgtc tgccagactg agcaagagca gacgcctgga    7980
aaatctgatc gcccagctgc ccggcgagaa gaagaatggc tgttcggca acctgattgc    8040
cctgagcctg ggcctgaccc ccaacttcaa gagcaacttc gacctggccg aggatgccaa    8100
actgcagctg agcaaggaca cctacgacga cgacctggac aacctgctgg cccagatcgg    8160
cgaccagtac gccgacctgt ttctggccgc caagaacctg tccgacgcca tcctgctgag    8220
```

```
cgacatcctg agagtgaaca ccgagatcac caaggccccc ctgagcgcct ctatgatcaa    8280
gagatacgac gagcaccacc aggacctgac cctgctgaaa gctctcgtgc ggcagcagct    8340
gcctgagaag tacaaagaga ttttcttcga ccagagcaag aacggctacg ccggctacat    8400
cgatggcgga gccagccagg aagagttcta caagttcatc aagcccatcc tggaaaagat    8460
ggacggcacc gaggaactgc tcgtgaagct gaacagagag gacctgctgc ggaagcagcg    8520
gaccttcgac aacggcagca tcccccacca gatccacctg ggagagctgc acgccattct    8580
gcggcggcag gaagattttt acccattcct gaaggacaac cgggaaaaga tcgagaagat    8640
cctgaccttc cgcatcccct actacgtggg ccctctggcc aggggaaaca gcagattcgc    8700
ctggatgacc agaaagagcg aggaaaccat cacccctgg aacttcgagg aagtggtgga    8760
caagggcgcc agcgcccaga gcttcatcga gcggatgacc aacttcgata gaacctgcc    8820 caacgagaag gtgctgccca gcacagcct gctgtacgag tacttcaccg tgtacaacga    8880
gctgaccaaa gtgaaatacg tgaccgaggg aatgagaaag cccgccttcc tgagcggcga    8940
gcagaaaaaa gccatcgtgg acctgctgtt caagaccaac cggaaagtga ccgtgaagca    9000
gctgaaagag gactacttca gaaaaatcga gtgcttcgac tccgtggaaa tctccggcgt    9060
ggaagatcgg ttcaacgcct ccctgggcac ataccacgat ctgctgaaaa ttatcaagga    9120
caaggacttc ctggacaatg aggaaaacga ggacattctg gaagatatcg tgctgaccct    9180
gacactgttt gaggacagag agatgatcga ggaacggctg aaaacctatg cccacctgtt    9240
cgacgacaaa gtgatgaagc agctgaagcg gcggagatac accggctggg gcaggctgag    9300
ccggaagctg atcaacggca tccgggacaa gcagtccggc aagacaatcc tggatttcct    9360
gaagtccgac ggcttcgcca acagaaactt catgcagctg atccacgacg acagcctgac    9420
ctttaaagag gacatccaga aagcccaggt gtccggccag ggcgatagcc tgcacgagca    9480
cattgccaat ctggccggca gccccgccat taagaagggc atcctgcaga cagtgaaggt    9540
ggtggacgag ctcgtgaaag tgatgggccg gcacaagccc gagaacatcg tgatcgaaat    9600
ggccagagag aaccagacca cccagaaggg acagaagaac agccgcgaga gaatgaagcg    9660
gatcgaagag ggcatcaaag agctgggcag ccagatcctg aaagaacacc ccgtggaaaa    9720
cacccagctg cagaacgaga agctgtacct gtactacctg cagaatgggc gggatatgta    9780
cgtggaccag gaactggaca tcaaccggct gtccgactac gatgtggacg ctatcgtgcc    9840
tcagagcttt ctgaaggacg actccatcga taacaaagtg ctgactcgga gcgacaagaa    9900
ccggggcaag agcgacaacg tgccctccga gaggtcgtg aagaagatga gaactactg    9960 gcgccagctg ctgaatgcca agctgattac ccagaggaag ttcgacaatc tgaccaaggc    10020
cgagagaggc ggcctgagcg aactggataa ggccggcttc atcaagagac agctggtgga    10080
aacccggcag atcacaaagc acgtggcaca gatcctggac tcccggatga cactaagta    10140 cgacgagaac gacaaactga tccgggaagt gaaagtgatc acccctgaagt ccaagctggt    10200 gtccgatttc cggaaggatt tccagttta caaagtgcgc gagatcaaca actaccacca    10260
cgcccacgac gcctacctga acgccgtcgt gggaaccgcc ctgatcaaaa agtaccctaa    10320
gctgaaaagc gagttcgtgt acggcgacta caaggtgtac gacgtgcgga agatgatcgc    10380
caagagcgag caggaaatcg gcaaggctac cgccaagtac ttcttctaca gcaacatcat    10440
gaactttttc aagaccgaga ttaccctggc caacggcgag atccggaagc ggcctctgat    10500
cgagacaaac ggcgaaacag gcgagatcgt gtgggataag ggccgggact tgccaccgt    10560 gcggaaagtg ctgtctatgc cccaagtgaa tatcgtgaaa aagaccgagg tgcagacagg    10620
```

| | | | |
|---|---|---|---|
| cggcttcagc | aaagagtcta | tcctgcccaa gaggaacagc gacaagctga tcgccagaaa | 10680 |
| gaaggactgg | gaccctaaga | agtacggcgg cttcgacagc cccaccgtgg cctattctgt | 10740 |
| gctggtggtg | gccaaagtgg | aaaagggcaa gtccaagaaa ctgaagagtg tgaaagagct | 10800 |
| gctgggatc | accatcatgg | aaagaagcag cttcgagaag atcccatcg actttctgga | 10860 |
| agccaagggc | tacaaagaag | tgaaaaagga cctgatcatc aagctgccta agtactccct | 10920 |
| gttcgagctg | aaaacggcc | ggaagagaat gctggcctct gccggcgaac tgcagaaggg | 10980 |
| aaacgaactg | gccctgccct | ccaaatatgt gaacttcctg tacctggcca gccactatga | 11040 |
| gaagctgaag | ggctcccccg | aggataatga gcagaaacag ctgtttgtgg aacagcacaa | 11100 |
| acactacctg | gacgagatca | tcgagcagat cagcgagttc tccaagagag tgatcctggc | 11160 |
| cgacgctaat | ctggacaagg | tgctgagcgc ctacaacaag cacagagaca agcctatcag | 11220 |
| agagcaggcc | gagaatatca | tccacctgtt taccctgacc aatctgggag cccctgccgc | 11280 |
| cttcaagtac | tttgacacca | ccatcgaccg gaagaggtac accagcacca agaggtgct | 11340 |
| ggacgccacc | ctgatccacc | agagcatcac cggcctgtac gagacacgga tcgacctgtc | 11400 |
| tcagctggga | ggcgacgcgg | ccgcggagca gaaactcatc tctgaagaag atctggaaca | 11460 |
| aaagttgatt | tcagaagaag | atctggaaca gaagctcatc tctgaggaag atctgtaata | 11520 |
| aggcgcgcct | ccttaatggg | acttgcagcc tcggtaccaa attccagaaa agacacccga | 11580 |
| aagggtgttt | tttcgttttg | gtcccacaga atgagcatca tggctctagt cgacatcgga | 11640 |
| gaagagtacg | gctcttttaa | ccgcctcaag aaccagataa gtgaaatcta gttccaaact | 11700 |
| attttgtcat | ttttaatttt | cgtattagct tacgacgcta cacccagttc ccatctattt | 11760 |
| tgtcactctt | ccctaaataa | tccttaaaaa ctccatttcc accctccca gttcccaact | 11820 |
| attttgtccg | cccacagcgg | ggcattttc ttcctgttat gtttgggcgc tgcattaatg | 11880 |
| aatcggccaa | cgcgcgggga | gaggcggttt gcgtattggg cgctcttccg cttcctcgct | 11940 |
| cactgacccg | ctgcgctcgg | tcgttcggct gcggcgagcg gtatcag | 11987 |

<210> SEQ ID NO 12
<211> LENGTH: 11861
<212> TYPE: DNA
<213> ORGANISM: Artificial sequence
<220> FEATURE:
<223> OTHER INFORMATION: Synthetic construct

<400> SEQUENCE: 12

| | | | |
|---|---|---|---|
| agcttatcgg | ccagcctcgc | agagcaggat tcccgttgag caccgccagg tgcgaataag | 60 |
| ggacagtgaa | gaaggaacac | ccgctcgcgg gtgggcctac ttcacctatc ctgcccggct | 120 |
| gacgccgttg | gatacaccaa | ggaaagtcta cacgaaccct ttggcaaaat cctgtatatc | 180 |
| gtgcgaaaaa | ggatggatat | accgaaaaaa tcgctataat gaccccgaag cagggttatg | 240 |
| cagcggaaag | tataccttaa | ggaatcccct gataacgcag gaaagaacat gtgagcaaaa | 300 |
| ggccagcaaa | aggccaggaa | ccgtaaaaag gccgcactcc ctgcctctgt catcacgata | 360 |
| ctgtgatgcc | atggctaatt | cccatgtcag ccgttaagtg ttcctgtgtc actcaaaatt | 420 |
| gctttgagag | gctctaaggg | cttctcagtg cgttacatcc ctggcttgtt gtccacaacc | 480 |
| gttaaacctt | aaaagcttta | aaagccttat atattctttt ttttcttata aaacttaaaa | 540 |
| ccttagaggc | tatttaagtt | gctgatttat attaatttta ttgttcaaac atgagagctt | 600 |
| agtacgtgaa | acatgagagc | ttagtacgtt agccatgaga gcttagtacg ttagccatga | 660 |

```
gggtttagtt cgttaaacat gagagcttag tacgttaaac atgagagctt agtacgtgaa    720
acatgagagc ttagtacgta ctatcaacag gttgaactgc tgatcttcag atcctctacg    780
ccggacgcat cgtggccgga tcttgcggcc gcaaaaatta aaaatgaagt tttaaatcaa    840
tctaaagtat atatgagtaa acttggtctg acagttacca atgcttaatc agtgaggcac    900
caataactgc ctttgatctt ttctacgggg tctgacgctc agtggaacga aaactcacgt    960
taagggattt tggtcatgag attatcaaaa aggatcttca cctagatcct tttaaattaa   1020
aaatgaagtt ttaaatcaat ctaaagtata tatgagtaaa cttggtctga cagttaccaa   1080
tgcttaatca gtgaggcacc tatctcagcg atctgtctat ttcgttcatc catagttgcc   1140
tgactccccg tcgtgtagat aactacgata cgggagggct taccatctgg ccccagtgct   1200
gcaatgatac cgcgggaccc acgctcaccg gctccagatt tatcagcaat aaaccagcca   1260
gccggaaggg ccgagcgcag aagtggtcct gcaactttat ccgcctccat ccagtctatt   1320
aattgttgcc gggaagctag agtaagtagt tcgccagtta atagtttgcg caacgttgtt   1380
gccattgcta caggcatcgt ggtgtcacgc tcgtcgtttg gtatggcttc attcagctcc   1440
ggttcccaac gatcaaggcg agttacatga tcccccatgt tgtgcaaaaa agcggttagc   1500
tccttcggtc ctccgatcgt tgtcagaagt aagttggccg cagtgttatc actcatggtt   1560
atggcagcac tgcataattc tcttactgtc atgccatccg taagatgctt ttctgtgact   1620
ggtgagtact caaccaagtc attctgagaa tagtgtatgc ggcgaccgag ttgctcttgc   1680
ccggcgtcaa tacgggataa taccgcgcca catagcagaa ctttaaaagt gctcatcatt   1740
ggaaaacgtt cttcggggcg aaaactctca aggatcttac cgctgttgag atccagttcg   1800
atgtaaccca ctcgtgcacc caactgatct tcagcatctt ttactttcac cagcgtttct   1860
gggtgagcaa aaacaggaag gcaaaatgcc gcaaaaaagg gaataagggc gacacggaaa   1920
tgttgaatac tcatactctt cctttttcaa tattattgaa gcatttatca gggttattgt   1980
ctcatgagcg gatacatatt tgaatgtatt tagaaaaata aacaaatagg ggttccgcgc   2040
acatttcccc gaaaagtgcc acctgacgtc taagaaacca ttattatcat gacattaacc   2100
tataaaaata ggcgtatcac gaggcccttt cgtctcgcgc gtttcggtga tgacggtgaa   2160
aacctctgac acatgcagct cccggagacg gtcacagctt gtctgtaagc ggatgccggg   2220
agcagacaag cccgtcaggg cgcgtcagcg ggtgttggcg ggtgtcgggg ctggcttaac   2280
tatgcggcat cagagcagat tgtactgaga gtgcaccata tgcggtgtga ataccgcac   2340 agatgcgtaa ggagaaaata ccgcatcagg cgccattcgc cattcaggct gcgcaactgt   2400
tgggaagggc gatcggtgcg ggcctcttcg ctattacgcc agctagagga ccagccgcgt   2460
aacctggcaa atcggttac ggttgagtaa taaatggatg ccctgcgtaa gcgggtgtgg   2520
gcggacaata aagtcttaaa ctgaacaaaa tagatctaaa ctatgacaat aaagtcttaa   2580
actagacaga atagttgtaa actgaaatca gtccagttat gctgtgaaaa agcatactgg   2640
acttttgtta tggctaaagc aaactcttca ttttctgaag tgcaaattgc ccgtcgtatt   2700 aaagagggc gtgggttcg aggtcgacgg tatcgataag ctagcttaat tagctgagct   2760
tggactcctg ttgatagatc cagtaatgac ctcagaactc catctggatt tgttcagaac   2820
gctcggttgc cgccgggcgt ttttattgg tgagaatcca agctagactg cgatgagtgg   2880
cagggcgggg cgtaatttt ttaaggcagt tattggtgcc cttaaacgcc tggggtaatg   2940
actctctagc ttgaggcatc aaataaaacg aaaggctcag tcgaaagact gggcctttcg   3000
ttttatctgt tgtttgtcgg tgaacgctct cctgagtagg acaaatccgc cgctaggagc   3060
```

-continued

| | |
|---|---|
| ttgcggcccg gacgatgagc tcgaattggg gatcttgaag tacctattcc gaagttccta | 3120 |
| ttctctagaa agtataggaa cttcagagcg cttttgaagc tgatgctcga gttccagtcg | 3180 |
| ggaaacctgt cgtgccagct gcattaatga atcggccaac gcgcggggag aggcggtttg | 3240 |
| cgtattgggc gcatgcataa aaactgttgt aattcattaa gcattctgcc gacatggaag | 3300 |
| ccatcacaaa cggcatgatg aacctgaatc gccagcggca tcagcacctt gtcgccttgc | 3360 |
| gtataatatt tgcccatggt gaaaacgggg gcgaagaagt tgtccatatt ggccacgttt | 3420 |
| aaatcaaaac tggtgaaact cacccaggga ttggctgaga cgaaaaacat attctcaata | 3480 |
| aaccctttag ggaaataggc caggttttca ccgtaacacg ccacatcttg cgaatatatg | 3540 |
| tgtagaaact gccggaaatc gtcgtggtat tcactccaga gcgatgaaaa cgtttcagtt | 3600 |
| tgctcatgga aaacggtgta acaagggtga acactatccc atatcaccag ctcaccgtct | 3660 |
| ttcattgcca tacgaactc cggatgagca ttcatcaggc gggcaagaat gtgaataaag | 3720 |
| gccggataaa acttgtgctt atttttcttt acggtcttta aaaaggccgt aatatccagc | 3780 |
| tgaacggtct ggttataggt acattgagca actgactgaa atgcctcaaa atgttcttta | 3840 |
| cgatgccatt gggatatatc aacggtggta tatccagtga tttttttctc cattttagct | 3900 |
| tccttagctc ctgaaaatct cgataactca aaaaatacgc ccggtagtga tgagcgcata | 3960 |
| cgctacttgc attacagttt acgaaccgaa caggcttatg tcaactgggt tcgtgccttc | 4020 |
| atccgtttcc acggctcgag agttcaacag acagccttcg ttcttatggc cgttcaggag | 4080 |
| gaagttccta ttccgaagtt cctattctct agaaagtata ggaacttctt gagaagagaa | 4140 |
| aagaaaaccg ccgatcctgt ccaccgcatt actgcaaggt agtggacaag accggcggtc | 4200 |
| ttaagttttt tggctgaaac gaatgacgaa aaggctgtct gagcaaatcc aggaggtcgt | 4260 |
| ttttattaag caccggtgga gtgacgacct tcagcacgtt cgtactgttc aacgatggtg | 4320 |
| tagtcttcgt tgtgggaggt gatgtccagt ttgatgtcgg ttttgtaagc acccggcagc | 4380 |
| tgaaccggtt ttttagccat gtaggtggtt ttaacttcag cgtcgtagtg accaccgtct | 4440 |
| ttcagtttca gacgcatttt gatttcacct ttcagagcac cgtcttccgg gtacatacgt | 4500 |
| tcggtggaag cttcccaacc catggttttt ttctgcataa ccggaccgtc ggacgggaag | 4560 |
| ttggtaccac gcagtttaac tttgtagatg aactcaccgt cttgcaggga ggagtcctgg | 4620 |
| gtaacggtaa caacaccacc gtcttcgaag ttcataacac gttcccattt gaaaccttcc | 4680 |
| gggaaggaca gtttcaggta gtccgggatg tcagccgggt gtttaacgta agctttggaa | 4740 |
| ccgtactgga actgcgggga caggatgtcc caagcgaacg gcagcggacc acctttggta | 4800 |
| actttcagtt tagcggtctg ggtaccttcg tacggacgac cttcaccttc accttcgatt | 4860 |
| tcgaactcgt gaccgttaac ggaaccttcc atacgaactt tgaaacgcat gaactctttg | 4920 |
| ataacgtctt cgctactcgc catggtacct ttctcctctt taattaattc agatctatta | 4980 |
| tacctaggac tgagctagct gtcaaattca ccaccctgaa ttgactctca accgtatta | 5040 |
| gcccggtatt ttggaaatag cggaagcact gacttttgtt atcaataaaa aaggcccccc | 5100 |
| gttagggagg ccttattgtt cgtctactcg gaagagcgag agacaacaga acggtcagcc | 5160 |
| acatgaattc aaaaaaaaag caccgactcg gtgccacttt ttcaagttga taacggacta | 5220 |
| gccttattta aacttgctat gctgtttcca gcatagctct taaacagacc gctaaactga | 5280 |
| aagttactag aagtatcttg ttatccgctc acaatgtcaa tgttatccgc tcacatttat | 5340 |
| agatctttag gaattctttc agctcagtcg ataggtagta ggcaagagta gtcgcacctt | 5400 |

```
tggtcgaaaa aaaaagcccg cactgtcagg tgcgggcttt tttctgtgtt tccccaaaag    5460
taaaaacccg ccgaagcggg ttttacgta  aaacaggtga aactgaccag acgagaaggc    5520
tttggaggtg ataatggggc tcaaggaccc tggggtgcct aatgagtgag ctaactcaca    5580
ttaattgcgt tgcgctcact gcccgctttc cagtcgggaa acctgtcgtg ccagctgcat    5640
taatgaatcg gccaacgcgc ggggagaggc ggtttgcgta ttgggcgcca gggtggtttt    5700
tcttttcacc agtgagacgg gcaacagctg attgcccttc accgcctggc cctgagagag    5760
ttgcagcaag cggtccacgc tggtttgccc cagcaggcga aaatcctgtt tgatggtggt    5820
taacggcggg atataacatg agctgtcttc ggtatcgtcg tatcccacta ccagatatc     5880
cgcaccaacg cgcagcccgg actcggtaat ggcgcgcatt gcgcccagcg ccatctgatc    5940
gttggcaacc agcatcgcag tgggaacgat gccctcattc agcatttgca tggtttgttg    6000
aaaaccggac atggcactcc agtcgccttc ccgttccgct atcggctgaa tttgattgcg    6060
agtgagatat ttatgccagc cagcagacg  cagacgcgcc gagacagaac ttaatgggcc    6120
cgctaacagc gcgatttgct ggtgacccaa tgcgaccaga tgctccacgc ccagtcgcgt    6180
accgtcttca tgggagaaaa taatactgtt gatgggtgtc tggtcagaga catcaagaaa    6240
taacgccgga acattagtgc aggcagcttc cacagcaatg gcatcctggt catccagcgg    6300
atagttaatg atcagcccac tgacgcgttg cgcgagaaga ttgtgcaccg ccgctttaca    6360
ggcttcgacg ccgcttcgtt ctaccatcga caccaccacg ctggcaccca gttgatcggc    6420
gcgagattta atcgccgcga caatttgcga cggcgcgtgc agggccagac tggaggtggc    6480
aacgccaatc agcaacgact gtttgcccgc cagttgttgt gccacgcggt tgggaatgta    6540
attcagctcc gccatcgccg cttccacttt ttcccgcgtt ttcgcagaaa cgtggctggc    6600
ctggttcacc acgcgggaaa cggtctgata agagacaccg gcatactctg cgacatcgta    6660
taacgttact ggtttcacat tcaccaccct gaattgactc tcttccgggc gctatcatgc    6720
cataccgcga aaggttttgc accattcgat ggtgtcaacg taaatgcatg ccgcttggga    6780
ggcagatagg taggcatggc ccccatttc  aatacaagca acgcatgaga aagcccccgg    6840
aagatcacct tccgggggct tttttattgc gctccggcaa ttaaaaaagc ggctaaccac    6900
gccgcttttt ttacgtctgc aggcgaattg atctggtttg acagcttatc accaagccag    6960
ttacctcggt tcaaagagtt ggtagctcag agaaccttcg aaaaaccgcc ctgcaaggcg    7020
gttttttcgt tttcagagca agagattacg cgcagaccaa acgatctca  agaagatcat    7080
cttattaatc agataaaata ttataaatgt gagcggataa cattgacatt gtgagcggat    7140
aacaagatac tgagcacatc agcaggtttc acacaggaaa actagtatgg ataagaaata    7200
ctcaataggc ttagctatcg gcacaaatag cgtcggatgg gcggtgatca ctgatgaata    7260
taaggttccg tctaaaaagt tcaaggttct gggaaataca gaccgccaca gtatcaaaaa    7320
aaatcttata ggggctcttt atttgacag  tggagagaca gcggaagcga ctcgtctcaa    7380
acggacagct cgtagaaggt atacacgtcg gaagaatcgt atttgttatc tacaggagat    7440
ttttt caaat gagatggcga aagtagatga tagtttcttt catcgacttg aagagtcttt    7500
tttggtggaa gaagacaaga agcatgaacg tcatcctatt tttggaaata tagtagatga    7560
agttgcttat catgagaaat atccaactat ctatcatctg cgaaaaaat  tggtagattc    7620
tactgataaa gcggatttgc gcttaatcta tttggcctta gcgcatatga ttaagtttcg    7680
tggtcatttt ttgattgagg gagatttaaa tcctgataat agtgatgtgg acaaactatt    7740
tatccagttg gtacaaacct acaatcaatt atttgaagaa aaccctatta acgcaagtgg    7800
```

```
agtagatgct aaagcgattc tttctgcacg attgagtaaa tcaagacgat tagaaaatct   7860
cattgctcag ctccccggtg agaagaaaaa tggcttattt gggaatctca ttgctttgtc   7920
attgggtttg acccctaatt ttaaatcaaa ttttgatttg gcagaagatg ctaaattaca   7980
gctttcaaaa gatacttacg atgatgattt agataattta ttggcgcaaa ttggagatca   8040
atatgctgat ttgttttggg cagctaagaa tttatcagat gctattttac tttcagatat   8100
cctaagagta aatactgaaa taactaaggc tccccctatca gcttcaatga ttaaacgcta   8160
cgatgaacat catcaagact tgactctttt aaaagcttta gttcgacaac aacttccaga   8220
aaagtataaa gaaatctttt ttgatcaatc aaaaaacgga tatgcaggtt atattgatgg   8280
gggagctagc caagaagaat tttataaatt tatcaaacca attttagaaa aaatggatgg   8340
tactgaggaa ttattggtga aactaaatcg tgaagatttg ctgcgcaagc aacgggacctt   8400
tgacaacggc tctattcccc atcaaattca cttgggtgag ctgcatgcta ttttgagaag   8460
acaagaagac ttttatccat ttttaaaaga caatcgtgag aagattgaaa aaatcttgac   8520
ttttcgaatc ccttattatg ttggtccatt ggcgcgtggc aatagtcgtt ttgcatggat   8580
gactcggaag tctgaagaaa caattacccc atggaatttt gaagaagttg tcgataaagg   8640
tgcttcagct caatcattta ttgaacgcat gacaaacttt gataaaaatc ttccaaatga   8700
aaaagtacta ccaaaacata gtttgcttta tgagtatttt acggtttata acgaattgac   8760
aaaggtcaaa tatgttactg aaggaatgcg aaaaccagca tttctttcag gtgaacagaa   8820
gaaagccatt gttgatttac tcttcaaaac aaatcgaaaa gtaaccgtta agcaattaaa   8880
agaagattat ttcaaaaaaa tagaatgttt tgatagtgtt gaaatttcag gagttgaaga   8940
tagatttaat gcttcattag gtacctacca tgatttgcta aaaattatta agataaaga   9000
ttttttggat aatgaagaaa atgaagatat cttagaggat attgtttaa cattgaccttt  9060
atttgaagat agggagatga ttgaggaaag acttaaaaca tatgctcacc tctttgatga   9120
taaggtgatg aaacagctta acgtcgccg ttatactggt tggggacgtt tgtctcgaaa    9180
attgattaat ggtattaggg ataagcaatc tggcaaaaca atattagatt ttttgaaatc   9240
agatggtttt gccaatcgca atttttatgca gctgatccat gatgatagtt tgacatttaa  9300
agaagacatt caaaaagcac aagtgtctgg acaaggcgat agtttacatg aacatattgc   9360
aaatttagct ggtagccctg ctattaaaaa aggtattta cagactgtaa aagttgttga    9420
tgaattggtc aaagtaatgg ggcggcataa gccagaaaat atcgttattg aaatggcacg   9480
tgaaaatcag acaactcaaa agggccagaa aaattcgcga gagcgtatga acgaatcga    9540
agaaggtatc aaagaattag gaagtcagat tcttaaagag catcctgttg aaaatactca   9600
attgcaaaat gaaaagctct atctctatta tctccaaaat ggaagagaca tgtatgtgga   9660
ccaagaatta gatattaatc gtttaagtga ttatgatgtc gatgccattg ttccacaaag   9720
tttccttaaa gacgattcaa tagacaataa ggtcttaacg cgttctgata aaaatcgtgg   9780
taaatcggat aacgttccaa gtgaagaagt agtcaaaaag atgaaaaact attggagaca   9840
acttctaaac gccaagttaa tcactcaacg taagtttgat aatttaacga agctgaacg    9900
tggaggtttg agtgaacttg ataaagctgg ttttatcaaa cgccaattgg ttgaaactcg   9960
ccaaatcact aagcatgtgg cacaaatttt ggatagtcgc atgaatacta atacgatga   10020
aaatgataaa cttattcgag aggttaaagt gattacctta aaatctaaat tagtttctga  10080
cttccgaaaa gatttccaat tctataaagt acgtgagatt aacaattacc atcatgccca  10140
```

-continued

```
tgatgcgtat ctaaatgccg tcgttggaac tgctttgatt aagaaatatc caaaacttga    10200
atcggagttt gtctatggtg attataaagt ttatgatgtt cgtaaaatga ttgctaagtc    10260
tgagcaagaa ataggcaaag caaccgcaaa atatttcttt tactctaata tcatgaactt    10320
cttcaaaaca gaaattacac ttgcaaatgg agagattcgc aaacgccctc taatcgaaac    10380
taatggggaa actggagaaa ttgtctggga taaagggcga gattttgcca cagtgcgcaa    10440
agtattgtcc atgccccaag tcaatattgt caagaaaaca gaagtacaga caggcggatt    10500
ctccaaggag tcaattttac caaaagaaa ttcggacaag cttattgctc gtaaaaaga     10560 ctgggatcca aaaaaatatg gtggttttga tagtccaacg gtagcttatt cagtcctagt    10620
ggttgctaag gtggaaaaag ggaaatcgaa gaagttaaaa tccgttaaag agttactagg    10680
gatcacaatt atggaagaa gttcctttga aaaaatccg attgactttt tagaagctaa      10740
aggatataag gaagttaaaa aagacttaat cattaaacta cctaaatata gtcttttga    10800 gttagaaaac ggtcgtaaac ggatgctggc tagtgccgga gaattacaaa aggaaatga     10860 gctggctctg ccaagcaaat atgtgaattt tttatattta gctagtcatt atgaaaagtt    10920
gaagggtagt ccagaagata acgaacaaaa acaattgttt gtggagcagc ataagcatta    10980
tttagatgag attattgagc aaatcagtga attttctaag cgtgttattt tagcagatgc    11040
caatttagat aaagttctta gtgcatataa caaacataga gacaaaccaa tacgtgaaca    11100
agcagaaaat attattcatt tatttacgtt gacgaatctt ggagctcccg ctgcttttaa    11160
atattttgat acaacaattg atcgtaaacg atatacgtct acaaaagaag ttttagatgc    11220
cactcttatc catcaatcca tcactggtct ttatgaaaca cgcattgatt tgagtcagct    11280
aggaggtgac gcggccgcgg agcagaaact catctctgaa gaagatctgg aacaaaagtt    11340
gatttcagaa gaagatctgg aacagaagct catctctgag gaagatctgt aataaggcgc    11400
gcctccttaa tgggacttgc agcctcggta ccaaattcca gaaagacac ccgaagggt     11460 gttttttcgt tttggtccca cagaatgagc atcatggctc tagtcgacat cggagaagag    11520
tacggctctt ttaaccgcct caagaaccag ataagtgaaa tctagttcca aactatttg    11580 tcatttttaa ttttcgtatt agcttacgac gctacaccca gttcccatct attttgtcac    11640
tcttccctaa ataatcctta aaaactccat ttccaccct cccagttccc aactattttg    11700
tccgcccaca gcggggcatt tttcttcctg ttatgtttgg gcgctgcatt aatgaatcgg    11760
ccaacgcgcg gggagaggcg gtttgcgtat tgggcgctct tccgcttcct cgctcactga    11820
cccgctgcgc tcggtcgttc ggctgcggcg agcggtatca g                        11861
```

<210> SEQ ID NO 13
<211> LENGTH: 11861
<212> TYPE: DNA
<213> ORGANISM: Artificial sequence
<220> FEATURE:
<223> OTHER INFORMATION: Synthetic construct

<400> SEQUENCE: 13

```
agcttatcgg ccagcctcgc agagcaggat tcccgttgag caccgccagg tgcgaataag     60
ggacagtgaa gaaggaacac ccgctcgcgg gtgggcctac ttcacctatc ctgcccggct    120
gacgccgttg gatacaccaa ggaaagtcta cacgaaccct ttggcaaaat cctgtatatc    180
gtgcgaaaaa ggatggatat accgaaaaaa tcgctataat gaccccgaag cagggttatg    240
cagcggaaag tataccttaa ggaatcccct gataacgcag gaaagaacat gtgagcaaa     300 ggccagcaaa aggccaggaa ccgtaaaaag gccgcactcc ctgcctctgt catcacgata    360
```

```
ctgtgatgcc atggctaatt cccatgtcag ccgttaagtg ttcctgtgtc actcaaaatt      420
gctttgagag gctctaaggg cttctcagtg cgttacatcc ctggcttgtt gtccacaacc      480
gttaaacctt aaaagcttta aaagccttat atattctttt ttttcttata aaacttaaaa      540
ccttagaggc tatttaagtt gctgatttat attaatttta ttgttcaaac atgagagctt      600
agtacgtgaa acatgagagc ttagtacgtt agccatgaga gcttagtacg ttagccatga      660
gggtttagtt cgttaaacat gagagcttag tacgttaaac atgagagctt agtacgtgaa      720
acatgagagc ttagtacgta ctatcaacag gttgaactgc tgatcttcag atcctctacg      780
ccggacgcat cgtggccgga tcttgcggcc gcaaaaatta aaaatgaagt tttaaatcaa      840
tctaaagtat atatgagtaa acttggtctg acagttacca atgcttaatc agtgaggcac      900
caataactgc ctttgatctt ttctacgggg tctgacgctc agtggaacga aaactcacgt      960
taagggattt tggtcatgag attatcaaaa aggatcttca cctagatcct tttaaattaa     1020
aaatgaagtt ttaaatcaat ctaaagtata tatgagtaaa cttggtctga cagttaccaa     1080
tgcttaatca gtgaggcacc tatctcagcg atctgtctat ttcgttcatc catagttgcc     1140
tgactccccg tcgtgtagat aactacgata cgggagggct taccatctgg ccccagtgct     1200
gcaatgatac cgcgggaccc acgctcaccg gctccagatt tatcagcaat aaaccagcca     1260
gccggaaggg ccgagcgcag aagtggtcct gcaactttat ccgcctccat ccagtctatt     1320
aattgttgcc gggaagctag agtaagtagt tcgccagtta atagtttgcg caacgttgtt     1380
gccattgcta caggcatcgt ggtgtcacgc tcgtcgtttg gtatggcttc attcagctcc     1440
ggttcccaac gatcaaggcg agttacatga tcccccatgt tgtgcaaaaa agcggttagc     1500
tccttcggtc ctccgatcgt tgtcagaagt aagttggccg cagtgttatc actcatggtt     1560
atggcagcac tgcataattc tcttactgtc atgccatccg taagatgctt ttctgtgact     1620
ggtgagtact caaccaagtc attctgagaa tagtgtatgc ggcgaccgag ttgctcttgc     1680
ccggcgtcaa tacgggataa taccgcgcca catagcagaa ctttaaaagt gctcatcatt     1740
ggaaaacgtt cttcggggcg aaaactctca aggatcttac cgctgttgag atccagttcg     1800
atgtaaccca ctcgtgcacc caactgatct tcagcatctt ttactttcac cagcgtttct     1860
gggtgagcaa aaacaggaag gcaaaatgcc gcaaaaaagg gaataagggc gacacggaaa     1920
tgttgaatac tcatactctt cctttttcaa tattattgaa gcatttatca gggttattgt     1980
ctcatgagcg gatacatatt tgaatgtatt tagaaaaata acaaataggg gttccgcgc      2040 acatttcccc gaaaagtgcc acctgacgtc taagaaacca ttattatcat gacattaacc     2100
tataaaaata ggcgtatcac gaggcccttt cgtctcgcgc gtttcggtga tgacggtgaa     2160
aacctctgac acatgcagct cccggagacg gtcacagctt gtctgtaagc ggatgccggg     2220
agcagacaag cccgtcaggg cgcgtcagcg ggtgttggcg ggtgtcgggg ctggcttaac     2280
tatgcggcat cagagcagat tgtactgaga gtgcaccata tgcggtgtga ataccgcac      2340 agatgcgtaa ggagaaaata ccgcatcagg cgccattcgc cattcaggct gcgcaactgt     2400
tgggaagggc gatcggtgcg ggcctcttcg ctattacgcc agctagagga ccagccgcgt     2460
aacctggcaa atcggttac ggttgagtaa taaatggatg ccctgcgtaa gcgggtgtgg      2520
gcggacaata aagtcttaaa ctgaacaaaa tagatctaaa ctatgacaat aaagtcttaa     2580
actagacaga atagttgtaa actgaaatca gtccagttat gctgtgaaaa agcatactgg     2640
acttttgtta tggctaaagc aaactcttca ttttctgaag tgcaaattgc ccgtcgtatt     2700
```

| | |
|---|---|
| aaagaggggc gtggggttcg aggtcgacgg tatcgataag ctagcttaat tagctgagct | 2760 |
| tggactcctg ttgatagatc cagtaatgac ctcagaactc catctggatt tgttcagaac | 2820 |
| gctcggttgc cgccgggcgt tttttattgg tgagaatcca agctagactg cgatgagtgg | 2880 |
| cagggcgggg cgtaattttt ttaaggcagt tattggtgcc cttaaacgcc tggggtaatg | 2940 |
| actctctagc ttgaggcatc aaataaaacg aaaggctcag tcgaaagact gggcctttcg | 3000 |
| ttttatctgt tgtttgtcgg tgaacgctct cctgagtagg acaaatccgc cgctaggagc | 3060 |
| ttgcggcccg gacgatgagc tcgaattggg gatcttgaag tacctattcc gaagttccta | 3120 |
| ttctctagaa agtataggaa cttcagagcg cttttgaagc tgatgctcga gttccagtcg | 3180 |
| ggaaacctgt cgtgccagct gcattaatga atcggccaac gcgcggggag aggcggtttg | 3240 |
| cgtattgggc gcatgcataa aaactgttgt aattcattaa gcattctgcc gacatggaag | 3300 |
| ccatcacaaa cggcatgatg aacctgaatc gccagcggca tcagcacctt gtcgccttgc | 3360 |
| gtataatatt tgcccatggt gaaaacgggg gcgaagaagt tgtccatatt ggccacgttt | 3420 |
| aaatcaaaac tggtgaaact cacccaggga ttggctgaga cgaaaaacat attctcaata | 3480 |
| aaccctttag ggaataggc caggttttca ccgtaacacg ccacatcttg cgaatatatg | 3540 |
| tgtagaaact gccggaaatc gtcgtggtat tcactccaga gcgatgaaaa cgtttcagtt | 3600 |
| tgctcatgga aaacggtgta acaagggtga acactatccc atatcaccag ctcaccgtct | 3660 |
| ttcattgcca tacggaactc cggatgagca ttcatcaggc gggcaagaat gtgaataaag | 3720 |
| gccggataaa acttgtgctt attttctttt acggtcttta aaaggccgt aatatccagc | 3780 |
| tgaacggtct ggttataggt acattgagca actgactgaa atgcctcaaa atgttctttta | 3840 |
| cgatgccatt gggatatatc aacggtggta tatccagtga ttttttctc cattttagct | 3900 |
| tccttagctc ctgaaaatct cgataactca aaaaatacgc ccggtagtga tgagcgcata | 3960 |
| cgctacttgc attacagttt acgaaccgaa caggcttatg tcaactgggt tcgtgccttc | 4020 |
| atccgttttcc acggctcgag agttcaacag acagccttcg ttcttatggc cgttcaggag | 4080 |
| gaagttccta ttccgaagtt cctattctct agaaagtata ggaacttctt gagaagagaa | 4140 |
| aagaaaaccg ccgatcctgt ccaccgcatt actgcaaggt agtggacaag accggcggtc | 4200 |
| ttaagttttt tggctgaaac gaatgacgaa aaggctgtct gagcaaatcc aggaggtcgt | 4260 |
| ttttattaag caccggtgga gtgacgacct cagcacgtt cgtactgttc aacgatggtg | 4320 |
| tagtcttcgt tgtgggaggt gatgtccagt ttgatgtcgg ttttgtaagc acccggcagc | 4380 |
| tgaaccggtt ttttagccat gtaggtggtt ttaacttcag cgtcgtagtg accaccgtct | 4440 |
| ttcagtttca gacgcatttt gatttcacct ttcagagcac cgtcttccgg gtacatacgt | 4500 |
| tcggtggaag cttcccaacc catggttttt ttctgcataa ccggaccgtc ggacgggaag | 4560 |
| ttggtaccac gcagtttaac tttgtagatg aactcaccgt cttgcaggga ggagtcctgg | 4620 |
| gtaacggtaa caacaccacc gtcttcgaag ttcataacac gttcccattt gaaaccttcc | 4680 |
| gggaaggaca gtttcaggta gtccgggatg tcagccgggt gtttaacgta agctttggaa | 4740 |
| ccgtactgga actgcgggga caggatgtcc caagcgaacg gcagcggacc acctttggta | 4800 |
| actttcagtt tagcggtctg ggtaccttcg tacggacgac cttcaccttc accttcgatt | 4860 |
| tcgaactcgt gaccgttaac ggaaccttcc atacgaactt tgaaacgcat gaactctttg | 4920 |
| ataacgtctt cgctactcgc catggtacct ttctcctctt taattaattc agatctatta | 4980 |
| tacctaggac tgagctagct gtcaaattca ccacctgaa ttgactctca aaccgtatta | 5040 |
| gcccggtatt ttggaaatag cggaagcact gactttgtt atcaataaaa aaggcccccc | 5100 |

```
gttagggagg ccttattgtt cgtctactcg aagagcgag agacaacaga acggtcagcc    5160
acatgaattc aaaaaaaaag caccgactcg gtgccacttt ttcaagttga taacggacta    5220
gccttattta aacttgctat gctgtttcca gcatagctct taaacagacc gctaaactga    5280
aagttactag aagtatcttg ttatccgctc acaatgtcaa tgttatccgc tcacatttat    5340
agatctttag gaattctttc agctcagtcg ataggtagta ggcaagagta gtcgcacctt    5400
tggtcgaaaa aaaagcccg cactgtcagg tgcgggcttt tttctgtgtt tccccaaaag    5460
taaaaacccg ccgaagcggg ttttttacgta aaacaggtga aactgaccag acgagaaggc    5520
tttggaggtg ataatgggc tcaaggaccc tggggtgcct aatgagtgag ctaactcaca    5580
ttaattgcgt tgcgctcact gcccgctttc cagtcgggaa acctgtcgtg ccagctgcat    5640
taatgaatcg gccaacgcgc ggggagaggc ggtttgcgta ttgggcgcca gggtggtttt    5700
tcttttcacc agtgagacgg gcaacagctg attgcccttc accgcctggc cctgagagag    5760
ttgcagcaag cggtccacgc tggtttgccc cagcaggcga aaatcctgtt tgatggtggt    5820
taacggcggg atataacatg agctgtcttc ggtatcgtcg tatcccacta ccgagatatc    5880
cgcaccaacg cgcagcccgg actcggtaat ggcgcgcatt gcgcccagcg ccatctgatc    5940
gttggcaacc agcatcgcag tgggaacgat gccctcattc agcatttgca tggtttgttg    6000
aaaaccggac atggcactcc agtcgccttc ccgttccgct atcggctgaa tttgattgcg    6060
agtgagatat ttatgccagc cagccagacg cagacgcgcc gagacagaac ttaatgggcc    6120
cgctaacagc gcgatttgct ggtgacccaa tgcgaccaga tgctccacgc ccagtcgcgt    6180
accgtcttca tgggagaaaa taatactgtt gatgggtgtc tggtcagaga catcaagaaa    6240
taacgccgga acattagtgc aggcagcttc cacagcaatg gcatcctggt catccagcgg    6300
atagttaatg atcagcccac tgacgcgttg cgcgagaaga ttgtgcaccg ccgctttaca    6360
ggcttcgacg ccgcttcgtt ctaccatcga caccaccacg ctggcaccca gttgatcggc    6420
gcgagattta atcgccgcga caatttgcga cggcgcgtgc agggccagac tggaggtggc    6480
aacgccaatc agcaacgact gtttgcccgc cagttgttgt gccacgcggt tgggaatgta    6540
attcagctcc gccatcgccg cttccacttt ttcccgcgtt ttcgcagaaa cgtggctggc    6600
ctggttcacc acgcgggaaa cggtctgata agagacaccg gcatactctg cgacatcgta    6660
taacgttact ggtttcacat tcaccaccct gaattgactc tcttccgggc gctatcatgc    6720
cataccgcga aggttttgc accattcgat ggtgtcaacg taaatgcatg ccgcttggga    6780
ggcagatagg taggcatggc ccccattttc aatacaagca acgcatgaga aagccccgg    6840 aagatcacct tccgggggct tttttattgc gctccggcaa ttaaaaaagc ggctaaccac    6900
gccgcttttt ttacgtctgc aggcgaattg atctggtttg acagcttatc accaagccag    6960
ttacctcggt tcaaagagtt ggtagctcag agaaccttcg aaaaaccgcc ctgcaaggcg    7020
gttttttcgt tttcagagca agagattacg cgcagaccaa aacgatctca agaagatcat    7080
cttattaatc agataaaata ttataaatgt gagcggataa cattgacatt gtgagcggat    7140
aacaagatac tgagcacatc agcaggtttc acacaggaaa actagtatgg acaagaagta    7200
cagcatcggc ctggccatcg gcaccaactc tgtgggctgg gccgtgatca ccgacgagta    7260
caaggtgccc agcaagaaat tcaaggtgct gggcaacacc gaccggcaca gcatcaagaa    7320
gaacctgatc ggcgccctgc tgttcgacag cggagaaaca gccgaggcca cccggctgaa    7380
gagaaccgcc agaagaagat acaccagacg gaagaaccgg atctgctatc tgcaagagat    7440
```

```
cttcagcaac gagatggcca aggtggacga cagcttcttc cacagactgg aagagtcctt    7500
cctggtggaa gaggataaga agcacgagcg gcaccccatc ttcggcaaca tcgtggacga    7560
ggtggcctac cacgagaagt accccaccat ctaccacctg agaaagaaac tggtggacag    7620
caccgacaag gccgacctgc ggctgatcta tctggccctg gcccacatga tcaagttccg    7680
gggccacttc ctgatcgagg gcgacctgaa ccccgacaac agcgacgtgg acaagctgtt    7740
catccagctg gtgcagacct acaaccagct gttcgaggaa aaccccatca cgccagcgg     7800 cgtggacgcc aaggccatcc tgtctgccag actgagcaag agcagacggc tggaaaatct    7860
gatcgcccag ctgcccggcg agaagaagaa tggcctgttc ggcaacctga ttgccctgag    7920
cctgggcctg acccccaact tcaagagcaa cttcgacctg gccgaggatg ccaaactgca    7980
gctgagcaag gacacctacg acgacgacct ggacaacctg ctggcccaga tcggcgacca    8040
gtacgccgac ctgtttctgg ccgccaagaa cctgtccgac gccatcctgc tgagcgacat    8100
cctgagagtg aacaccgaga tcaccaaggc cccccctgagc gcctctatga tcaagagata    8160
cgacgagcac caccaggacc tgaccctgct gaaagctctc gtgcggcagc agctgcctga    8220
gaagtacaaa gagattttct cgaccagag caagaacggc tacgccggct acatcgatgg    8280
cggagccagc caggaagagt tctacaagtt catcaagccc atcctggaaa agatggacgg    8340
caccgaggaa ctgctcgtga agctgaacag agaggacctg ctgcggaagc agcggaccttt  8400 cgacaacggc agcatccccc accagatcca cctgggagag ctgcacgcca ttctgcggcg    8460
gcaggaagat ttttacccat tcctgaagga caaccgggaa aagatcgaga agatcctgac    8520
cttccgcatc ccctactacg tgggccctct ggccagggga aacagcagat cgcctggat     8580 gaccagaaag agcgaggaaa ccatcacccc ctggaacttc gaggaagtgg tggacaaggg    8640
cgccagcgcc cagagcttca tcgagcggat gaccaacttc gataagaacc tgcccaacga    8700
gaaggtgctg cccaagcaca gcctgctgta cgagtacttc accgtgtaca acgagctgac    8760
caaagtgaaa tacgtgaccg agggaatgag aaagcccgcc ttcctgagcg gcgagcagaa    8820
aaaagccatc gtggacctgc tgttcaagac caaccggaaa gtgaccgtga gcagctgaa     8880 agaggactac ttcaagaaaa tcgagtgctt cgactccgtg gaaatctccg gcgtggaaga    8940
tcggttcaac gcctccctgg gcacatacca cgatctgctg aaaattatca aggacaagga    9000
cttcctggac aatgaggaaa acgaggacat tctggaagat atcgtgctga ccctgacact    9060
gtttgaggac agagagatga tcgaggaacg gctgaaaacc tatgcccacc tgttcgacga    9120
caaagtgatg aagcagctga gcggcggag atacaccggc tggggcaggc tgagccggaa    9180
gctgatcaac ggcatccggg acaagcagtc cggcaagaca atcctggatt tcctgaagtc    9240
cgacggcttc gccaacagaa acttcatgca gctgatccac gacgcagcc tgacctttaa     9300 agaggacatc cagaaagccc aggtgtccgg ccagggcgat agcctgcacg agcacattgc    9360
caatctggcc ggcagccccg ccattaagaa gggcatcctg cagacagtga aggtggtgga    9420
cgagctcgtg aaagtgatgg gccggcacaa gcccgagaac atcgtgatcg aaatggccag    9480
agagaaccag accacccaga agggacagaa gaacagccgc gagagaatga agcggatcga    9540
agagggcatc aaagagctgg gcagccagat cctgaaagaa caccccgtgg aaaacaccca    9600
gctgcagaac gagaagctgt acctgtacta cctgcagaat gggcgggata tgtacgtgga    9660
ccaggaactg gacatcaacc ggctgtccga ctacgatgtg gacgctatcg tgcctcagag    9720
ctttctgaag gacgactcca tcgataacaa agtgctgact cggagcgaca gaaccgggg     9780 caagagcgac aacgtgccct ccgaagaggt cgtgaagaag atgaagaact actggcgcca    9840
```

```
gctgctgaat gccaagctga ttacccagag gaagttcgac aatctgacca aggccgagag    9900
aggcggcctg agcgaactgg ataaggccgg cttcatcaag agacagctgg tggaaacccg    9960
gcagatcaca aagcacgtgg cacagatcct ggactccgg atgaacacta agtacgacga    10020
gaacgacaaa ctgatccggg aagtgaaagt gatcaccctg aagtccaagc tggtgtccga    10080
tttccggaag gatttccagt tttacaaagt gcgcgagatc aacaactacc accacgccca    10140
cgacgcctac ctgaacgccg tcgtgggaac cgccctgatc aaaaagtacc ctaagctgga    10200
aagcgagttc gtgtacggcg actacaaggt gtacgacgtg cggaagatga tcgccaagag    10260
cgagcaggaa atcggcaagg ctaccgccaa gtacttcttc tacagcaaca tcatgaactt    10320
tttcaagacc gagattaccc tggccaacgg cgagatccgg aagcggcctc tgatcgagac    10380
aaacggcgaa acaggcgaga tcgtgtggga taagggccgg gactttgcca ccgtgcgaa    10440
agtgctgtct atgccccaag tgaatatcgt gaaaagacc gaggtgcaga caggcggctt    10500
cagcaaagag tctatcctgc ccaagaggaa cagcgacaag ctgatcgcca gaaagaagga    10560
ctgggaccct aagaagtacg gcggcttcga cagccccacc gtggcctatt ctgtgctggt    10620
ggtggccaaa gtgaaaaagg gcaagtccaa gaaactgaag agtgtgaaag agctgctggg    10680
gatcaccatc atggaaagaa gcagcttcga gaagaatccc atcgactttc tggaagccaa    10740
gggctacaaa gaagtgaaaa aggacctgat catcaagctg cctaagtact ccctgttcga    10800
gctggaaaac ggccggaaga gaatgctggc ctctgccggc gaactgcaga agggaaacga    10860
actgcccctg ccctccaaat atgtgaactt cctgtacctg gccagccact atgagaagct    10920
gaagggctcc cccgaggata tgagcagaa acagctgttt gtggaacagc acaaacacta    10980
cctggacgag atcatcgagc agatcagcga gttctccaag agagtgatcc tggccgacgc    11040
taatctggac aaggtgctga gcgcctacaa caagcacaga gacaagccta tcagagagca    11100
ggccgagaat atcatccacc tgtttaccct gaccaatctg ggagccctg ccgccttcaa    11160
gtactttgac accaccatcg accggaagag gtacaccagc accaagagg tgctggacgc    11220
caccctgatc caccagagca tcaccggcct gtacgagaca cggatcgacc tgtctcagct    11280
gggaggcgac gcggccgcgg agcagaaact catctctgaa gaagatctgg aacaaaagtt    11340
gatttcagaa gaagatctgg aacagaagct catctctgag gaagatctgt aataaggcgc    11400
gcctccttaa tgggacttgc agcctcggta ccaaattcca gaaagacac ccgaaagggt    11460
gttttttcgt tttggtccca cagaatgagc atcatggctc tagtcgacat cggagaagag    11520
tacggctctt ttaaccgcct caagaaccag ataagtgaaa tctagttcca aactatttg    11580
tcattttaa ttttcgtatt agcttacgac gctacaccca gttcccatct attttgtcac    11640
tcttccctaa ataatcctta aaaactccat ttccacccct cccagttccc aactatttg    11700
tccgcccaca gcggggcatt tttcttcctg ttatgtttgg gcgctgcatt aatgaatcgg    11760
ccaacgcgcg gggagaggcg gtttgcgtat tgggcgctct ccgcttcct cgctcactga    11820
cccgctgcgc tcggtcgttc ggctgcggcg agcggtatca g                        11861
```

<210> SEQ ID NO 14  
<211> LENGTH: 10856  
<212> TYPE: DNA  
<213> ORGANISM: Artificial sequence  
<220> FEATURE:  
<223> OTHER INFORMATION: Synthetic construct

<400> SEQUENCE: 14

```
agcttatcgg ccagcctcgc agagcaggat tcccgttgag caccgccagg tgcgaataag    60
ggacagtgaa gaaggaacac ccgctcgcgg gtgggcctac ttcacctatc ctgcccggct   120
gacgccgttg gatacaccaa ggaaagtcta cacgaaccct ttggcaaaat cctgtatatc   180
gtgcgaaaaa ggatggatat accgaaaaaa tcgctataat gaccccgaag cagggttatg   240
cagcggaaag tataccttaa ggaatcccct gataacgcag gaaagaacat gtgagcaaaa   300
ggccagcaaa aggccaggaa ccgtaaaaag gccgcactcc ctgcctctgt catcacgata   360
ctgtgatgcc atggctaatt cccatgtcag ccgttaagtg ttcctgtgtc actcaaaatt   420
gctttgagag gctctaaggg cttctcagtg cgttacatcc ctggcttgtt gtccacaacc   480
gttaaacctt aaaagcttta aaagccttat atattctttt ttttcttata aacttaaaa    540
ccttagaggc tatttaagtt gctgatttat attaatttta ttgttcaaac atgagagctt   600
agtacgtgaa acatgagagc ttagtacgtt agccatgaga gcttagtacg ttagccatga   660
gggtttagtt cgttaaacat gagagcttag tacgttaaac atgagagctt agtacgtgaa   720
acatgagagc ttagtacgta ctatcaacag gttgaactgc tgatcttcag atcctctacg   780
ccggacgcat cgtggccgga tcttgcggcc gcaaaaatta aaaatgaagt tttaaatcaa   840
tctaaagtat atatgagtaa acttggtctg acagttacca atgcttaatc agtgaggcac   900
caataactgc ctttgatctt ttctacgggg tctgacgctc agtggaacga aaactcacgt   960
taagggattt tggtcatgag attatcaaaa aggatcttca cctagatcct tttaaattaa  1020
aaatgaagtt ttaaatcaat ctaaagtata tatgagtaaa cttggtctga cagttaccaa  1080
tgcttaatca gtgaggcacc tatctcagcg atctgtctat ttcgttcatc catagttgcc  1140
tgactccccg tcgtgtagat aactacgata cgggagggct taccatctgg ccccagtgct  1200
gcaatgatac cgcgggaccc acgctcaccg gctccagatt tatcagcaat aaaccagcca  1260
gccggaaggg ccgagcgcag aagtggtcct gcaactttat ccgcctccat ccagtctatt  1320
aattgttgcc gggaagctag agtaagtagt tcgccagtta atagtttgcg caacgttgtt  1380
gccattgcta caggcatcgt ggtgtcacgc tcgtcgtttg gtatggcttc attcagctcc  1440
ggttcccaac gatcaaggcg agttacatga tcccccatgt tgtgcaaaaa agcggttagc  1500
tccttcggtc ctccgatcgt tgtcagaagt aagttggccg cagtgttatc actcatggtt  1560
atggcagcac tgcataattc tcttactgtc atgccatccg taagatgctt ttctgtgact  1620
ggtgagtact caaccaagtc attctgagaa tagtgtatgc ggcgaccgag ttgctcttgc  1680
ccggcgtcaa tacgggataa taccgcgcca catagcagaa ctttaaaagt gctcatcatt  1740
ggaaaacgtt cttcggggcg aaaactctca aggatcttac cgctgttgag atccagttcg  1800
atgtaaccca ctcgtgcacc caactgatct tcagcatctt ttactttcac cagcgtttct  1860
gggtgagcaa aaacaggaag gcaaaatgcc gcaaaaaagg gaataagggc gacacggaaa  1920
tgttgaatac tcatactctt cctttttcaa tattattgaa gcatttatca gggttattgt  1980
ctcatgagcg gatacatatt tgaatgtatt tagaaaaata aacaataggg gttccgcgc   2040
acatttcccc gaaaagtgcc acctgacgtc taagaaacca ttattatcat gacattaacc  2100
tataaaaata ggcgtatcac gaggcccttt cgtctcgcgc gtttcggtga tgacggtgaa  2160
aacctctgac acatgcagct cccggagacg gtcacagctt gtctgtaagc ggatgccggg  2220
agcagacaag cccgtcaggg cgcgtcagcg ggtgttggcg ggtgtcgggg ctggcttaac  2280
tatgcggcat cagagcagat tgtactgaga gtgcaccata tgcggtgtga aataccgcac  2340
agatgcgtaa ggagaaaata ccgcatcagg cgccattcgc cattcaggct gcgcaactgt  2400
```

| | |
|---|---|
| tgggaagggc gatcggtgcg ggcctcttcg ctattacgcc agctagagga ccagccgcgt | 2460 |
| aacctggcaa aatcggttac ggttgagtaa taaatggatg ccctgcgtaa gcgggtgtgg | 2520 |
| gcggacaata aagtcttaaa ctgaacaaaa tagatctaaa ctatgacaat aaagtcttaa | 2580 |
| actagacaga atagttgtaa actgaaatca gtccagttat gctgtgaaaa agcatactgg | 2640 |
| acttttgtta tggctaaagc aaactcttca ttttctgaag tgcaaattgc ccgtcgtatt | 2700 |
| aaagaggggc gtggggttcg aggtcgacgg tatcgataag ctagcttaat tagctgagct | 2760 |
| tggactcctg ttgatagatc cagtaatgac ctcagaactc catctggatt tgttcagaac | 2820 |
| gctcggttgc cgccgggcgt tttttattgg tgagaatcca agctagactg cgatgagtgg | 2880 |
| cagggcgggg cgtaattttt ttaaggcagt tattggtgcc cttaaacgcc tggggtaatg | 2940 |
| actctctagc ttgaggcatc aaataaaacg aaaggctcag tcgaaagact gggccttttcg | 3000 |
| ttttatctgt tgtttgtcgg tgaacgctct cctgagtagg acaaatccgc cgctaggagc | 3060 |
| ttgcggcccg gacgatgagc tcgaattggg gatcttgaag tacctattcc gaagttccta | 3120 |
| ttctctagaa agtataggaa cttcagagcg cttttgaagc tgatgctcga gatctcggct | 3180 |
| tgaacgaatt gttaggtggc ggtacttggg tcgatatcaa agtgcatcac ttcttcccgt | 3240 |
| atgcccaact ttgtatagag agccactgcg ggatcgtcac cgtaatctgc ttgcacgtag | 3300 |
| atcacataag caccaagcgc gttggcctca tgcttgagga gattgatgag cgcggtggca | 3360 |
| atgccctgcc tccggtgctc tccggagact gcgagatcat agatatagat ctcactacgc | 3420 |
| ggctgctcaa acttgggcag aacgtaagcc gcgagagcgc caacaaccgc ttcttggtcg | 3480 |
| aaggcagcaa gcgcgatgaa tgtcttacta cggagcaagt tcccgaggta atcggagtcc | 3540 |
| ggctgatgtt gggagtaggt ggctacgtct ccgaactcac gaccgaaaag atcaagagca | 3600 |
| gcccgcatgg atttgacttg gtcagggccg agcctacatg tgcgaatgat gcccatactt | 3660 |
| gagccaccta actttgtttt agggcgactg ccctgctgcg taacatcgtt gctgctgcgt | 3720 |
| aacatcgttg ctgctccata acatcaaaca tcgacccacg gcgtaacgcg cttgctgctt | 3780 |
| ggatgcccga ggcatagact gtacaaaaaa acagtcataa caagccatga aaaccgccac | 3840 |
| tgcgccgtta ccaccgctgc gttcggtcaa ggttctggac cagttgcgtg agcgcatacg | 3900 |
| ctacttgcat tacagtttac gaaccgaaca ggcttatgtc aactgggttc gtgccttcat | 3960 |
| ccgtttccac ggtgtgcgtc catgggcaaa tattatacgc aaggcgacaa ggctcgagag | 4020 |
| ttcaacagac agccttcgtt cttatggccg ttcaggagga agttcctatt ccgaagttcc | 4080 |
| tattctctag aaagtatagg aacttcttga aagagaaaa gaaaaccgcc gatcctgtcc | 4140 |
| accgcattac tgcaaggtag tggacaagac cggcggtctt aagttttttg gctgaaacga | 4200 |
| atgacgaaaa ggctgtctga gcaaatccag gaggtcgttt aaaccgtatt agcccggtat | 4260 |
| tttggaaata gcggaagcac tgacttttgt tatcaataaa aaaggccccc cgttagggag | 4320 |
| gccttattgt tcgtctactc ggaagagcga gagacaacag aacggtcagc cacatgaatt | 4380 |
| caaaaaaaaa gcaccgactc ggtgccactt tttcaagttg ataacggact agccttattt | 4440 |
| aaacttgcta tgctgtttcc agcatagctc ttaaacagag accgaccgct atggtggaga | 4500 |
| ccaaagttgg tctcaactag aattatacga gccggatgat taattgtcaa cagctcattt | 4560 |
| cagaatattt gccagaaccg gaattctttc agctcagtcg ataggtagta ggcaagagta | 4620 |
| gtcgcacctt tggtcgaaaa aaaaagcccg cactgtcagg tgcgggcttt tttctgtgtt | 4680 |
| tccccaaaag taaaaacccg ccgaagcggg tttttacgta aaacaggtga aactgaccag | 4740 |

```
acgagaaggc tttggaggtg ataatgggc tcaaggaccc gggaggcaga taggtaggca    4800
tggcccccat tttcaataca agcaacgcat gagaaagccc ccggaagatc accttccggg    4860 ggcttttta ttgcgctccg gcaattaaaa aagcggctaa ccacgccgct tttttacgt     4920 ctgcagacta gttatgaca acttgacggc tacatcattc acttttctt cacaaccggc     4980 acggaactcg ctcgggctgg ccccggtgca ttttttaaat acccgcgaga aatagagttg    5040
atcgtcaaaa ccaacattgc gaccgacggt ggcgatagc atccgggtgg tgctcaaaag    5100
cagcttcgcc tggctgatac gttggtcctc gcgccagctt aagacgctaa tccctaactg    5160
ctggcggaaa agatgtgaca gacgcgacgg cgacaagcaa acatgctgtg cgacgctggc    5220
gatatcaaaa ttgctgtctg ccaggtgatc gctgatgtac tgacaagcct cgcgtacccg    5280
attatccatc ggtggatgga gcgactcgtt aatcgcttcc atgcgccgca gtaacaattg    5340
ctcaagcaga tttatcgcca gcagctccga atagcgccct tcccctttgcc cggcgttaat    5400 gatttgccca aacaggtcgc tgaaatgcgg ctggtgcgct tcatccgggc gaaagaaccc    5460
cgtattggca aatattgacg gccagttaag ccattcatgc cagtaggcgc gcggacgaaa    5520
gtaaacccac tggtgatacc attcgcgagc ctccggatga cgaccgtagt gatgaatctc    5580
tcctggcggg aacagcaaaa tatcacccgg tcggcaaaca aattctcgtc cctgattttt    5640 caccacccc tgaccgcgaa tggtgagatt gagaatataa cctttcattc ccagcggtcg    5700
gtcgataaaa aaatcgagat aaccgttggc ctcaatcggc gttaaacccg ccaccagatg    5760
ggcattaaac gagtatcccg gcagcagggg atcattttgc gcttcagcca tactttcat    5820 actcccgcca ttcagagaag aaaccaattg tccatattgc atcagacatt gccgtcactg    5880 cgtctttac tggctcttct cgctaaccaa accggtaacc ccgcttatta aaagcattct    5940
gtaacaaagc gggaccaaag ccatgacaaa aacgcgtaac aaaagtgtct ataatcacgg    6000
cagaaaagtc cacattgatt atttgcacgg cgtcacactt tgctatgcca tagcattttt    6060
atccataaga ttagcggatc ctacctgacg ctttttatcg caactctcta ctgttttctcc    6120 atacccgttt ttttgggcta gaaataattt tgtttaactt taagaaggag atatacatac    6180
ccatggacaa gaagtacagc atcggcctgg ccatcggcac caactctgtg ggctgggccg    6240
tgatcaccga cgagtacaag gtgcccagca agaaattcaa ggtgctgggc aacaccgacc    6300
ggcacagcat caagaagaac ctgatcggcg ccctgctgtt cgacagcgga gaaacagccg    6360
aggccacccg gctgaagaga accgccagaa gaagatacac cagacggaag aaccggatct    6420
gctatctgca agagatcttc agcaacgaga tggccaaggt ggacgacagc ttcttccaca    6480
gactggaaga gtccttcctg gtggaagagg ataagaagca cgagcggcac cccatcttcg    6540
gcaacatcgt ggacgaggtg gcctaccacg agaagtaccc caccatctac acctgagaa    6600 agaaactggt ggacagcacc gacaaggccg acctgcggct gatctatctg gccctggccc    6660
acatgatcaa gttccggggc cacttcctga tcgagggcga cctgaacccc gacaacagcg    6720
acgtggacaa gctgttcatc cagctggtgc agacctacaa ccagctgttc gaggaaaacc    6780
ccatcaacgc cagcggcgtg gacgccaagg ccatcctgtc tgccagactg agcaagagca    6840
gacggctgga aaatctgatc gcccagctgc ccggcgagaa gaagaatggc ctgttcggca    6900
acctgattgc cctgagcctg ggcctgaccc ccaacttcaa gagcaacttc gacctggccg    6960
aggatgccaa actgcagctg agcaaggaca ctctacgacga cgacctggac aacctgctgg    7020
cccagatcgg cgaccagtac gccgacctgt ttctggccgc caagaacctg tccgacgcca    7080
tcctgctgag cgacatcctg agagtgaaca ccgagatcac caaggccccc ctgagcgcct    7140
```

```
ctatgatcaa gagatacgac gagcaccacc aggacctgac cctgctgaaa gctctcgtgc   7200
ggcagcagct gcctgagaag tacaaagaga ttttcttcga ccagagcaag aacggctacg   7260
ccggctacat cgatggcgga gccagccagg aagagttcta caagttcatc aagcccatcc   7320
tggaaaagat ggacggcacc gaggaactgc tcgtgaagct gaacagagag gacctgctgc   7380
ggaagcagcg gaccttcgac aacggcagca tcccccacca gatccacctg ggagagctgc   7440
acgccattct cgcgcggcag gaagattttt acccattcct gaaggacaac cgggaaaaga   7500
tcgagaagat cctgaccttc cgcatcccct actacgtggg ccctctggcc aggggaaaca   7560
gcagattcgc ctggatgacc agaaagagcg aggaaaccat caccccctgg aacttcgagg   7620
aagtggtgga caagggcgcc agcgcccaga gcttcatcga gcggatgacc aacttcgata   7680
agaacctgcc caacgagaag gtgctgccca agcacagcct gctgtacgag tacttcaccg   7740
tgtacaacga gctgaccaaa gtgaaatacg tgaccgaggg aatgagaaag cccgccttcc   7800
tgagcggcga gcagaaaaaa gccatcgtgg acctgctgtt caagaccaac cggaaagtga   7860
ccgtgaagca gctgaaagag gactacttca gaaaaatcga gtgcttcgac tccgtggaaa   7920
tctccggcgt ggaagatcgg ttcaacgcct ccctgggcac ataccacgat ctgctgaaaa   7980
ttatcaagga caaggacttc ctggacaatg aggaaaacga ggacattctg gaagatatcg   8040
tgctgaccct gacactgttt gaggacagag agatgatcga ggaacggctg aaaacctatg   8100
cccacctgtt cgacgacaaa gtgatgaagc agctgaagcg gcggagatac accggctggg   8160
gcaggctgag ccggaagctg atcaacggca tccgggacaa gcagtccggc aagacaatcc   8220
tggatttcct gaagtccgac ggcttcgcca acagaaactt catgcagctg atccacgacg   8280
acagcctgac ctttaaagag gacatccaga aagcccaggt gtccggccag gccgatagcc   8340
tgcacgagca cattgccaat ctggccggca gccccgccat taagaagggc atcctgcaga   8400
cagtgaaggt ggtggacgag ctcgtgaaag tgatgggccg gcacaagccc gagaacatcg   8460
tgatcgaaat ggccagagag aaccagacca cccagaaggg acagaagaac agccgcgaga   8520
gaatgaagcg gatcgaagag ggcatcaaag agctgggcag ccagatcctg aaagaacacc   8580
ccgtggaaaa cacccagctg cagaacgaga agctgtacct gtactacctg cagaatgggc   8640
gggatatgta cgtggaccag gaactggaca tcaaccggct gtccgactac gatgtggacg   8700
ctatcgtgcc tcagagcttt ctgaaggacg actccatcga taacaaagtg ctgactcgga   8760
gcgacaagaa ccggggcaag agcgacaacg tgccctccga agaggtcgtg aagaagatga   8820
agaactactg gcgccagctg ctgaatgcca agctgattac ccagaggaag ttcgacaatc   8880
tgaccaaggc cgagagaggc ggcctgagcg aactggataa ggccggcttc atcaagagac   8940
agctggtgga aacccggcag atcacaaagc acgtggcaca gatcctggac tcccggatga   9000
acactaagta cgacgagaac gacaaactga tccgggaagt gaaagtgatc accctgaagt   9060
ccaagctggt gtccgatttc cggaaggatt tccagtttta caaagtgcgc gagatcaaca   9120
actaccacca cgcccacgac gcctacctga acgccgtcgt gggaaccgcc ctgatcaaaa   9180
agtaccctaa gctggaaagc gagttcgtgt acggcgacta caaggtgtac gacgtgcgga   9240
agatgatcgc caagagcgag caggaaatcg gcaaggctac cgccaagtac ttcttctaca   9300
gcaacatcat gaacttttc aagaccgaga ttaccctggc caacggcgag atccggaagc   9360
ggcctctgat cgagacaaac ggcgaaacag gcgagatcgt gtgggataag gccgggact   9420 ttgccaccgt gcggaaagtg ctgtctatgc cccaagtgaa tatcgtgaaa aagaccgagg   9480
```

| | |
|---|---|
| tgcagacagg cggcttcagc aaagagtcta tcctgcccaa gaggaacagc gacaagctga | 9540 |
| tcgccagaaa gaaggactgg gaccctaaga agtacggcgg cttcgacagc ccaccgtgg | 9600 |
| cctattctgt gctggtggtg gccaaagtgg aaaagggcaa gtccaagaaa ctgaagagtg | 9660 |
| tgaaagagct gctggggatc accatcatgg aagaagcag cttcgagaag aatcccatcg | 9720 |
| actttctgga agccaagggc tacaagaag tgaaaaagga cctgatcatc aagctgccta | 9780 |
| agtactccct gttcgagctg gaaaacggcc ggaagagaat gctggcctct gccggcgaac | 9840 |
| tgcagaaggg aaacgaactg gccctgccct ccaaatatgt gaacttcctg tacctggcca | 9900 |
| gccactatga gaagctgaag ggctcccccg aggataatga gcagaaacag ctgtttgtgg | 9960 |
| aacagcacaa acactacctg gacgagatca tcgagcagat cagcgagttc tccaagagag | 10020 |
| tgatcctggc cgacgctaat ctggacaagg tgctgagcgc ctacaacaag cacagagaca | 10080 |
| agcctatcag agagcaggcc gagaatatca tccacctgtt taccctgacc aatctgggag | 10140 |
| cccctgccgc cttcaagtac tttgacacca ccatcgaccg gaagaggtac accagcacca | 10200 |
| aagaggtgct ggacgccacc ctgatccacc agagcatcac cggcctgtac gagacacgga | 10260 |
| tcgacctgtc tcagctggga ggcgacgcgg ccgcggagca gaaactcatc tctgaagaag | 10320 |
| atctggaaca aaagttgatt tcagaagaag atctggaaca gaagctcatc tctgaggaag | 10380 |
| atctgtaata aggcgcgcct ccttaatggg acttgcagcc tcggtaccaa attccagaaa | 10440 |
| agacacccga aagggtgttt tttcgttttg gtcccacaga atgagcatca tggcctagtc | 10500 |
| gacatcggag aagagtacgg ctcttttaac cgcctcaaga accagataag tgaaatctag | 10560 |
| ttccaaacta ttttgtcatt tttaatttc gtattagctt acgacgctac acccagttcc | 10620 |
| catctatttt gtcactcttc cctaaataat ccttaaaaac tccatttcca cccctcccag | 10680 |
| ttcccaacta ttttgtccgc ccacagcggg gcatttttct tcctgttatg tttgggcgct | 10740 |
| gcattaatga atcggccaac gcgcgggag aggcggtttg cgtattgggc gctcttccgc | 10800 |
| ttcctcgctc actgacccgc tgcgctcggt cgttcggctg cggcgagcgg tatcag | 10856 |

<210> SEQ ID NO 15
<211> LENGTH: 10837
<212> TYPE: DNA
<213> ORGANISM: Artificial sequence
<220> FEATURE:
<223> OTHER INFORMATION: Synthetic construct

<400> SEQUENCE: 15

| | |
|---|---|
| ctgataccgc tcgccgcagc cgaacgaccg agcgcagcgg gtcagtgagc gaggaagcgg | 60 |
| aagagcgccc aatacgcaaa ccgcctctcc ccgcgcgttg gccgattcat taatgcagcg | 120 |
| cccaaacata acaggaagaa aaatgccccg ctgtgggcgg acaaaatagt tgggaactgg | 180 |
| gaggggtgga aatggagttt ttaaggatta tttagggaag agtgacaaaa tagatgggaa | 240 |
| ctgggtgtag cgtcgtaagc taatacgaaa attaaaaatg acaaaatagt ttggaactag | 300 |
| atttcactta tctggttctt gaggcggtta aaagagccgt actcttctcc gatgtcgact | 360 |
| aggccatgat gctcattctg tgggaccaaa acgaaaaaac ccctttcgg gtgtcttttc | 420 |
| tggaatttgg taccgaggct gcaagtccca ttaaggaggc gcgccttatt acagatcttc | 480 |
| ctcagagatg agcttctgtt ccagatcttc ttctgaaatc aacttttgtt ccagatcttc | 540 |
| ttcagagatg agtttctgct ccgcggccgc gtcgcctccc agctgagaca ggtcgatccg | 600 |
| tgtctcgtac aggccggtga tgctctggtg gatcagggtg gcgtccagca cctctttggt | 660 |
| gctggtgtac ctcttccggt cgatggtggt gtcaaagtac ttgaaggcgg caggggctcc | 720 |

```
cagattggtc agggtaaaca ggtggatgat attctcggcc tgctctctga taggcttgtc    780
tctgtgcttg ttgtaggcgc tcagcacctt gtccagatta gcgtcggcca ggatcactct    840
cttggagaac tcgctgatct gctcgatgat ctcgtccagg tagtgtttgt gctgttccac    900
aaacagctgt ttctgctcat tatcctcggg ggagcccttc agcttctcat agtggctggc    960
caggtacagg aagttcacat atttggaggg cagggccagt tcgtttccct tctgcagttc    1020
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttcttttcat gatggtgatc cccagcagct ctttcacact    1200
cttcagtttc ttggacttgc ccttttccac tttggccacc accagcacag aataggccac    1260
ggtggggctg tcgaagccgc cgtacttctt agggtcccag tccttctttc tggcgatcag    1320
cttgtcgctg ttcctcttgg gcaggataga ctctttgctg aagccgcctg tctgcacctc    1380
ggtcttttc acgatattca cttggggcat agacagcact ttccgcacgg tggcaaagtc    1440
ccggccctta tcccacacga tctcgcctgt ttcgccgttt gtctcgatca gaggccgctt    1500
ccggatctcg ccgttggcca gggtaatctc ggtcttgaaa aagttcatga tgttgctgta    1560
gaagaagtac ttggcggtag ccttgccgat ttcctgctcg ctcttggcga tcatcttccg    1620
cacgtcgtac accttgtagt cgccgtacac gaactcgctt tccagcttag ggtacttttt    1680
gatcagggcg gttcccacga cggcgttcag gtaggcgtcg tgggcgtggt ggtagttgtt    1740
gatctcgcgc actttgtaaa actgaaaatc cttccggaaa tcggacacca gcttggactt    1800
cagggtgatc actttcactt cccggatcag tttgtcgttc tcgtcgtact tagtgttcat    1860
ccggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atcggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccgacacct gggctttctg gatgtcctct ttaaaggtca ggctgtcgtc    2580
gtggatcagc tgcatgaagt ttctgttggc gaagccgtcg acttcagga aatccaggat    2640
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccagggaggc gttgaaccga tcttccacgc cggagatttc    2940
cacgagtcaa agcactcga ttttcttgaa gtagtcctct ttcagctgct tcacggtcac    3000
tttccggttg gtcttgaaca gcaggtccac gatggctttt ttctgctcgc cgctcaggaa    3060
```

-continued

```
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300 tccctggcc agagggccca cgtagtaggg gatgcggaag gtcaggatct tctcgatctt    3360 ttccggttg tccttcagga atgggtaaaa atcttcctgc cgccgcagaa tggcgtgcag    3420
ctctcccagg tggatctggt ggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720 gctcagggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatggggtt    4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtcacga tgttgccgaa    4320 gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatgggtat    4680
gtatatctcc ttcttaaagt taaacaaaat tatttctagc ccaaaaaaac gggtatggag    4740
aaacagtaga gagttgcgat aaaaagcgtc aggtaggatc cgctaatctt atggataaaa    4800
atgctatggc atagcaaagt gtgacgccgt gcaaataatc aatgtggact tttctgccgt    4860
gattatagac acttttgtta cgcgttttg tcatggcttt ggtcccgctt tgttacagaa    4920
tgcttttaat aagcggggtt accggtttgg ttagcgagaa gagccagtaa aagacgcagt    4980
gacggcaatg tctgatgcaa tatggacaat tggtttcttc tctgaatggc gggagtatga    5040
aaagtatggc tgaagcgcaa aatgatcccc tgctgccggg atactcgttt aatgcccatc    5100
tggtggcggg tttaacgccg attgaggcca acggttatct cgattttttt atcgaccgac    5160
cgctgggaat gaaaggttat attctcaatc tcaccattcg cggtcagggg gtggtgaaaa    5220
atcagggacg agaatttgtt tgccgaccgg gtgatatttt gctgttcccg ccaggagaga    5280
ttcatcacta cggtcgtcat ccggaggctc gcgaatggta tcaccagtgg gtttactttc    5340
gtccgcgcgc ctactggcat gaatggctta actggccgtc aatatttgcc aatacggggt    5400 tcttcgccc ggatgaagcg caccagccgc atttcagcga cctgtttggg caaatcatta    5460
```

```
acgccgggca aggggaaggg cgctattcgg agctgctggc gataaatctg cttgagcaat    5520
tgttactgcg gcgcatggaa gcgattaacg agtcgctcca tccaccgatg gataatcggg    5580
tacgcgaggc ttgtcagtac atcagcgatc acctggcaga cagcaatttt gatatcgcca    5640
gcgtcgcaca gcatgtttgc ttgtcgccgt cgcgtctgtc acatcttttc cgccagcagt    5700
tagggattag cgtcttaagc tggcgcgagg accaacgtat cagccaggcg aagctgcttt    5760
tgagcaccac ccgatgcct atcgccaccg tcggtcgcaa tgttggtttt gacgatcaac     5820
tctatttctc gcgggtattt aaaaaatgca ccggggccag cccgagcgag ttccgtgccg    5880
gttgtgaaga aaaagtgaat gatgtagccg tcaagttgtc ataaactagt ctgcagacgt    5940
aaaaaaagcg gcgtggttag ccgctttttt aattgccgga gcgcaataaa aaagcccccg    6000
gaaggtgatc ttccgggggc tttctcatgc gttgcttgta ttgaaaatgg gggccatgcc    6060
tacctatctg cctcccgggt ccttgagccc cattatcacc tccaaagcct tctcgtctgg    6120
tcagtttcac ctgttttacg taaaaacccg cttcggcggg ttttttacttt tggggaaaca   6180
cagaaaaaag cccgcacctg acagtgcggg cttttttttt cgaccaaagg tgcgactact   6240
cttgcctact acctatcgac tgagctgaaa gaattccggt tctggcaaat attctgaaat   6300
gagctgttga caattaatca tccggctcgt ataattctag tcgcgcggtt ctcgccaagg   6360
ggtttaagag ctatgctgga aacagcatag caagtttaaa taaggctagt ccgttatcaa   6420
cttgaaaaag tggaccgag tcggtgcttt tttttttgaat tcatgtggct gaccgttctg   6480
ttgtctctcg ctcttccgag tagacgaaca ataaggcctc cctaacgggg ggcctttttt   6540
attgataaca aaagtcagtg cttccgctat ttccaaaata ccgggctaat acggtttaaa   6600
cgacctcctg gatttgctca gacagccttt tcgtcattcg tttcagccaa aaaacttaag   6660
accgccggtc ttgtccacta ccttgcagta atgcggtgga caggatcggc ggttttcttt   6720
tctcttctca agaagttcct atactttcta gagaatagga acttcggaat aggaacttcc   6780
tcctgaacgg ccataagaac gaaggctgtc tgttgaactc tcgagccttg tcgccttgcg   6840
tataatattt gcccatggac gcacaccgtg gaaacggatg aaggcacgaa cccagttgac   6900
ataagcctgt tcggttcgta aactgtaatg caagtagcgt atgcgctcac gcaactggtc   6960
cagaaccttg accgaacgca gcggtggtaa cggcgcagtg gcggttttca tggcttgtta   7020
tgactgtttt tttgtacagt ctatgcctcg ggcatccaag cagcaagcgc gttacgccgt   7080
gggtcgatgt ttgatgttat ggagcagcaa cgatgttacg cagcagcaac gatgttacgc   7140
agcagggcag tcgccctaaa acaaagttag gtggctcaag tatgggcatc attcgcacat   7200
gtaggctcgg ccctgaccaa gtcaaatcca tgcgggctgc tcttgatctt tcggtcgtg    7260
agttcggaga cgtagccacc tactcccaac atcagccgga ctccgattac tcgggaact    7320
tgctccgtag taagacattc atcgcgcttg ctgccttcga ccaagaagcg gttgttggcg    7380
ctctcgcggc ttacgttctg cccaagtttg agcagccgcg tagtgagatc tatatctatg    7440
atctcgcagt ctccggagag caccggaggc agggcattgc caccgcgctc atcaatctcc    7500
tcaagcatga ggccaacgcg cttggtgctt atgtgatcta cgtgcaagca gattacggtg    7560
acgatcccgc agtggctctc tatacaaagt tgggcatacg ggaagaagtg atgcactttg    7620
atatcgaccc aagtaccgcc acctaacaat tcgttcaagc cgagatctcg agcatcagct    7680
tcaaaagcgc tctgaagttc ctatactttc tagagaatag gaacttcgga ataggtactt    7740
caagatcccc aattcgagct catcgtccgg gccgcaagct cctagcggcg gatttgtcct    7800
```

```
actcaggaga gcgttcaccg acaaacaaca gataaaacga aaggcccagt ctttcgactg   7860
agcctttcgt tttatttgat gcctcaagct agagagtcat tacccaggc gtttaagggc    7920 accaataact gccttaaaaa aattacgccc cgccctgcca ctcatcgcag tctagcttgg   7980
attctcacca ataaaaaacg cccggcggca accgagcgtt ctgaacaaat ccagatggag   8040
ttctgaggtc attactggat ctatcaacag gagtccaagc tcagctaatt aagctagctt   8100
atcgataccg tcgacctcga accccacgcc cctctttaat acgacgggca atttgcactt   8160
cagaaaatga agagtttgct ttagccataa caaaagtcca gtatgctttt tcacagcata   8220
actggactga tttcagttta caactattct gtcagttta agactttatt gtcatagttt     8280
agatctattt tgttcagttt aagactttat tgtccgccca cacccgctta cgcagggcat   8340
ccatttatta ctcaaccgta accgattttg ccaggttacg cggctggtcc tctagctggc   8400
gtaatagcga agaggcccgc accgatcgcc cttcccaaca gttgcgcagc ctgaatggcg   8460
aatggcgcct gatgcggtat tttctcctta cgcatctgtg cggtatttca caccgcatat   8520
ggtgcactct cagtacaatc tgctctgatg ccgcatagtt aagccagccc cgacacccgc   8580
caacacccgc tgacgcgccc tgacgggctt gtctgctccc ggcatccgct tacagacaag   8640
ctgtgaccgt ctccgggagc tgcatgtgtc agaggttttc accgtcatca ccgaaacgcg   8700
cgagacgaaa gggcctcgtg atacgcctat ttttataggt taatgtcatg ataataatgg   8760
tttcttagac gtcaggtggc acttttcggg gaaatgtgcg cggaacccct atttgtttat   8820
ttttctaaat acattcaaat atgtatccgc tcatgagaca ataaccctga taaatgcttc   8880
aataatattg aaaaggaag agtatgagta ttcaacattt ccgtgtcgcc cttattccct   8940
tttttgcggc attttgcctt cctgtttttg ctcacccaga aacgctggtg aaagtaaaag   9000
atgctgaaga tcagttgggt gcacgagtgg gttacatcga actggatctc aacagcggta   9060
agatccttga gagttttcgc cccgaagaac gttttccaat gatgagcact tttaaagttc   9120
tgctatgtgg cgcggtatta cccgtattg acgccgggca agagcaactc ggtcgccgca   9180
tacactattc tcagaatgac ttggttgagt actcaccagt cacagaaaag catcttacgg   9240
atggcatgac agtaagagaa ttatgcagtg ctgccataac catgagtgat aacactgcgg   9300
ccaacttact tctgacaacg atcggaggac cgaaggagct aaccgctttt ttgcacaaca   9360
tgggggatca tgtaactcgc cttgatcgtt gggaaccgga gctgaatgaa gccataccaa   9420
acgacgagcg tgacaccacg atgcctgtag caatggcaac aacgttgcgc aaactattaa   9480
ctggcgaact acttactcta gcttcccggc aacaattaat agactggatg gaggcggata   9540
aagttgcagg accacttctg cgctcggccc ttccggctgg ctggtttatt gctgataaat   9600
ctggagccgg tgagcgtggg tcccgcggta tcattgcagc actggggcca gatggtaagc   9660
cctcccgtat cgtagttatc tacacgacgg ggagtcaggc aactatggat gaacgaaata   9720
gacagatcgc tgagataggt gcctcactga ttaagcattg gtaactgtca gaccaagttt   9780
actcatatat actttagatt gatttaaaac ttcatttta atttaaaagg atctaggtga   9840
agatcctttt tgataatctc atgaccaaaa tcccttaacg tgagttttcg ttccactgag   9900
cgtcagaccc cgtagaaaag atcaaaggca gttattggtg cctcactgat taagcattgg   9960
taactgtcag accaagttta ctcatatata ctttagattg atttaaaact tcattttaa  10020 tttttgcggc gcaagatcc ggccacgatg cgtccggcgt agaggatctg aagatcagca   10080
gttcaacctt ttgatagtac gtactaagct ctcatgtttc acgtactaag ctctcatgtt   10140
taacgtacta agctctcatg tttaacgaac taaaccctca tggctaacgt actaagctct   10200
```

```
catggctaac gtactaagct ctcatgtttc acgtactaag ctctcatgtt tgaacaataa    10260
aattaatata aatcagcaac ttaaatagcc tctaaggttt taagttttat aagaaaaaaa    10320
agaatatata aggcttttaa agcttttaag gtttaacggt tgtggacaac aagccaggga    10380
tgtaacgcac tgagaagccc ttagagcctc tcaaagcaat tttgagtgac acaggaacac    10440
ttaacggctg acatgggaat tagccatggc atcacagtat cgtgatgaca gaggcaggga    10500
gtgcggcctt tttacggttc ctggcctttt gctggccttt tgctcacatg ttctttcctg    10560
cgttatcagg ggattcctta aggtatactt tccgctgcat aaccctgctt cggggtcatt    10620
atagcgattt tttcggtata tccatccttt tcgcacgat atacaggatt ttgccaaagg    10680
gttcgtgtag actttccttg gtgtatccaa cggcgtcagc cgggcaggat aggtgaagta    10740
ggcccacccg cgagcgggtg ttccttcttc actgtccctt attcgcacct ggcggtgctc    10800
aacgggaatc ctgctctgcg aggctggccg ataagct                             10837

<210> SEQ ID NO 16
<211> LENGTH: 10347
<212> TYPE: DNA
<213> ORGANISM: Artificial sequence
<220> FEATURE:
<223> OTHER INFORMATION: Synthetic construct

<400> SEQUENCE: 16
ttctaactac ttattttaaa gcagtctgga ttgtttgggt aattcataaa aaaataaaag      60
aaagaaggag gaatagagtt tttcttttt ttgtttgcaa tgttactgtc aagtcgcaaa     120
agaattgcta tgaccgaaaa aaaaccgcaa aggaatagat ataaggtacc tttttgcaat     180
tcatctttgt aaaataaagg ttattctgac ataatacaat taatgtaaaa attcgcacaa     240
ttttatgtaa ggatggggga attttcttgc ggggtgtttt cttagataaa gataaaattc     300
cgtacgactt agtcacgaaa aagttaaatg aatggtatac atcaataaaa aatgatcaag     360
ttgagcaagc cgagattata aaaacagaag tagagaaaga attgttaaac atggaagaaa     420
atcaagatgc cctgttatat tatcaactat tagaatttag acatgagata atgctgagtt     480
atatgaaatc taaggaaata gaagatctca ataatgctta tgagactata aaagaaattg     540
agaagcaagg gcaattaact ggcatgttgg aatactattt ttactttttt aagggtatgt     600
acgagtttag gcgtaaagaa ttaatttcag cgataagtgc ttatcgaata gctgaatcaa     660
agttgtcaga agttgaggat gaaatagaga aagcagagtt ttttttcaaa gtgtcctatg     720
tatattatta tatgaaacaa acatacttct ccatgaatta tgcaaatcgt gcactcaaaa     780
tatttagaga gtatgaagaa tatgctgtcc agactgtgcg ttgtcaattt attgtagcag     840
gaaacttgat cgagtgaatc gataagctag cttaattagc tgagcttgga ctcctgttga     900
tagatccagt aatgacctca gaactccatc tggatttgtt cagaacgctc ggttgccgcc     960
gggcgttttt tattggtgag aatccaagct agactgcgat gagtggcagg gcggggcgta    1020 attttttaa ggcagttatt ggtgccctta aacgcctggg gtaatgactc tctagcttga    1080
ggcatcaaat aaaacgaaag gctcagtcga agactgggc ctttcgtttt atctgttgtt    1140
tgtcggtgaa cgctctcctg agtaggacaa atccgccgct aggagcttgc ggcccggacg    1200
atgagctcga attggggatc ttgaagtacc tattccgaag ttcctattct ctagaaagta    1260
taggaacttc agagcgcttt tgaagctgat gctcgagtgc ttaaaaactt actcaatgga    1320
ataattctag ataattctta ggccacacgt tcaagtgcag ccacaggata aatttgcact    1380
```

```
gagcctgggt gggattcgga ctcgaccgca tagccttcag gagtgagttt tgtgcaatac    1440
caaccgacga cttgaccctg ccaagcggca ccagatttct tgcgtacgcg atcccctaag    1500
ccaaaggtgg cactcagggg aagcgcaaac tgccctgcaa cgggagcgtt ggcttcatcg    1560
ctactttgac ccatgtcgaa tccttcttgt gaatctatta tggcgacaag caaatcgagc    1620
tctgactgcc taccccacaa caactatcag aaagcaccag cacaacggct gcctaacttt    1680
gttttagggc gactgccctg ctgcgtaaca tcgttgctgc tccataacat caaacatcga    1740
cccacggcgt aacgcgcttg ctgcttggat gcccgaggca tagactgtac aaaaaaacag    1800
tcataacaag ccatgaaaac cgccactgcg ccgttaccac cgctgcgttc ggtcaaggtt    1860
ctggaccagt tgcgtgagcg catacgctac ttgcattaca gtttacgaac cgaacaggct    1920
tatgtcaact gggttcgtga attatccatt gctgttgaca aagggaatca ggctcgagag    1980
ttcaacagac agccttcgtt cttatggccg ttcaggagga agttcctatt ccgaagttcc    2040
tattctctag aaagtatagg aacttcttga gaagagaaaa gaaaaccgcc gatcctgtcc    2100
accgcattac tgcaaggtag tggacaagac cggcggtctt aagttttttg gctgaaacga    2160
atgacgaaaa ggctgtctga gcaaatccag gaggtcgttt aaaccgtatt agcccggtat    2220
tttgaaaata gcggaagcac tgacttttgt tatcaataaa aaaggccccc cgttagggag    2280
gccttattgt tcgtctactc ggaagagcga gagacaacag aacggtcagc cacatgaatt    2340
caaaaaaaaa gcaccgactc ggtgccactt tttcaagttg ataacggact agccttattt    2400
aaacttgcta tgctgtttcc agcatagctc ttaaacagac cgctaaactg aaagttccac    2460
acattatacg agccggatga ttaattgtca acagctcatt tcagaatatt tgccagaacc    2520
ggaattcttt cagctcagtc gataggtagt aggcaagagt agtcgcacct ttggtcgaaa    2580
aaaaaagccc gcactgtcag gtgcgggctt ttttctgtgt ttccccaaaa gtaaaaaccc    2640
gccgaagcgg gttttacgt aaaacaggtg aaactgacca gacgagaagg ctttggaggt    2700
gataatgggg ctcaaggacc cgggaggcag ataggtaggc atggccccca ttttcaatac    2760
aagcaacgca tgagaaagcc cccggaagat caccttccgg gggctttttt attgcgctcc    2820
ggcaattaaa aaagcggcta accacgccgc tttttttacg tctgcagagc tcataggcaa    2880
gcgaatcgtg atgcctctta gccagtacta gtatggataa gaaatactca ataggcttag    2940
ctatcggcac aaatagcgtc ggatgggcgg tgatcactga tgaatataag gttccgtcta    3000
aaaagttcaa ggttctggga aatacagacc gccacagtat caaaaaaaat cttataggg    3060 ctctttatt tgacagtgga gagacagcgg aagcgactcg tctcaaacgg acagctcgta    3120
gaaggtatac acgtcggaag aatcgtattt gttatctaca ggagattttt tcaaatgaga    3180
tggcgaaagt agatgatagt ttctttcatc gacttgaaga gtcttttttg gtggaagaag    3240
acaagaagca tgaacgtcat cctatttttg gaaatatagt agatgaagtt gcttatcatg    3300
agaaatatcc aactatctat catctgcgaa aaaaattggt agattctact gataaagcgg    3360
atttgcgctt aatctatttg gccttagcgc atatgattaa gtttcgtggt catttttga    3420 ttgagggaga tttaaatcct gataatagtg atgtggacaa actatttatc cagttggtac    3480
aaacctacaa tcaattattt gaagaaaacc ctattaacgc aagtggagta gatgctaaag    3540
cgattctttc tgcacgattg agtaaatcaa gacgattaga aaatctcatt gctcagctcc    3600
ccggtgagaa gaaaaatggc ttatttggga atctcattgc tttgtcattg ggtttgaccc    3660
ctaattttaa atcaaatttt gatttggcag aagatgctaa attacagctt tcaaaagata    3720
cttacgatga tgatttagat aatttattgg cgcaaattgg agatcaatat gctgatttgt    3780
```

```
ttttggcagc taagaattta tcagatgcta ttttactttc agatatccta agagtaaata   3840
ctgaaataac taaggctccc ctatcagctt caatgattaa acgctacgat gaacatcatc   3900
aagacttgac tcttttaaaa gctttagttc gacaacaact tccagaaaag tataaagaaa   3960
tcttttttga tcaatcaaaa aacgatatg caggttatat tgatggggga gctagccaag    4020
aagaattta taaatttatc aaaccaattt tagaaaaaat ggatggtact gaggaattat    4080
tggtgaaact aaatcgtgaa gatttgctgc gcaagcaacg gacctttgac aacggctcta   4140
ttccccatca aattcacttg ggtgagctgc atgctatttt gagaagacaa gaagactttt   4200
atccattttt aaaagacaat cgtgagaaga ttgaaaaaat cttgactttt cgaatcccctt  4260
attatgttgg tccattggcg cgtggcaata gtcgttttgc atggatgact cggaagtctg   4320
aagaaacaat tacccccatgg aattttgaag aagttgtcga taaaggtgct tcagctcaat  4380
catttattga acgcatgaca aactttgata aaaatcttcc aaatgaaaaa gtactaccaa   4440
aacatagttt gctttatgag tattttacgg tttataacga attgacaaag gtcaaatatg  4500
ttactgaagg aatgcgaaaa ccagcatttc tttcaggtga acagaagaaa gccattgttg  4560
atttactctt caaaacaaat cgaaaagtaa ccgttaagca attaaaagaa gattatttca  4620
aaaaaataga atgttttgat agtgttgaaa tttcaggagt tgaagataga tttaatgctt  4680
cattaggtac ctaccatgat ttgctaaaaa ttattaaaga taaagatttt ttggataatg  4740
aagaaaatga agatatctta gaggatattg ttttaacatt gaccttattt gaagatagg   4800
agatgattga ggaaagactt aaaacatatg ctcacctctt tgatgataag gtgatgaaac  4860
agcttaaacg tcgccgttat actggttggg gacgtttgtc tcgaaaattg attaatggta  4920
ttagggataa gcaatctggc aaaacaatat tagatttttt gaaatcagat ggttttgcca  4980
atcgcaattt tatgcagctg atccatgatg atagtttgac atttaaagaa gacattcaaa  5040
aagcacaagt gtctggacaa ggcgatagtt tacatgaaca tattgcaaat ttagctggta  5100
gccctgctat taaaaaaggt attttacaga ctgtaaaagt tgttgatgaa ttggtcaaag  5160
taatggggcg gcataagcca gaaaatatcg ttattgaaat ggcacgtgaa aatcagacaa  5220
ctcaaaaggg ccagaaaaat tcgcgagagc gtatgaaacg aatcgaagaa ggtatcaaag  5280
aattaggaag tcagattctt aaagagcatc ctgttgaaaa tactcaattg caaaatgaaa  5340
agctctatct ctattatctc caaaatggaa gagacatgta tgtggaccaa gaattagata  5400
ttaatcgttt aagtgattat gatgtcgatg ccattgttcc acaaagtttc cttaaagacg  5460
attcaataga caataaggtc ttaacgcgtt ctgataaaaa tcgtggtaaa tcggataacg  5520
ttccaagtga agaagtagtc aaaaagatga aaaactattg gagacaactt ctaaacgcca  5580
agttaatcac tcaacgtaag tttgataatt taacgaaagc tgaacgtgga ggtttgagtg  5640
aacttgataa agctggtttt atcaaacgcc aattggttga aactcgccaa atcactaagc  5700
atgtggcaca aattttggat agtcgcatga atactaaata cgatgaaaat gataaactta  5760
ttcgagaggt taaagtgatt accttaaaat ctaaattagt ttctgacttc cgaaaagatt  5820
tccaattcta taagtacgt gagattaaca attaccatca tgcccatgat gcgtatctaa  5880
atgccgtcgt tggaactgct ttgattaaga atatccaaa acttgaatcg gagtttgtct   5940
atggtgatta taaagtttat gatgttcgta aaatgattgc taagtctgag caagaaatag  6000
gcaaagcaac cgcaaaatat ttcttttact ctaatatcat gaacttcttc aaaacagaaa  6060
ttacacttgc aaatggagag attcgcaaac gccctctaat cgaaactaat ggggaaactg  6120
```

```
gagaaattgt ctgggataaa gggcgagatt ttgccacagt gcgcaaagta ttgtccatgc    6180
cccaagtcaa tattgtcaag aaaacagaag tacagacagg cggattctcc aaggagtcaa    6240
ttttaccaaa aagaaattcg gacaagctta ttgctcgtaa aaaagactgg gatccaaaaa    6300
aatatggtgg ttttgatagt ccaacggtag cttattcagt cctagtggtt gctaaggtgg    6360
aaaaagggaa atcgaagaag ttaaaatccg ttaaagagtt actagggatc acaattatgg    6420
aaagaagttc ctttgaaaaa aatccgattg acttttttaga agctaaagga tataaggaag    6480
ttaaaaaaga cttaatcatt aaactaccta aatatagtct ttttgagtta gaaaacggtc    6540
gtaaacggat gctggctagt gccggagaat acaaaaagg aaatgagctg gctctgccaa     6600
gcaaatatgt gaattttta tatttagcta gtcattatga aaagttgaag ggtagtccag      6660
aagataacga acaaaaacaa ttgtttgtgg agcagcataa gcattattta gatgagatta    6720
ttgagcaaat cagtgaattt tctaagcgtg ttatttagc agatgccaat ttagataaag      6780
ttcttagtgc atataacaaa catagagaca aaccaatacg tgaacaagca gaaaatatta    6840
ttcatttatt tacgttgacg aatcttggag ctcccgctgc ttttaaatat tttgatacaa    6900
caattgatcg taaacgatat acgtctacaa aagaagtttt agatgccact cttatccatc    6960
aatccatcac tggtctttat gaaacacgca ttgatttgag tcagctagga ggtgacgcgg    7020
ccgcggagca gaaactcatc tctgaagaag atctggaaca aaagttgatt tcagaagaag    7080
atctggaaca gaagctcatc tctgaggaag atctgtaata aggcgcgcct ccttaatggg    7140
acttgcagcc tcggtaccaa attccagaaa agacacccga aagggtgttt tttcgttttg    7200
gtcccacaga atgagcatca tggctctagt cgaccgggta ggggcatagc ttagataatt    7260
ggaaaagagg aaaaaagctt aatcttttt cgaaggttaa gcttttcctt ttatttataa      7320
aaagtgaact aactatcaga aagaaattat attaaatttt atttttttgt ttaaaaagta    7380
gattatataa aggcaagcta ggtggggaa aatatgtta aaaagaaaa agtcacagaa        7440 tacatttgga ctatactaat accaacaatc atcacttta tcattagttg ggttgggtct      7500
tattacaatg gtacttcgac agttagtatt ggacaaccta caaaagtttc cggtcagtat    7560
atcacgccaa taaatataag tccctatcat gatattaagg aattaagaat aacttttccg    7620
caaaaactag atgtaaaaca aattagttca aatgagccta taatgtaaa atcagataag      7680 aacaatatag gagttgaaag taattccact tttgagattg cgaaaatcgt tgaaaataat    7740
agcgttcagt tgctaattac aacacaaaaa aagttaaacg ataaggaaat tagaattgat    7800
aaaaatggaa ataacatttc tgtaaattat gaatctcaga ttgttaatcc tgcaaaaaaa    7860
caattaatca atcttataat tacgtcatct atttatttta taatgcttaa tatactagca    7920
ttgattatga acaaaagatg ggataagtat tatgcaaaaa tgaaaatga aatcaaagaa      7980 tttgaggata atgcaaaaga tcttgataaa aaatcaaaga agaaaagcga ggaattatcg    8040
gagctgcgaa agaccttgaa ccaagcgttt gaggaaactg ataggataaa atatcatgag    8100 aagaaaaac aaatcctcct cttagctaag ttaaacgatt ataaaaaaga actaaccttt     8160
tggagaaata caataagaaa agttctttat gaacttcctg atggagataa aaaagcagat    8220
aaactaatag ggacagttac atcatcttta aaaacgtacg gtacagtcga aagtaaagc     8280 ttatcggcca gcctcgcaga gcaggattcc cgttgagcac cgccaggtgc gaataaggga    8340
cagtgaagaa ggaacacccg ctcgcgggtg ggccttcttc acctatcctg cccggctgac    8400
gccgttggat acaccaagga aagtctacac gaacccttg gcaaaatcct gtatatcgtg     8460
cgaaaaagga tggatatacc gaaaaaatcg ctataatgac cccgaagcag ggttatgcag    8520
```

```
cggaaagtat accttaagga atccctgat aacgcaggaa agaacatgtg agcaaaaggc      8580
cagcaaaagg ccaggaaccg taaaaaggcc gcactccctg cctctgtcat cacgatactg      8640
tgatgccatg gctaattccc atgtcagccg ttaagtgttc ctgtgtcact caaaattgct      8700
ttgagaggct ctaagggctt ctcagtgcgt tacatccctg gcttgttgtc cacaaccgtt      8760
aaaccttaaa agctttaaaa gccttatata ttcttttttt tcttataaaa cttaaaacct      8820
tagaggctat ttaagttgct gatttatatt aattttattg ttcaaacatg agagcttagt      8880
acgtgaaaca tgagagctta gtacgttagc catgagagct tagtacgtta gccatgaggg      8940
tttagttcgt taaacatgag agcttagtac gttaaacatg agagcttagt acgtgaaaca      9000
tgagagctta gtacgtacta tcaacaggtt gaactgctga tcttcagatc ctctacgccg      9060
gacgcatcgt ggccggatct tgcggccgca aaaattaaaa atgaagtttt aaatcaatct      9120
aaagtatata tgagtaaact tggtctgaca gttaccaatg cttaatcagt gaggcaccaa      9180
taactgcctt tgatcttttc tacggggtct gacgctcagt ggaacgaaaa ctcacgttaa      9240
gggattttgg tcatgagatt atcaaaaagg atcttcacct agatcctttt aaattaaaaa      9300
tgaagtttta aatcaatcta agtatatat gagtaaactt ggtctgacag ttaccaatgc      9360
ttaatcagtg aggcacctat ctcagcgatc tgtctatttc gttcatccat agttgcctga      9420
ctccccgtcg tgtagataac tacgatacgg gagggcttac catctggccc cagtgctgca      9480
atgataccgc gagacccacg ctcaccggct ccagatttat cagcaataaa ccagccagcc      9540
ggaagggccg agcgcagaag tggtcctgca actttatccg cctccatcca gtctattaat      9600
tgttgccggg aagctagagt aagtagttcg ccagttaata gtttgcgcaa cgttgttgcc      9660
attgctacag gcatcgtggt gtcacgctcg tcgtttggta tggcttcatt cagctccggt      9720
tcccaacgat caaggcgagt tacatgatcc cccatgttgt gcaaaaaagc ggttagctcc      9780
ttcggtcctc cgatcgttgt cagaagtaag ttggccgcag tgttatcact catggttatg      9840
gcagcactgc ataattctct tactgtcatg ccatccgtaa gatgcttttc tgtgactggt      9900
gagtactcaa ccaagtcatt ctgagaatag tgtatgcggc gaccgagttg ctcttgcccg      9960
gcgtcaatac gggataatac cgcgccacat agcagaactt taaaagtgct catcattgga     10020
aaacgttctt cggggcgaaa actctcaagg atcttaccgc tgttgagatc cagttcgatg     10080
taacccactc gtgcacccaa ctgatcttca gcatctttta ctttcaccag cgtttctggg     10140
tgagcaaaaa caggaaggca aaatgccgca aaaagggaa taagggcgac acggaaatgt     10200
tgaatactca tactcttcct ttttcaatat tattgaagca tttatcaggg ttattgtctc     10260
atgagcggat acatatttga atgtatttag aaaaataaac aaatagggt tccgcgcaca     10320 tttccccgaa aagtgccacc tgacgtc                                       10347
```

<210> SEQ ID NO 17
<211> LENGTH: 12711
<212> TYPE: DNA
<213> ORGANISM: Artificial sequence
<220> FEATURE:
<223> OTHER INFORMATION: Synthetic construct

<400> SEQUENCE: 17

```
ttctaactac ttattttaaa gcagtctgga ttgtttgggt aattcataaa aaaataaaag        60
aaagaaggag gaatagagtt tttctttttt ttgtttgcaa tgttactgtc aagtcgcaaa       120
agaattgcta tgaccgaaaa aaaaccgcaa aggaatagat ataaggtacc tttttgcaat       180
```

-continued

| | |
|---|---|
| tcatctttgt aaaataaagg ttattctgac ataatacaat taatgtaaaa attcgcacaa | 240 |
| ttttatgtaa ggatggggga attttcttgc ggggtgtttt cttagataaa gataaaattc | 300 |
| cgtacgactt agtcacgaaa agttaaatg aatggtatac atcaataaaa aatgatcaag | 360 |
| ttgagcaagc cgagattata aaacagaag tagagaaaga attgttaaac atggaagaaa | 420 |
| atcaagatgc cctgttatat tatcaactat tagaatttag acatgagata atgctgagtt | 480 |
| atatgaaatc taaggaaata gaagatctca ataatgctta tgagactata aagaaattg | 540 |
| agaagcaagg gcaattaact ggcatgttgg aatactattt ttactttttt aagggtatgt | 600 |
| acgagtttag gcgtaaagaa ttaatttcag cgataagtgc ttatcgaata gctgaatcaa | 660 |
| agttgtcaga agttgaggat gaaatagaga aagcagagtt ttttttcaaa gtgtcctatg | 720 |
| tatattatta tatgaaacaa acatacttct ccatgaatta tgcaaatcgt gcactcaaaa | 780 |
| tatttagaga gtatgaagaa tatgctgtcc agactgtgcg ttgtcaattt attgtagcag | 840 |
| gaaacttgat cgagtgaatc gataagctag cttaattagc tgagcttgga ctcctgttga | 900 |
| tagatccagt aatgacctca gaactccatc tggatttgtt cagaacgctc ggttgccgcc | 960 |
| gggcgttttt tattggtgag aatccaagct agactgcgat gagtggcagg gcggggcgta | 1020 |
| attttttaa ggcagttatt ggtgcccta acgcctggg gtaatgactc tctagcttga | 1080 |
| ggcatcaaat aaaacgaaag gctcagtcga aagactgggc ctttcgtttt atctgttgtt | 1140 |
| tgtcggtgaa cgctctcctg agtaggacaa atccgccgct aggagcttgc ggccccggacg | 1200 |
| atgagctcga attggggatc ttgaagtacc tattccgaag ttcctattct ctagaaagta | 1260 |
| taggaacttc agagcgcttt tgaagctgat gctcgaggat cctctagaca tcagagtatg | 1320 |
| gacagttgcg gatgtacttc agaaaagatt agatgtctaa aaagcttgta gttaaagctt | 1380 |
| tttagacatc taaatctagg tactaaaaca attcatccag taaatataaa tattttattt | 1440 |
| tctcccaatc aggcttgatc cccagtaagt caaaaaatag ctcgacatac tgttcttccc | 1500 |
| cgatatcctc cctgatcgac cggacgcaga aggcaatgtc ataccacttg tccgccctgc | 1560 |
| cgcttctccc aagatcaata aagccactta ctttgccatc tttcacaaag atgttgctgt | 1620 |
| ctcccaggtc gccgtgggaa aagacaagtt cctcttcggg cttttccgtc tttaaaaaat | 1680 |
| catacagctc gcgcggatct ttaaatggag tgtcttcttc ccagttttcg caatccacat | 1740 |
| cggccagatc gttattcagt aagtaatcca attcggctaa gcggctgtct aagctattcg | 1800 |
| tatagggaca atccgatatg tcgatggagt gaaagagcct gatgcactcc gcatacagct | 1860 |
| cgataatctt ttcagggctt tgttcatctt catactcttc cgagcaaagg acgccatcgg | 1920 |
| cctcactcat gagcagattg ctccagccat catgccgttc aaagtgcagg acctttggaa | 1980 |
| caggcagctt tccttccagc catagcatca tgtcctttc ccgttccaca tcataggtgg | 2040 |
| tcccttata ccggctgtcc gtcattttta aatataggtt ttcattttct cccaccagct | 2100 |
| tatataccct agcaggagac attccttccg tatctttac gcagcggtat ttttcgatca | 2160 |
| gttttttcaa ttccggtgat attctcattt tagccattta ttatttcctt cctcttttct | 2220 |
| acagtattta agataccccc aagaagctaa ttataacaag acgaactcca attcactgtt | 2280 |
| ccttgcattc taaaacctta aataccagaa aacagctttt tcaagttgt tttgaaagtt | 2340 |
| ggcgtataac atagtatcga cggagccgat tttgaaacca caattatgat agaatttaca | 2400 |
| agctataagg ttattgtcct gggtttcaag cattagtcca tgcaagtttt tatgctttgc | 2460 |
| ccattctata gatatattga taagcgcgct gcctatgcct tgcccctga atccttaca | 2520 |
| tacggcgata tcttctatat aaaagatata ttatcttatc agtattgtca atatattcaa | 2580 |

-continued

```
ggcaatctgc ctcctcatcc tcttcatcct cttcgtcttg gtagcttttt aaatatggcg    2640
cttcatagag taattctgta aaggtccaat tctcgttttc atacctcggt ataatcttac    2700
ctatcacctc aaatggttct ctagactcga gagttcaaca gacagccttc gttcttatgg    2760
ccgttcagga ggaagttcct attccgaagt tcctattctc tagaaagtat aggaacttct    2820
tgagaagaga aaagaaaacc gccgatcctg tccaccgcat tactgcaagg tagtggacaa    2880
gaccggcggt cttaagtttt ttggctgaaa cgaatgacga aaaggctgtc tgagcaaatc    2940
caggaggtcg tttaaactta agcaccggtg gagtgacgac cttcagcacg ttcgtactgt    3000
tcaacgatgt tgtagtcttc gttgtgggag gtgatgtcca gtttgatgtc ggttttgtaa    3060
gcacccggca gctgaaccgg ttttttagcc atgtaggtgg ttttaacttc agcgtcgtag    3120
tgaccaccgt ctttcagttt cagacgcatt ttgatttcac ctttcagagc accgtcttcc    3180
gggtacatac gttcggtgga agcttcccaa cccatggttt ttttctgcat aaccggaccg    3240
tcggacggga agttggtacc acgcagttta actttgtaga tgaactcacc gtcttgcagg    3300
gaggagtcct gggtaacggt aacaacacca ccgtcttcga agttcataac acgttcccat    3360
ttgaaacctt ccgggaagga cagtttcagg tagtccggga tgtcagccgg gtgtttaacg    3420
taagctttgg aaccgtactg gaactgcggg gacaggatgt cccaagcgaa cggcagcgga    3480
ccacctttgg taactttcag tttagcggtc tgggtacctt cgtacggacg accttcacct    3540
tcaccttcga tttcgaactc gtgaccgtta acggaacctt ccatacgaac tttgaaacgc    3600
atgaactctt tgataacgtc ttcgctactc gccatagtag ttcctcctta tgtactatta    3660
gttacattta ttgtacaaca cgagcccatt tttgtcaaat aaaatttaaa ttatatcaac    3720
gttaataagg aattgataag cgtttaaacc gtattagccc ggtattttgg aaatagcgga    3780
agcactgact tttgttatca ataaaaaagg ccccccgtta gggaggcctt attgttcgtc    3840
tactcggaag agcgagagac aacagaacgg tcagccacat gaattccgct attcagatcc    3900
tcttctgaga tgagtttttg ttcgggccca agcttcaaaa aaagcaccga ctcggtgcca    3960 cttttttcaag ttgataacgg actagcctta ttttaacttg ctatttctag ctctaaaaca    4020
gaccgctaaa ctgaaagtta catttattgt acaacacgag cccattttg tcaaataaaa    4080 tttaaattat atcaacgtta ataaggaatt ctttcagctc agtcgatagg tagtaggcaa    4140
gagtagtcgc accttggtc gaaaaaaaaa gcccgcactg tcaggtgcgg gcttttttct    4200
gtgtttcccc aaaagtaaaa acccgccgaa gcgggttttt acgtaaaaca ggtgaaactg    4260
accagacgag aaggctttgg aggtgataat ggggctcaag gacccgggtt aagacccact    4320
ttcacattta agttgttttt ctaatccgca tatgatcaat tcaaggccga ataagaaggc    4380
tggctctgca ccttggtgat caaataattc gatagcttgt cgtaataatg gcggcatact    4440
atcagtagta ggtgtttccc tttcttcttt agcgacttga tgctcttgat cttccaatac    4500
gcaacctaaa gtaaaatgcc ccacagcgct gagtgcatat aatgcattct ctagtgaaaa    4560
accttgttgg cataaaaagg ctaattgatt ttcgagagtt tcatactgtt tttctgtagg    4620
ccgtgtacct aaatgtactt tgctccatc gcgatgactt agtaaagcac atctaaaact    4680
tttagcgtta ttacgtaaaa aatcttgcca gctttcccct tctaaagggc aaaagtgagt    4740
atggtgccta tctaacatct caatggctaa ggcgtcgagc aaagcccgct tattttttac    4800
atgccaatac aatgtaggct gctctacacc tagcttctgg gcgagtttac gggttgttaa    4860
accttcgatt ccgacctcat taagcagctc taatgcgctg ttaatcactt tacttttatc    4920
```

```
taatctagac atcattaatt cctccttttt gttgacatta tatcattgat agagttattt    4980
gtcaaactat tttttattt ggatccccc gggaggcaga taggtaggca tggcccccat     5040
tttcaataca agcaacgcat gagaaagccc ccggaagatc accttccggg ggctttttta    5100
ttgcgctccg gcaattaaaa aagcggctaa ccacgccgct ttttttacgt ctgcagacta    5160
gtgtcgagtt catgaaaaac taaaaaaaat attgacactc tatcattgat agagtataat    5220
taaaataagc tctctatcat tgatagagta ctaatagtac ataaggagga actagtatgg    5280
ataagaaata ctcaataggc ttagctatcg gcacaaatag cgtcggatgg gcggtgatca    5340
ctgatgaata taaggttccg tctaaaaagt tcaaggttct gggaaataca gaccgccaca    5400
gtatcaaaaa aaatcttata ggggctcttt tatttgacag tggagagaca gcggaagcga    5460
ctcgtctcaa acggacagct cgtagaaggt atacacgtcg gaagaatcgt atttgttatc    5520
tacaggagat ttttcaaat gagatggcga aagtagatga tagtttcttt catcgacttg    5580
aagagtcttt tttggtggaa gaagacaaga agcatgaacg tcatcctatt tttggaaata    5640
tagtagatga agttgcttat catgagaaat atccaactat ctatcatctg cgaaaaaaat    5700
tggtagattc tactgataaa gcggatttgc gcttaatcta tttggcctta gcgcatatga    5760
ttaagtttcg tggtcatttt ttgattgagg agatttaaa tcctgataat agtgatgtgg    5820
acaaactatt tatccagttg gtacaaacct acaatcaatt atttgaagaa accctatta    5880
acgcaagtgg agtagatgct aaagcgattc tttctgcacg attgagtaaa tcaagacgat    5940
tagaaaatct cattgctcag ctccccggtg agaagaaaaa tggcttattt gggaatctca    6000
ttgctttgtc attgggtttg accctaatt ttaaatcaaa ttttgatttg gcagaagatg     6060
ctaaattaca gctttcaaaa gatacttacg atgatgattt agataattta ttggcgcaaa    6120
ttggagatca atatgctgat ttgttttgg cagctaagaa tttatcagat gctatttac      6180
tttcagatat cctaagagta aatactgaaa taactaaggc tccctatca gcttcaatga    6240
ttaaacgcta cgatgaacat catcaagact tgactcttt aaaagcttta gttcgacaac     6300
aacttccaga aaagtataaa gaaatctttt ttgatcaatc aaaaaacgga tatgcaggtt    6360
atattgatgg gggagctagc caagaagaat tttataaatt tatcaaacca attttagaaa    6420
aaatggatgg tactgaggaa ttattggtga actaaatcg tgaagatttg ctgcgcaagc    6480
aacgaccttt tgacaacggc tctattcccc atcaaattca cttgggtgag ctgcatgcta    6540
ttttgagaag acaagaagac ttttatccat ttttaaaaga caatcgtgag aagattgaaa    6600
aaatcttgac ttttcgaatc ccttattatg ttggtccatt ggcgcgtggc aatagtcgtt    6660
ttgcatggat gactcggaag tctgaagaaa caattacccc atggaattt gaagaagttg    6720
tcgataaagg tgcttcagct caatcattta ttgaacgcat gacaaacttt gataaaaatc    6780
ttccaaatga aaagtacta ccaaaacata gtttgcttta tgagtatttt acggtttata    6840
acgaattgac aaaggtcaaa tatgttactg aaggaatgcg aaaaccagca tttctttcag    6900
gtgaacagaa gaaagccatt gttgatttac tcttcaaaac aaatcgaaaa gtaaccgtta    6960
agcaattaaa agaagattat ttcaaaaaaa tagaatgttt tgatagtgtt gaaatttcag    7020
gagttgaaga tagatttaat gcttcattag gtacctacca tgatttgcta aaaattatta    7080
aagataaaga tttttggat aatgaagaaa atgaagatat cttagaggat attgttttaa    7140
cattgacctt atttgaagat agggagatga ttgaggaaag acttaaaaca tatgctcacc    7200
tctttgatga taaggtgatg aaacagctta acgtcgccg ttatactggt tggggacgtt     7260
tgtctcgaaa attgattaat ggtattaggg ataagcaatc tggcaaaaca atattagatt    7320
```

```
ttttgaaatc agatggtttt gccaatcgca attttatgca gctgatccat gatgatagtt   7380
tgacatttaa agaagacatt caaaaagcac aagtgtctgg acaaggcgat agtttacatg   7440
aacatattgc aaatttagct ggtagccctg ctattaaaaa aggtatttta cagactgtaa   7500
aagttgttga tgaattggtc aaagtaatgg ggcggcataa gccagaaaat atcgttattg   7560
aaatggcacg tgaaaatcag acaactcaaa agggccagaa aaattcgcga gagcgtatga   7620
aacgaatcga agaaggtatc aaagaattag gaagtcagat tcttaaagag catcctgttg   7680
aaaatactca attgcaaaat gaaaagctct atctctatta tctccaaaat ggaagagaca   7740
tgtatgtgga ccaagaatta gatattaatc gtttaagtga ttatgatgtc gatgccattg   7800
ttccacaaag tttccttaaa gacgattcaa tagacaataa ggtcttaacg cgttctgata   7860
aaaatcgtgg taaatcggat aacgttccaa gtgaagaagt agtcaaaaag atgaaaaact   7920
attggagaca acttctaaac gccaagttaa tcactcaacg taagtttgat aatttaacga   7980
aagctgaacg tggaggtttg agtgaacttg ataaagctgg ttttatcaaa cgccaattgg   8040
ttgaaactcg ccaaatcact aagcatgtgg cacaaatttt ggatagtcgc atgaatacta   8100
aatacgatga aaatgataaa cttattcgag aggttaaagt gattacctta aaatctaaat   8160
tagtttctga cttccgaaaa gatttccaat tctataaagt acgtgagatt aacaattacc   8220
atcatgccca tgatgcgtat ctaaatgccg tcgttggaac tgctttgatt aagaaatatc   8280
caaaacttga atcggagttt gtctatggtg attataaagt ttatgatgtt cgtaaaatga   8340
ttgctaagtc tgagcaagaa ataggcaaag caaccgcaaa atatttcttt tactctaata   8400
tcatgaactt cttcaaaaca gaaattacac ttgcaaatgg agagattcgc aaacgccctc   8460
taatcgaaac taatgggaa actggagaaa ttgtctggga taagggcga gattttgcca   8520
cagtgcgcaa agtattgtcc atgccccaag tcaatattgt caagaaaaca gaagtacaga   8580
caggcggatt ctccaaggag tcaatttac caaaaagaaa ttcggacaag cttattgctc   8640
gtaaaaaaga ctgggatcca aaaaaatatg gtggttttga tagtccaacg gtagcttatt   8700
cagtcctagt ggttgctaag gtggaaaaag ggaaatcgaa gaagtaaaaa tccgttaaag   8760
agttactagg gatcacaatt atggaaagaa gttcctttga aaaaaatccg attgactttt   8820
tagaagctaa aggatataag gaagttaaaa aagacttaat cattaaacta cctaaatata   8880
gtcttttttga gttagaaaac ggtcgtaaac ggatgctggc tagtgccgga gaattacaaa   8940
aaggaaatga gctggctctg ccaagcaaat atgtgaattt tttatattta gctagtcatt   9000
atgaaaagtt gaagggtagt ccagaagata acgaacaaaa acaattgttt gtggagcagc   9060
ataagcatta tttagatgag attattgagc aaatcagtga atttctaag cgtgttattt   9120
tagcagatgc caatttagat aaagttctta gtgcatataa caaacataga acaaaccaa   9180
tacgtgaaca agcagaaaat attattcatt tatttacgtt gacgaatctt ggagctccg   9240
ctgcttttaa atattttgat acaacaattg atcgtaaacg atatacgtct acaaaagaag   9300
ttttagatgc cactcttatc catcaatcca tcactggtct ttatgaaaca cgcattgatt   9360
tgagtcagct aggaggtgac gcggccgcgg agcagaaact catctctgaa gaagatctgg   9420
aacaaaagtt gatttcagaa gaagatctgg aacagaagct catctctgag gaagatctgt   9480
aataaggcgc gcctccttaa tgggacttgc agcctcggta ccaaattcca gaaaagacac   9540
ccgaaagggt gttttttcgt tttggtccca cagaatgagc atcatggctc tagtcgaccg   9600
ggtaggggca tagcttagat aattggaaaa gaggaaaaaa gcttaatctt ttttcgaagg   9660
```

```
ttaagctttt tcttttattt ataaaaagtg aactaactat cagaaagaaa ttatattaaa    9720
ttttatttt ttgtttaaaa agtagattat ataaaggcaa gctaggtggg ggaaaatatg    9780
tttaaaaag aaaaagtcac agaatacatt tggactatac taataccaac aatcatcact    9840
tttatcatta gttgggttgg gtcttattac aatggtactt cgacagttag tattggacaa    9900
cctacaaaag tttccggtca gtatatcacg ccaataaata taagtcccta tcatgatatt    9960
aaggaattaa gaataacttt tccgcaaaaa ctagatgtaa aacaaattag ttcaaatgag   10020
cctataaatg taaaatcaga taagaacaat ataggagttg aaagtaattc cacttttgag   10080
attgcgaaaa tcgttgaaaa taatagcgtt cagttgctaa ttacaacaca aaaaaagtta   10140
aacgataagg aaattagaat tgataaaaat ggaaataaca tttctgtaaa ttatgaatct   10200
cagattgtta atcctgcaaa aaaacaatta atcaatctta taattacgtc atctatttat   10260
tttataatgc ttaatatact agcattgatt atgaacaaaa gatgggataa gtattatgca   10320
aaaatgaaaa atgaaatcaa agaatttgag gataatgcaa aagatcttga taaaaaatca   10380
aagaagaaaa gcgaggaatt atcggagctg cgaaagacct tgaaccaagc gtttgaggaa   10440
actgatagga taaatatca tgagaagaaa aaacaaatcc tcctcttagc taagttaaac   10500
gattataaaa aagaactaac cttttggaga aatacaataa gaaaagttct ttatgaactt   10560
cctgatggag ataaaaagc agataaacta ataggacag ttacatcatc tttaaaaacg   10620
tacggtacag tcgaaaagta aagcttatcg gccagcctcg cagagcagga ttcccgttga   10680
gcaccgccag gtgcgaataa gggacagtga agaaggaaca cccgctcgcg ggtgggccta   10740
cttcacctat cctgcccggc tgacgccgtt ggatacacca aggaaagtct acacgaaccc   10800
tttggcaaaa tcctgtatat cgtgcgaaaa aggatggata taccgaaaaa atcgctataa   10860
tgaccccgaa gcagggttat gcagcggaaa gtataccta aggaatcccc tgataacgca   10920
ggaaagaaca tgtgagcaaa aggccagcaa aaggccagga accgtaaaaa ggccgcactc   10980
cctgcctctg tcatcacgat actgtgatgc catggctaat tcccatgtca gccgttaagt   11040
gttcctgtgt cactcaaaat tgctttgaga ggctctaagg gcttctcagt gcgttacatc   11100
cctggcttgt tgtccacaac cgttaaacct taaaagcttt aaaagcctta tatattcttt   11160
tttttcttat aaaacttaaa accttagagg ctatttaagt tgctgattta tattaatttt   11220
attgttcaaa catgagagct tagtacgtga aacatgagag cttagtacgt tagccatgag   11280
agcttagtac gttagccatg agggtttagt tcgttaaaca tgagagctta gtacgttaaa   11340
catgagagct tagtacgtga aacatgagag cttagtacgt actatcaaca ggttgaactg   11400
ctgatcttca gatcctctac gccggacgca tcgtggccgg atcttgcggc cgcaaaaatt   11460
aaaaatgaag ttttaaatca atctaaagta tatatgagta aacttggtct gacagttacc   11520
aatgcttaat cagtgaggca ccaataactg cctttgatct tttctacggg gtctgacgct   11580
cagtggaacg aaaactcacg ttaagggatt ttggtcatga gattatcaaa aaggatcttc   11640
acctagatcc ttttaaatta aaaatgaagt tttaaatcaa tctaaagtat atatgagtaa   11700
acttggtctg acagttacca atgcttaatc agtgaggcac ctatctcagc gatctgtcta   11760
tttcgttcat ccatagttgc ctgactcccc gtcgtgtaga taactacgat acgggagggc   11820
ttaccatctg gccccagtgc tgcaatgata ccgcgggacc cacgctcacc ggctccagat   11880
ttatcagcaa taaccagcc agccggaagg gccgagcgca gaagtggtcc tgcaacttta   11940
tccgcctcca tccagtctat taattgttgc cgggaagcta gagtaagtag ttcgccagtt   12000
aatagtttgc gcaacgttgt tgccattgct acaggcatcg tggtgtcacg ctcgtcgttt   12060
```

```
ggtatggctt cattcagctc cggttcccaa cgatcaaggc gagttacatg atcccccatg    12120
ttgtgcaaaa aagcggttag ctccttcggt cctccgatcg ttgtcagaag taagttggcc    12180
gcagtgttat cactcatggt tatggcagca ctgcataatt ctcttactgt catgccatcc    12240
gtaagatgct tttctgtgac tggtgagtac tcaaccaagt cattctgaga atagtgtatg    12300
cggcgaccga gttgctcttg cccggcgtca atacgggata ataccgcgcc acatagcaga    12360
actttaaaag tgctcatcat tggaaaacgt tcttcggggc gaaaactctc aaggatctta    12420
ccgctgttga gatccagttc gatgtaaccc actcgtgcac ccaactgatc ttcagcatct    12480
tttactttca ccagcgtttc tgggtgagca aaaacaggaa ggcaaaatgc cgcaaaaaag    12540
ggaataaggg cgacacggaa atgttgaata ctcatactct tcctttttca atattattga    12600
agcatttatc agggttattg tctcatgagc ggatacatat ttgaatgtat ttagaaaaat    12660
aaacaaatag gggttccgcg cacatttccc cgaaaagtgc cacctgacgt c             12711
```

<210> SEQ ID NO 18
<211> LENGTH: 11888
<212> TYPE: DNA
<213> ORGANISM: Artificial sequence
<220> FEATURE:
<223> OTHER INFORMATION: Synthetic construct

<400> SEQUENCE: 18

```
ttctaactac ttattttaaa gcagtctgga ttgtttgggt aattcataaa aaaataaaag      60
aaagaaggag gaatagagtt tttctttttt ttgtttgcaa tgttactgtc aagtcgcaaa     120
agaattgcta tgaccgaaaa aaaaccgcaa aggaatagat ataaggtacc tttttgcaat     180
tcatctttgt aaaataaagg ttattctgac ataatacaat taatgtaaaa attcgcacaa     240
ttttatgtaa ggatggggga attttcttgc ggggtgtttt cttagataaa gataaaattc     300
cgtacgactt agtcacgaaa aagttaaatg aatggtatac atcaataaaa aatgatcaag     360
ttgagcaagc cgagattata aaaacagaag tagagaaaga attgttaaac atggaagaaa     420
atcaagatgc cctgttatat tatcaactat tagaatttag acatgagata atgctgagtt     480
atatgaaatc taaggaaata gaagatctca ataatgctta tgagactata aaagaaattg     540
agaagcaagg gcaattaact ggcatgttgg aatactattt ttactttttt aagggtatgt     600
acgagtttag gcgtaaagaa ttaatttcag cgataagtgc ttatcgaata gctgaatcaa     660
agttgtcaga agttgaggat gaaatagaga aagcagagtt tttttcaaa gtgtcctatg     720 tatattatta tatgaaacaa acatacttct ccatgaatta tgcaaatcgt gcactcaaaa     780
tatttagaga gtatgaagaa tatgctgtcc agactgtgcg ttgtcaattt attgtagcag     840
gaaacttgat cgagtgaatc gataagctag cttaattagc tgagcttgga ctcctgttga     900
tagatccagt aatgacctca gaactccatc tggatttgtt cagaacgctc ggttgccgcc     960
gggcgttttt tattggtgag aatccaagct agactgcgat gagtggcagg gcggggcgta    1020
atttttttaa ggcagttatt ggtgccctta aacgcctggg gtaatgactc tctagcttga    1080
ggcatcaaat aaaacgaaag gctcagtcga agactgggc ctttcgtttt atctgttgtt    1140
tgtcggtgaa cgctctcctg agtaggacaa atccgccgct aggagcttgc ggcccggacg    1200
atgagctcga attggggatc ttgaagtacc tattccgaag ttcctattct ctagaaagta    1260
taggaacttc agagcgcttt tgaagctgat gctcgaggat cctctagaca tcagagtatg    1320
gacagttgcg gatgtacttc agaaaagatt agatgtctaa aaagcttgta gttaaagctt    1380
```

-continued

```
tttagacatc taaatctagg tactaaaaca attcatccag taaaatataa tattttattt    1440
tctcccaatc aggcttgatc cccagtaagt caaaaaatag ctcgacatac tgttcttccc    1500
cgatatcctc cctgatcgac cggacgcaga aggcaatgtc ataccacttg tccgccctgc    1560
cgcttctccc aagatcaata aagccactta ctttgccatc tttcacaaag atgttgctgt    1620
ctcccaggtc gccgtgggaa aagacaagtt cctcttcggg cttttccgtc tttaaaaaat    1680
catacagctc gcgcggatct ttaaatggag tgtcttcttc ccagttttcg caatccacat    1740
cggccagatc gttattcagt aagtaatcca attcggctaa gcggctgtct aagctattcg    1800
tatagggaca atccgatatg tcgatggagt gaaagagcct gatgcactcc gcatacagct    1860
cgataatctt ttcagggctt tgttcatctt catactcttc cgagcaaagg acgccatcgg    1920
cctcactcat gagcagattg ctccagccat catgccgttc aaagtgcagg acctttggaa    1980
caggcagctt tccttccagc catagcatca tgtcctttc ccgttccaca tcataggtgg    2040
tccctttata ccggctgtcc gtcatttta aatataggtt ttcattttct cccaccagct    2100
tatataccctt agcaggagac attccttccg tatcttttac gcagcggtat ttttcgatca    2160
gttttttcaa ttccggtgat attctcattt tagccattta ttatttcctt cctctttct    2220
acagtattta aagataccccc aagaagctaa ttataacaag acgaactcca attcactgtt    2280
ccttgcattc taaaaccta aataccagaa aacagctttt tcaaagttgt tttgaaagtt    2340
ggcgtataac atagtatcga cggagccgat tttgaaacca caattatgat agaatttaca    2400
agctataagg ttattgtcct gggtttcaag cattagtcca tgcaagtttt tatgctttgc    2460
ccattctata gatatattga taagcgcgct gcctatgcct tgcccctga atccttaca    2520
tacggcgata tcttctatat aaaagatata ttatcttatc agtattgtca atatattcaa    2580
ggcaatctgc ctcctcatcc tcttcatcct cttcgtcttg gtagcttttt aaatatggcg    2640
cttcatagag taattctgta aaggtccaat tctcgttttc atacctcggt ataatcttac    2700
ctatcacctc aaatggttct ctagactcga gagttcaaca gacagccttc gttcttatgg    2760
ccgttcagga ggaagttcct attccgaagt tcctattctc tagaaagtat aggaacttct    2820
tgagaagaga aaagaaaacc gccgatcctg tccaccgcat tactgcaagg tagtggacaa    2880
gaccggcggt cttaagtttt ttggctgaaa cgaatgacga aaaggctgtc tgagcaaatc    2940
caggaggtcg tttaaaccgt attagcccgg tattttggaa atagcggaag cactgacttt    3000
tgttatcaat aaaaaaggcc ccccgttagg gaggcttat tgttcgtcta ctcggaagag    3060
cgagagacaa cagaacggtc agccacatga attcctagta aaaaaagcac cgactcggtg    3120
ccacttttc aagttgataa cggactagcc ttatttaac ttgctatttc tagctctaaa    3180
accgagaccg ggtctcccga agggtctcga catttattgt acaacacgag cccatttttg    3240
tcaaataaaa tttaaattat atcaacgtta ataaagacg cggaattctt tcagctcagt    3300
cgataggtag taggcaagag tagtcgcacc tttggtcgaa aaaaaagcc cgcactgtca    3360
ggtgcgggct ttttctgtg tttccccaaa agtaaaaacc cgccgaagcg ggttttacg    3420
taaaacaggt gaaactgacc agacgagaag gctttggagg tgataatggg gctcaaggac    3480
ccgggttaag acccactttc acatttaagt tgttttcta atccgcatat gatcaattca    3540
aggccgaata agaaggctgg ctctgcacct tggtgatcaa ataattcgat agcttgtcgt    3600
aataatggcg gcatactatc agtagtaggt gtttcccttt cttctttagc gacttgatgc    3660
tcttgatctt ccaatacgca acctaaagta aaatgcccca cagcgctgag tgcatataat    3720
gcattctcta gtgaaaaacc ttgttggcat aaaaaggcta attgattttc gagagtttca    3780
```

```
tactgttttt ctgtaggccg tgtacctaaa tgtacttttg ctccatcgcg atgacttagt   3840
aaagcacatc taaaactttt agcgttatta cgtaaaaaat cttgccagct ttccccttct   3900
aaagggcaaa agtgagtatg gtgcctatct aacatctcaa tggctaaggc gtcgagcaaa   3960
gcccgcttat tttttacatg ccaatacaat gtaggctgct ctacacctag cttctgggcg   4020
agtttacggg ttgttaaacc ttcgattccg acctcattaa gcagctctaa tgcgctgtta   4080
atcactttac ttttatctaa tctagacatc attaattcct ccttttttgtt gacattatat   4140 cattgataga gttatttgtc aaactatttt tttatttgga tcccccgggg aggcagatag   4200
gtaggcatgg cccccatttt caatacaagc aacgcatgag aaagccccg gaagatcacc    4260 ttccgggggc ttttttattg cgctccggca attaaaaaag cggctaacca cgccgctttt   4320
tttacgtctg cagactagtg tcgagttcat gaaaaactaa aaaaaatatt gacactctat   4380
cattgataga gtataattaa aataagctct ctatcattga tagagtacta atagtacata   4440
aggaggaact agtatggata agaaatactc aataggctta gctatcggca caaatagcgt   4500
cggatgggcg gtgatcactg atgaatataa ggttccgtct aaaaagttca aggttctggg   4560
aaatacagac cgccacagta tcaaaaaaaa tcttataggg gctcttttat ttgacagtgg   4620
agagacagcg gaagcgactc gtctcaaacg acagctcgt agaaggtata cacgtcggaa     4680
gaatcgtatt tgttatctac aggagatttt ttcaaatgag atggcgaaag tagatgatag   4740
tttctttcat cgacttgaag agtctttttt ggtggaagaa gacaagaagc atgaacgtca   4800 tcctatttttt ggaaatatag tagatgaagt tgcttatcat gagaaatatc caactatcta   4860
tcatctgcga aaaaaattgg tagattctac tgataaagcg gatttgcgct taatctatt   4920 ggccttagcg catatgatta agttt cgtgg tcatttttttg attgagggag atttaaatcc   4980
tgataatagt gatgtggaca aactatttat ccagttggta caaacctaca atcaattatt   5040
tgaagaaaac cctattaacg caagtggagt agatgctaaa gcgattcttt ctgcacgatt   5100
gagtaaatca agacgattag aaaatctcat tgctcagctc cccggtgaga agaaaaatgg   5160
cttatttggg aatctcattg ctttgtcatt gggtttgacc cctaatttta aatcaaattt   5220
tgatttggca gaagatgcta aattacagct ttcaaaagat acttacgatg atgatttaga   5280
taatttattg gcgcaaattg gagatcaata tgctgatttg ttttttggcag ctaagaattt   5340 atcagatgct attttacttt cagatatcct aagagtaaat actgaaataa ctaaggctcc   5400
cctatcagct tcaatgatta aacgctacga tgaacatcat caagacttga ctcttttaaa   5460
agctttagtt cgacaacaac ttccagaaaa gtataaagaa atcttttttg atcaatcaaa   5520
aaacggatat gcaggttata ttgatggggg agctagccaa gaagaatttt ataaatttat   5580
caaaccaatt ttagaaaaaa tggatggtac tgaggaatta ttggtgaaac taaatcgtga   5640
agatttgctg cgcaagcaac ggacctttga caacggctct attccccatc aaattcactt   5700
gggtgagctg catgctattt tgagaagaca agaagacttt tatccatttt taaaagacaa   5760
tcgtgagaag attgaaaaaa tcttgacttt tcgaatccct tattatgttg gtccattggc   5820
gcgtggcaat agtcgttttg catggatgac tcggaagtct gaagaaacaa ttaccccatg   5880
gaattttgaa gaagttgtcg ataaaggtgc ttcagctcaa tcatttattg aacgcatgac   5940
aaactttgat aaaaatcttc caaatgaaaa agtactacca aaacatagtt tgctttatga   6000
gtattttacg gttataacg aattgacaaa ggtcaaatat gttactgaag gaatgcgaaa    6060
accagcattt ctttcaggtg aacagaagaa agccattgtt gatttactct tcaaaacaaa   6120
```

```
tcgaaaagta accgttaagc aattaaaaga agattatttc aaaaaaatag aatgttttga      6180
tagtgttgaa atttcaggag ttgaagatag atttaatgct tcattaggta cctaccatga      6240
tttgctaaaa attattaaag ataaagattt tttggataat gaagaaaatg aagatatctt      6300
agaggatatt gttttaacat tgaccttatt tgaagatagg gagatgattg aggaaagact      6360
taaaacatat gctcacctct tgatgataaa ggtgatgaaa cagcttaaac gtcgccgtta      6420
tactggttgg ggacgtttgt ctcgaaaatt gattaatggt attagggata agcaatctgg      6480
caaaacaata ttagattttt tgaaatcaga tggttttgcc aatcgcaatt ttatgcagct      6540
gatccatgat gatagtttga catttaaaga agacattcaa aaagcacaag tgtctggaca      6600
aggcgatagt ttacatgaac atattgcaaa tttagctggt agccctgcta ttaaaaaagg      6660
tattttacag actgtaaaag ttgttgatga attggtcaaa gtaatggggc ggcataagcc      6720
agaaaatatc gttattgaaa tggcacgtga aaatcagaca actcaaaagg gccagaaaaa      6780
ttcgcgagag cgtatgaaac gaatcgaaga aggtatcaaa gaattaggaa gtcagattct      6840
taaagagcat cctgttgaaa atactcaatt gcaaaatgaa aagctctatc tctattatct      6900
ccaaaatgga agagacatgt atgtggacca agaattagat attaatcgtt aagtgatta      6960
tgatgtcgat gccattgttc cacaaagttt ccttaaagac gattcaatag acaataaggt      7020
cttaacgcgt tctgataaaa atcgtggtaa atcggataac gttccaagtg aagaagtagt      7080
caaaagatg aaaaactatt ggagacaact tctaaacgcc aagttaatca ctcaacgtaa      7140
gtttgataat ttaacgaaag ctgaacgtgg aggtttgagt gaacttgata agctggttt      7200
tatcaaacgc caattggttg aaactcgcca aatcactaag catgtggcac aaattttgga      7260
tagtcgcatg aatactaaat acgatgaaaa tgataaactt attcgagagg ttaaagtgat      7320
taccttaaaa tctaaattag tttctgactt ccgaaaagat ttccaattct ataaagtacg      7380
tgagattaac aattaccatc atgcccatga tgcgtatcta aatgccgtcg ttggaactgc      7440
tttgattaag aaatatccaa aacttgaatc ggagtttgtc tatggtgatt ataaagttta      7500
tgatgttcgt aaaatgattg ctaagtctga gcaagaaata ggcaaagcaa ccgcaaaata      7560
tttctttttac tctaatatca tgaacttctt caaaacagaa attacacttg caaatggaga      7620
gattcgcaaa cgccctctaa tcgaaactaa tggggaaact ggagaaattg tctgggataa      7680
agggcgagat tttgccacag tgcgcaaagt attgtccatg ccccaagtca atattgtcaa      7740
gaaaacagaa gtacagacag gcggattctc caaggagtca attttaccaa aaagaaattc      7800
ggacaagctt attgctcgta aaaaagactg ggatccaaaa aaatatggtg gttttgatag      7860
tccaacggta gcttattcag tcctagtggt tgctaaggtg gaaaaaggga atcgaagaa      7920
gttaaaatcc gttaaagagt tactagggat cacaattatg gaagaagtt cctttgaaaa      7980
aaatccgatt gactttttag aagctaaagg atataaggaa gttaaaaaag acttaatcat      8040
taaactacct aaatatagtc tttttgagtt agaaaacggt cgtaaacgga tgctggctag      8100
tgccggagaa ttacaaaaag gaaatgagct ggctctgcca agcaaatatg tgaatttttt      8160
atatttagct agtcattatg aaaagttgaa gggtagtcca gaagataacg aacaaaaaca      8220
attgtttgtg gagcagcata agcattattt agatgagatt attgagcaaa tcagtgaatt      8280
ttctaagcgt gttatttag cagatgccaa tttagataaa gttcttagtg catataacaa      8340
acatagagac aaaccaatac gtgaacaagc agaaaatatt attcatttat ttacgttgac      8400
gaatcttgga gctcccgctg cttttaaata ttttgataca acaattgatc gtaaacgata      8460
tacgtctaca aaagaagttt tagatgccac tcttatccat caatccatca ctggtctta      8520
```

```
tgaaacacgc attgatttga gtcagctagg aggtgacgcg gccgcggagc agaaactcat    8580
ctctgaagaa gatctggaac aaaagttgat ttcagaagaa gatctggaac agaagctcat    8640
ctctgaggaa gatctgtaat aaggcgcgcc tccttaatgg gacttgcagc ctcggtacca    8700
aattccagaa aagacacccg aaagggtgtt ttttcgtttt ggtcccacag aatgagcatc    8760
atggctctag tcgaccgggt aggggcatag cttagataat tggaaagag gaaaaaagct    8820 taatcttttt tcgaaggtta agcttttct tttatttata aaaagtgaac taactatcag    8880
aaagaaatta tattaaattt tatttttttg tttaaaaagt agattatata aaggcaagct    8940
aggtggggga aatatgttt aaaaagaaa aagtcacaga atacatttgg actatactaa    9000
taccaacaat catcactttt atcattagtt gggttgggtc ttattacaat ggtacttcga    9060
cagttagtat tggacaacct acaaaagttt ccggtcagta tatcacgcca ataaatataa    9120
gtccctatca tgatattaag gaattaagaa taacttttcc gcaaaaacta gatgtaaaac    9180
aaattagttc aaatgagcct ataaatgtaa aatcagataa gaacaatata ggagttgaaa    9240
gtaattccac ttttgagatt gcgaaaatcg ttgaaaataa tagcgttcag ttgctaatta    9300
caacacaaaa aaagttaaac gataaggaaa ttagaattga taaaaatgga ataacatttt    9360
ctgtaaatta tgaatctcag attgttaatc ctgcaaaaaa acaattaatc aatcttataa    9420
ttacgtcatc tatttatttt ataatgctta atatactagc attgattatg aacaaaagat    9480
gggataagta ttatgcaaaa atgaaaaatg aaatcaaaga atttgaggat aatgcaaaag    9540
atcttgataa aaaatcaaag aagaaaagcg aggaattatc ggagctgcga aagaccttga    9600
accaagcgtt tgaggaaact gataggataa aatatcatga gaagaaaaaa caaatcctcc    9660
tcttagctaa gttaaacgat tataaaaaag aactaacctt ttggagaaat acaataagaa    9720 aagttctta tgaacttcct gatggagata aaaaagcaga taaactaata gggacagtta    9780
catcatcttt aaaaacgtac ggtacagtcg aaaagtaaag cttatcggcc agcctcgcag    9840
agcaggattc ccgttgagca ccgccaggtg cgaataaggg acagtgaaga aggaacaccc    9900
gctcgcgggt gggcctactt cacctatcct gcccggctga cgccgttgga tacaccaagg    9960
aaagtctaca cgaacccttt ggcaaaatcc tgtatatcgt gcgaaaaagg atggatatac   10020 cgaaaaatc gctataatga ccccgaagca gggttatgca gcggaaagta taccttaagg   10080
aatcccctga taacgcagga aagaacatgt gagcaaaagg ccagcaaaag gccaggaacc   10140
gtaaaaaggc cgcactccct gcctctgtca tcacgatact gtgatgccat ggctaattcc   10200
catgtcagcc gttaagtgtt cctgtgtcac tcaaaattgc tttgagaggc tctaaggggct   10260 tctcagtgcg ttacatccct ggcttgttgt ccacaaccgt taaaccttaa agctttaaa   10320 agccttatat attcttttttt ttcttataaa acttaaaacc ttagaggcta tttaagttgc   10380
tgatttatat taattttatt gttcaaacat gagagcttag tacgtgaaac atgagagctt   10440
agtacgttag ccatgagagc ttagtacgtt agccatgagg gtttagttcg ttaaacatga   10500
gagcttagta cgttaaacat gagagcttag tacgtgaaac atgagagctt agtacgtact   10560
atcaacaggt tgaactgctg atcttcagat cctctacgcc ggacgcatcg tggccggatc   10620
ttgcggccgc aaaaattaaa aatgaagttt taaatcaatc taaagtatat atgagtaaac   10680
ttggtctgac agttaccaat gcttaatcag tgaggcacca ataactgcct ttgatctttt   10740
ctacggggtc tgacgctcag tggaacgaaa actcacgtta agggattttg gtcatgagat   10800
tatcaaaaag gatcttcacc tagatccttt taaattaaaa atgaagtttt aaatcaatct   10860
```

| | |
|---|---|
| aaagtatata tgagtaaact tggtctgaca gttaccaatg cttaatcagt gaggcaccta | 10920 |
| tctcagcgat ctgtctattt cgttcatcca tagttgcctg actccccgtc gtgtagataa | 10980 |
| ctacgatacg ggagggctta ccatctggcc ccagtgctgc aatgataccg cgggacccac | 11040 |
| gctcaccggc tccagattta tcagcaataa accagccagc cggaagggcc gagcgcagaa | 11100 |
| gtggtcctgc aactttatcc gcctccatcc agtctattaa ttgttgccgg gaagctagag | 11160 |
| taagtagttc gccagttaat agtttgcgca acgttgttgc cattgctaca ggcatcgtgg | 11220 |
| tgtcacgctc gtcgtttggt atggcttcat tcagctccgg ttcccaacga tcaaggcgag | 11280 |
| ttacatgatc ccccatgttg tgcaaaaaag cggttagctc cttcggtcct ccgatcgttg | 11340 |
| tcagaagtaa gttggccgca gtgttatcac tcatggttat ggcagcactg cataattctc | 11400 |
| ttactgtcat gccatccgta agatgctttt ctgtgactgg tgagtactca accaagtcat | 11460 |
| tctgagaata gtgtatgcgg cgaccgagtt gctcttgccc ggcgtcaata cgggataata | 11520 |
| ccgcgccaca tagcagaact ttaaaagtgc tcatcattgg aaaacgttct cggggcgaa | 11580 |
| aactctcaag gatcttaccg ctgttgagat ccagttcgat gtaacccact cgtgcaccca | 11640 |
| actgatcttc agcatctttt actttcacca gcgtttctgg gtgagcaaaa acaggaaggc | 11700 |
| aaaatgccgc aaaaagggga ataagggcga cacggaaatg ttgaatactc atactcttcc | 11760 |
| tttttcaata ttattgaagc atttatcagg gttattgtct catgagcgga tacatatttg | 11820 |
| aatgtattta gaaaaataaa caaataggg ttccgcgcac atttccccga aagtgccac | 11880 |
| ctgacgtc | 11888 |

<210> SEQ ID NO 19
<211> LENGTH: 11249
<212> TYPE: DNA
<213> ORGANISM: Artificial sequence
<220> FEATURE:
<223> OTHER INFORMATION: Synthetic construct

<400> SEQUENCE: 19

| | |
|---|---|
| ctgataccgc tcgccgcagc cgaacgaccg agcgcagcgg gtcagtgagc gaggaagcgg | 60 |
| aagagcgccc aatacgcaaa ccgcctctcc ccgcgcgttg gccgattcat taatgcagcg | 120 |
| cccaaacata acaggaagaa aaatgccccg ctgtgggcgg acaaaatagt tgggaactgg | 180 |
| gaggggtgga aatggagttt ttaaggatta tttaggaag agtgacaaaa tagatgggaa | 240 |
| ctgggtgtag cgtcgtaagc taatacgaaa attaaaaatg acaaaatagt ttggaactag | 300 |
| atttcactta tctggttctt gaggcggtta aaagagccgt actcttctcc gatgtcgact | 360 |
| aggccatgat gctcattctg tgggaccaaa acgaaaaaac acccttcgg gtgtcttttc | 420 |
| tggaatttgg taccgaggct gcaagtccca ttaaggaggc gcgccttatt acagatcttc | 480 |
| ctcagagatg agcttctgtt ccagatcttc ttctgaaatc aacttttgtt ccagatcttc | 540 |
| ttcagagatg agtttctgct ccgcggccgc gtcgcctccc agctgagaca ggtcgatccg | 600 |
| tgtctcgtac aggccggtga tgctctggtg gatcagggtg gcgtccagca cctctttggt | 660 |
| gctggtgtac ctcttccggt cgatggtggt gtcaaagtac ttgaaggcgg caggggctcc | 720 |
| cagattggtc agggtaaaca ggtggatgat attctcggcc tgctctctga taggcttgtc | 780 |
| tctgtgcttg ttgtaggcgc tcagcacctt gtccagatta gcgtcggcca ggatcactct | 840 |
| cttggagaac tcgctgatct gctcgatgat ctcgtccagg tagtgtttgt gctgttccac | 900 |
| aaacagctgt ttctgctcat tatcctcggg ggagcccttc agcttctcat agtggctggc | 960 |
| caggtacagg aagttcacat atttggaggg cagggccagt tcgtttccct tctgcagttc | 1020 |

```
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttctttccat gatggtgatc cccagcagct ctttcacact    1200
cttcagtttc ttggacttgc ccttttccac tttggccacc accagcacag aataggccac    1260
ggtggggctg tcgaagccgc cgtacttctt agggtcccag tccttctttc tggcgatcag    1320
cttgtcgctg ttcctcttgg gcaggataga ctctttgctg aagccgcctg tctgcacctc    1380
ggtcttttc  acgatattca cttggggcat agacagcact ttccgcacgg tggcaaagtc    1440
ccggccctta tcccacacga tctcgcctgt ttcgccgttt gtctcgatca gaggccgctt    1500
ccggatctcg ccgttggcca gggtaatctc ggtcttgaaa aagttcatga tgttgctgta    1560
gaagaagtac ttggcggtag ccttgccgat ttcctgctcg ctcttggcga tcatcttccg    1620
cacgtcgtac accttgtagt cgccgtacac gaactcgctt tccagcttag ggtactttt    1680
gatcagggcg gttcccacga cggcgttcag gtaggcgtcg tgggcgtggt ggtagttgtt    1740
gatctcgcgc actttgtaaa actggaaatc cttccggaaa tcggacacca gcttggactt    1800
cagggtgatc actttcactt cccggatcag tttgtcgttc tcgtcgtact tagtgttcat    1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccggacacct gggctttctg gatgtcctct ttaaaggtca ggctgtcgtc    2580
gtggatcagc tgcatgaagt ttctgttggc gaagccgtcg gacttcagga aatccaggat    2640
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccagggaggc gttgaaccga tcttccacgc cggagatttc    2940
cacggagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tccctggcc  agagggccca cgtagtaggg gatgcggaag gtcaggatct tctcgatctt    3360
```

```
ttcccggttg tccttcagga atgggtaaaa atcttcctgc cgccgcagaa tggcgtgcag    3420
ctctcccagg tggatctggt gggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720
gctcaggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatggggtt    4080
ttcctcgaac agctggttgt aggtctgcac cagctgatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa cgaaaaaac cgccttgcag gccggttttt    4860
cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccggaaggt gatcttccgg gggctttctc    5040
atgcgttgct tgtattgaaa atgggggcca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc cgctggatga    5580
ccaggatgcc attgctgtgg aagctgcctg cactaatgtt ccggcgttat ttcttgatgt    5640
ctctgaccag acaccatca acagtattat tttctcccat gaagacgta cgcgactggg    5700 cgtggagcat ctggtcgcat tgggtcacca gcaaatcgcg ctgttagcgg cccattaagc    5760
```

```
ttctgtctcg gcgcgtctgc gtctggctgg ctggcataaa tatctcactc gcaatcaaat    5820
tcagccgata gcggaacggg aaggcgactg gagtgccatg tccggttttc aacaaaccat    5880
gcaaatgctg aatgagggca tcgttcccac tgcgatgctg gttgccaacg atcagatggc    5940
gctgggcgca atgcgcgcca ttaccgagtc cgggctgcgc gttggtgcgg atatctcggt    6000
agtgggatac gacgataccg aagacagctc atgttatatc ccgccgttaa ccaccatcaa    6060
acaggatttt cgcctgctgg ggcaaaccag cgtggaccgc ttgctgcaac tctctcaggg    6120
ccaggcggtg aagggcaatc agctgttgcc cgtctcactg gtgaaaagaa aaaccaccct    6180
ggcgcccaat acgcaaaccg cctctccccg cgcgttggcc gattcattaa tgcagctggc    6240
acgacaggtt tcccgactgg aaagcgggca gtgagcgcaa cgcaattaat gtaagttagc    6300
tcactcatta ggcaccccac ccgggtcctt gagccccatt atcacctcca aagccttctc    6360
gtctggtcag tttcacctgt tttacgtaaa aacccgcttc ggcgggtttt tacttttggg    6420
gaaacacaga aaaagcccg cacctgacag tgcgggcttt ttttttcgac caaaggtgcg    6480
actactcttg cctactacct atcgactgag ctgaaagaat tcctaaagat ctataaatgt    6540
gagcggataa cattgacatt gtgagcggat aacaagatac ttctagttga ccaactttt    6600 ggtctccacc atagcggtcg gtctctgttt aagagctatg ctggaaacag catagcaagt    6660
ttaaataagg ctagtccgtt atcaacttga aaaagtggca ccgagtcggt gcttttttt    6720 tgaattcatg tggctgaccg ttctgttgtc tctcgctctt ccgagtagac gaacaataag    6780
gcctccctaa cggggggcct tttttattga taacaaaagt cagtgcttcc gctatttcca    6840
aaataccggg ctaatacggt ttaaacgacc tcctggattt gctcagacag ccttttcgtc    6900
attcgtttca gccaaaaaac ttaagaccgc cggtcttgtc cactaccttg cagtaatgcg    6960
gtggacagga tcggcggttt tcttttctct tctcaagaag ttcctatact ttctagagaa    7020
taggaacttc ggaataggaa cttcctcctg aacggccata agaacgaagg ctgtctgttg    7080
aactctcgag ccgtggaaac ggatgaaggc acgaacccag ttgacataag cctgttcggt    7140
tcgtaaactg taatgcaagt agcgtatgcg ctcaaaactg gatggctttc ttgccgccaa    7200
ggatctgatg gcgcagggga tcaagatctg atcaagagac aggatgagga tcgtttcgca    7260
tgattgaaca agatggattg cacgcaggtt ctccggccgc ttgggtggag aggctattcg    7320
gctatgactg ggcacaacag acaatcggct gctctgatgc cgccgtgttc cggctgtcag    7380
cgcaggggcg cccggttctt tttgtcaaga ccgacctgtc cggtgccctg aatgaactgc    7440
aggacgagga agcgcggcta tcgtggctgg ccacgacggg cgttccttgc gcagctgtgc    7500
tcgacgttgt cactgaagcg ggaagggact ggctgctatt gggcgaagtg ccggggcagg    7560
atctcctgtc atctcacctt gctcctgccg agaaagtatc catcatggct gatgcaatgc    7620
ggcggctgca tacgcttgat ccggctacct gcccattcga ccaccaagcg aaacatcgca    7680
tcgagcgagc acgtactcgg atggaagccg gtcttgtcga tcaggatgat ctggacgaag    7740
agcatcaggg gctcgcgcca gccgaactgt tcgccaggct caaggcgcgc atgcccgacg    7800
gcgaggatct cgtcgtgacc catggcgatg cctgcttgcc gaatatcatg gtggaaaatg    7860
gccgcttttc tggattcatc gactgtggcc ggctgggtgt ggcggaccgc tatcaggaca    7920
tagcgttggc tacccgtgat attgctgaag agcttggcgg cgaatgggct gaccgcttcc    7980
tcgtgcttta cggtatcgcc gctcccgatt cgcagcgcat cgccttctat cgccttcttg    8040
acgagttctt ctgagcggga ctctggggtt cgaaatgact cgagcatcag cttcaaaagc    8100
```

```
gctctgaagt tcctatactt tctagagaat aggaacttcg gaataggtac ttcaagatcc    8160
ccaattcgag ctcatcgtcc gggccgcaag ctcctagcgg cggatttgtc ctactcagga    8220
gagcgttcac cgacaaacaa cagataaaac gaaaggccca gtctttcgac tgagcctttc    8280
gttttatttg atgcctcaag ctagagagtc attaccccag cgtttaagg gcaccaataa     8340 ctgccttaaa aaattacgc cccgccctgc cactcatcgc agtctagctt ggattctcac     8400
caataaaaaa cgcccggcgg caaccgagcg ttctgaacaa atccagatgg agttctgagg    8460
tcattactgg atctatcaac aggagtccaa gctcagctaa ttaagctagc ttatcgatac    8520
cgtcgacctc gaaccccacg ccctctttta atacgacggg caatttgcac ttcagaaaat    8580
gaagagtttg ctttagccat aacaaaagtc cagtatgctt tttcacagca taactggact    8640
gatttcagtt tacaactatt ctgtctagtt taagacttta ttgtcatagt ttagatctat    8700
tttgttcagt ttaagacttt attgtccgcc cacacccgct tacgcagggc atccatttat    8760
tactcaaccg taaccgattt tgccaggtta cgcggctggt cctctagctg gcgtaatagc    8820
gaagaggccc gcaccgatcg ccctcccaa cagttgcgca gcctgaatgg cgaatggcgc     8880
ctgatgcggt atttttctcct tacgcatctg tgcggtattt cacaccgcat atggtgcact   8940
ctcagtacaa tctgctctga tgccgcatag ttaagccagc cccgacaccc gccaacaccc    9000
gctgacgcgc cctgacgggc ttgtctgctc ccggcatccg cttacagaca agctgtgacc    9060
gtctccggga gctgcatgtg tcagaggttt tcaccgtcat caccgaaacg cgcgagacga    9120
aagggcctcg tgatacgcct atttttatag gttaatgtca tgataataat ggtttcttag    9180
acgtcaggtg gcacttttcg gggaaatgtg cgcggaaccc ctatttgttt attttttctaa   9240 atacattcaa atatgtatcc gctcatgaga caataaccct gataaatgct tcaataatat    9300
tgaaaaagga agagtatgag tattcaacat ttccgtgtcg cccttattcc cttttttgcg    9360 gcatttttgcc ttcctgtttt tgctcaccca gaaacgctgg tgaaagtaaa agatgctgaa    9420
gatcagttgg gtgcacgagt gggttacatc gaactggatc tcaacagcgg taagatcctt    9480
gagagttttc gccccgaaga acgttttcca atgatgagca cttttaaagt tctgctatgt    9540
ggcgcggtat tatcccgtat tgacgccggg caagagcaac tcggtcgccg catacactat    9600
tctcagaatg acttggttga gtactcacca gtcacagaaa agcatcttac ggatggcatg    9660
acagtaagag aattatgcag tgctgccata accatgagtg ataacactgc ggccaactta    9720
cttctgacaa cgatcggagg accgaaggag ctaaccgctt ttttgcacaa catgggggat    9780
catgtaactc gccttgatcg ttgggaaccg gagctgaatg aagccatacc aaacgacgag    9840
cgtgacacca cgatgcctgt agcaatggca acaacgttgc gcaaactatt aactggcgaa    9900
ctacttactc tagcttcccg gcaacaatta atagactgga tggaggcgga taaagttgca    9960
ggaccacttc tgcgctcggc ccttccggct ggctggttta ttgctgataa atctggagcc   10020
ggtgagcgtg ggtccgcgg tatcattgca gcactgggc cagatggtaa gccctcccgt     10080
atcgtagtta tctacacgac ggggagtcag gcaactatgg atgaacgaaa tagacagatc   10140
gctgagatag gtgcctcact gattaagcat tggtaactgt cagaccaagt ttactcatat   10200
atactttaga ttgatttaaa acttcatttt taatttaaaa ggatctaggt gaagatcctt   10260
tttgataatc tcatgaccaa aatcccttaa cgtgagtttt cgttccactg agcgtcagac   10320
cccgtagaaa agatcaaagg cagttattgg tgcctcactg attaagcatt ggtaactgtc   10380
agaccaagtt tactcatata ctttagat tgatttaaaa cttcattttt aattttttgcg    10440 gccgcaagat ccggccacga tgcgtccggc gtagaggatc tgaagatcag cagttcaacc   10500
```

```
tgttgatagt acgtactaag ctctcatgtt tcacgtacta agctctcatg tttaacgtac    10560
taagctctca tgtttaacga actaaaccct catggctaac gtactaagct ctcatggcta    10620
acgtactaag ctctcatgtt tcacgtacta agctctcatg tttgaacaat aaaattaata    10680
taaatcagca acttaaatag cctctaaggt tttaagtttt ataagaaaaa aagaatata     10740 taaggctttt aaagctttta aggtttaacg gttgtggaca acaagccagg gatgtaacgc    10800
actgagaagc ccttagagcc tctcaaagca attttgagtg acacaggaac acttaacggc    10860
tgacatggga attagccatg gcatcacagt atcgtgatga cagaggcagg gagtgcggcc    10920
tttttacggt tcctggcctt tgctggcct tttgctcaca tgttctttcc tgcgttatca     10980
ggggattcct taaggtatac tttccgctgc ataaccctgc ttcggggtca ttatagcgat    11040
tttttcggta tatccatcct ttttcgcacg atatacagga ttttgccaaa gggttcgtgt    11100
agactttcct tggtgtatcc aacggcgtca gccgggcagg ataggtgaag taggcccacc    11160
cgcgagcggg tgttccttct tcactgtccc ttattcgcac ctggcggtgc tcaacgggaa    11220
tcctgctctg cgaggctggc cgataagct                                      11249
```

<210> SEQ ID NO 20
<211> LENGTH: 11230
<212> TYPE: DNA
<213> ORGANISM: Artificial sequence
<220> FEATURE:
<223> OTHER INFORMATION: Synthetic construct

<400> SEQUENCE: 20

```
ctgataccgc tcgccgcagc cgaacgaccg agcgcagcgg gtcagtgagc gaggaagcgg      60
aagagcgccc aatacgcaaa ccgcctctcc ccgcgcgttg gccgattcat taatgcagcg     120
cccaaacata acaggaagaa aaatgccccg ctgtgggcgg acaaaatagt tgggaactgg     180 gagggggtgga aatggagttt ttaaggatta tttaggaag agtgacaaaa tagatgggaa     240
ctgggtgtag cgtcgtaagc taatacgaaa attaaaaatg acaaaatagt ttggaactag     300
atttcactta tctggttctt gaggcggtta aaagagccgt actcttctcc gatgtcgact     360
aggccatgat gctcattctg tgggaccaaa acgaaaaaac accctttcgg gtgtcttttc     420
tggaatttgg taccgaggct gcaagtccca ttaaggaggc gcgccttatt acagatcttc     480
ctcagagatg agcttctgtt ccagatcttc ttctgaaatc aacttttgtt ccagatcttc     540
ttcagagatg agtttctgct ccgcggccgc gtcgcctccc agctgagaca ggtcgatccg     600
tgtctcgtac aggccggtga tgctctggtg gatcagggtg gcgtccagca cctctttggt     660
gctggtgtac ctcttccggt cgatggtggt gtcaaagtac ttgaaggcgg caggggctcc     720
cagattggtc agggtaaaca ggtggatgat attctcggcc tgctctctga taggcttgtc     780
tctgtgcttg ttgtaggcgc tcagcacctt gtccagatta gcgtcggcca ggatcactct     840
cttggagaac tcgctgatct gctcgatgat ctcgtccagg tagtgtttgt gctgttccac     900
aaacagctgt ttctgctcat tatcctcggg ggagcccttc agcttctcat agtggctggc     960
caggtacagg aagttcacat atttggaggg cagggccagt tcgtttccct tctgcagttc    1020
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttcttttcat gatggtgatc cccagcagct ctttcacact    1200
cttcagtttc ttggacttgc cctttttccac tttggccacc accagcacag aataggccac    1260
```

-continued

| | |
|---|---|
| ggtggggctg tcgaagccgc cgtacttctt agggtcccag tccttctttc tggcgatcag | 1320 |
| cttgtcgctg ttcctcttgg gcaggataga ctctttgctg aagccgcctg tctgcacctc | 1380 |
| ggtcttttc acgatattca cttggggcat agacagcact ttccgcacgg tggcaaagtc | 1440 |
| ccggcccta tcccacacga tctcgcctgt ttcgccgttt gtctcgatca gaggccgctt | 1500 |
| ccggatctcg ccgttggcca gggtaatctc ggtcttgaaa aagttcatga tgttgctgta | 1560 |
| gaagaagtac ttggcggtag ccttgccgat ttcctgctcg ctcttggcga tcatcttccg | 1620 |
| cacgtcgtac accttgtagt cgccgtacac gaactcgctt ccagcttag ggtacttttt | 1680 |
| gatcagggcg gttcccacga cggcgttcag gtaggcgtcg tgggcgtggt ggtagttgtt | 1740 |
| gatctcgcgc actttgtaaa actggaaatc cttccggaaa tcggacacca gcttggactt | 1800 |
| cagggtgatc actttcactt cccggatcag tttgtcgttc tcgtcgtact tagtgttcat | 1860 |
| ccgggagtcc aggatctgtg ccacgtgctt tgtgatctgc cgggtttcca ccagctgtct | 1920 |
| cttgatgaag ccggccttat ccagttcgct caggccgcct ctctcggcct tggtcagatt | 1980 |
| gtcgaacttc ctctgggtaa tcagcttggc attcagcagc tggcgccagt agttcttcat | 2040 |
| cttcttcacg acctcttcgg agggcacgtt gtcgctcttg ccccggttct tgtcgctccg | 2100 |
| agtcagcact ttgttatcga tggagtcgtc cttcagaaag ctctgaggca cgatagcgtc | 2160 |
| cacatcgtag tcggacagcc ggttgatgtc cagttcctgg tccacgtaca tatcccgccc | 2220 |
| attctgcagg tagtacaggt acagcttctc gttctgcagc tgggtgtttt ccacggggtg | 2280 |
| ttctttcagg atctggctgc ccagctcttt gatgccctct tcgatccgct tcattctctc | 2340 |
| gcggctgttc ttctgtccct tctgggtggt ctggttctct ctggccattt cgatcacgat | 2400 |
| gttctcgggc ttgtgccggc ccatcacttt cacgagctcg tccaccacct tcactgtctg | 2460 |
| caggatgccc ttcttaatgg cggggctgcc ggccagattg gcaatgtgct cgtgcaggct | 2520 |
| atcgccctgg ccggacacct gggctttctg gatgtcctct ttaaaggtca ggctgtcgtc | 2580 |
| gtggatcagc tgcatgaagt ttctgttggc gaagccgtcg gacttcagga aatccaggat | 2640 |
| tgtcttgccg gactgcttgt cccggatgcc gttgatcagc ttccggctca gcctgcccca | 2700 |
| gccggtgtat ctccgccgct tcagctgctt catcactttg tcgtcgaaca ggtgggcata | 2760 |
| ggttttcagc cgttcctcga tcatctctct gtcctcaaac agtgtcaggg tcagcacgat | 2820 |
| atcttccaga atgtcctcgt tttcctcatt gtccaggaag tccttgtcct tgataatttt | 2880 |
| cagcagatcg tggtatgtgc cagggaggc gttgaaccga tcttccacgc cggagatttc | 2940 |
| cacggagtcg aagcactcga ttttcttgaa gtagtcctct ttcagctgct tcacggtcac | 3000 |
| tttccggttg gtcttgaaca gcaggtccac gatggctttt ttctgctcgc cgctcaggaa | 3060 |
| ggcgggcttt ctcattccct cggtcacgta tttcactttg gtcagctcgt tgtacacggt | 3120 |
| gaagtactcg tacagcaggc tgtgcttggg cagcaccttc tcgttgggca ggttcttatc | 3180 |
| gaagttggtc atccgctcga tgaagctctg ggcgctggcg ccttgtcca ccacttcctc | 3240 |
| gaagttccag ggggtgatgg tttcctcgct ctttctggtc atccaggcga atctgctgtt | 3300 |
| tcccctggcc agagggccca cgtagtaggg gatgcggaag gtcaggatct tctcgatctt | 3360 |
| ttcccggttg tccttcagga atgggtaaaa atcttcctgc cgccgcagaa tggcgtgcag | 3420 |
| ctctcccagg tggatctggt gggggatgct gccgttgtcg aaggtccgct gcttccgcag | 3480 |
| caggtcctct ctgttcagct tcacgagcag ttcctcggtg ccgtccatct ttccaggat | 3540 |
| gggcttgatg aacttgtaga actcttcctg gctggctccg ccatcgatgt agccggcgta | 3600 |
| gccgttcttg ctctggtcga agaaaatctc tttgtacttc tcaggcagct gctgccgcac | 3660 |

```
gagagctttc agcagggtca ggtcctggtg gtgctcgtcg tatctcttga tcatagaggc    3720 gctcagggg  gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt     4080 ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320 gatgggtgc  cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa cgaaaaaac  cgccttgcag gcggttttt     4860 cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccggaaggt gatcttccgg gggctttctc    5040
atgcgttgct tgtattgaaa atgggggcca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc gctggatga    5580 ccaggatgcc attgctgtgg aagctgcctg cactaatgtt ccggcgttat ttcttgatgt    5640
ctctgaccag acacccatca acagtattat tttctcccat gaagacggta cgcgactggg    5700
cgtggagcat ctggtcgcat tgggtcacca gcaaatcgcg ctgttagcgg cccattaag     5760 ttctgtctcg gcgcgtctgc gtctggctgg ctggcataaa tatctcactc gcaatcaaat    5820
tcagccgata gcggaacggg aaggcgactg gagtgccatg tccggttttc aacaaaccat    5880
gcaaatgctg aatgagggca tcgttcccac tgcgatgctg gttgccaacg atcagatggc    5940
gctgggcgca atgcgcgcca ttaccgagtc cgggctgcgc gttggtgcgg atatctcggt    6000
```

| | |
|---|---|
| agtgggatac gacgataccg aagacagctc atgttatatc ccgccgttaa ccaccatcaa | 6060 |
| acaggatttt cgcctgctgg ggcaaaccag cgtggaccgc ttgctgcaac tctctcaggg | 6120 |
| ccaggcggtg aagggcaatc agctgttgcc cgtctcactg gtgaaaagaa aaaccaccct | 6180 |
| ggcgcccaat acgcaaaccg cctctccccg cgcgttggcc gattcattaa tgcagctggc | 6240 |
| acgacaggtt tcccgactgg aaagcgggca gtgagcgcaa cgcaattaat gtaagttagc | 6300 |
| tcactcatta ggcaccccac ccgggtcctt gagcccatt atcacctcca aagccttctc | 6360 |
| gtctggtcag tttcacctgt tttacgtaaa aacccgcttc ggcgggtttt tacttttggg | 6420 |
| gaaacacaga aaaagcccg cacctgacag tgcgggcttt tttttcgac caaaggtgcg | 6480 |
| actactcttg cctactacct atcgactgag ctgaaagaat tcctaaagat ctataaatgt | 6540 |
| gagcggataa cattgacatt gtgagcggat aacaagatac ttctagtaac tttcagttta | 6600 |
| gcggtctgtt taagagctat gctggaaaca gcatagcaag tttaaataag gctagtccgt | 6660 |
| tatcaacttg aaaagtggc accgagtcgg tgcttttttt ttgaattcat gtggctgacc | 6720 |
| gttctgttgt ctctcgctct tccgagtaga cgaacaataa ggcctcccta acgggggcc | 6780 |
| ttttttattg ataacaaaag tcagtgcttc cgctatttcc aaaataccgg gctaatacgg | 6840 |
| tttaaacgac ctcctggatt tgctcagaca gccttttcgt cattcgtttc agccaaaaaa | 6900 |
| cttaagaccg ccggtcttgt ccactacctt gcagtaatgc ggtggacagg atcggcggtt | 6960 |
| ttctttctc ttctcaagaa gttcctatac tttctagaga ataggaactt cggaatagga | 7020 |
| acttcctcct gaacggccat aagaacgaag gctgtctgtt gaactctcga gccgtggaaa | 7080 |
| cggatgaagg cacgaaccca gttgacataa gcctgttcgg ttcgtaaact gtaatgcaag | 7140 |
| tagcgtatgc gctcaaaact ggatggcttt cttgccgcca aggatctgat ggcgcagggg | 7200 |
| atcaagatct gatcaagaga caggatgagg atcgtttcgc atgattgaac aagatggatt | 7260 |
| gcacgcaggt tctccggccg cttgggtgga gaggctattc ggctatgact gggcacaaca | 7320 |
| gacaatcggc tgctctgatg ccgccgtgtt ccggctgtca gcgcaggggc gcccggttct | 7380 |
| ttttgtcaag accgacctgt ccggtgccct gaatgaactg caggacgagg cagcgcggct | 7440 |
| atcgtggctg gccacgacgg gcgttccttg cgcagctgtg ctcgacgttg tcactgaagc | 7500 |
| gggaagggac tggctgctat tgggcgaagt gccggggcag gatctcctgt catctcacct | 7560 |
| tgctcctgcc gagaaagtat ccatcatggc tgatgcaatg cggcggctgc atacgcttga | 7620 |
| tccggctacc tgcccattcg accaccaagc gaaacatcgc atcgagcgag cacgtactcg | 7680 |
| gatggaagcc ggtcttgtcg atcaggatga tctggacgaa gagcatcagg gctcgcgcc | 7740 |
| agccgaactg ttcgccaggc tcaaggcgcg catgcccgac ggcgaggatc tcgtcgtgac | 7800 |
| ccatggcgat gcctgcttgc cgaatatcat ggtggaaaat ggccgctttt ctggattcat | 7860 |
| cgactgtggc cggctgggtg tggcggaccg ctatcaggac atagcgttgg ctacccgtga | 7920 |
| tattgctgaa gagcttggcg gcgaatgggc tgaccgcttc ctcgtgcttt acggtatcgc | 7980 |
| cgctcccgat tcgcagcgca tcgccttcta tcgccttctt gacgagttct tctgagcggg | 8040 |
| actctggggt tcgaaatgac tcgagcatca gcttcaaaag cgctctgaag ttcctatact | 8100 |
| ttctagagaa taggaacttc ggaataggta cttcaagatc cccaattcga gctcatcgtc | 8160 |
| cgggccgcaa gctcctagcg gcggatttgt cctactcagg agagcgttca ccgacaaaca | 8220 |
| acagataaaa cgaaaggccc agtctttcga ctgagccttt cgttttattt gatgcctcaa | 8280 |
| gctagagagt cattacccca ggcgtttaag ggcaccaata actgccttaa aaaaattacg | 8340 |
| ccccgccctg ccactcatcg cagtctagct tggattctca ccaataaaaa acgcccggcg | 8400 |

```
gcaaccgagc gttctgaaca aatccagatg gagttctgag gtcattactg gatctatcaa   8460
caggagtcca agctcagcta attaagctag cttatcgata ccgtcgacct cgaaccccac   8520
gcccctcttt aatacgacgg gcaatttgca cttcagaaaa tgaagagttt gctttagcca   8580
taacaaaagt ccagtatgct ttttcacagc ataactggac tgatttcagt ttacaactat   8640
tctgtctagt ttaagacttt attgtcatag tttagatcta ttttgttcag tttaagactt   8700
tattgtccgc ccacacccgc ttacgcaggg catccattta ttactcaacc gtaaccgatt   8760
ttgccaggtt acgcggctgg tcctctagct ggcgtaatag cgaagaggcc cgcaccgatc   8820
gcccttccca acagttgcgc agcctgaatg gcgaatggcg cctgatgcgg tattttctcc   8880
ttacgcatct gtgcggtatt tcacaccgca tatggtgcac tctcagtaca atctgctctg   8940
atgccgcata gttaagccag ccccgacacc cgccaacacc cgctgacgcg ccctgacggg   9000
cttgtctgct cccggcatcc gcttacagac aagctgtgac cgtctccggg agctgcatgt   9060
gtcagaggtt ttcaccgtca tcaccgaaac gcgcgagacg aaagggcctc gtgatacgcc   9120
tatttttata ggttaatgtc atgataataa tggtttctta gacgtcaggt ggcacttttc   9180
ggggaaatgt gcgcggaacc cctatttgtt tatttttcta aatacattca aatatgtatc   9240
cgctcatgag acaataaccc tgataaatgc ttcaataata ttgaaaaagg aagagtatga   9300
gtattcaaca tttccgtgtc gcccttattc ccttttttgc ggcattttgc cttcctgttt   9360
ttgctcaccc agaaacgctg gtgaaagtaa aagatgctga agatcagttg ggtgcacgag   9420
tgggttacat cgaactggat ctcaacagcg gtaagatcct tgagagtttt cgccccgaag   9480
aacgttttcc aatgatgagc acttttaaag ttctgctatg tggcgcggta ttatcccgta   9540
ttgacgccgg gcaagagcaa ctcggtcgcc gcatacacta ttctcagaat gacttggttg   9600
agtactcacc agtcacagaa aagcatctta cggatggcat gacagtaaga gaattatgca   9660
gtgctgccat aaccatgagt gataacactg cggccaactt acttctgaca acgatcggag   9720
gaccgaagga gctaaccgct tttttgcaca acatggggga tcatgtaact cgccttgatc   9780
gttgggaacc ggagctgaat gaagccatac caaacgacga gcgtgacacc acgatgcctg   9840
tagcaatggc aacaacgttg cgcaaactat taactggcga actacttact ctagcttccc   9900
ggcaacaatt aatagactgg atggaggcgg ataaagttgc aggaccactt ctgcgctcgg   9960
cccttccggc tggctggttt attgctgata aatctggagc cggtgagcgt gggtcccgcg  10020
gtatcattgc agcactgggg ccagatggta agccctcccg tatcgtagtt atctacacga  10080
cggggagtca ggcaactatg gatgaacgaa atagacagat cgctgagata ggtgcctcac  10140
tgattaagca ttggtaactg tcagaccaag tttactcata tatactttag attgatttaa  10200
aacttcattt ttaatttaaa aggatctagg tgaagatcct ttttgataat ctcatgacca  10260
aaatccctta acgtgagttt tcgttccact gagcgtcaga ccccgtagaa aagatcaaag  10320
gcagttattg gtgcctcact gattaagcat tggtaactgt cagaccaagt ttactcatat  10380
atactttaga ttgatttaaa acttcatttt taattttgc ggccgcaaga tccggccacg  10440
atgcgtccgg cgtagaggat ctgaagatca gcagttcaac ctgttgatag tacgtactaa  10500
gctctcatgt ttcacgtact aagctctcat gtttaacgta ctaagctctc atgtttaacg  10560
aactaaaccc tcatggctaa cgtactaagc tctcatggct aacgtactaa gctctcatgt  10620
ttcacgtact aagctctcat gtttgaacaa taaaattaat ataaatcagc aacttaaata  10680
gcctctaagg ttttaagttt tataagaaaa aaaagaatat ataaggcttt taaagctttt  10740
```

| | |
|---|---:|
| aaggtttaac ggttgtggac aacaagccag ggatgtaacg cactgagaag cccttagagc | 10800 |
| ctctcaaagc aattttgagt gacacaggaa cacttaacgg ctgacatggg aattagccat | 10860 |
| ggcatcacag tatcgtgatg acagaggcag ggagtgcggc ctttttacgg ttcctggcct | 10920 |
| tttgctggcc ttttgctcac atgttctttc ctgcgttatc aggggattcc ttaaggtata | 10980 |
| cttccgctg cataaccctg cttcggggtc attatagcga ttttttcggt atatccatcc | 11040 |
| tttttcgcac gatatacagg attttgccaa agggttcgtg tagactttcc ttggtgtatc | 11100 |
| caacggcgtc agccgggcag gataggtgaa gtaggcccac ccgcgagcgg gtgttccttc | 11160 |
| ttcactgtcc cttattcgca cctggcggtg ctcaacggga atcctgctct gcgaggctgg | 11220 |
| ccgataagct | 11230 |

<210> SEQ ID NO 21
<211> LENGTH: 11230
<212> TYPE: DNA
<213> ORGANISM: Artificial sequence
<220> FEATURE:
<223> OTHER INFORMATION: Synthetic construct

<400> SEQUENCE: 21

| | |
|---|---:|
| ctgataccgc tcgccgcagc cgaacgaccg agcgcagcgg gtcagtgagc gaggaagcgg | 60 |
| aagagcgccc aatacgcaaa ccgcctctcc ccgcgcgttg gccgattcat taatgcagcg | 120 |
| cccaaacata acaggaagaa aaatgccccg ctgtgggcgg acaaaatagt tgggaactgg | 180 |
| gaggggtgga aatggagttt ttaaggatta tttaggggaag agtgacaaaa tagatgggaa | 240 |
| ctgggtgtag cgtcgtaagc taatacgaaa attaaaaatg acaaaatagt ttggaactag | 300 |
| atttcactta tctggttctt gaggcggtta aaagagccgt actcttctcc gatgtcgact | 360 |
| aggccatgat gctcattctg tgggaccaaa acgaaaaaac cccctttcgg gtgtcttttc | 420 |
| tggaatttgg taccgaggct gcaagtccca ttaaggaggc gcgccttatt acagatcttc | 480 |
| ctcagagatt agcttctgtt ccagatcttc ttctgaaatc aacttttgtt ccagatcttc | 540 |
| ttcagagatg agtttctgct ccgcggccgc gtcgcctccc agctgagaca ggtcgatccg | 600 |
| tgtctcgtac aggccggtga tgctctggtg gatcagggtg gcgtccagca cctcttggt | 660 |
| gctggtgtac ctcttccggt cgatggtggt gtcaaagtac ttgaaggcgg caggggctcc | 720 |
| cagattggtc agggtaaaca ggtggatgat attctcggcc tgctctctga taggcttgtc | 780 |
| tctgtgcttg ttgtaggcgc tcagcaacctt gtccagatta gcgtcggcca ggatcactct | 840 |
| cttggagaac tcgctgatct gctcgatgat ctcgtccagg tagtgtttgt gctgttccac | 900 |
| aaacagctgt ttctgctcat tatcctcggg ggagcccttc agcttctcat agtggctggc | 960 |
| caggtacagg aagttcacat atttggaggg cagggccagt tcgtttccct tctgcagttc | 1020 |
| gccggcagag gccagcattc tcttccggcc gttttccagc tcgaacaggg agtacttagg | 1080 |
| cagcttgatg atcaggtcct tttttcacttc tttgtagccc ttggcttcca gaaagtcgat | 1140 |
| gggattcttc tcgaagctgc ttcttttccat gatggtgatc cccagcagct ctttcacact | 1200 |
| cttcagtttc ttggacttgc ccttttccac tttggccacc accagcacag aataggccac | 1260 |
| ggtggggctc tcgaagccgc cgtacttctt agggtcccag tccttctttc tggcgatcag | 1320 |
| cttgtcgctg ttcctcttgg gcaggataga ctctttgctg aagccgcctg tctgcacctc | 1380 |
| ggtcttttc acgatattca cttggggcat agacagcact ttccgcacgg tggcaaagtc | 1440 |
| ccggccctta tcccacacga tctcgcctgt ttcgccgttt gtctcgatca gaggccgctt | 1500 |
| ccggatctcg ccgttggcca gggtaatctc ggtcttgaaa aagttcatga tgttgctgta | 1560 |

```
gaagaagtac ttggcggtag ccttgccgat ttcctgctcg ctcttggcga tcatcttccg    1620
cacgtcgtac accttgtagt cgccgtacac gaactcgctt tccagcttag ggtactttt     1680 gatcagggcg gttcccacga cggcgttcag gtaggcgtcg tgggcgtggt ggtagttgtt    1740
gatctcgcgc actttgtaaa actggaaatc cttccggaaa tcggacacca gcttggactt    1800
cagggtgatc actttcactt cccggatcag tttgtcgttc tcgtcgtact tagtgttcat    1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccggacacct gggctttctg gatgtcctct ttaaaggtca ggctgtcgtc    2580
gtggatcagc tgcatgaagt ttctgttggc gaagccgtcg gacttcagga aatccaggat    2640
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccagggaggc gttgaaccga tcttccacgc cggagatttc    2940 cacgagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tcccctggcc agagggccca cgtagtaggg gatgcggaag gtcaggatct tctcgatctt    3360 ttccggttg tccttcagga atgggtaaaa atcttcctgc cgccgcagaa tggcgtgcag    3420
ctctcccagg tggatctggt ggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtc tatctcttga tcatagaggc    3720
gctcaggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
```

```
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatggggtt    4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcaggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa acgaaaaaac cgccttgcag gcggtttttt    4860
cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccggaaggt gatcttccgg gggctttctc    5040
atgcgttgct tgtattgaaa atgggggcca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc cgctggatga    5580
ccaggatgcc attgctgtgg aagctgcctg cactaatgtt ccggcgttat tcttgatgt    5640
ctctgaccag acacccatca acagtattat tttctcccat gaagacggta cgcgactggg    5700
cgtggagcat ctggtcgcat tgggtcacca gcaaatcgcg ctgttagcgg cccattaag    5760
ttctgtctcg gcgcgtctgc gtctggctgg ctggcataaa tatctcactc gcaatcaaat    5820
tcagccgata gcggaacggg aaggcgactg gagtgccatg tccggttttc aacaaaccat    5880
gcaaatgctg aatgagggca tcgttcccac tgcgatgctg gttgccaacg atcagatggc    5940
gctgggcgca atgcgcgcca ttaccgagtc cgggctgcgc gttggtgcgg atatctcggt    6000
agtgggatac gacgataccg aagacagctc atgttatatc ccgccgttaa ccaccatcaa    6060
acaggatttt cgcctgctgg ggcaaaccag cgtggaccgc ttgctgcaac tctctcaggg    6120
ccaggcggtg aagggcaatc agctgttgcc cgtctcactg gtgaaaagaa aaccaccct    6180
ggcgcccaat acgcaaaccg cctctccccg cgcgttggcc gattcattaa tgcagctggc    6240
acgacaggtt tcccgactgg aaagcgggca gtgagcgcaa cgcaattaat gtaagttagc    6300
```

```
tcactcatta ggcacccac ccgggtcctt gagccccatt atcacctcca aagccttctc    6360
gtctggtcag tttcacctgt tttacgtaaa aacccgcttc ggcgggtttt tacttttggg    6420
gaaacacaga aaaagcccg cacctgacag tgcgggcttt tttttcgac caaaggtgcg     6480 actactcttg cctactacct atcgactgag ctgaaagaat tcctaaagat ctataaatgt    6540
gagcggataa cattgacatt gtgagcggat aacaagatac ttctagtaga tcggcaggca    6600
agtcccagtt taagagctat gctggaaaca gcatagcaag tttaaataag gctagtccgt    6660
tatcaacttg aaaagtggc accgagtcgg tgcttttttt ttgaattcat gtggctgacc     6720
gttctgttgt ctctcgctct tccgagtaga cgaacaataa ggcctcccta acgggggcc     6780 tttttattg ataacaaaag tcagtgcttc cgctatttcc aaaataccgg ctaatacgg      6840 tttaaacgac ctcctggatt tgctcagaca gccttttcgt cattcgtttc agccaaaaaa    6900
cttaagaccg ccggtcttgt ccactacctt gcagtaatgc ggtggacagg atcggcggtt    6960
ttcttttctc ttctcaagaa gttcctatac tttctagaga ataggaactt cggaatagga    7020
acttcctcct gaacggccat aagaacgaag gctgtctgtt gaactctcga gccgtggaaa    7080
cggatgaagg cacgaaccca gttgacataa gcctgttcgg ttcgtaaact gtaatgcaag    7140
tagcgtatgc gctcaaaact ggatggcttt cttgccgcca aggatctgat ggcgcagggg    7200
atcaagatct gatcaagaga caggatgagg atcgtttcgc atgattgaac aagatggatt    7260
gcacgcaggt tctccggccg cttgggtgga gaggctattc ggctatgact gggcacaaca    7320
gacaatcggc tgctctgatg ccgccgtgtt ccggctgtca gcgcaggggc gcccggttct    7380
ttttgtcaag accgacctgt ccggtgccct gaatgaactg caggacgagg cagcgcggct    7440
atcgtggctg gccacgacgg gcgttccttg cgcagctgtg ctcgacgttg tcactgaagc    7500
gggaagggac tggctgctat tgggcgaagt gccggggcag gatctcctgt catctcacct    7560
tgctcctgcc gagaaagtat ccatcatggc tgatgcaatg cggcggctgc atacgcttga    7620
tccggctacc tgcccattcg accaccaagc gaaacatcgc atcgagcgag cacgtactcg    7680
gatggaagcc ggtcttgtcg atcaggatga tctggacgaa gagcatcagg ggctcgcgcc    7740
agccgaactg ttcgccaggc tcaaggcgcg catgcccgac ggcgaggatc tcgtcgtgac    7800
ccatggcgat gcctgcttgc cgaatatcat ggtggaaaat ggccgctttt ctggattcat    7860
cgactgtggc cggctgggtg tggcggaccg ctatcaggac atagcgttgg ctacccgtga    7920
tattgctgaa gagcttggcg gcgaatgggc tgaccgcttc ctcgtgcttt acggtatcgc    7980
cgctcccgat tcgcagcgca tcgccttcta tcgccttctt gacgagttct tctgagcggg    8040
actctggggt tcgaaatgac tcgagcatca gcttcaaaag cgctctgaag ttcctatact    8100 ttctagaaa taggaacttc ggaataggta cttcaagatc cccaattcga gctcatcgtc    8160
cgggccgcaa gctcctagcg gcggatttgt cctactcagg agagcgttca ccgacaaaca    8220
acagataaaa cgaaggccc agtctttcga ctgagccttt cgttttattt gatgcctcaa    8280
gctagagagt cattacccca ggcgtttaag ggcaccaata actgccttaa aaaaattacg    8340
ccccgccctg ccactcatcg cagtctagct tggattctca ccaataaaaa acgcccggcg    8400
gcaaccgagc gttctgaaca atccagatg gagttctgag gtcattactg gatctatcaa    8460
caggagtcca agctcagcta attaagctag cttatcgata ccgtcgacct cgaaccccac    8520
gcccctcttt aatacgacgg gcaatttgca cttcagaaaa tgaagagttt gctttagcca    8580
taacaaaagt ccagtatgct ttttcacagc ataactggac tgatttcagt ttacaactat    8640
```

```
tctgtctagt ttaagacttt attgtcatag tttagatcta ttttgttcag tttaagactt    8700
tattgtccgc ccacacccgc ttacgcaggg catccattta ttactcaacc gtaaccgatt    8760
ttgccaggtt acgcggctgg tcctctagct ggcgtaatag cgaagaggcc cgcaccgatc    8820
gcccttccca acagttgcgc agcctgaatg gcgaatggcg cctgatgcgg tattttctcc    8880
ttacgcatct gtgcggtatt tcacaccgca tatggtgcac tctcagtaca atctgctctg    8940
atgccgcata gttaagccag ccccgacacc cgccaacacc cgctgacgcg ccctgacggg    9000
cttgtctgct cccggcatcc gcttacagac aagctgtgac cgtctccggg agctgcatgt    9060
gtcagaggtt ttcaccgtca tcaccgaaac gcgcgagacg aaagggcctc gtgatacgcc    9120
tatttttata ggttaatgtc atgataataa tggtttctta gacgtcaggt ggcacttttc    9180
ggggaaatgt gcgcggaacc cctatttgtt tatttttcta atacattca aatatgtatc     9240
cgctcatgag acaataaccc tgataaatgc ttcaataata ttgaaaaagg aagagtatga    9300
gtattcaaca tttccgtgtc gcccttattc cctttttgc ggcattttgc cttcctgttt     9360
ttgctcaccc agaaacgctg gtgaaagtaa aagatgctga agatcagttg ggtgcacgag    9420
tgggttacat cgaactggat ctcaacagcg gtaagatcct tgagagtttt cgccccgaag    9480
aacgttttcc aatgatgagc acttttaaag ttctgctatg tggcgcggta ttatcccgta    9540
ttgacgccgg gcaagagcaa ctcggtcgcc gcatacacta ttctcagaat gacttggttg    9600
agtactcacc agtcacagaa aagcatctta cggatggcat gacagtaaga gaattatgca    9660
gtgctgccat aaccatgagt gataacactg cggccaactt acttctgaca acgatcggag    9720
gaccgaagga gctaaccgct tttttgcaca acatggggga tcatgtaact cgccttgatc    9780
gttgggaacc ggagctgaat gaagccatac caaacgacga gcgtgacacc acgatgcctg    9840
tagcaatggc aacaacgttg cgcaaactat taactggcga actacttact ctagcttccc    9900
ggcaacaatt aatagactgg atggaggcgg ataaagttgc aggaccactt ctgcgctcgg    9960
cccttccggc tggctggttt attgctgata aatctggagc cggtgagcgt gggtcccgcg    10020
gtatcattgc agcactgggg ccagatggta agccctcccg tatcgtagtt atctacacga    10080
cggggagtca ggcaactatg gatgaacgaa atagacagat cgctgagata ggtgcctcac    10140
tgattaagca ttggtaactg tcagaccaag tttactcata tatactttag attgatttaa    10200
aacttcattt taatttaaa aggatctagg tgaagatcct ttttgataat ctcatgacca     10260
aaatccctta acgtgagttt tcgttccact gagcgtcaga ccccgtagaa aagatcaaag    10320
gcagttattg gtgcctcact gattaagcat tggtaactgt cagaccaagt ttactcatat    10380
atactttaga ttgatttaaa acttcatttt taatttttgc ggccgcaaga tccggccacg    10440
atgcgtccgg cgtagaggat ctgaagatca gcagttcaac ctgttgatag tacgtactaa    10500
gctctcatgt ttcacgtact aagctctcat gtttaacgta ctaagctctc atgtttaacg    10560
aactaaaccc tcatggctaa cgtactaagc tctcatggct aacgtactaa gctctcatgt    10620
ttcacgtact aagctctcat gtttgaacaa taaaattaat ataaatcagc aacttaaata    10680
gcctctaagg ttttaagttt tataagaaaa aaagaatat ataaggcttt taaagctttt    10740
aaggtttaac ggttgtggac aacaagccag ggatgtaacg cactgagaag cccttagagc    10800
ctctcaaagc aattttgagt gacacaggaa cacttaacgg ctgacatggg aattagccat    10860
ggcatcacag tatcgtgatg acagaggcag ggagtgcggc ctttttacgg ttcctggcct    10920
tttgctggcc ttttgctcac atgttctttc ctgcgttatc aggggattcc ttaaggtata    10980
ctttccgctg cataaccctg cttcggggtc attatagcga tttttcggt atatccatcc     11040
```

```
tttttcgcac gatatacagg attttgccaa agggttcgtg tagactttcc ttggtgtatc    11100
caacggcgtc agccgggcag gataggtgaa gtaggcccac ccgcgagcgg gtgttccttc    11160
ttcactgtcc cttattcgca cctggcggtg ctcaacggga atcctgctct gcgaggctgg    11220
ccgataagct                                                           11230
```

<210> SEQ ID NO 22
<211> LENGTH: 11230
<212> TYPE: DNA
<213> ORGANISM: Artificial sequence
<220> FEATURE:
<223> OTHER INFORMATION: Synthetic construct

<400> SEQUENCE: 22

```
ctgataccgc tcgccgcagc cgaacgaccg agcgcagcgg gtcagtgagc gaggaagcgg      60
aagagcgccc aatacgcaaa ccgcctctcc ccgcgcgttg gccgattcat taatgcagcg    120
cccaaacata acaggaagaa aaatgccccg ctgtgggcgg acaaaatagt tgggaactgg    180
gaggggtgga aatggagttt ttaaggatta tttaggaag  agtgacaaaa tagatgggaa    240
ctgggtgtag cgtcgtaagc taatacgaaa attaaaaatg acaaaatagt ttggaactag    300
atttcactta tctggttctt gaggcggtta aaagagccgt actcttctcc gatgtcgact    360
aggccatgat gctcattctg tgggaccaaa acgaaaaaac cccttttcgg gtgtcttttc    420
tggaatttgg taccgaggct gcaagtccca ttaaggaggc gcgccttatt acagatcttc    480
ctcagagatg agcttctgtt ccagatcttc ttctgaaatc aacttttgtt ccagatcttc    540
ttcagagatg agtttctgct ccgcggccgc gtcgcctccc agctgagaca ggtcgatccg    600
tgtctcgtac aggccggtga tgctctggtg gatcagggtg gcgtccagca cctctttggt    660
gctggtgtac ctcttccggt cgatggtggt gtcaaagtac ttgaaggcgg caggggctcc    720
cagattggtc agggtaaaca ggtggatgat attctcggcc tgctctctga taggcttgtc    780
tctgtgcttg ttgtaggcgc tcagcacctt gtccagatta gcgtcggcca ggatcactct    840
cttggagaac tcgctgatct gctcgatgat ctcgtccagg tagtgtttgt gctgttccac    900
aaacagctgt ttctgctcat tatcctcggg ggagcccttc agcttctcat agtggctggc    960
caggtacagg aagttcacat atttggaggg cagggccagt tcgtttccct tctgcagttc   1020
gccggcagag gccagcattc tcttccggcc gttttccagc tcgaacaggg agtacttagg   1080
cagcttgatg atcaggtcct ttttcacttc tttgtagccc ttggcttcca gaaagtcgat   1140
gggattcttc tcgaagctgc ttcttttcat gatggtgatc cccagcagct ctttcacact   1200
cttcagtttc ttggacttgc ccttttccac tttggccacc accagcacag aataggccac   1260
ggtgggggctg tcgaagccgc cgtacttctt agggtcccag tccttctttc tggcgatcag   1320
cttgtcgctg ttcctcttgg gcaggataga ctctttgctg aagccgcctg tctgcacctc   1380
ggtcttttttc acgatattca cttggggcat agacagcact ttccgcacgg tggcaaagtc   1440
ccggccctta tcccacacga tctcgcctgt ttcgccgttt gtctcgatca gaggccgctt   1500
ccggatctcg ccgttggcca gggtaatctc ggtcttgaaa aagttcatga tgttgctgta   1560
gaagaagtac ttggcggtag ccttgccgat ttcctgctcg ctcttggcga tcatcttccg   1620
cacgtcgtac accttgtagt cgccgtacac gaactcgctt tccagcttag ggtactttt   1680
gatcagggcg gttcccacga cggcgttcag gtaggcgtcg tgggcgtggt ggtagttgtt   1740
gatctcgcgc actttgtaaa actggaaatc cttccggaaa tcggacacca gcttggactt   1800
```

```
cagggtgatc actttcactt cccggatcag tttgtcgttc tcgtcgtact tagtgttcat    1860
ccggagtcc  aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact tgttatcga  tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccggacacct gggctttctg gatgtcctct ttaaaggtca ggctgtcgtc    2580
gtggatcagc tgcatgaagt ttctgttggc gaagccgtcg gacttcagga aatccaggat    2640
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccagggaggc gttgaaccga tcttccacgc cggagatttc    2940
cacggagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tccctggcc  agagggccca cgtagtaggg gatgcggaag gtcaggatct tctcgatctt    3360
ttccggttg  tccttcagga atgggtaaaa atcttcctgc cgccgcagaa tggcgtgcag    3420
ctctcccagg tggatctggt gggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720
gctcagggg  gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttggggt  caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt    4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
```

```
cagggccaga tagatcagcc gcaggtcggc cttgtcggtg ctgtccacca gtttctttct   4260
caggtggtag atggtggggt acttctcgtg gtaggccacc tcgtccacga tgttgccgaa   4320
gatggggtgc cgctcgtgct tcttatcctc ttccaccagg aaggactctt ccagtctgtg   4380
gaagaagctg tcgtccacct tggccatctc gttgctgaag atctcttgca gatagcagat   4440
ccggttcttc cgtctggtgt atcttcttct ggcggttctc ttcagccggg tggcctcggc   4500
tgtttctccg ctgtcgaaca gcagggcgcc gatcaggttc ttcttgatgc tgtgccggtc   4560
ggtgttgccc agcaccttga atttcttgct gggcaccttg tactcgtcgg tgatcacggc   4620
ccagcccaca gagttggtgc cgatggccag gccgatgctg tacttcttgt ccatactagt   4680
tttcctgtgt gaaacctgct gatgtgctca gtatcttgtt atccgctcac aatgtcaatg   4740
ttatccgctc acatttataa tattttatct gattaataag atgatcttct tgagatcgtt   4800
ttggtctgcg cgtaatctct tgctctgaaa cgaaaaaac cgccttgcag ggcggttttt    4860
cgaaggttct ctgagctacc aactctttga accgaggtaa ctggcttggt gataagctgt   4920
caaaccagat caattcgcac tagtctgcag acgtaaaaaa agcggcgtgg ttagccgctt   4980
ttttaattgc cggagcgcaa taaaaaagcc cccggaaggt gatcttccgg ggctttctc    5040
atgcgttgct tgtattgaaa atgggggcca tgcctaccta tctgcctccc gggaagcggc   5100
atgcatttac gttgacacca tcgaatggtg caaaaccttt cgcggtatgg catgatagcg   5160
cccggaagag agtcaattca gggtggtgaa tgtgaaacca gtaacgttat acgatgtcgc   5220
agagtatgcc ggtgtctctt atcagaccgt ttcccgcgtg gtgaaccagg ccagccacgt   5280
ttctgcgaaa acgcgggaaa aagtggaagc ggcgatggcg gagctgaatt acattcccaa   5340
ccgcgtggca caacaactgg cgggcaaaca gtcgttgctg attggcgttg ccacctccag   5400
tctggccctg cacgcgccgt cgcaaattgt cgcggcgatt aaatctcgcg ccgatcaact   5460
gggtgccagc gtggtggtgt cgatggtaga acgaagcggc gtcgaagcct gtaaagcggc   5520
ggtgcacaat cttctcgcgc aacgcgtcag tgggctgatc attaactatc cgctggatga   5580
ccaggatgcc attgctgtgg aagctgcctg cactaatgtt ccggcgttat ttcttgatgt   5640
ctctgaccag acacccatca acagtattat tttctcccat gaagacggta cgcgactggg   5700
cgtggagcat ctggtcgcat tgggtcacca gcaaatcgcg ctgttagcgg cccattaag    5760
ttctgtctcg gcgcgtctgc gtctggctgg ctggcataaa tatctcactc gcaatcaaat   5820
tcagccgata gcggaacggg aaggcgactg gagtgccatg tccggttttc aacaaaccat   5880
gcaaatgctg aatgagggca tcgttcccac tgcgatgctg gttgccaacg atcagatggc   5940
gctgggcgca atgcgcgcca ttaccgagtc cgggctgcgc gttggtgcgg atatctcggt   6000
agtgggatac gacgataccg aagacagctc atgttatatc cgccgttaa ccaccatcaa    6060
acaggatttt cgcctgctgg ggcaaaccag cgtggaccgc ttgctgcaac tctctcaggg   6120
ccaggcggtg aagggcaatc agctgttgcc cgtctcactg gtgaaagaa aaaccaccct    6180
ggcgcccaat acgcaaaccg cctctccccg cgcgttggcc gattcattaa tgcagctggc   6240
acgacaggtt tcccgactgg aaagcgggca gtgagcgcaa cgcaattaat gtaagttagc   6300
tcactcatta ggcaccccac ccgggtcctt gagcccatt atcacctcca aagccttctc    6360
gtctggtcag tttcacctgt tttacgtaaa acccgcttc ggcgggtttt tacttttggg    6420
gaaacacaga aaaagcccg cacctgacag tgcgggcttt ttttttcgac caaaggtgcg    6480
actactcttg cctactacct atcgactgag ctgaagaat tcctaaagat ctataaatgt    6540
```

```
gagcggataa cattgacatt gtgagcggat aacaagatac ttctagtggc aggcaggttc    6600
catggcagtt taagagctat gctggaaaca gcatagcaag tttaaataag gctagtccgt    6660
tatcaacttg aaaaagtggc accgagtcgg tgcttttttt ttgaattcat gtggctgacc    6720
gttctgttgt ctctcgctct tccgagtaga cgaacaataa ggcctcccta acgggggggcc   6780 tttttttattg ataacaaaag tcagtgcttc cgctatttcc aaaataccgg gctaatacgg   6840
tttaaacgac ctcctggatt tgctcagaca gccttttcgt cattcgtttc agccaaaaaa    6900
cttaagaccg ccggtcttgt ccactacctt gcagtaatgc ggtggacagg atcggcggtt    6960
ttcttttctc ttctcaagaa gttcctatac tttctagaga ataggaactt cggaatagga    7020
acttcctcct gaacggccat aagaacgaag gctgtctgtt gaactctcga gccgtggaaa    7080
cggatgaagg cacgaaccca gttgacataa gcctgttcgg ttcgtaaact gtaatgcaag    7140
tagcgtatgc gctcaaaact ggatggcttt cttgccgcca aggatctgat ggcgcagggg    7200
atcaagatct gatcaagaga caggatgagg atcgtttcgc atgattgaac aagatggatt    7260
gcacgcaggt tctccggccg cttgggtgga gaggctattc ggctatgact gggcacaaca    7320
gacaatcggc tgctctgatg ccgccgtgtt ccggctgtca gcgcaggggc gcccggttct    7380
ttttgtcaag accgacctgt ccggtgccct gaatgaactg caggacgagg cagcgcggct    7440
atcgtggctg gccacgacgg gcgttccttg cgcagctgtg ctcgacgttg tcactgaagc    7500
gggaagggac tggctgctat tgggcgaagt gccggggcag gatctcctgt catctcacct    7560
tgctcctgcc gagaaagtat ccatcatggc tgatgcaatg cggcggctgc atacgcttga    7620
tccggctacc tgcccattcg accaccaagc gaaacatcgc atcgagcgag cacgtactcg    7680
gatggaagcc ggtcttgtcg atcaggatga tctggacgaa gagcatcagg gctcgcgcc    7740 agccgaactg ttcgccaggc tcaaggcgcg catgcccgac ggcgaggatc tcgtcgtgac    7800
ccatggcgat gcctgcttgc cgaatatcat ggtggaaaat ggccgctttt ctggattcat    7860
cgactgtggc cggctgggtg tggcggaccg ctatcaggac atagcgttgg ctacccgtga    7920
tattgctgaa gagcttggcg gcgaatgggc tgaccgcttc ctcgtgcttt acggtatcgc    7980
cgctcccgat tcgcagcgca tcgccttcta tcgccttctt gacgagttct tctgagcggg    8040
actctggggt tcgaaatgac tcgagcatca gcttcaaaag cgctctgaag ttcctatact    8100
ttctagagaa taggaacttc ggaataggta cttcaagatc cccaattcga gctcatcgtc    8160
cgggccgcaa gctcctagcg gcggatttgt cctactcagg agagcgttca ccgacaaaca    8220
acagataaaa cgaaaggccc agtctttcga ctgagccttt cgttttattt gatgcctcaa    8280
gctagagagt cattacccca ggcgtttaag ggcaccaata actgccttaa aaaaattacg    8340
ccccgccctg ccactcatcg cagtctagct tggattctca ccaataaaaa acgcccggcg    8400
gcaaccgagc gttctgaaca aatccagatg gagttctgag gtcattactg gatctatcaa    8460
caggagtcca agctcagcta attaagctag cttatcgata ccgtcgacct cgaaccccac    8520
gcccctcttt aatacgacgg gcaatttgca cttcagaaaa tgaagagttt gctttagcca    8580
taacaaaagt ccagtatgct ttttcacagc ataactggac tgatttcagt ttacaactat    8640
tctgtctagt ttaagacttt attgtcatag tttagatcta ttttgttcag tttaagactt    8700
tattgtccgc ccacacccgc ttacgcaggg catccattta ttactcaacc gtaaccgatt    8760
ttgccaggtt acgcggctgg tcctctagct ggcgtaatag cgaagaggcc cgcaccgatc    8820
gcccttccca acagttgcgc agcctgaatg gcgaatggcg cctgatgcgg tattttctcc    8880
ttacgcatct gtgcggtatt tcacaccgca tatggtgcac tctcagtaca atctgctctg    8940
```

```
atgccgcata gttaagccag ccccgacacc cgccaacacc cgctgacgcg ccctgacggg    9000
cttgtctgct cccggcatcc gcttacagac aagctgtgac cgtctccggg agctgcatgt    9060
gtcagaggtt ttcaccgtca tcaccgaaac gcgcgagacg aaagggcctc gtgatacgcc    9120
tattttttata ggttaatgtc atgataataa tggtttctta gacgtcaggt ggcactttc    9180
ggggaaatgt gcgcggaacc cctatttgtt tattttttcta aatacattca aatatgtatc    9240
cgctcatgag acaataaccc tgataaatgc ttcaataata ttgaaaaagg aagagtatga    9300
gtattcaaca tttccgtgtc gcccttattc ccttttttgc ggcattttgc cttcctgttt    9360
ttgctcaccc agaaacgctg gtgaaagtaa aagatgctga agatcagttg ggtgcacgag    9420
tgggttacat cgaactggat ctcaacagcg gtaagatcct tgagagtttt cgccccgaag    9480
aacgttttcc aatgatgagc acttttaaag ttctgctatg tggcgcggta ttatcccgta    9540
ttgacgccgg gcaagagcaa ctcggtcgcc gcatacacta ttctcagaat gacttggttg    9600
agtactcacc agtcacagaa aagcatctta cggatggcat gacagtaaga gaattatgca    9660
gtgctgccat aaccatgagt gataacactg cggccaactt acttctgaca acgatcggag    9720
gaccgaagga gctaaccgct tttttgcaca acatggggga tcatgtaact cgccttgatc    9780
gttgggaacc ggagctgaat gaagccatac caaacgacga gcgtgacacc acgatgcctg    9840
tagcaatggc aacaacgttg cgcaaactat taactggcga actacttact ctagcttccc    9900
ggcaacaatt aatagactgg atggaggcgg ataaagttgc aggaccactt ctgcgctcgg    9960
cccttccggc tggctggttt attgctgata atctggagc cggtgagcgt gggtcccgcg   10020
gtatcattgc agcactgggg ccagatggta agccctcccg tatcgtagtt atctacacga   10080
cggggagtca ggcaactatg gatgaacgaa atagacagat cgctgagata ggtgcctcac   10140
tgattaagca ttggtaactg tcagaccaag tttactcata tatactttag attgatttaa   10200
aacttcattt ttaatttaaa aggatctagg tgaagatcct ttttgataat ctcatgacca   10260
aaatccctta acgtgagttt tcgttccact gagcgtcaga ccccgtagaa aagatcaaag   10320
gcagttattg gtgcctcact gattaagcat tggtaactgt cagaccaagt ttactcatat   10380
atactttaga ttgatttaaa acttcatttt taattttgc ggccgcaaga tccggccacg   10440
atgcgtccgg cgtagaggat ctgaagatca gcagttcaac ctgttgatag tacgtactaa   10500
gctctcatgt ttcacgtact aagctctcat gtttaacgta ctaagctctc atgtttaacg   10560
aactaaaccc tcatggctaa cgtactaagc tctcatggct aacgtactaa gctctcatgt   10620
ttcacgtact aagctctcat gtttgaacaa taaaattaat ataaatcagc aacttaaata   10680
gcctctaagg ttttaagttt tataagaaaa aaagaatat ataaggcttt taaagcttt     10740
aaggtttaac ggttgtggac aacaagccag ggatgtaacg cactgagaag cccttagagc   10800
ctctcaaagc aattttgagt gacacaggaa cacttaacgg ctgacatggg aattagccat   10860
ggcatcacag tatcgtgatg acagaggcag ggagtgcggc cttttacgg ttcctggcct    10920
tttgctggcc ttttgctcac atgttctttc ctgcgttatc agggattcc ttaaggtata    10980
ctttccgctg cataaccctg cttcggggtc attatagcga ttttttcggt atatccatcc   11040
tttttcgcac gatatacagg attttgccaa agggttcgtg tagactttcc ttggtgtatc   11100
caacggcgtc agccgggcag gataggtgaa gtaggcccac ccgcgagcgg gtgttccttc   11160
ttcactgtcc cttattcgca cctggcggtg ctcaacggga atcctgctct gcgaggctgg   11220
ccgataagct                                                          11230
```

<210> SEQ ID NO 23
<211> LENGTH: 10936
<212> TYPE: DNA
<213> ORGANISM: Artificial sequence
<220> FEATURE:
<223> OTHER INFORMATION: Synthetic construct

<400> SEQUENCE: 23

| | | | | | |
|---|---|---|---|---|---|
| ctgataccgc | tcgccgcagc | cgaacgaccg | agcgcagcgg | gtcagtgagc | gaggaagcgg | 60 |
| aagagcgccc | aatacgcaaa | ccgcctctcc | ccgcgcgttg | gccgattcat | taatgcagcg | 120 |
| cccaaacata | acaggaagaa | aaatgccccg | ctgtgggcgg | acaaaatagt | tgggaactgg | 180 |
| gaggggtgga | aatggagttt | ttaaggatta | tttagggaag | agtgacaaaa | tagatgggaa | 240 |
| ctgggtgtag | cgtcgtaagc | taatacgaaa | attaaaaatg | acaaaatagt | ttggaactag | 300 |
| atttcactta | tctggttctt | gaggcggtta | aaagagccgt | actcttctcc | gatgtcgact | 360 |
| aggccatgat | gctcattctg | tgggaccaaa | acgaaaaaac | accctttcgg | gtgtcttttc | 420 |
| tggaatttgg | taccgaggct | gcaagtccca | ttaaggaggc | gcgccttatt | acagatcttc | 480 |
| ctcagagatg | agcttctgtt | ccagatcttc | ttctgaaatc | aacttttgtt | ccagatcttc | 540 |
| ttcagagatg | agtttctgct | ccgcggccgc | gtcgcctccc | agctgagaca | ggtcgatccg | 600 |
| tgtctcgtac | aggccggtga | tgctctggtg | gatcagggtg | gcgtccagca | cctctttggt | 660 |
| gctggtgtac | ctcttccggt | cgatggtggt | gtcaaagtac | ttgaaggcgg | caggggctcc | 720 |
| cagattggtc | agggtaaaca | ggtggatgat | attctcggcc | tgctctctga | taggcttgtc | 780 |
| tctgtgcttg | ttgtaggcgc | tcagcacctt | gtccagatta | gcgtcggcca | ggatcactct | 840 |
| cttggagaac | tcgctgatct | gctcgatgat | ctcgtccagg | tagtgtttgt | gctgttccac | 900 |
| aaacagctgt | ttctgctcat | tatcctcggg | ggagcccttc | agcttctcat | agtggctggc | 960 |
| caggtacagg | aagttcacat | atttggaggg | cagggccagt | tcgtttccct | tctgcagttc | 1020 |
| gccggcagag | gccagcattc | tcttccggcc | gttttccagc | tcgaacaggg | agtacttagg | 1080 |
| cagcttgatg | atcaggtcct | ttttcacttc | tttgtagccc | ttggcttcca | gaaagtcgat | 1140 |
| gggattcttc | tcgaagctgc | ttcttttccat | gatggtgatc | cccagcagct | ctttcacact | 1200 |
| cttcagtttc | ttggacttgc | ccttttccac | tttggccacc | accagcacag | aataggccac | 1260 |
| ggtgggctg | tcgaagccgc | cgtacttctt | agggtcccag | tccttctttc | tggcgatcag | 1320 |
| cttgtcgctg | ttcctcttgg | gcaggataga | ctctttgctg | aagccgcctg | tctgcacctc | 1380 |
| ggtcttttc | acgatattca | cttggggcat | agacagcact | ttccgcacgg | tggcaaagtc | 1440 |
| ccggccctta | tcccacacga | tctcgcctgt | ttcgccgttt | gtctcgatca | gaggccgctt | 1500 |
| ccggatctcg | ccgttggcca | gggtaatctc | ggtcttgaaa | agttcatga | tgttgctgta | 1560 |
| gaagaagtac | ttggcggtag | ccttgccgat | ttcctgctcg | ctcttggcga | tcatcttccg | 1620 |
| cacgtcgtac | accttgtagt | cgccgtacac | gaactcgctt | tccagcttag | ggtacttttt | 1680 |
| gatcagggcg | gttcccacga | cggcgttcag | gtaggcgtcg | tgggcgtggt | ggtagttgtt | 1740 |
| gatctcgcgc | actttgtaaa | actggaaatc | cttccggaaa | tcggacacca | gcttggactt | 1800 |
| cagggtgatc | actttcactt | cccgatcag | tttgtcgttc | tcgtcgtact | tagtgttcat | 1860 |
| ccgggagtcc | aggatctgtg | ccacgtgctt | tgtgatctgc | cgggtttcca | ccagctgtct | 1920 |
| cttgatgaag | ccggccttat | ccagttcgct | caggccgcct | ctctcggcct | tggtcagatt | 1980 |
| gtcgaacttc | ctctgggtaa | tcagcttggc | attcagcagc | tggcgccagt | agttcttcat | 2040 |
| cttcttcacg | acctcttcgg | agggcacgtt | gtcgctcttg | ccccggttct | tgtcgctccg | 2100 |

```
agtcagcact tgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg caatgtgct cgtgcaggct    2520 atcgccctgg ccggacacct gggctttctg gatgtcctct ttaaaggtca ggctgtcgtc    2580
gtggatcagc tgcatgaagt ttctgttggc gaagccgtcg acttcagga aatccaggat    2640 tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccagggaggc gttgaaccga tcttccacgc cggagatttc    2940
cacggagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tcccctggcc agagggccca cgtagtaggg gatgcggaag gtcaggatct tctcgatctt    3360
ttcccggttg tccttcagga atgggtaaaa atcttcctgc cgccgcagaa tggcgtgcag    3420
ctctcccagg tggatctggt gggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720 gctcagggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt    4080 ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320 gatgggtgc cgctcgtgct tcttatcctc ttccaccagg aaggactctt ccagtctgtg    4380
gaagaagctg tcgtccacct tggccatctc gttgctgaag atctcttgca gatagcagat    4440
```

```
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa acgaaaaaac cgccttgcag gcggtttttt    4860
cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccggaaggt gatcttccgg ggctttctc    5040 atgcgttgct tgtattgaaa atgggggcca tgcctaccta tctgcctccc gggaagcggg    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc cgctggatga    5580
ccaggatgcc attgctgtgg aagctgcctg cactaatgtt ccggcgttat tcttgatgt    5640 ctctgaccag acacccatca acagtattat tttctcccat gaagacggta cgcgactggg    5700
cgtggagcat ctggtcgcat tgggtcacca gcaaatcgcg ctgttagcgg cccattaag    5760 ttctgtctcg gcgcgtctgc gtctggctgg ctggcataaa tatctcactc gcaatcaaat    5820
tcagccgata gcggaacggg aaggcgactg gagtgccatg tccggttttc aacaaaccat    5880
gcaaatgctg aatgagggca tcgttcccac tgcgatgctg gttgccaacg atcagatggc    5940
gctgggcgca atgcgcgcca ttaccgagtc cgggctgcgc gttggtgcgg atatctcggt    6000
agtgggatac gacgataccg aagacagctc atgttatatc cgccgttaa ccaccatcaa    6060 acaggatttt cgcctgctgg ggcaaaccag cgtggaccgc ttgctgcaac tctctcaggg    6120
ccaggcggtg aagggcaatc agctgttgcc cgtctcactg gtgaaaagaa aaaccaccct    6180
ggcgcccaat acgcaaaccg cctctccccg cgcgttggcc gattcattaa tgcagctggc    6240
acgacaggtt tcccgactgg aaagcgggca gtgagcgcaa cgcaattaat gtaagttagc    6300
tcactcatta ggcaccccac ccgggtcctt gagccccatt atcacctcca aagccttctc    6360
gtctggtcag tttcacctgt tttacgtaaa aacccgcttc ggcggttttt acttttggg    6420 gaaacacaga aaaaagcccg cacctgacag tgcgggcttt ttttttcgac caaaggtgcg    6480
actactcttg cctactacct atcgactgag ctgaaagaat tcctaaagat ctataaatgt    6540
gagcggataa cattgacatt gtgagcggat aacaagatac ttctagttga dccaacttt    6600 ggtctccacc atagcggtcg gtctctgttt aagagctatg ctggaaacag catagcaagt    6660
ttaaataagg ctagtccgtt atcaacttga aaaagtggca ccgagtcggt gcttttttt    6720 tgaattcatg tggctgaccg ttctgttgtc tctcgctctt ccgagtagac gaacaataag    6780
gcctccctaa cgggggggcct tttttattga taacaaaagt cagtgcttcc gctatttcca    6840
```

```
aaataccggg ctaatacggt ttaaacgacc tcctggattt gctcagacag ccttttcgtc   6900
attcgtttca gccaaaaaac ttaagaccgc cggtcttgtc cactaccttg cagtaatgcg   6960
gtggacagga tcggcggttt tcttttctct tctcaagaag ttcctatact ttctagagaa   7020
taggaacttc ggaataggaa cttcctcctg aacggccata agaacgaagg ctgtctgttg   7080
aactctcgag cctgattccc tttgtcaaca gcaatggata attcacgaac ccagttgaca   7140
taagcctgtt cggttcgtaa actgtaatgc aagtagcgta tgcgctcacg caactggtcc   7200
agaaccttga ccgaacgcag cggtggtaac ggcgcagtgg cggttttcat ggcttgttat   7260
gactgttttt ttgtacagtc tatgcctcgg gcatccaagc agcaagcgcg ttacgccgtg   7320
ggtcgatgtt tgatgttatg gagcagcaac gatgttacgc agcagggcag tcgccctaaa   7380
acaaagttag gcagccgttg tgctggtgct ttctgatagt tgttgtgggg taggcagtca   7440
gagctcgatt tgcttgtcgc cataatagat tcacaagaag gattcgacat gggtcaaagt   7500
agcgatgaag ccaacgctcc cgttgcaggg cagtttgcgc ttcccctgag tgccaccttt   7560
ggcttagggg atcgcgtacg caagaaatct ggtgccgctt ggcagggtca gtcgtcggt    7620
tggtattgca caaaactcac tcctgaaggc tatgcggtcg agtccgaatc ccacccaggc   7680
tcagtgcaaa tttatcctgt ggctgcactt gaacgtgtgg cctaagaatt atctagaatt   7740
attccattga gtaagttttt aagcactcga gcatcagctt caaaagcgct ctgaagttcc   7800
tatactttct agagaatagg aacttcggaa taggtacttc aagatcccca attcgagctc   7860
atcgtccggg ccgcaagctc ctagcggcgg atttgtccta ctcaggagag cgttcaccga   7920
caaacaacag ataaaacgaa aggcccagtc tttcgactga gcctttcgtt ttatttgatg   7980
cctcaagcta gagagtcatt accccaggcg tttaagggca ccaataactg ccttaaaaaa   8040
attacgcccc gccctgccac tcatcgcagt ctagcttgga ttctcaccaa taaaaaacgc   8100
ccggcggcaa ccgagcgttc tgaacaaatc cagatggagt tctgaggtca ttactggatc   8160
tatcaacagg agtccaagct cagctaatta agctagctta tcgataccgt cgacctcgaa   8220
ccccacgccc ctctttaata cgacgggcaa tttgcacttc agaaaatgaa gagtttgctt   8280
tagccataac aaaagtccag tatgcttttt cacagcataa ctggactgat ttcagtttac   8340
aactattctg tctagtttaa gactttattg tcatagttta gatctatttt gttcagttta   8400
agactttatt gtccgcccac acccgcttac gcagggcatc catttattac tcaaccgtaa   8460
ccgattttgc caggttacgc ggctggtcct ctagctggcg taatagcgaa gaggcccgca   8520
ccgatcgccc ttcccaacag ttgcgcagcc tgaatggcga atggcgcctg atgcggtatt   8580
ttctccttac gcatctgtgc ggtatttcac accgcatatg gtgcactctc agtacaatct   8640
gctctgatgc cgcatagtta agccagcccc gacacccgcc aacacccgct gacgcgccct   8700
gacgggcttg tctgctcccg gcatccgctt acagacaagc tgtgaccgtc tccgggagct   8760
gcatgtgtca gaggttttca ccgtcatcac cgaaacgcgc gagacgaaag gcctcgtga   8820
tacgcctatt tttataggtt aatgtcatga taataatggt ttcttagacg tcaggtggca   8880
cttttcgggg aaatgtgcgc ggaaccccta tttgtttatt tttctaaata cattcaaata   8940
tgtatccgct catgagacaa taaccctgat aaatgcttca ataatattga aaaggaaga   9000
gtatgagtat tcaacatttc cgtgtcgccc ttattccctt ttttgcggca ttttgccttc   9060
ctgttttgc tcacccagaa acgctggtga agtaaaaga tgctgaagat cagttgggtg    9120
cacgagtggg ttacatcgaa ctggatctca acagcggtaa gatccttgag agttttcgcc   9180
```

```
ccgaagaacg tttttccaatg atgagcactt ttaaagttct gctatgtggc gcggtattat    9240
cccgtattga cgccgggcaa gagcaactcg gtcgccgcat acactattct cagaatgact    9300
tggttgagta ctcaccagtc acagaaaagc atcttacgga tggcatgaca gtaagagaat    9360
tatgcagtgc tgccataacc atgagtgata acactgcggc caacttactt ctgacaacga    9420
tcggaggacc gaaggagcta accgcttttt tgcacaacat gggggatcat gtaactcgcc    9480
ttgatcgttg ggaaccggag ctgaatgaag ccataccaaa cgacgagcgt gacaccacga    9540
tgcctgtagc aatggcaaca cgttgcgca aactattaac tggcgaacta cttactctag    9600
cttcccggca caattaata gactggatgg aggcggataa agttgcagga ccacttctgc    9660
gctcggccct tccggctggc tggtttattg ctgataaatc tggagccggt gagcgtgggt    9720
cccgcggtat cattgcagca ctggggccag atggtaagcc ctcccgtatc gtagttatct    9780
acacgacggg gagtcaggca actatggatg aacgaaatag acagatcgct gagataggtg    9840
cctcactgat taagcattgg taactgtcag accaagttta ctcatatata ctttagattg    9900
atttaaaact tcatttttaa tttaaaagga tctaggtgaa gatcctttt gataatctca    9960 tgaccaaaat cccttaacgt gagttttcgt tccactgagc gtcagacccc gtagaaaaga   10020
tcaaaggcag ttattggtgc ctcactgatt aagcattggt aactgtcaga ccaagtttac   10080
tcatatatac tttagattga tttaaaactt catttttaat ttttgcggcc gcaagatccg   10140
gccacgatgc gtccggcgta gaggatctga agatcagcag ttcaacctgt tgatagtacg   10200
tactaagctc tcatgtttca cgtactaagc tctcatgttt aacgtactaa gctctcatgt   10260
ttaacgaact aaaccctcat ggctaacgta ctaagctctc atggctaacg tactaagctc   10320
tcatgtttca cgtactaagc tctcatgttt gaacaataaa attaatataa atcagcaact   10380
taaatagcct ctaaggtttt aagttttata agaaaaaaaa gaatatataa ggcttttaaa   10440
gcttttaagg tttaacggtt gtggacaaca agccagggat gtaacgcact gagaagccct   10500
tagagcctct caaagcaatt ttgagtgaca caggaacact taacggctga catgggaatt   10560
agccatggca tcacagtatc gtgatgacag aggcagggag tgcggccttt ttacggttcc   10620
tggccttttg ctggcctttt gctcacatgt tctttcctgc gttatcaggg gattccttaa   10680
ggtatacttt ccgctgcata accctgcttc ggggtcatta tagcgatttt ttcggtatat   10740
ccatcctttt tcgcacgata tacaggattt tgccaaaggg ttcgtgtaga ctttccttgg   10800
tgtatccaac ggcgtcagcc gggcaggata ggtgaagtag gcccacccgc gagcgggtgt   10860
tccttcttca ctgtccctta ttcgcacctg gcggtgctca acgggaatcc tgctctgcga   10920
ggctggccga taagct                                                   10936
```

<210> SEQ ID NO 24
<211> LENGTH: 11124
<212> TYPE: DNA
<213> ORGANISM: Artificial sequence
<220> FEATURE:
<223> OTHER INFORMATION: Synthetic construct

<400> SEQUENCE: 24

```
ctgataccgc tcgccgcagc cgaacgaccg agcgcagcgg gtcagtgagc gaggaagcgg      60
aagagcgccc aatacgcaaa ccgcctctcc ccgcgcgttg gccgattcat taatgcagcg     120
cccaaacata acaggaagaa aaatgccccg ctgtgggcgg acaaaatagt tgggaactgg     180
gaggggtgga aatggagttt ttaaggatta tttaggaag agtgacaaaa tagatgggaa     240
ctgggtgtag cgtcgtaagc taatacgaaa attaaaaatg acaaaatagt ttggaactag     300
```

```
atttcactta tctggttctt gaggcggtta aaagagccgt actcttctcc gatgtcgact    360
aggccatgat gctcattctg tgggaccaaa acgaaaaaac ccctttcgg gtgtcttttc     420 tggaatttgg taccgaggct gcaagtccca ttaaggaggc gcgccttatt acagatcttc    480
ctcagagatg agcttctgtt ccagatcttc ttctgaaatc aacttttgtt ccagatcttc    540
ttcagagatg agtttctgct ccgcggccgc gtcgcctccc agctgagaca ggtcgatccg    600
tgtctcgtac aggccggtga tgctctggtg gatcagggtg gcgtccagca cctctttggt    660
gctggtgtac ctcttccggt cgatggtggt gtcaaagtac ttgaaggcgg caggggctcc    720
cagattggtc agggtaaaca ggtggatgat attctcggcc tgctctctga taggcttgtc    780
tctgtgcttg ttgtaggcgc tcagcacctt gtccagatta gcgtcggcca ggatcactct    840
cttggagaac tcgctgatct gctcgatgat ctcgtccagg tagtgtttgt gctgttccac    900
aaacagctgt ttctgctcat tatcctcggg ggagccttc agcttctcat agtggctggc     960
caggtacagg aagttcacat atttggaggg caggccagt tcgtttccct tctgcagttc    1020
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttcttttccat gatggtgatc cccagcagct ctttcacact    1200
cttcagtttc ttggacttgc ccttttccac tttggccacc accagcacag aataggccac    1260
ggtggggctg tcgaagccgc cgtacttctt agggtcccag tccttctttc tggcgatcag    1320
cttgtcgctg ttcctcttgg gcaggataga ctctttgctg aagccgcctg tctgcacctc    1380 ggtcttttc acgatattca cttggggcat agacagcact ttccgcacgg tggcaaagtc     1440
ccggccctta tcccacacga tctcgcctgt tcgccgtttt gtctcgatca gaggccgctt    1500
ccggatctcg ccgttggcca gggtaatctc ggtcttgaaa aagttcatga tgttgctgta    1560
gaagaagtac ttggcggtag ccttgccgat ttcctgctcg ctcttggcga tcatcttccg    1620
cacgtcgtac accttgtagt cgccgtacac gaactcgctt tccagcttag ggtactttt    1680 gatcagggcg gttcccacga cggcgttcag gtaggcgtcg tgggcgtggt ggtagttgtt    1740
gatctcgcgc actttgtaaa actggaaatc cttccggaaa tcggacacca gcttggactt    1800
cagggtgatc actttcactt cccggatcag tttgtcgttc tcgtcgtact tagtgttcat    1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccgacacct gggctttctg gatgtcctct ttaaaggtca ggctgtcgtc    2580
gtggatcagc tgcatgaagt ttctgttggc gaagccgtcg gacttcagga aatccaggat    2640
```

```
tgtcttgccg gactgcttgt cccggatgcc gttgatcagc ttccggctca gcctgcccca    2700
gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc cagggaggc gttgaaccga tcttccacgc cggagatttc     2940
cacggagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tcccctggcc agagggccca cgtagtaggg gatgcggaag gtcaggatct tctcgatctt    3360
ttcccggttg tccttcagga atgggtaaaa atcttcctgc cgccgcagaa tggcgtgcag    3420
ctctcccagg tggatctggt ggggatgct gccgttgtcg aaggtccgct gcttccgcag     3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720
gctcaggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt     4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa acgaaaaaac cgccttgcag gcggtttttt    4860
cgaaggttct ctgagctacc aactctttga accgaggtaa ctggcttggt gataagctgt    4920
caaaccgat caattcgcac tagtctgcag acgtaaaaaa agcggcgtgg ttagccgctt     4980
ttttaattgc cggagcgcaa taaaaaagcc cccggaaggt gatcttccgg gggctttctc    5040
```

```
atgcgttgct tgtattgaaa atggggccca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg agctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc cgctggatga    5580
ccaggatgcc attgctgtgg aagctgcctg cactaatgtt ccggcgttat ttcttgatgt    5640
ctctgaccag acacccatca acagtattat tttctcccat gaagacggta cgcgactggg    5700
cgtggagcat ctggtcgcat tgggtcacca gcaaatcgcg ctgttagcgg cccattaag    5760
ttctgtctcg gcgcgtctgc gtctggctgg ctggcataaa tatctcactc gcaatcaaat    5820
tcagccgata gcgaacggg aaggcgactg gagtgccatg tccggttttc aacaaaccat    5880
gcaaatgctg aatgagggca tcgttcccac tgcgatgctg gttgccaacg atcagatggc    5940
gctgggcgca atgcgcgcca ttaccgagtc cgggctgcgc gttggtgcgg atatctcggt    6000
agtgggatac gacgataccg aagacagctc atgttatatc ccgccgttaa ccaccatcaa    6060
acaggatttt cgcctgctgg ggcaaaccag cgtggaccgc ttgctgcaac tctctcaggg    6120
ccaggcggtg aagggcaatc agctgttgcc cgtctcactg gtgaaaagaa aaccaccct    6180
ggcgcccaat acgcaaaccg cctctccccg cgcgttggcc gattcattaa tgcagctggc    6240
acgacaggtt tcccgactgg aaagcgggca gtgagcgcaa cgcaattaat gtaagttagc    6300
tcactcatta ggcacccac ccgggtcctt gagccccatt atcacctcca aagccttctc    6360
gtctggtcag tttcacctgt tttacgtaaa aacccgcttc ggcgggtttt acttttggg    6420
gaaacacaga aaaagcccg cacctgacag tgcgggcttt ttttttcgac caaaggtgcg    6480
actactcttg cctactacct atcgactgag ctgaaagaat tcctaaagat ctataaatgt    6540
gagcggataa cattgacatt gtgagcggat aacaagatac ttctagttga ccaacttt    6600
ggtctccacc atagcggtcg gtctctgttt aagagctatg ctggaaacag catagcaagt    6660
ttaaataagg ctagtccgtt atcaacttga aaaagtggca ccgagtcggt gcttttttt    6720
tgaattcatg tggctgaccg ttctgttgtc tctcgctctt ccgagtagac gaacaataag    6780
gcctccctaa cggggggcct ttttattga taacaaaagt cagtgcttcc gctatttcca    6840
aaataccggg ctaatacggt ttaaacgacc tcctggattt gctcagacag ccttttcgtc    6900
attcgtttca gccaaaaaac ttaagaccgc cggtcttgtc cactaccttg cagtaatgcg    6960
gtggacagga tcggcggttt ctttttctct tctcaagaag ttcctatact ttctagagaa    7020
taggaacttc ggaataggaa cttcctcctg aacggccata agaacgaagg ctgtctgttg    7080
aactctcgag ccgtggaaac ggatgaaggc acgaacccag ttgacataag cctgttcggt    7140
tcgtaaactg taatgcaagt agcgtatgcg ctcatcacta ccgggcgtat ttttgagtt    7200
atcgagattt tcaggagcta aggaagctaa aatggagaaa aaatcactg gatataccac    7260
cgttgatata tcccaatggc atcgtaaaga acattttgag gcatttcagt cagttgctca    7320
atgtacctat aaccagaccg ttcagctgga tattacggcc ttttttaaga ccgtaaagaa    7380
```

```
aaataagcac aagtttatc cggcctttat tcacattctt gcccgcctga tgaatgctca    7440
tccggagttc cgtatggcaa tgaaagacgg tgagctggtg atatgggata gtgttcaccc   7500
ttgttacacc gttttccatg agcaaactga aacgttttca tcgctctgga gtgaatacca   7560
cgacgatttc cggcagtttc tacacatata ttcgcaagat gtggcgtgtt acggtgaaaa   7620
cctggcctat ttccctaaag ggtttattga aatatgttt ttcgtctcag ccaatccctg    7680
ggtgagtttc accagttttg atttaaacgt ggccaatatg acaacttct tcgccccgt     7740 tttcaccatg ggcaaatatt atacgcaagg cgacaaggtg ctgatgccgc tggcgattca   7800
ggttcatcat gccgtttgtg atggcttcca tgtcggcaga atgcttaatg aattacaaca   7860 gttttatgc atgcgcccaa tacgcaaacc gcctctcccc gcgcgttggc cgattcatta    7920
atgcagctgg cacgacaggt ttcccgactg gaactcgagc atcagcttca aaagcgctct   7980
gaagttccta tactttctag agaataggaa cttcggaata ggtacttcaa gatccccaat   8040
tcgagctcat cgtccgggcc gcaagctcct agcggcggat ttgtcctact caggagagcg   8100
ttcaccgaca acaacagat aaaacgaaag gcccagtctt tcgactgagc cttcgttt     8160 atttgatgcc tcaagctaga gagtcattac cccaggcgtt taagggcacc aataactgcc   8220 ttaaaaaat tacgccccgc cctgccactc atcgcagtct agcttggatt ctcaccaata    8280
aaaaacgccc ggcggcaacc gagcgttctg aacaaatcca gatggagttc tgaggtcatt   8340
actggatcta tcaacaggag tccaagctca gctaattaag ctagcttatc gataccgtcg   8400
acctcgaacc ccacgcccct ctttaatacg acgggcaatt tgcacttcag aaaatgaaga   8460
gtttgcttta gccataacaa aagtccagta tgctttttca cagcataact ggactgattt   8520
cagtttacaa ctattctgtc tagtttaaga ctttattgtc atagtttaga tctattttgt   8580
tcagtttaag actttattgt ccgcccacac ccgcttacgc agggcatcca tttattactc   8640
aaccgtaacc gattttgcca ggttacgcgg ctggtcctct agctggcgta atagcgaaga   8700
ggcccgcacc gatcgccctt cccaacagtt gcgcagcctg aatggcgaat ggcgcctgat   8760 gcggtattt ctccttacgc atctgtgcgg tatttcacac cgcatatggt gcactctcag    8820
tacaatctgc tctgatgccg catagttaag ccagccccga cacccgccaa cacccgctga   8880
cgcgccctga cgggcttgtc tgctcccggc atccgcttac agacaagctg tgaccgtctc   8940
cgggagctga atgtgtcaga ggttttcacc gtcatcaccg aaacgcgcga cgcgaaaggg   9000
cctcgtgata cgcctatttt tataggttaa tgtcatgata ataatggttt cttagacgtc   9060
aggtggcact tttcggggaa atgtgcgcgg aaccccctatt tgtttatttt tctaaataca   9120
ttcaaatatg tatccgctca tgagacaata accctgataa atgcttcaat aatattgaaa   9180
aaggaagagt atgagtattc aacatttccg tgtcgccctt attccctttt ttgcggcatt   9240
ttgccttcct gtttttgctc acccagaaac gctggtgaaa gtaaaagatg ctgaagatca   9300
gttgggtgca cgagtgggtt acatcgaact ggatctcaac agcggtaaga tccttgagag   9360
ttttcgcccc gaagaacgtt ttccaatgat gagcactttt aaagttctgc tatgtggcgc   9420
ggtattatcc cgtattgacg ccgggcaaga gcaactcggt cgccgcatac actattctca   9480
gaatgacttg gttgagtact caccagtcac agaaaagcat cttacggatg gcatgacagt   9540
aagagaatta tgcagtgctg ccataaccat gagtgataac actgcggcca acttacttct   9600
gacaacgatc ggaggaccga aggagctaac cgcttttttg cacaacatgg ggatcatgt    9660 aactcgcctt gatcgttggg aaccggagct gaatgaagcc ataccaaacg acgagcgtga   9720
caccacgatg cctgtagcaa tggcaacaac gttgcgcaaa ctattaactg gcgaactact   9780
```

```
tactctagct tcccggcaac aattaataga ctggatggag gcggataaag ttgcaggacc    9840
acttctgcgc tcggcccttc cggctggctg gtttattgct gataaatctg gagccggtga    9900
gcgtgggtcc cgcggtatca ttgcagcact ggggccagat ggtaagccct cccgtatcgt    9960
agttatctac acgacgggga gtcaggcaac tatggatgaa cgaaatagac agatcgctga    10020
gataggtgcc tcactgatta agcattggta actgtcagac caagtttact catatatact    10080
ttagattgat ttaaaacttc atttttaatt taaaaggatc taggtgaaga tcctttttga    10140
taatctcatg accaaaatcc cttaacgtga gttttcgttc cactgagcgt cagaccccgt    10200
agaaaagatc aaaggcagtt attggtgcct cactgattaa gcattggtaa ctgtcagacc    10260
aagtttactc atatatactt tagattgatt taaaacttca tttttaattt tgcggccgc     10320
aagatccggc cacgatgcgt ccggcgtaga ggatctgaag atcagcagtt caacctgttg    10380
atagtacgta ctaagctctc atgtttcacg tactaagctc tcatgtttaa cgtactaagc    10440
tctcatgttt aacgaactaa accctcatgg ctaacgtact aagctctcat ggctaacgta    10500
ctaagctctc atgtttcacg tactaagctc tcatgtttga acaataaaat taatataaat    10560
cagcaactta aatagcctct aaggttttaa gttttataag aaaaaaaaga atatataagg    10620
cttttaaagc ttttaaggtt taacggttgt ggacaacaag ccagggatgt aacgcactga    10680
gaagccctta gagcctctca aagcaatttt gagtgacaca ggaacactta acggctgaca    10740
tgggaattag ccatggcatc acagtatcgt gatgacagag gcagggagtg cggccttttt    10800
acggttcctg gccttttgct ggccttttgc tcacatgttc tttcctgcgt tatcagggga    10860
ttccttaagg tatactttcc gctgcataac cctgcttcgg ggtcattata gcgattttt     10920
cggtatatcc atcctttttc gcacgatata caggattttg ccaaagggtt cgtgtagact    10980
ttccttggtg tatccaacgg cgtcagccgg gcaggatagg tgaagtaggc ccacccgcga    11040
gcgggtgttc cttcttcact gtcccttatt cgcacctggc ggtgctcaac gggaatcctg    11100
ctctgcgagg ctggccgata agct                                           11124
```

<210> SEQ ID NO 25
<211> LENGTH: 11362
<212> TYPE: DNA
<213> ORGANISM: Artificial sequence
<220> FEATURE:
<223> OTHER INFORMATION: Synthetic construct

<400> SEQUENCE: 25

```
ctgataccgc tcgccgcagc cgaacgaccg agcgcagcgg gtcagtgagc gaggaagcgg     60
aagagcgccc aatacgcaaa ccgcctctcc ccgcgcgttg gccgattcat taatgcagcg    120
cccaaacata acaggaagaa aaatgccccg ctgtgggcgg acaaaatagt tgggaactgg    180
gagggggtgga aatggagttt ttaaggatta tttaggaag agtgacaaaa tagatgggaa    240
ctgggtgtag cgtcgtaagc taatacgaaa attaaaaatg acaaaatagt ttggaactag    300
atttcactta tctggttctt gaggcggtta aaagagccgt actcttctcc gatgtcgact    360
aggccatgat gctcattctg tgggaccaaa acgaaaaaac accctttcgg gtgtctttc     420
tggaatttgg taccgaggct gcaagtccca ttaaggaggc gcgccttatt acagatcttc    480
ctcagagatg agcttctgtt ccagatcttc ttctgaaatc aacttttgtt ccagatcttc    540
ttcagagatg agtttctgct ccgcggccgc gtcgcctccc agctgagaca ggtcgatccg    600
tgtctcgtac aggccggtga tgctctggtg gatcagggtg gcgtccagca cctctttggt    660
```

```
gctggtgtac ctcttccggt cgatggtggt gtcaaagtac ttgaaggcgg caggggctcc    720
cagattggtc agggtaaaca ggtggatgat attctcggcc tgctctctga taggcttgtc    780
tctgtgcttg ttgtaggcgc tcagcacctt gtccagatta gcgtcggcca ggatcactct    840
cttggagaac tcgctgatct gctcgatgat ctcgtccagg tagtgtttgt gctgttccac    900
aaacagctgt ttctgctcat tatcctcggg ggagcccttc agcttctcat agtggctggc    960
caggtacagg aagttcacat atttggaggg cagggccagt tcgtttccct tctgcagttc   1020
gccggcagag gccagcattc tcttccggcc gttttccagc tcgaacaggg agtacttagg   1080
cagcttgatg atcaggtcct tttcacttc tttgtagccc ttggcttcca gaaagtcgat   1140
gggattcttc tcgaagctgc ttcttccat gatggtgatc cccagcagct ctttcacact   1200
cttcagtttc ttggacttgc ccttttccac tttggccacc accagcacag aataggccac   1260
ggtggggctg tcgaagccgc cgtacttctt agggtcccag tccttctttc tggcgatcag   1320
cttgtcgctg ttcctcttgg gcaggataga ctctttgctg aagccgcctg tctgcacctc   1380
ggtctttttc acgatattca cttggggcat agacagcact ttccgcacgg tggcaaagtc   1440
ccggccctta tcccacacga tctcgcctgt ttcgccgttt gtctcgatca gaggccgctt   1500
ccggatctcg ccgttggcca gggtaatctc ggtcttgaaa agttcatga tgttgctgta   1560
gaagaagtac ttggcggtag ccttgccgat ttcctgctcg ctcttggcga tcatcttccg   1620
cacgtcgtac accttgtagt cgccgtacac gaactcgctt ccagcttag ggtacttttt   1680
gatcagggcg gttcccacga cggcgttcag gtaggcgtcg tgggcgtggt ggtagttgtt   1740
gatctcgcgc actttgtaaa actggaaatc cttccggaaa tcggacacca gcttggactt   1800
cagggtgatc actttcactt cccggatcag tttgtcgttc tcgtcgtact tagtgttcat   1860
ccgggagtcc aggatctgtg ccacgtgctt tgtgatctgc cgggtttcca ccagctgtct   1920
cttgatgaag ccggccttat ccagttcgct caggccgcct ctctcggcct tggtcagatt   1980
gtcgaacttc ctctgggtaa tcagcttggc attcagcagc tggcgccagt agttcttcat   2040
cttcttcacg acctcttcgg agggcacgtt gtcgctcttg ccccggttct tgtcgctccg   2100
agtcagcact ttgttatcga tggagtcgtc cttcagaaag ctctgaggca cgatagcgtc   2160
cacatcgtag tcggacagcc ggttgatgtc cagttcctgg tccacgtaca tatcccgccc   2220
attctgcagg tagtacaggt acagcttctc gttctgcagc tgggtgtttt ccacggggtg   2280
ttctttcagg atctggctgc ccagctcttt gatgccctct tcgatccgct tcattctctc   2340
gcggctgttc ttctgtccct tctgggtggt ctggttctct ctggccattt cgatcacgat   2400
gttctcgggc ttgtgccggc ccatcacttt cacgagctcg tccaccacct tcactgtctg   2460
caggatgccc ttcttaatgg cggggctgcc ggccagattg gcaatgtgct cgtgcaggct   2520
atcgccctgg ccggacacct gggctttctg gatgtcctct ttaaaggtca ggctgtcgtc   2580
gtggatcagc tgcatgaagt ttctgttggc gaagccgtcg acttcagga atccaggat    2640
tgtcttgccg gactgcttgt cccggatgcc gttgatcagc ttccggctca gcctgcccca   2700
gccggtgtat ctccgccgct tcagctgctt catcactttg tcgtcgaaca ggtgggcata   2760
ggttttcagc cgttcctcga tcatctctct gtcctcaaac agtgtcaggg tcagcacgat   2820
atcttccaga atgtcctcgt tttcctcatt gtccaggaag tccttgtcct tgataatttt   2880
cagcagatcg tggtatgtgc ccaggggaggc gttgaaccga tcttccacgc cggagatttc   2940
cacggagtcg aagcactcga ttttcttgaa gtagtcctct ttcagctgct tcacggtcac   3000
tttccggttg gtcttgaaca gcaggtccac gatggctttt ttctgctcgc cgctcaggaa   3060
```

```
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300 tccccctggcc agagggccca cgtagtaggg gatgcggaag gtcaggatct tctcgatctt    3360
ttcccggttg tccttcagga atgggtaaaa atcttcctgc cgccgcagaa tggcgtgcag    3420
ctctcccagg tggatctggt ggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720 gctcagggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt    4080 ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tatttttatct gattaataag atgatcttct tgagatcgtt    4800
ttggtctgcg cgtaatctct tgctctgaaa acgaaaaaac cgccttgcag ggcggttttt    4860
cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccgaaggt gatcttccgg gggctttctc    5040
atgcgttgct tgtattgaaa atgggggcca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
```

-continued

```
tctggccctg cacgcgccgt cgcaaattgt cgcggcgatt aaatctcgcg ccgatcaact      5460
gggtgccagc gtggtggtgt cgatggtaga acgaagcggc gtcgaagcct gtaaagcggc      5520
ggtgcacaat cttctcgcgc aacgcgtcag tgggctgatc attaactatc cgctggatga      5580
ccaggatgcc attgctgtgg aagctgcctg cactaatgtt ccggcgttat ttcttgatgt      5640
ctctgaccag acacccatca acagtattat tttctcccat gaagacggta cgcgactggg      5700
cgtggagcat ctggtcgcat tgggtcacca gcaaatcgcg ctgttagcgg cccattaag      5760 ttctgtctcg gcgcgtctgc gtctggctgg ctggcataaa tatctcactc gcaatcaaat      5820
tcagccgata gcggaacggg aaggcgactg gagtgccatg tccggttttc aacaaaccat      5880
gcaaatgctg aatgagggca tcgttcccac tgcgatgctg gttgccaacg atcagatggc      5940
gctgggcgca atgcgcgcca ttaccgagtc cgggctgcgc gttggtgcgg atatctcggt      6000
agtgggatac gacgataccg aagacagctc atgttatatc ccgccgttaa ccaccatcaa      6060
acaggatttt cgcctgctgg ggcaaaccag cgtggaccgc ttgctgcaac tctctcaggg      6120
ccaggcggtg aagggcaatc agctgttgcc cgtctcactg gtgaaaagaa aaaccaccct      6180
ggcgcccaat acgcaaaccg cctctccccg cgcgttggcc gattcattaa tgcagctggc      6240
acgacaggtt cccgactgg aaagcgggca gtgagcgcaa cgcaattaat gtaagttagc      6300
tcactcatta ggcaccccac ccgggtcctt gagccccatt atcacctcca aagccttctc      6360
gtctggtcag tttcacctgt tttacgtaaa aacccgcttc ggcgggtttt acttttggg      6420 gaaacacaga aaaagcccg cacctgacag tgcgggcttt ttttttcgac caaaggtgcg      6480
actactcttg cctactacct atcgactgag ctgaaagaat tcctaaagat ctataaatgt      6540
gagcggataa cattgacatt gtgagcggat aacaagatac ttctagttga ccaactttt      6600 ggtctccacc atagcggtcg gtctctgttt aagagctatg ctggaaacag catagcaagt      6660
ttaaataagg ctagtccgtt atcaacttga aaaagtggca ccgagtcggt gctttttttt      6720
tgaattcatg tggctgaccg ttctgttgtc tctcgctctt ccgagtagac gaacaataag      6780
gcctccctaa cgggggggcct tttttattga taacaaaagt cagtgcttcc gctatttcca      6840
aaataccggg ctaatacggt ttaaacgacc tcctggattt gctcagacag ccttttcgtc      6900
attcgtttca gccaaaaaac ttaagaccgc cggtcttgtc cactaccttg cagtaatgcg      6960
gtggacagga tcgcggtttt cttttctct tctcaagaag ttcctatact ttctagagaa      7020
taggaacttc ggaataggaa cttcctcctg aacggccata agaacgaagg ctgtctgttg      7080
aactctcgag ccgtggaaac ggatgaaggc acgaacccag ttgacataag cctgttcggt      7140
tcgtaaactg taatgcagtg atctaaagag gagaaaggat ctatgcgctc acgcaactgg      7200
tccagaacct tgaccgaacg cagcggtggt aacggcgcag tggcggtttt catggcttgt      7260
tatgactgtt ttttggggt acagtctatg cctcgggcat ccaagcagca agcgcgttac      7320
gccgtgggtc gatgtttgat gttatggagc agcaacgatg ttacgcagca gggcagtcgc      7380
cctaaaacaa agttaaacat catgagggaa gcggtgatcg ccgaagtatc gactcaacta      7440
tcagaggtag ttggcgtcat cgagcgccat ctcgaaccga cgttgctggc cgtacatttg      7500 tacgctccg cagtggatgg cggcctgaag ccacacagtg atattgattt gctggttacg      7560
gtgaccgtaa ggcttgatga aacaacgcgg cgagctttga tcaacgacct tttggaaact      7620
tcggcttccc ctggagagag cgagattctc cgcgctgtag aagtcaccat tgttgtgcac      7680
gacgacatca ttccgtggcg ttatccagct aagcgcgaac tgcaatttgg agaatggcag      7740
cgcaatgaca ttcttgcagg tatcttcgag ccagccacga tcgacattga tctggctatc      7800
```

```
ttgctgacaa aagcaagaga acatagcgtt gccttggtag gtccagcggc ggaggaactc    7860
tttgatccgg ttcctgaaca ggatctattt gaggcgctaa atgaaacctt aacgctatgg    7920
aactcgccgc ccgactgggc tggcgatgag cgaaatgtag tgcttacgtt gtcccgcatt    7980
tggtacagcg cagtaaccgg caaaatcgcg ccgaaggatg tcgctgccga ctgggcaatg    8040
gagcgcctgc cggcccagta tcagcccgtc atacttgaag ctagacaggc ttatcttgga    8100
caagaagaag atcgcttggc ctcgcgcgca gatcagttgg aagaatttgt ccactacgtg    8160
aaaggcgaga tcaccaaggt agtcggcaaa tctcgagcat cagcttcaaa agcgctctga    8220
agttcctata ctttctagag aataggaact tcggaatagg tacttcaaga tccccaattc    8280
gagctcatcg tccgggccgc aagctcctag cggcggattt gtcctactca ggagagcgtt    8340
caccgacaaa caacagataa aacgaaaggc ccagtctttc gactgagcct ttcgttttat    8400
ttgatgcctc aagctagaga gtcattaccc caggcgttta agggcaccaa taactgcctt    8460
aaaaaaatta cgccccgccc tgccactcat cgcagtctag cttggattct caccaataaa    8520
aaacgcccgg cggcaaccga gcgttctgaa caaatccaga tggagttctg aggtcattac    8580
tggatctatc aacaggagtc caagctcagc taattaagct agcttatcga taccgtcgac    8640
ctcgaacccc acgcccctct ttaatacgac gggcaatttg cacttcagaa aatgaagagt    8700
ttgctttagc cataacaaaa gtccagtatg cttttcaca gcataactgg actgatttca    8760
gtttacaact attctgtcta gtttaagact ttattgtcat agtttagatc tattttgttc    8820
agtttaagac tttattgtcc gcccacaccc gcttacgcag ggcatccatt tattactcaa    8880
ccgtaaccga ttttgccagg ttacgcggct ggtcctctag ctggcgtaat agcgaagagg    8940
cccgcaccga tcgcccttcc caacagttgc gcagcctgaa tggcgaatgg cgcctgatgc    9000
ggtattttct ccttacgcat ctgtgcggta tttcacaccg catatggtgc actctcagta    9060
caatctgctc tgatgccgca tagttaagcc agccccgaca cccgccaaca cccgctgacg    9120
cgccctgacg ggcttgtctg ctcccggcat ccgcttacag acaagctgtg accgtctccg    9180
ggagctgcat gtgtcagagg ttttcaccgt catcaccgaa acgcgcgaga cgaaagggcc    9240
tcgtgatacg cctatttta taggttaatg tcatgataat aatggtttct tagacgtcag    9300
gtggcacttt tcggggaaat gtgcgcggaa cccctatttg tttatttttc taaatacatt    9360
caaatatgta tccgctcatg agacaataac cctgataaat gcttcaataa tattgaaaaa    9420
ggaagagtat gagtattcaa catttccgtg tcgcccttat cccttttttt gcggcatttt    9480
gccttcctgt ttttgctcac ccagaaacgc tggtgaaagt aaaagatgct gaagatcagt    9540
tgggtgcacg agtgggttac atcgaactgg atctcaacag cggtaagatc cttgagagtt    9600
ttcgccccga agaacgtttt ccaatgatga gcacttttaa agttctgcta tgtggcgcgg    9660
tattatcccg tattgacgcc gggcaagagc aactcggtcg ccgcatacac tattctcaga    9720
atgacttggt tgagtactca ccagtcacag aaaagcatct tacggatggc atgacagtaa    9780
gagaattatg cagtgctgcc ataaccatga gtgataacac tgcggccaac ttacttctga    9840
caacgatcgg aggaccgaag gagctaaccg cttttttgca caacatgggg gatcatgtaa    9900
ctcgccttga tcgttgggaa ccggagctga atgaagccat accaaacgac gagcgtgaca    9960
ccacgatgcc tgtagcaatg gcaacaacgt tgcgcaaact attaactggc gaactactta   10020
ctctagcttc ccggcaacaa ttaatagact ggatggaggc ggataaagtt gcaggaccac   10080
ttctgcgctc ggcccttccg gctggctggt ttattgctga taaatctgga gccggtgagc   10140
```

```
gtgggtcccg cggtatcatt gcagcactgg ggccagatgg taagccctcc cgtatcgtag    10200
ttatctacac gacggggagt caggcaacta tggatgaacg aaatagacag atcgctgaga    10260
taggtgcctc actgattaag cattggtaac tgtcagacca agtttactca tatatacttt    10320
agattgattt aaaacttcat ttttaattta aaaggatcta ggtgaagatc cttttttgata   10380 atctcatgac caaaatccct taacgtgagt tttcgttcca ctgagcgtca gaccccgtag    10440
aaaagatcaa aggcagttat tggtgcctca ctgattaagc attggtaact gtcagaccaa    10500
gtttactcat atatacttta gattgattta aaacttcatt tttaattttt gcggccgcaa    10560
gatccggcca cgatgcgtcc ggcgtagagg atctgaagat cagcagttca acctgttgat    10620
agtacgtact aagctctcat gtttcacgta ctaagctctc atgtttaacg tactaagctc    10680
tcatgtttaa cgaactaaac cctcatggct aacgtactaa gctctcatgg ctaacgtact    10740
aagctctcat gtttcacgta ctaagctctc atgtttgaac aataaaatta atataaatca    10800
gcaacttaaa tagcctctaa ggttttaagt tttataagaa aaaaagaat atataaggct    10860 tttaaagctt ttaaggttta acggttgtgg acaacaagcc agggatgtaa cgcactgaga    10920
agcccttaga gcctctcaaa gcaattttga gtgacacagg aacacttaac ggctgacatg    10980
ggaattagcc atggcatcac agtatcgtga tgacagaggc agggagtgcg gccttttac    11040 ggttcctggc cttttgctgg ccttttgctc acatgttctt tcctgcgtta tcagggatt    11100 ccttaaggta tactttccgc tgcataaccc tgcttcgggg tcattatagc gattttttcg    11160
gtatatccat cctttttcgc acgatataca ggattttgcc aaagggttcg tgtagacttt    11220
ccttggtgta tccaacggcg tcagccgggc aggataggtg aagtaggccc acccgcgagc    11280
gggtgttcct tcttcactgt cccttattcg cacctggcgg tgctcaacgg aatcctgct    11340 ctgcgaggct ggccgataag ct                                             11362

<210> SEQ ID NO 26
<211> LENGTH: 11102
<212> TYPE: DNA
<213> ORGANISM: Artificial sequence
<220> FEATURE:
<223> OTHER INFORMATION: Synthetic construct

<400> SEQUENCE: 26
ctgataccgc tcgccgcagc cgaacgaccg agcgcagcgg gtcagtgagc gaggaagcgg     60
aagagcgccc aatacgcaaa ccgcctctcc ccgcgcgttg gccgattcat taatgcagcg    120
cccaaacata acaggaagaa aaatgccccg ctgtgggcgg acaaaatagt tgggaactgg    180 gagggggtgga aatggagttt ttaaggatta tttagggaag agtgacaaaa tagatgggaa    240
ctgggtgtag cgtcgtaagc taatacgaaa attaaaaatg acaaaatagt ttggaactag    300
atttcactta tctggttctt gaggcggtta aaagagccgt actcttctcc gatgtcgact    360
aggccatgat gctcattctg tgggaccaaa acgaaaaaac ccctttcgg gtgtcttttc     420 tggaatttgg taccgaggct gcaagtccca ttaaggaggc gcgccttatt acagatcttc    480
ctcagagatg agcttctgtt ccagatcttc ttctgaaatc aacttttgtt ccagatcttc    540
ttcagagatg agtttctgct ccgcggccgc gtcgcctccc agctgagaca ggtcgatccg    600
tgtctcgtac aggccggtga tgctctggtg gatcagggtg gcgtccagca cctctttggt    660
gctggtgtac ctcttccggt cgatggtggt gtcaaagtac ttgaaggcgg caggggctcc    720
cagattggtc agggtaaaca ggtggatgat attctcggcc tgctctctga taggcttgtc    780
tctgtgcttg ttgtaggcgc tcagcacctt gtccagatta gcgtcggcca ggatcactct    840
```

```
cttggagaac tcgctgatct gctcgatgat ctcgtccagg tagtgtttgt gctgttccac    900
aaacagctgt ttctgctcat tatcctcggg ggagcccttc agcttctcat agtggctggc    960
caggtacagg aagttcacat atttggaggg cagggccagt tcgtttccct tctgcagttc   1020
gccggcagag gccagcattc tcttccggcc gttttccagc tcgaacaggg agtacttagg   1080
cagcttgatg atcaggtcct ttttcacttc tttgtagccc ttggcttcca gaaagtcgat   1140
gggattcttc tcgaagctgc ttcttttcat gatggtgatc cccagcagct ctttcacact   1200
cttcagtttc ttggacttgc ccttttccac tttggccacc accagcacag aataggccac   1260
ggtggggctg tcgaagccgc cgtacttctt agggtcccag tccttctttc tggcgatcag   1320
cttgtcgctg ttcctcttgg gcaggataga ctctttgctg aagccgcctg tctgcacctc   1380 ggtcttttc acgatattca cttggggcat agacagcact ttccgcacgg tggcaaagtc   1440
ccggccctta tcccacacga tctcgcctgt ttcgccgttt gtctcgatca gaggccgctt   1500
ccggatctcg ccgttggcca gggtaatctc ggtcttgaaa aagttcatga tgttgctgta   1560
gaagaagtac ttggcggtag ccttgccgat ttcctgctcg ctcttggcga tcatcttccg   1620
cacgtcgtac accttgtagt cgccgtacac gaactcgctt tccagcttag ggtactttt   1680 gatcagggcg gttcccacga cggcgttcag gtaggcgtcg tgggcgtggt ggtagttgtt   1740
gatctcgcgc actttgtaaa actgaaaatc cttccggaaa tcggacacca gcttggactt   1800
cagggtgatc actttcactt cccggatcag tttgtcgttc tcgtcgtact tagtgttcat   1860 ccggagtcc aggatctgtg ccacgtgctt tgtgatctgc cgggtttcca ccagctgtct   1920
cttgatgaag ccggccttat ccagttcgct caggccgcct ctctcggcct tggtcagatt   1980
gtcgaacttc ctctgggtaa tcagcttggc attcagcagc tggcgccagt agttcttcat   2040
cttcttcacg acctcttcgg agggcacgtt gtcgctcttg ccccggttct tgtcgctccg   2100
agtcagcact ttgttatcga tggagtcgtc cttcagaaag ctctgaggca cgatagcgtc   2160
cacatcgtag tcggacagcc ggttgatgtc cagttcctgg tccacgtaca tatcccgccc   2220
attctgcagg tagtacaggt acagcttctc gttctgcagc tgggtgtttt ccacggggtg   2280
ttctttcagg atctggctgc ccagctcttt gatgccctct tcgatccgct tcattctctc   2340
gcggctgttc ttctgtccct tctgggtggt ctggttctct ctggccattt cgatcacgat   2400
gttctcgggc ttgtgccggc ccatcacttt cacgagctcg tccaccacct tcactgtctg   2460
caggatgccc ttcttaatgg cggggctgcc ggccagattg gcaatgtgct cgtgcaggct   2520
atcgccctgg ccggacacct gggctttctg gatgtcctct ttaaaggtca ggctgtcgtc   2580
gtggatcagc tgcatgaagt ttctgttggc gaagccgtcg gacttcagga aatccaggat   2640
tgtcttgccg gactgcttgt cccggatgcc gttgatcagc ttccggctca gcctgcccca   2700
gccggtgtat ctccgccgct tcagctgctt catcactttg tcgtcgaaca ggtgggcata   2760
ggttttcagc cgttcctcga tcatctctct gtcctcaaac agtgtcaggg tcagcacgat   2820
atcttccaga atgtcctcgt tttcctcatt gtccaggaag tccttgtcct tgataatttt   2880
cagcagatcg tggtatgtgc ccagggaggc gttgaaccga tcttccacgc cggagatttc   2940
cacggagtcg aagcactcga tttttcttgaa gtagtcctct ttcagctgct tcacggtcac   3000
tttccggttg tcttgaaca gcaggtccac gatggctttt ttctgctcgc cgctcaggaa   3060
ggcgggcttt ctcattccct cggtcacgta tttcactttg gtcagctcgt tgtacacggt   3120
gaagtactcg tacagcaggc tgtgcttggg cagcaccttc tcgttgggca ggttcttatc   3180
```

```
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300
tccccctggcc agagggccca cgtagtaggg gatgcggaag gtcaggatct tctcgatctt   3360
ttccggttg tccttcagga atgggtaaaa atcttcctgc cgccgcagaa tggcgtgcag     3420
ctctcccagg tggatctggt ggggggatgct gccgttgtcg aaggtccgct gcttccgcag   3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720
gctcaggggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatggggtt    4080
ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320
gatggggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttcctgtgt gaaacctgct gatgtgctca gtatcttgtt atccgctcac aatgtcaatg    4740
ttatccgctc acatttataa tattttatct gattaataag atgatcttct tgagatcgtt    4800
ttggtctgcg cgtaatctct tgctctgaaa acgaaaaaac cgccttgcag gcggtttttt    4860
cgaaggttct ctgagctacc aactctttga accgaggtaa ctggcttggt gataagctgt    4920
caaaccagat caattcgcac tagtctgcag acgtaaaaaa agcggcgtgg ttagccgctt    4980
ttttaattgc cggagcgcaa taaaaaagcc cccggaaggt gatcttccgg gggctttctc    5040
atgcgttgct tgtattgaaa atggggggcca tgcctaccta tctgcctccc gggaagcggc    5100
atgcatttac gttgacacca tcgaatggtg caaaaccttt cgcggtatgg catgatagcg    5160
cccggaagag agtcaattca gggtggtgaa tgtgaaacca gtaacgttat acgatgtcgc    5220
agagtatgcc ggtgtctctt atcagaccgt ttcccgcgtg gtgaaccagg ccagccacgt    5280
ttctgcgaaa acgcgggaaa aagtggaagc ggcgatggcg gagctgaatt acattcccaa    5340
ccgcgtggca caacaactgg cgggcaaaca gtcgttgctg attggcgttg ccacctccag    5400
tctggccctg cacgcgccgt cgcaaattgt cgcggcgatt aaatctcgcg ccgatcaact    5460
gggtgccagc gtggtggtgt cgatggtaga acgaagcggc gtcgaagcct gtaaagcggc    5520
ggtgcacaat cttctcgcgc aacgcgtcag tgggctgatc attaactatc cgctggatga    5580
```

```
ccaggatgcc attgctgtgg aagctgcctg cactaatgtt ccggcgttat ttcttgatgt   5640
ctctgaccag acacccatca acagtattat tttctcccat gaagacggta cgcgactggg   5700
cgtggagcat ctggtcgcat tgggtcacca gcaaatcgcg ctgttagcgg gcccattaag   5760
ttctgtctcg gcgcgtctgc gtctggctgg ctggcataaa tatctcactc gcaatcaaat   5820
tcagccgata gcggaacggg aaggcgactg gagtgccatg tccggttttc aacaaaccat   5880
gcaaatgctg aatgagggca tcgttcccac tgcgatgctg gttgccaacg atcagatggc   5940
gctgggcgca atgcgcgcca ttaccgagtc cgggctgcgc gttggtgcgg atatctcggt   6000
agtgggatac gacgataccg aagacagctc atgttatatc ccgccgttaa ccaccatcaa   6060
acaggatttt cgcctgctgg ggcaaaccag cgtggaccgc ttgctgcaac tctctcaggg   6120
ccaggcggtg aagggcaatc agctgttgcc cgtctcactg gtgaaaagaa aaaccaccct   6180
ggcgcccaat acgcaaaccg cctctccccg cgcgttggcc gattcattaa tgcagctggc   6240
acgacaggtt tcccgactgg aaagcgggca gtgagcgcaa cgcaattaat gtaagttagc   6300
tcactcatta ggcaccccac ccgggtcctt gagccccatt atcacctcca aagccttctc   6360
gtctggtcag tttcacctgt tttacgtaaa aacccgcttc ggcgggtttt tacttttggg   6420
gaaacacaga aaaagcccgc acctgacagt gcgggctttt ttttttcgac caaaggtgcg   6480
actactcttg cctactacct atcgactgag ctgaaagaat tcctaaagat ctataaatgt   6540
gagcggataa cattgacatt gtgagcggat aacaagatac ttctagttga gaccaacttt   6600
ggtctccacc atagcggtcg gtctctgttt aagagctatg ctggaaacag catagcaagt   6660
ttaaataagg ctagtccgtt atcaacttga aaaagtggca ccgagtcggt gcttttttt   6720 tgaattcatg tggctgaccg ttctgttgtc tctcgctctt ccgagtagac gaacaataag   6780
gcctccctaa cgggggggcct tttttattga taacaaaagt cagtgcttcc gctatttcca   6840
aaataccggg ctaatacggt ttaaacgacc tcctggattt gctcagacag cctttcgtc    6900 attcgtttca gccaaaaaac ttaagaccgc cggtcttgtc cactaccttg cagtaatgcg   6960
gtggacagga tcggcggttt tcttttctct tctcaagaag ttcctatact ttctagagaa   7020
taggaacttc ggaataggaa cttcctcctg aacggccata agaacgaagg ctgtctgttg   7080
aactctcgag ccttgtcgcc ttgcgtataa tatttgccca tggacgcaca ccgtggaaac   7140
ggatgaaggc acgaacccag ttgacataag cctgttcggt tcgtaaactg taatgcaagt   7200
agcgtatgcg ctcacgcaac tggtccagaa ccttgaccga acgcagcggt ggtaacggcg   7260
cagtggcggt tttcatggct tgttatgact gttttttgt acagtctatg cctcgggcat    7320
ccaagcagca agcgcgttac gccgtgggtc gatgtttgat gttatggagc agcaacgatg   7380
ttacgcagca gcaacgatgt tacgcagcag gcagtcgccc taaaacaaa gttaggtggc    7440 tcaagtatgg gcatcattcg cacatgtagg ctcggccctg accaagtcaa atccatgcgg   7500
gctgctcttg atcttttcgg tcgtgagttc ggagacgtag ccacctactc ccaacatcag   7560
ccggactccg attacctcgg aacttgctcc gtagtaaga cattcatcgc gcttgctgcc    7620
ttcgaccaag aagcggttgt tggcgctctc gcggcttacg ttctgcccaa gtttgagcag   7680
ccgcgtagtg agatctatat ctatgatctc gcagtctccg gagagcaccg gaggcagggc   7740
attgccaccg cgctcatcaa tctcctcaag catgaggcca acgcgcttgg tgcttatgtg   7800
atctacgtgc aagcagatta cggtgacgat cccgcagtgg ctctctatac aaagttgggc   7860
atacgggaag aagtgatgca ctttgatatc gacccaagta ccgccaccta acaattcgtt   7920
```

```
caagccgaga tctcgagcat cagcttcaaa agcgctctga agttcctata ctttctagag    7980
aataggaact tcggaatagg tacttcaaga tccccaattc gagctcatcg tccgggccgc    8040
aagctcctag cggcggattt gtcctactca ggagagcgtt caccgacaaa caacagataa    8100
aacgaaaggc ccagtctttc gactgagcct ttcgttttat ttgatgcctc aagctagaga    8160
gtcattaccc caggcgttta agggcaccaa taactgcctt aaaaaaatta cgccccgccc    8220
tgccactcat cgcagtctag cttggattct caccaataaa aaacgcccgg cggcaaccga    8280
gcgttctgaa caaatccaga tggagttctg aggtcattac tggatctatc aacaggagtc    8340
caagctcagc taattaagct agcttatcga taccgtcgac ctcgaacccc acgcccctct    8400
ttaatacgac gggcaatttg cacttcagaa aatgaagagt ttgctttagc cataacaaaa    8460
gtccagtatg cttttttcaca gcataactgg actgatttca gtttacaact attctgtcta    8520
gtttaagact ttattgtcat agtttagatc tattttgttc agtttaagac tttattgtcc    8580
gcccacaccc gcttacgcag ggcatccatt tattactcaa ccgtaaccga ttttgccagg    8640
ttacgcggct ggtcctctag ctggcgtaat agcgaagagg cccgcaccga tcgcccttcc    8700
caacagttgc gcagcctgaa tggcgaatgg cgcctgatgc ggtattttct ccttacgcat    8760
ctgtgcggta tttcacaccg catatggtgc actctcagta caatctgctc tgatgccgca    8820
tagttaagcc agccccgaca cccgccaaca cccgctgacg cgccctgacg gcttgtctg    8880
ctcccggcat ccgcttacag acaagctgtg accgtctccg ggagctgcat gtgtcagagg    8940
ttttcaccgt catcaccgaa acgcgcgaga cgaaagggcc tcgtgatacg cctattttta    9000
taggttaatg tcatgataat aatggtttct tagacgtcag gtggcacttt tcggggaaat    9060
gtgcgcggaa cccctatttg tttatttttc taaatacatt caaatatgta tccgctcatg    9120
agacaataac cctgataaat gcttcaataa tattgaaaaa ggaagagtat gagtattcaa    9180
catttccgtg tcgcccttat tccctttttt gcggcatttt gccttcctgt ttttgctcac    9240
ccagaaacgc tggtgaaagt aaaagatgct gaagatcagt tgggtgcacg agtgggttac    9300
atcgaactgg atctcaacag cggtaagatc cttgagagtt ttcgccccga agaacgtttt    9360
ccaatgatga gcacttttaa agttctgcta tgtggcgcgg tattatcccg tattgacgcc    9420
gggcaagagc aactcggtcg ccgcatacac tattctcaga atgacttggt tgagtactca    9480
ccagtcacag aaaagcatct tacggatggc atgacagtaa gagaattatg cagtgctgcc    9540
ataaccatga gtgataacac tgcggccaac ttacttctga caacgatcgg aggaccgaag    9600
gagctaaccg cttttttgca caacatgggg gatcatgtaa ctcgccttga tcgttgggaa    9660
ccggagctga atgaagccat accaaacgac gagcgtgaca ccacgatgcc tgtagcaatg    9720
gcaacaacgt tgcgcaaact attaactggc gaactactta ctctagcttc ccggcaacaa    9780
ttaatagact ggatggaggc ggataaagtt gcaggaccac ttctgcgctc ggcccttccg    9840
gctggctggt ttattgctga taaatctgga gccggtgagc gtgggtcccg cggtatcatt    9900
gcagcactgg ggccagatgg taagccctcc cgtatcgtag ttatctacac gacggggagt    9960
caggcaacta tggatgaacg aaatagacag atcgctgaga taggtgcctc actgattaag   10020
cattggtaac tgtcagacca agtttactca tatatacttt agattgattt aaaacttcat   10080
ttttaattta aaaggatcta ggtgaagatc ctttttgata atctcatgac caaaatccct   10140
taacgtgagt tttcgttcca ctgagcgtca gaccccgtag aaaagatcaa aggcagttat   10200
tggtgcctca ctgattaagc attggtaact gtcagaccaa gtttactcat atactttta    10260
gattgattta aaacttcatt tttaattttt gcggccgcaa gatccggcca cgatgcgtcc   10320
```

```
ggcgtagagg atctgaagat cagcagttca acctgttgat agtacgtact aagctctcat    10380
gtttcacgta ctaagctctc atgtttaacg tactaagctc tcatgtttaa cgaactaaac    10440
cctcatggct aacgtactaa gctctcatgg ctaacgtact aagctctcat gtttcacgta    10500
ctaagctctc atgtttgaac aataaaatta atataaatca gcaacttaaa tagcctctaa    10560
ggttttaagt tttataagaa aaaaagaat atataaggct tttaaagctt ttaaggttta     10620
acggttgtgg acaacaagcc agggatgtaa cgcactgaga agcccttaga gcctctcaaa    10680
gcaattttga gtgacacagg aacacttaac ggctgacatg gaattagcc atggcatcac     10740 agtatcgtga tgacagaggc agggagtgcg gccttttttac ggttcctggc cttttgctgg   10800
ccttttgctc acatgttctt tcctgcgtta tcagggatt ccttaaggta actttccgc      10860 tgcataaccc tgcttcgggg tcattatagc gattttttcg gtatatccat ccttttttcgc  10920 acgatataca ggattttgcc aaagggttcg tgtagacttt ccttggtgta tccaacggcg    10980
tcagccgggc aggataggtg aagtaggccc acccgcgagc gggtgttcct tcttcactgt    11040
cccttattcg cacctggcgg tgctcaacgg gaatcctgct ctgcgaggct ggccgataag    11100
ct                                                                   11102

<210> SEQ ID NO 27
<211> LENGTH: 5143
<212> TYPE: DNA
<213> ORGANISM: Artificial sequence
<220> FEATURE:
<223> OTHER INFORMATION: Synthetic construct

<400> SEQUENCE: 27
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc    180
gtgcgaaaaa ggatggatat accgaaaaaa tcgctataat gaccccgaag cagggttatg    240
cagcggaaag tataccttaa ggaatccccct gataacgcag gaaagaacat gtgagcaaaa   300
ggccagcaaa aggccaggaa ccgtaaaaag gccgcactcc tgcctctgt catcacgata     360 ctgtgatgcc atggctaatt cccatgtcag ccgttaagtg ttcctgtgtc actcaaaatt    420
gctttgagag gctctaaggg cttctcagtg cgttacatcc ctggcttgtt gtccacaacc    480
gttaaacctt aaaagcttta aaagccttat atattctttt ttttcttata aaacttaaaa    540
ccttagaggc tatttaagtt gctgatttat attaatttta ttgttcaaac atgagagctt    600
agtacgtgaa acatgagagc ttagtacgtt agccatgaga gcttagtacg ttagccatga    660
gggtttagtt cgttaaacat gagagcttag tacgttaaac atgagagctt agtacgtgaa    720
acatgagagc ttagtacgta ctatcaacag gttgaactgc tgatcttcag atcctctacg    780
ccggacgcat cgtggccgga tcttgcggcc gcaaaaatta aaatgaagt tttaaatcaa     840 tctaaagtat atatgagtaa acttggtctg acagttacca atgcttaatc agtgaggcac    900
caataactgc ctttgatctt ttctacgggg tctgacgctc agtggaacga aaactcacgt    960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140
tgactccccg tcgtgtagat aactacgata cgggagggct taccatctgg ccccagtgct   1200
```

```
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggcccttt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac     2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa atcggttac ggttgagtaa taaatggatg ccctgcgtaa gcgggtgtgg     2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtgggttcg aggtcgacgg tatcgataag ctagcttaat tagctgagct      2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gtgcttaaaa    3180
acttactcaa tggaataatt ctagataatt cttaggccac acgttcaagt gcagccacag    3240
gataaatttg cactgagcct gggtgggatt cggactcgac cgcatagcct tcaggagtga    3300
gttttgtgca ataccaaccg acgacttgac cctgccaagc ggaccagat tcttgcgta      3360 cgcgatcccc taagccaaag gtggcactca ggggaagcgc aaactgccct gcaacgggag    3420
cgttggcttc atcgctactt tgacccatgt cgaatccttc ttgtgaatct attatggcga    3480
caagcaaatc gagctctgac tgcctacccc acaacaacta tcagaaagca ccagcacaac    3540
ggctgcctaa cttgttttta gggcgactgc cctgctgcgt aacatcgttg ctgctccata    3600
```

| | |
|---|---|
| acatcaaaca tcgacccacg gcgtaacgcg cttgctgctt ggatgcccga ggcatagact | 3660 |
| gtacaaaaaa acagtcataa caagccatga aaaccgccac tgcgccgtta ccaccgctgc | 3720 |
| gttcggtcaa ggttctggac cagttgcgtg agcgcatacg ctacttgcat tacagtttac | 3780 |
| gaaccgaaca ggcttatgtc aactgggttc gtgaattatc cattgctgtt gacaaaggga | 3840 |
| atcaggctcg agagttcaac agacagcctt cgttcttatg gccgttcagg aggaagttcc | 3900 |
| tattccgaag ttcctattct ctagaaagta taggaacttc ttgagaagag aaagaaaac | 3960 |
| cgccgatcct gtccaccgca ttactgcaag gtagtggaca agaccggcgg tcttaagttt | 4020 |
| tttggctgaa acgaatgacg aaaaggctgt ctgagcaaat ccaggaggtc gtttaaaccg | 4080 |
| tattagcccg gtattttgga aatagcggaa gcactgactt ttgttatcaa taaaaaaggc | 4140 |
| cccccgttag ggaggcctta ttgttcgtct actcggaaga gcgagagaca acagaacggt | 4200 |
| cagccacatg aattcaaaaa aaaagcaccg actcggtgcc acttttttcaa gttgataacg | 4260 |
| gactagcctt atttaaactt gctatgctgt ttccagcata gctcttaaac agaccgctaa | 4320 |
| actgaaagtt ccacacatta tacgagccgg atgattaatt gtcaacagct catttcagaa | 4380 |
| tatttgccag aaccggaatt cctttcagctc agtcgatagg tagtaggcaa gagtagtcgc | 4440 |
| accttttggtc gaaaaaaaaa gcccgcactg tcaggtgcgg gctttttttct gtgtttcccc | 4500 |
| aaaagtaaaa acccgccgaa gcgggttttt acgtaaaaca ggtgaaactg accagacgag | 4560 |
| aaggctttgg aggtgataat ggggctcaag gacccgggag gcagataggt aggcatggcc | 4620 |
| cccatttttca atacaagcaa cgcatgagaa agccccgga agatcacctt ccggggggctt | 4680 |
| ttttattgcg ctccggcaat taaaaaagcg gctaaccacg ccgcttttt tacgtctgca | 4740 |
| gagctcatag gcaagcgaat cgtgatgcct cttagccagt actagtcgac atcggagaag | 4800 |
| agtacggctc ttttaaccgc tcaagaacc agataagtga aatctagttc caaactattt | 4860 |
| tgtcattttt aatttttcgta ttagcttacg acgctacacc cagttcccat ctatttttgtc | 4920 |
| actcttccct aaataatcct taaaaactcc atttccaccc ctcccagttc ccaactatttt | 4980 |
| tgtccgccca cagcggggca ttttttcttcc tgttatgttt gggcgctgca ttaatgaatc | 5040 |
| ggccaacgcg cggggagagg cggtttgcgt attgggcgct cttccgcttc ctcgctcact | 5100 |
| gacccgctgc gctcggtcgt tcggctgcgg cgagcggtat cag | 5143 |

<210> SEQ ID NO 28
<211> LENGTH: 9795
<212> TYPE: DNA
<213> ORGANISM: Artificial sequence
<220> FEATURE:
<223> OTHER INFORMATION: Synthetic construct

<400> SEQUENCE: 28

| | |
|---|---|
| gaagtaccta ttccgaagtt cctattctct agaaagtata ggaacttcag agcgcttttg | 60 |
| aagctgatgc tcgaggcgta gaggatctgg agctgtaata taaaaccctt cttcaactaa | 120 |
| cggggcaggt tagtgacatt agaaaaccga ctgtaaaaag tacagtcggc attatctcat | 180 |
| attataaaag ccagtcatta ggcctatctg acaattcctg aatagagttc ataaacaatc | 240 |
| ctgcatgata accatcacaa acagaatgat gtacctgtaa agatagcggt aaatatattg | 300 |
| aattaccttt attaatgaat tttcctgctg taataatggg tagaaggtaa ttactattat | 360 |
| tattgatatt taagttaaac ccagtaaatg aagtccatgg aataatagaa agagaaaaag | 420 |
| cattttcagg tataggtgtt ttgggaaaca atttccccga accattatat ttctctacat | 480 |

```
cagaaaggta taaatcataa aactctttga agtcattctt tacaggagtc caaataccag    540
agaatgtttt agatacacca tcaaaaattg tataaagtgg ctctaactta tcccaataac    600
ctaactctcc gtcgctattg taaccagttc taaaagctgt atttgagttt atcacccttg    660
tcactaagaa aataaatgca gggtaaaatt tatatccttc ttgttttatg tttcggtata    720
aaacactaat atcaatttct gtggttatac taaaagtcgt tgttggttc aaataatgat     780 taaatatctc ttttctcttc caattgtcta aatcaatttt attaaagttc atttgatatg    840
cctcctaaat ttttatctaa agtgaattta ggaggcttac ttgtctgctt tcttcattag    900
aatcaatcct ttttttaaaag tcaatattac tgtaacataa atatatattt taaaaatatc   960
ccactttatc caattttcgt tgttgaact aatgggtgct ttagttgaag aataaagacc     1020
acattaaaaa atgtggtctt ttgtgttttt taaaggatt tgagcgtagc gaaaatcct      1080 tttctttctt atcttgataa taagggtaac tattgccgat gataagctgt caactagtat   1140
ggataagaaa tactcaatag gcttagctat cggcacaaat agcgtcggat gggcggtgat   1200
cactgatgaa tataaggttc cgtctaaaaa gttcaaggtt ctgggaaata cagaccgcca   1260
cagtatcaaa aaaaatctta tagggctct tttatttgac agtggagaga cagcggaagc    1320
gactcgtctc aaacggacag ctcgtagaag gtatacacgt cggaagaatc gtatttgtta   1380
tctacaggag attttttcaa atgagatggc gaaagtagat gatagtttct ttcatcgact   1440
tgaagagtct ttttttggtgg aagaagacaa gaagcatgaa cgtcatccta tttttggaaa  1500
tatagtagat gaagttgctt atcatgagaa atatccaact atctatcatc tgcgaaaaaa   1560
attggtagat tctactgata aagcggattt gcgcttaatc tatttggcct tagcgcatat   1620
gattaagttt cgtggtcatt ttttgattga gggagattta aatcctgata atagtgatgt   1680
ggacaaacta tttatccagt tggtacaaac ctacaatcaa ttatttgaag aaaaccctat   1740
taacgcaagt ggagtagatg ctaaagcgat tctttctgca cgattgagta aatcaagacg   1800
attagaaaat ctcattgctc agctccccgg tgagaagaaa aatggcttat ttgggaatct   1860
cattgctttg tcattgggtt tgaccctaa ttttaaatca aattttgatt tggcagaaga    1920
tgctaaatta cagcttttcaa aagatactta cgatgatgat ttagataatt tattggcgca  1980
aattggagat caatatgctg atttgttttt ggcagctaag aatttatcag atgctatttt   2040
actttcagat atcctaagag taaatactga aataactaag gctcccctat cagcttcaat   2100
gattaaacgc tacgatgaac atcatcaaga cttgactctt ttaaaagctt tagttcgaca   2160
acaacttcca gaaagtata aagaaatctt ttttgatcaa tcaaaaaacg gatatgcagg    2220
ttatattgat gggggagcta gccaagaaga attttataaa tttatcaaac caattttaga    2280
aaaaatggag ggtactgagg aattattggt gaaactaaat cgtgaagatt tgctgcgcaa    2340
gcaacggacc tttgacaacg gctctattcc ccatcaaatt cacttgggtg agctgcatgc   2400 tatttgaga agacaagaag actttttatcc atttttaaaa gacaatcgtg agaagattga   2460
aaaaatcttg acttttcgaa tcccttatta tgttggtcca ttggcgcgtg gcaatagtcg   2520 tttttgcatgg atgactcgga agtctgaaga acaattacc ccatggaatt ttgaagaagt    2580
tgtcgataaa ggtgcttcag ctcaatcatt tattgaacgc atgacaaact tgataaaaa    2640 tcttccaaat gaaaaagtac taccaaaaca tagtttgctt tatgagtatt ttacggttta    2700
taacgaattg acaaaggtca aatatgttac tgaaggaatg cgaaaccag catttctttc     2760 aggtgaacag aagaaagcca ttgttgattt actcttcaaa acaaatcgaa aagtaaccgt    2820
taagcaatta aaagaagatt atttcaaaaa aatagaatgt tttgatagtg ttgaaatttc    2880
```

```
aggagttgaa gatagattta atgcttcatt aggtacctac catgatttgc taaaaattat    2940
taaagataaa gatttttttgg ataatgaaga aaatgaagat atcttagagg atattgttttt   3000
```

```
aggagttgaa gatagattta atgcttcatt aggtacctac catgatttgc taaaaattat    2940
taaagataaa gattttttgg ataatgaaga aaatgaagat atcttagagg atattgtttt    3000
aacattgacc ttatttgaag atagggagat gattgaggaa agacttaaaa catatgctca    3060
cctctttgat gataaggtga tgaaacagct taaacgtcgc cgttatactg gttgggacg     3120
tttgtctcga aaattgatta atggtattag ggataagcaa tctggcaaaa caatattaga    3180
tttttttgaaa tcagatggtt ttgccaatcg caattttatg cagctgatcc atgatgatag   3240
tttgacattt aaagaagaca ttcaaaaagc acaagtgtct ggacaaggcg atagtttaca    3300
tgaacatatt gcaaatttag ctggtagccc tgctattaaa aaaggtatttt tacagactgt   3360
aaaagttgtt gatgaattgg tcaaagtaat ggggcggcat aagccagaaa atatcgttat    3420
tgaaatggca cgtgaaaatc agacaactca aaagggccag aaaaattcgc gagagcgtat    3480
gaaacgaatc gaagaaggta tcaaagaatt aggaagtcag attcttaaag agcatcctgt    3540
tgaaaatact caattgcaaa atgaaaagct ctatctctat tatctccaaa atggaagaga    3600
catgtatgtg gaccaagaat tagatattaa tcgtttaagt gattatgatg tcgatgccat    3660
tgttccacaa agtttcctta agacgattc aatagacaat aaggtcttaa cgcgttctga    3720
taaaaatcgt ggtaaatcgg ataacgttcc aagtgaagaa gtagtcaaaa agatgaaaaa    3780
ctattggaga caacttctaa acgccaagtt aatcactcaa cgtaagtttg taattttaac    3840
gaaagctgaa cgtggaggtt tgagtgaact tgataaagct ggttttatca acgccaatt    3900
ggttgaaact cgccaaatca ctaagcatgt ggcacaaatt ttggatagtc gcatgaatac    3960
taaatacgat gaaaatgata aacttattcg agaggttaaa gtgattaccctt aaaatctaa   4020
attagtttct gacttccgaa aagatttcca attctataaa gtacgtgaga ttaacaatta    4080
ccatcatgcc catgatgcgt atctaaatgc cgtcgttgga actgctttga ttaagaaata    4140
tccaaaactt gaatcggagt ttgtctatgg tgattataaa gtttatgatg ttcgtaaaaat   4200
gattgctaag tctgagcaag aaataggcaa agcaaccgca aaatattttct tttactctaa   4260
tatcatgaac ttcttcaaaa cagaaattac acttgcaaat ggagagattc gcaaacgccc    4320
tctaatcgaa actaatgggg aaactggaga aattgtctgg gataaagggc gagattttgc    4380
cacagtgcgc aaagtattgt ccatgcccca agtcaatatt gtcaagaaaa cagaagtaca    4440
gacaggcgga ttctccaagg agtcaatttt accaaaaaga aattcggaca gcttattgc     4500
tcgtaaaaaa gactgggatc caaaaaaata tggtggtttt gatagtccaa cggtagctta    4560
ttcagtccta gtggttgcta aggtggaaaa agggaaatcg aagaagttaa aatccgttaa    4620
agagttacta gggatcacaa ttatggaaag aagttccttt gaaaaaaatc gattgactt     4680
tttagaagct aaaggatata aggaagttaa aaaagactta atcattaaac tacctaaata    4740
tagtctttttt gagttagaaa acggtcgtaa acggatgctg gctagtgccg gagaattaca    4800
aaaaggaaat gagctggctc tgccaagcaa atatgtgaat tttttatatt tagctagtca    4860
ttatgaaaag ttgaagggta gtccagaaga taacgaacaa aaacaattgt tgtggagca     4920
gcataagcat tatttagatg agattattga gcaaatcagt gaattttcta agcgtgttat    4980
tttagcagat gccaatttag ataaagttct tagtgcatat aacaaacata gagacaaacc    5040
aatacgtgaa caagcagaaa atattattca ttttatttacg ttgacgaatc ttggagctcc    5100
cgctgctttt aaatattttg atacaacaat tgatcgtaaa cgatatacgt ctacaaaaga    5160
agttttagat gccactctta tccatcaatc catcactggt ctttatgaaa cacgcattga    5220
```

```
tttgagtcag ctaggaggtg acgcggccgc ggagcagaaa ctcatctctg aagaagatct    5280
ggaacaaaag ttgatttcag aagaagatct ggaacagaag ctcatctctg aggaagatct    5340
gtaataaggc gcgcctcctt aatgggactt gcagcctcgg taccaaattc cagaaaagac    5400
acccgaaagg gtgttttttc gttttggtcc cacagaatga gcatcatggc tctagtcgac    5460
cgggtagggg catagcttag ataattggaa aagaggaaaa aagcttaatc ttttttcgaa    5520
ggttaagctt tttctttat ttataaaaag tgaactaact atcagaaaga aattatatta     5580
aattttattt ttttgtttaa aaagtagatt atataaaggc aagctaggtg ggggaaaata    5640
tgtttaaaaa agaaaaagtc acagaataca tttggactat actaatacca acaatcatca    5700
cttttatcat tagttgggtt gggtcttatt acaatggtac ttcgacagtt agtattggac    5760
aacctacaaa agtttccggt cagtatatca cgccaataaa tataagtccc tatcatgata    5820
ttaaggaatt aagaataact tttccgcaaa aactagatgt aaaacaaatt agttcaaatg    5880
agcctataaa tgtaaaatca gataagaaca atataggagt tgaaagtaat tccacttttg    5940
agattgcgaa aatcgttgaa aataatagcg ttcagttgct aattacaaca caaaaaaagt    6000
taaacgataa ggaaattaga attgataaaa atggaaataa catttctgta aattatgaat    6060
ctcagattgt taatcctgca aaaaaacaat taatcaatct tataattacg tcatctattt    6120
attttataat gcttaatata ctagcattga ttatgaacaa aagatgggat aagtattatg    6180
caaaaatgaa aaatgaaatc aaagaatttg aggataatgc aaaagatctt gataaaaaat    6240
caaagaagaa aagcgaggaa ttatcggagc tgcgaaagac cttgaaccaa gcgtttgagg    6300
aaactgatag gataaaatat catgagaaga aaaacaaat cctcctctta gctaagttaa     6360
acgattataa aaagaacta accttttgga gaaatacaat aagaaaagtt ctttatgaac     6420
ttcctgatgg agataaaaaa gcagataaac taataggac agttacatca tctttaaaaa     6480
cgtacggtac agtcgaaaag taaagcttat cggccagcct cgcagagcag gattcccgtt    6540
gagcaccgcc aggtgcgaat aagggacagt gaagaaggaa cacccgctcg cgggtgggcc    6600
tacttcacct atcctgcccg gctgacgccg ttggatacac caaggaaagt ctacacgaac    6660
cctttggcaa aatcctgtat atcgtgcgaa aaaggatgga tataccgaaa aaatcgctat    6720
aatgaccccg aagcagggtt atgcagcgga agtataccct aaggaatcc cctgataacg     6780 caggaaagaa catgtgagca aaaggccagc aaaaggccag gaaccgtaaa aaggccgcac    6840
tccctgcctc tgtcatcacg atactgtgat gccatggcta attcccatgt cagccgttaa    6900
gtgttcctgt gtcactcaaa attgctttga gaggctctaa gggcttctca gtgcgttaca    6960
tccctggctt gttgtccaca accgttaaac cttaaaagct ttaaaagcct tatatattct    7020 ttttttctt ataaaactta aaaccttaga ggctatttaa gttgctgatt tatattaatt     7080
ttattgttca acatgagag cttagtacgt gaaacatgag agcttagtac gttagccatg     7140
agagcttagt acgttagcca tgagggttta gttcgttaaa catgagagct tagtacgtta    7200
aacatgagag cttagtacgt gaaacatgag agcttagtac gtactatcaa caggttgaac    7260
tgctgatctt cagatcctct acgccggacg catcgtggcc ggatcttgcg gccgcaaaaa    7320
ttaaaaatga agttttaaat caatctaaag tatatatgag taaacttggt ctgacagtta    7380
ccaatgctta atcagtgagg caccaataac tgcctttgat cttttctacg ggtctgacg     7440 ctcagtggaa cgaaaactca cgttaaggga ttttggtcat gagattatca aaaaggatct    7500
tcacctagat cctttaaat taaaaatgaa gttttaaatc aatctaaagt atatatgagt    7560
aaacttggtc tgacagttac caatgcttaa tcagtgaggc acctatctca gcgatctgtc    7620
```

```
tatttcgttc atccatagtt gcctgactcc ccgtcgtgta gataactacg atacgggagg    7680
gcttaccatc tggccccagt gctgcaatga taccgcgaga cccacgctca ccggctccag    7740
atttatcagc aataaaccag ccagccggaa gggccgagcg cagaagtggt cctgcaactt    7800
tatccgcctc catccagtct attaattgtt gccgggaagc tagagtaagt agttcgccag    7860
ttaatagttt gcgcaacgtt gttgccattg ctacaggcat cgtggtgtca cgctcgtcgt    7920
ttggtatggc ttcattcagc tccggttccc aacgatcaag gcgagttaca tgatccccca    7980
tgttgtgcaa aaaagcggtt agctccttcg gtcctccgat cgttgtcaga agtaagttgg    8040
ccgcagtgtt atcactcatg gttatggcag cactgcataa ttctcttact gtcatgccat    8100
ccgtaagatg cttttctgtg actggtgagt actcaaccaa gtcattctga atagtgta     8160
tgcggcgacc gagttgctct tgcccggcgt caatacggga taataccgcg ccacatagca    8220
gaactttaaa agtgctcatc attggaaaac gttcttcggg gcgaaaactc tcaaggatct    8280
taccgctgtt gagatccagt tcgatgtaac ccactcgtgc acccaactga tcttcagcat    8340
cttttacttt caccagcgtt tctgggtgag caaaaacagg aaggcaaaat gccgcaaaaa    8400
agggaataag ggcgacacgg aaatgttgaa tactcatact cttcctttt caatattatt     8460
gaagcattta tcagggttat tgtctcatga gcggatacat atttgaatgt atttagaaaa    8520
ataaacaaat aggggttccg cgcacatttc cccgaaaagt gccacctgac gtcttctaac    8580
tacttatttt aaagcagtct ggattgtttg ggtaattcat aaaaaaataa aagaaagaag    8640
gaggaataga gttttctttt ttttgtttg caatgttact gtcaagtcgc aaaagaattg      8700
ctatgaccga aaaaaaccg caaaggaata gatataaggt accttttttgc aattcatctt    8760
tgtaaaataa aggttattct gacataatac aattaatgta aaaattcgca caattttatg    8820
taaggatggg ggaattttct tgcggggtgt tttcttagat aaagataaaa ttccgtacga    8880
cttagtcacg aaaagttaa atgaatggta tacatcaata aaaatgatc aagttgagca     8940
agccgagatt ataaaacag aagtagagaa agaattgtta aacatggaag aaaatcaaga     9000
tgccctgtta tattatcaac tattagaatt tagacatgag ataatgctga gttatatgaa    9060
atctaaggaa atagaagatc tcaataatgc ttatgagact ataaaagaaa ttgagaagca    9120
agggcaatta actggcatgt tggaatacta ttttacttt tttaagggta tgtacgagtt     9180
taggcgtaaa gaattaattt cagcgataag tgcttatcga atagctgaat caaagttgtc    9240
agaagttgag gatgaaatag agaaagcaga ttttttttc aaagtgtcct atgtatatta     9300
ttatatgaaa caaacatact tctccatgaa ttatgcaaat cgtgcactca aatatttag     9360
agagtatgaa gaatatgctg tccagactgt gcgttgtcaa tttattgtag caggaaactt    9420
gatcgagtga atcgataagc tagcttaatt agctgagctt ggactcctgt tgatagatcc    9480
agtaatgacc tcagaactcc atctggattt gttcagaacg ctcggttgcc gccgggcgtt    9540
ttttattggt gagaatccaa gctagactgc gatgagtggc agggcgggc gtaatttttt      9600
taaggcagtt attggtgccc ttaaacgcct ggggtaatga ctctctagct tgaggcatca    9660
aataaaacga aaggctcagt cgaaagactg ggcctttcgt tttatctgtt gtttgtcggt    9720
gaacgctctc ctgagtagga caaatccgcc gctaggagct tgcggcccgg acgatgagct    9780
cgaattgggg atctt                                                     9795
```

<210> SEQ ID NO 29
<211> LENGTH: 9714
<212> TYPE: DNA

<210> ORGANISM: Artificial sequence
<220> FEATURE:
<223> OTHER INFORMATION: Synthetic construct

<400> SEQUENCE: 29

```
ctgataccgc tcgccgcagc cgaacgaccg agcgcagcgg gtcagtgagc gaggaagcgg      60
aagagcgccc aatacgcaaa ccgcctctcc ccgcgcgttg gccgattcat taatgcagcg     120
cccaaacata acaggaagaa aaatgccccg ctgtgggcgg acaaaatagt tgggaactgg     180
gaggggtgga aatggagttt ttaaggatta tttagggaag agtgacaaaa tagatgggaa     240
ctgggtgtag cgtcgtaagc taatacgaaa attaaaaatg acaaaatagt ttggaactag     300
atttcactta tctggttctt gaggcggtta aaagagccgt actcttctcc gatgtcgact     360
aggccatgat gctcattctg tgggaccaaa acgaaaaaac ccctttcgg gtgtcttttc      420
tggaatttgg taccgaggct gcaagtccca ttaaggaggc gcgccttatt acagatcttc     480
ctcagagatg agcttctgtt ccagatcttc ttctgaaatc aacttttgtt ccagatcttc     540
ttcagagatg agtttctgct ccgcggccgc gtcgcctccc agctgagaca ggtcgatccg     600
tgtctcgtac aggccggtga tgctctggtg gatcagggtg gcgtccagca cctctttggt     660
gctggtgtac ctcttccggt cgatggtggt gtcaaagtac ttgaaggcgg cagggggctcc    720
cagattggtc agggtaaaca ggtggatgat attctcggcc tgctctctga taggcttgtc     780
tctgtgcttg ttgtaggcgc tcagcacctt gtccagatta gcgtcggcca ggatcactct     840
cttggagaac tcgctgatct gctcgatgat ctcgtccagg tagtgtttgt gctgttccac     900
aaacagctgt ttctgctcat tatcctcggg ggagcccttc agcttctcat agtggctggc     960
caggtacagg aagttcacat atttggaggg cagggccagt tcgtttccct tctgcagttc    1020
gccggcagag gccagcattc tcttccggcc gttttccagc tcgaacaggg agtacttagg    1080
cagcttgatg atcaggtcct ttttcacttc tttgtagccc ttggcttcca gaaagtcgat    1140
gggattcttc tcgaagctgc ttcttttccat gatggtgatc cccagcagct ctttcacact    1200
cttcagtttc ttggacttgc ccttttccac tttggccacc accagcacag aataggccac    1260
ggtgggggctg tcgaagccgc cgtacttctt agggtcccag tccttcttc tggcgatcag    1320
cttgtcgctg ttcctcttgg gcaggataga ctctttgctg aagccgcctg tctgcacctc    1380
ggtcttttc acgatattca cttggggcat agacagcact ttccgcacgg tggcaaagtc     1440
ccggccctta tcccacacga tctcgcctgt ttcgccgttt gtctcgatca gaggccgctt    1500
ccggatctcg ccgttggcca gggtaatctc ggtcttgaaa aagttcatga tgttgctgta    1560
gaagaagtac ttggcggtag ccttgccgat ttcctgctcg ctcttggcga tcatcttccg    1620
cacgtcgtac accttgtagt cgccgtacac gaactcgctt tccagcttag ggtacttttt    1680
gatcagggcg gttcccacga cggcgttcag gtaggcgtcg tgggcgtggt ggtagttgtt    1740
gatctcgcgc actttgtaaa actgaaaatc cttccggaaa tcggacacca gcttggactt    1800
cagggtgatc actttcactt cccggatcag tttgtcgttc tcgtcgtact tagtgttcat    1860
ccgggagtcc aggatctgtg ccacgtgctt tgtgatctgc cgggtttcca ccagctgtct    1920
cttgatgaag ccggccttat ccagttcgct caggccgcct ctctcggcct tggtcagatt    1980
gtcgaacttc ctctgggtaa tcagcttggc attcagcagc tggcgccagt agttcttcat    2040
cttcttcacg acctcttcgg agggcacgtt gtcgctcttg ccccggttct tgtcgctccg    2100
agtcagcact ttgttatcga tggagtcgtc cttcagaaag ctctgaggca cgatagcgtc    2160
cacatcgtag tcggacagcc ggttgatgtc cagttcctgg tccacgtaca tatcccgccc    2220
```

```
attctgcagg tagtacaggt acagcttctc gttctgcagc tgggtgtttt ccacggggtg    2280
ttctttcagg atctggctgc ccagctcttt gatgccctct tcgatccgct tcattctctc    2340
gcggctgttc ttctgtccct tctgggtggt ctggttctct ctggccattt cgatcacgat    2400
gttctcgggc ttgtgccggc ccatcacttt cacgagctcg tccaccacct tcactgtctg    2460
caggatgccc ttcttaatgg cggggctgcc ggccagattg gcaatgtgct cgtgcaggct    2520
atcgccctgg ccggacacct gggctttctg gatgtcctct ttaaaggtca ggctgtcgtc    2580
gtggatcagc tgcatgaagt ttctgttggc gaagccgtcg acttcagga aatccaggat    2640 tgtcttgccg gactgcttgt cccggatgcc gttgatcagc ttccggctca gcctgccca    2700 gccggtgtat ctccgccgct tcagctgctt catcactttg tcgtcgaaca ggtgggcata    2760
ggttttcagc cgttcctcga tcatctctct gtcctcaaac agtgtcaggg tcagcacgat    2820
atcttccaga atgtcctcgt tttcctcatt gtccaggaag tccttgtcct tgataatttt    2880
cagcagatcg tggtatgtgc ccaggggaggc gttgaaccga tcttccacgc cggagatttc    2940
cacggagtcg aagcactcga ttttcttgaa gtagtcctct ttcagctgct tcacggtcac    3000
tttccggttg gtcttgaaca gcaggtccac gatggctttt ttctgctcgc cgctcaggaa    3060
ggcgggcttt ctcattccct cggtcacgta tttcactttg gtcagctcgt tgtacacggt    3120
gaagtactcg tacagcaggc tgtgcttggg cagcaccttc tcgttgggca ggttcttatc    3180
gaagttggtc atccgctcga tgaagctctg ggcgctggcg cccttgtcca ccacttcctc    3240
gaagttccag ggggtgatgg tttcctcgct ctttctggtc atccaggcga atctgctgtt    3300 tccctggcc agagggccca cgtagtaggg gatgcggaag gtcaggatct tctcgatctt    3360 ttccgttg tccttcagga atgggtaaaa atcttcctgc cgccgcagaa tggcgtgcag    3420
ctctcccagg tggatctggt gggggatgct gccgttgtcg aaggtccgct gcttccgcag    3480
caggtcctct ctgttcagct tcacgagcag ttcctcggtg ccgtccatct tttccaggat    3540
gggcttgatg aacttgtaga actcttcctg gctggctccg ccatcgatgt agccggcgta    3600
gccgttcttg ctctggtcga agaaaatctc tttgtacttc tcaggcagct gctgccgcac    3660
gagagctttc agcagggtca ggtcctggtg gtgctcgtcg tatctcttga tcatagaggc    3720 gctcagggg gccttggtga tctcggtgtt cactctcagg atgtcgctca gcaggatggc    3780
gtcggacagg ttcttggcgg ccagaaacag gtcggcgtac tggtcgccga tctgggccag    3840
caggttgtcc aggtcgtcgt cgtaggtgtc cttgctcagc tgcagtttgg catcctcggc    3900
caggtcgaag ttgctcttga agttgggggt caggcccagg ctcagggcaa tcaggttgcc    3960
gaacaggcca ttcttcttct cgccgggcag ctgggcgatc agattttcca gccgtctgct    4020
cttgctcagt ctggcagaca ggatggcctt ggcgtccacg ccgctggcgt tgatgggtt    4080 ttcctcgaac agctggttgt aggtctgcac cagctggatg aacagcttgt ccacgtcgct    4140
gttgtcgggg ttcaggtcgc cctcgatcag gaagtggccc cggaacttga tcatgtgggc    4200
cagggccaga tagatcagcc gcaggtcggc cttgtcggtg ctgtccacca gtttctttct    4260
caggtggtag atggtggggt acttctcgtg gtaggccacc tcgtccacga tgttgccgaa    4320 gatgggtgc cgctcgtgct tcttatcctc ttccaccagg aaggactctt ccagtctgtg    4380
gaagaagctg tcgtccacct tggccatctc gttgctgaag atctcttgca gatagcagat    4440
ccggttcttc cgtctggtgt atcttcttct ggcggttctc ttcagccggg tggcctcggc    4500
tgtttctccg ctgtcgaaca gcagggcgcc gatcaggttc ttcttgatgc tgtgccggtc    4560
```

```
ggtgttgccc agcaccttga atttcttgct gggcaccttg tactcgtcgg tgatcacggc    4620
ccagcccaca gagttggtgc cgatggccag gccgatgctg tacttcttgt ccatactagt    4680
tttctcctct ttagatcgct agcacaatcc ctaggactga gctagctgtc aagaaccgag    4740
gtaactggct tggtgataag ctgtcaaacc agatcaattc gcactagtct gcagacgtaa    4800
aaaaagcggc gtggttagcc gcttttttaa ttgccggagc gcaataaaaa agccccggga    4860
aggtgatctt ccgggggctt tctcatgcgt tgcttgtatt gaaaatgggg gccatgccta    4920
cctatctgcc tcccgggtcc ttgagcccca ttatcacctc caaagccttc tcgtctggtc    4980
agtttcacct gttttacgta aaacccgct tcggcgggtt tttacttttg gggaaacaca    5040
gaaaaaagcc cgcacctgac agtgcgggct ttttttttcg accaaggtg cgactactct    5100 tgcctactac ctatcgactg agctgaaaga attccggttc tggcaaatat tctgaaatga    5160
gctgttgaca attaatcatc cggctcgtat aattctagtt gagaccaact ttggtctcca    5220
ccatagcggt cggtctctgt ttaagagcta tgctggaaac agcatagcaa gtttaaataa    5280
ggctagtccg ttatcaactt gaaaaagtgg caccgagtcg gtgctttttt tttgaattca    5340
tgtggctgac cgttctgttg tctctcgctc ttccgagtag acgaacaata aggcctccct    5400 aacgggggc ctttttttatt gataacaaaa gtcagtgctt ccgctatttc caaaataccg    5460
ggctaatacg gtttaaacga cctcctggat ttgctcagac agccttttcg tcattcgttt    5520
cagccaaaaa acttaagacc gccggtcttg tccactacct tgcagtaatg cggtggacag    5580
gatcggcggt tttcttttct cttctcaaga agttcctata ctttctagag aataggaact    5640
tcggaatagg aacttcctcc tgaacggcca taagaacgaa ggctgtctgt tgaactctcg    5700
agccttgtcg ccttgcgtat aatatttgcc catggacgca caccgtggaa acggatgaag    5760
gcacgaaccc agttgacata agccgttcg gttcgtaaac tgtaatgcaa gtagcgtatg    5820
cgctcacgca actggtccag aaccttgacc gaacgcagcg gtggtaacgg cgcagtggcg    5880
gttttcatgg cttgttatga ctgttttttt gtacagtcta tgcctcgggc atccaagcag    5940
caagcgcgtt acgccgtggg tcgatgtttg atgttatgga gcagcaacga tgttacgcag    6000
cagcaacgat gttacgcagc agggcagtcg ccctaaaaca aagttaggtg gctcaagtat    6060
gggcatcatt cgcacatgta ggctcggccc tgaccaagtc aaatccatgc gggctgctct    6120
tgatcttttc ggtcgtgagt tcggagacgt agccacctac tcccaacatc agccggactc    6180
cgattacctc gggaacttgc tccgtagtaa gacattcatc gcgcttgctg ccttcgacca    6240
agaagcggtt gttggcgctc tcgcggctta cgttctgccc aagtttgagc agccgcgtag    6300
tgagatctat atctatgatc tcgcagtctc cggagagcac cggaggcagg gcattgccac    6360
cgcgctcatc aatctcctca agcatgaggc caacgcgctt ggtgcttatg tgatctacgt    6420
gcaagcagat tacggtgacg atcccgcagt ggctctctat acaaagttgg gcatacggga    6480
agaagtgatg cactttgata tcgacccaag taccgccacc taacaattcg ttcaagccga    6540
gatctcgagc atcagcttca aaagcgctct gaagttccta tactttctag agaataggaa    6600
cttcggaata ggtacttcaa gatccccaat tcgagctcat cgtccgggcc gcaagctcct    6660
agcggcggat ttgtcctact caggagagcg ttcaccgaca acaacagat aaaacgaaag    6720 gcccagtctt tcgactgagc ctttcgtttt atttgatgcc tcaagctaga gagtcattac    6780
cccaggcgtt taagggcacc aataactgcc ttaaaaaaat tacgccccgc cctgccactc    6840
atcgcagtct agcttggatt ctcaccaata aaaacgccc ggcggcaacc gagcgttctg    6900
aacaaatcca gatggagttc tgaggtcatt actggatcta tcaacaggag tccaagctca    6960
```

```
gctaattaag ctagcttatc gataccgtcg acctcgaacc ccacgcccct ctttaatacg   7020
acgggcaatt tgcacttcag aaaatgaaga gtttgcttta gccataacaa agtccagta    7080 tgcttttca cagcataact ggactgattt cagtttacaa ctattctgtc tagtttaaga    7140
ctttattgtc atagtttaga tctatttgt tcagtttaag actttattgt ccgcccacac    7200
ccgcttacgc agggcatcca tttattactc aaccgtaacc gattttgcca ggttacgcgg   7260
ctggtcctct agctggcgta atagcgaaga ggcccgcacc gatcgccctt cccaacagtt   7320
gcgcagcctg aatggcgaat ggcgcctgat gcggtatttt ctccttacgc atctgtgcgg   7380
tatttcacac cgcatatggt gcactctcag tacaatctgc tctgatgccg catagttaag   7440
ccagccccga cacccgccaa cacccgctga cgcgccctga cgggcttgtc tgctcccggc   7500
atccgcttac agacaagctg tgaccgtctc cgggagctgc atgtgtcaga ggttttcacc   7560
gtcatcaccg aaacgcgcga cgaaaggg cctcgtgata cgcctatttt tataggttaa    7620
tgtcatgata taatggttt cttagacgtc aggtggcact tttcggggaa atgtgcgcgg    7680 aaccccctatt tgtttatttt tctaaataca ttcaaatatg tatccgctca tgagacaata   7740
accctgataa atgcttcaat aatattgaaa aaggaagagt atgagtattc aacatttccg    7800
tgtcgccctt attcccttt ttgcggcatt ttgccttcct gttttgctc acccagaaac     7860 gctggtgaaa gtaaaagatg ctgaagatca gttgggtgca cgagtgggtt acatcgaact    7920
ggatctcaac agcggtaaga tccttgagag ttttcgcccc gaagaacgtt ttccaatgat   7980 gagcacttt aaagttctgc tatgtggcgc ggtattatcc cgtattgacg ccgggcaaga   8040
gcaactcggt cgccgcatac actattctca gaatgacttg gttgagtact caccagtcac   8100
agaaaagcat cttacggatg gcatgacagt aagagaatta tgcagtgctg ccataaccat   8160
gagtgataac actgcggcca acttacttct gacaacgatc ggaggaccga aggagctaac   8220
cgcttttttg cacaacatgg gggatcatgt aactcgcctt gatcgttggg aaccggagct   8280
gaatgaagcc ataccaaacg acgagcgtga caccacgatg cctgtagcaa tggcaacaac   8340
gttgcgcaaa ctattaactg gcgaactact tactctagct tcccggcaac aattaataga   8400
ctggatggag gcggataaag ttgcaggacc acttctgcgc tcggcccttc cggctggctg   8460
gtttattgct gataaatctg gagccggtga gcgtgggtcc cgcggtatca ttgcagcact   8520
ggggccagat ggtaagccct cccgtatcgt agttatctac acgacgggga gtcaggcaac   8580
tatggatgaa cgaaatagac agatcgctga gataggtgcc tcactgatta agcattggta   8640
actgtcagac caagtttact catatatact ttagattgat ttaaaacttc atttttaatt   8700
taaaaggatc taggtgaaga tcctttttga atctcatg accaaaatcc cttaacgtga   8760
gttttcgttc cactgagcgt cagaccccgt agaaaagatc aaaggcagtt attggtgcct   8820
cactgattaa gcattggtaa ctgtcagacc aagtttactc atatatactt tagattgatt    8880
taaaacttca tttttaattt ttgcggccgc aagatccggc cacgatgcgt ccggcgtaga   8940
ggatctgaag atcagcagtt caacctgttg atagtacgta ctaagctctc atgtttcacg   9000
tactaagctc tcatgtttaa cgtactaagc tctcatgttt aacgaactaa accctcatgg   9060
ctaacgtact aagctctcat ggctaacgta ctaagctctc atgtttcacg tactaagctc   9120
tcatgtttga acaataaaat taatataaat cagcaactta aatagcctct aaggttttaa   9180
gttttataag aaaaaaaga atatataagg cttttaaagc ttttaaggtt taacggttgt   9240
ggacaacaag ccagggatgt aacgcactga gaagccctta gagcctctca aagcaatttt   9300
```

```
gagtgacaca ggaacactta acggctgaca tgggaattag ccatggcatc acagtatcgt    9360
gatgacagag gcagggagtg cggcttttt acggttcctg cctttgct ggcctttgc        9420 tcacatgttc tttcctgcgt tatcagggga ttccttaagg tatactttcc gctgcataac    9480
cctgcttcgg ggtcattata gcgatttttt cggtatatcc atccttttc gcacgatata     9540 caggattttg ccaaagggtt cgtgtagact ttccttggtg tatccaacgg cgtcagccgg    9600
gcaggatagg tgaagtaggc ccacccgcga gcgggtgttc cttcttcact gtcccttatt    9660
cgcacctggc ggtgctcaac gggaatcctg ctctgcgagg ctggccgata agct          9714

<210> SEQ ID NO 30
<211> LENGTH: 9714
<212> TYPE: DNA
<213> ORGANISM: Artificial sequence
<220> FEATURE:
<223> OTHER INFORMATION: Synthetic construct

<400> SEQUENCE: 30
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc     180
gtgcgaaaaa ggatggatat accgaaaaaa tcgctataat gaccccgaag cagggttatg     240
cagcggaaag tataccttaa ggaatcccct gataacgcag gaagaacat gtgagcaaaa      300 ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagccttat atattctttt ttttcttata aaacttaaaa     540
ccttagaggc tatttaagtt gctgatttat attaatttta ttgttcaaac atgagagctt     600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaatgaagt tttaaatcaa      840 tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140 tgactcccg tcgtgtagat aactacgata cgggagggct taccatctgg ccccagtgct     1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
```

```
ccggcgtcaa tacgggataa taccgcgcca catagcagaa ctttaaaagt gctcatcatt   1740
ggaaaacgtt cttcggggcg aaaactctca aggatcttac cgctgttgag atccagttcg   1800
atgtaaccca ctcgtgcacc caactgatct tcagcatctt ttactttcac cagcgtttct   1860
gggtgagcaa aaacaggaag gcaaaatgcc gcaaaaagg gaataagggc gacacggaaa    1920
tgttgaatac tcatactctt ccttttcaa tattattgaa gcatttatca gggttattgt    1980
ctcatgagcg gatacatatt tgaatgtatt tagaaaaata aacaaatagg ggttccgcgc   2040
acatttcccc gaaaagtgcc acctgacgtc taagaaacca ttattatcat gacattaacc   2100
tataaaaata ggcgtatcac gaggccctt cgtctcgcgc gtttcggtga tgacggtgaa    2160
aacctctgac acatgcagct cccggagacg gtcacagctt gtctgtaagc ggatgccggg   2220
agcagacaag cccgtcaggg cgcgtcagcg ggtgttggcg ggtgtcgggg ctggcttaac   2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt   2400
tgggaagggc gatcggtgcg ggcctcttcg ctattacgcc agctagagga ccagccgcgt   2460
aacctggcaa atcggttac ggttgagtaa taaatggatg ccctgcgtaa gcgggtgtgg    2520
gcggacaata aagtcttaaa ctgaacaaaa tagatctaaa ctatgacaat aaagtcttaa   2580
actagacaga atagttgtaa actgaaatca gtccagttat gctgtgaaaa agcatactgg   2640 actttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac   2820
gctcggttgc cgccgggcgt tttttattgg tgagaatcca agctagactg cgatgagtgg   2880
cagggcgggg cgtaattttt ttaaggcagt tattggtgcc cttaaacgcc tggggtaatg   2940
actctctagc ttgaggcatc aaataaaacg aaaggctcag tcgaaagact gggcctttcg   3000
ttttatctgt tgtttgtcgg tgaacgctct cctgagtagg acaaatccgc cgctaggagc   3060
ttgcggcccg gacgatgagc tcgaattggg gatcttgaag tacctattcc gaagttccta   3120
ttctctagaa agtataggaa cttcagagcg cttttgaagc tgatgctcga gatctcggct   3180
tgaacgaatt gttaggtggc ggtacttggg tcgatatcaa agtgcatcac ttcttcccgt   3240
atgcccaact ttgtatagag agccactgcg ggatcgtcac cgtaatctgc ttgcacgtag   3300
atcacataag caccaagcgc gttggcctca tgcttgagga gattgatgag cgcggtggca   3360
atgccctgcc tccggtgctc tccggagact gcgagatcat agatatagat ctcactacgc   3420
ggctgctcaa acttgggcag aacgtaagcc gcgagagcgc caacaaccgc ttcttggtcg   3480
aaggcagcaa gcgcgatgaa tgtcttacta cggagcaagt tcccgaggta atcggagtcc   3540
ggctgatgtt gggagtaggt ggctacgtct ccgaactcac gaccgaaaag atcaagagca   3600
gcccgcatgg atttgacttg gtcagggccg agcctacatg tgcgaatgat gcccatactt   3660
gagccaccta actttgtttt agggcgactg ccctgctgcg taacatcgtt gctgctgcgt   3720
aacatcgttg ctgctccata acatcaaaca tcgacccacg gcgtaacgcg cttgctgctt   3780
ggatgcccga ggcatagact gtacaaaaaa acagtcataa caagccatga aaaccgccac   3840
tgcgccgtta ccaccgctgc gttcggtcaa ggttctggac cagttgcgtg agcgcatacg   3900
ctacttgcat tacagtttac gaaccgaaca ggcttatgtc aactgggttc gtgccttcat   3960
ccgtttccac ggtgtgcgtc catgggcaaa tattatacgc aaggcgacaa ggctcgagag   4020
```

```
ttcaacagac agccttcgtt cttatggccg ttcaggagga agttcctatt ccgaagttcc    4080
tattctctag aaagtatagg aacttcttga gaagagaaaa gaaaaccgcc gatcctgtcc    4140
accgcattac tgcaaggtag tggacaagac cggcggtctt aagttttttg gctgaaacga    4200
atgacgaaaa ggctgtctga gcaaatccag gaggtcgttt aaaccgtatt agcccggtat    4260
tttggaaata gcggaagcac tgacttttgt tatcaataaa aaaggccccc cgttagggag    4320
gccttattgt tcgtctactc ggaagagcga gagacaacag aacggtcagc cacatgaatt    4380
caaaaaaaaa gcaccgactc ggtgccactt tttcaagttg ataacggact agccttattt    4440
aaacttgcta tgctgtttcc agcatagctc ttaaacagag accgaccgct atggtggaga    4500
ccaaagttgg tctcaactag aattatacga gccggatgat taattgtcaa cagctcattt    4560
cagaatattt gccagaaccg gaattctttc agctcagtcg ataggtagta ggcaagagta    4620
gtcgcacctt tggtcgaaaa aaaaagcccg cactgtcagg tgcgggcttt tttctgtgtt    4680
tccccaaaag taaaaacccg ccgaagcggg ttttttacgta aaacaggtga aactgaccag    4740
acgagaaggc tttggaggtg ataatggggc tcaaggaccc gggaggcaga taggtaggca    4800
tggcccccat tttcaataca agcaacgcat gagaaagccc ccggaagatc accttccggg    4860
ggcttttta ttgcgctccg gcaattaaaa aagcggctaa ccacgccgct ttttttacgt    4920
ctgcagacta gtgcgaattg atctggtttg acagcttatc accaagccag ttacctcggt    4980
tctttatggc tagctcagtc ctaggtacaa tgctagcgat ctaaagagga gaaaactagt    5040
atggacaaga agtacagcat cggcctggcc atcggcacca actctgtggg ctgggccgtg    5100
atcaccgacg agtacaaggt gcccagcaag aaattcaagg tgctgggcaa caccgaccgg    5160
cacagcatca agaagaacct gatcggcgcc ctgctgttcg acagcggaga acagccgag    5220
gccaccggc tgaagagaac cgccagaaga agatacacca cacggaagaa ccggatctgc    5280
tatctgcaag agatcttcag caacgagatg gccaaggtgg acgacagctt cttccacaga    5340
ctggaagagt ccttcctggt ggaagaggat aagaagcacg agcggcaccc catcttcggc    5400
aacatcgtgg acgaggtggc ctaccacgag aagtacccca ccatctacca cctgagaaag    5460
aaactggtgg acagcaccga caaggccgac ctgcggctga tctatctggc cctggcccac    5520
atgatcaagt tccggggcca cttcctgatc gagggcgacc tgaacccga acagcgac     5580
gtggacaagc tgttcatcca gctggtgcag acctacaacc agctgttcga ggaaaacccc    5640
atcaacgcca gcggcgtgga cgccaaggcc atcctgtctg ccagactgag caagagcaga    5700
cggctggaaa atctgatcgc ccagctgccc ggcgagaaga gaatggcct gttcggcaac    5760
ctgattgccc tgagcctggg cctgaccccc aacttcaaga gcaacttcga cctggccgag    5820
gatgccaaac tgcagctgag caaggacacc tacgacgacg acctggacaa cctgctggcc    5880
cagatcggcg accagtacgc cgacctgttt ctggccgcca agaacctgtc cgacgccatc    5940
ctgctgagcg acatcctgag agtgaacacc gagatcacca aggcccccct gagcgcctct    6000
atgatcaaga gatacgacga gcaccaccag gacctgaccc tgctgaaagc tctcgtgcgg    6060
cagcagctgc ctgagaagta caaagagatt tcttcgacc agagcaagaa cggctacgcc    6120
ggctacatcg atggcggagc cagccaggaa gagttctaca gttcatcaa gcccatcctg    6180
gaaagatgg acggcaccga ggaactgctc gtgaagctga acagagagga cctgctgcgg    6240
aagcagcgga ccttcgacaa cggcagcatc ccccaccaga tccacctggg agagctgcac    6300
gccattctgc ggcggcagga agattttac ccattcctga aggacaaccg ggaaaagatc    6360
gagaagatcc tgaccttccg catcccctac tacgtgggcc ctctggccag ggaaacagc    6420
```

```
agattcgcct ggatgaccag aaagagcgag gaaaccatca cccctggaa cttcgaggaa    6480 gtggtggaca agggcgccag cgcccagagc ttcatcgagc ggatgaccaa cttcgataag    6540
aacctgccca acgagaaggt gctgcccaag cacagcctgc tgtacgagta cttcaccgtg    6600
tacaacgagc tgaccaaagt gaaatacgtg accgagggaa tgagaaagcc cgccttcctg    6660
agcggcgagc agaaaaaagc catcgtggac ctgctgttca agaccaaccg gaaagtgacc    6720
gtgaagcagc tgaaagagga ctacttcaag aaaatcgagt gcttcgactc cgtggaaatc    6780
tccggcgtgg aagatcggtt caacgcctcc ctgggcacat accacgatct gctgaaaatt    6840
atcaaggaca aggacttcct ggacaatgag gaaaacgagg acattctgga agatatcgtg    6900
ctgaccctga cactgtttga ggacagagag atgatcgagg aacggctgaa aacctatgcc    6960
cacctgttcg acgacaaagt gatgaagcag ctgaagcggc ggagatacac cggctggggc    7020
aggctgagcc ggaagctgat caacggcatc cgggacaagc agtccggcaa gacaatcctg    7080
gatttcctga gtccgacgg cttcgccaac agaaacttca tgcagctgat ccacgacgac    7140
agcctgacct ttaaagagga catccagaaa gcccaggtgt ccggccaggg cgatagcctg    7200
cacgagcaca ttgccaatct ggccggcagc cccgccatta agaagggcat cctgcagaca    7260
gtgaaggtgg tggacgagct cgtgaaagtg atgggccggc acaagcccga acatcgtg    7320 atcgaaatgg ccagagagaa ccagaccacc cagaagggac agaagaacag ccgcgagaga    7380
atgaagcgga tcgaagaggg catcaaagag ctgggcagcc agatcctgaa agaacacccc    7440
gtggaaaaca cccagctgca gaacgagaag ctgtacctgt actacctgca gaatgggcgg    7500
gatatgtacg tggaccagga actggacatc aaccggctgt ccgactacga tgtggacgct    7560
atcgtgcctc agagctttct gaaggacgac tccatcgata caaagtgct gactcggagc    7620 gacaagaacc ggggcaagag cgacaacgtg ccctccgaag aggtcgtgaa gaagatgaag    7680
aactactggc gccagctgct gaatgccaag ctgattaccc agaggaagtt cgacaatctg    7740
accaaggccg agagaggcgg cctgagcgaa ctggataagg ccggcttcat caagagacag    7800
ctggtggaaa cccggcagat cacaaagcac gtggcacaga tcctggactc ccggatgaac    7860
actaagtacg acgagaacga caaactgatc cgggaagtga agtgatcac cctgaagtcc    7920 aagctggtgt ccgatttccg gaaggatttc cagttttaca agtgcgcga gatcaacaac    7980 taccaccacg cccacgacgc ctacctgaac gccgtcgtgg gaaccgccct gatcaaaaag    8040 tacccctaagc tggaaagcga gttcgtgtac ggcgactaca aggtgtacga cgtgcggaag    8100
atgatcgcca agagcgagca ggaaatcggc aaggctaccg ccaagtactt cttctacagc    8160
aacatcatga cttttttcaa gaccgagatt accctggcca acggcgagat ccggaagcgg    8220
cctctgatcg agacaaacgg cgaaacaggc gagatcgtgt gggataaggg ccgggacttt    8280
gccaccgtgc ggaaagtgct gtctatgccc caagtgaata tcgtgaaaaa gaccgaggtg    8340
cagacaggcg gcttcagcaa agagtctatc ctgcccaaga ggaacagcga caagctgatc    8400
gccagaaaga aggactggga ccctaagaag tacgcggct cgacagccc accgtggcc    8460 tattctgtgc tggtggtggc caaagtggaa aagggcaagt ccaagaaact gaagagtgtg    8520
aaagagctgc tggggatcac catcatggaa agaagcagct cgagaagaa tcccatcgac    8580 tttctggaag ccaagggcta caaagaagtg aaaaaggacc tgatcatcaa gctgcctaag    8640
tactccctgt tcgagctgga aaacggccgg aagagaatgc tggcctctgc cggcgaactg    8700
cagaagggaa acgaactggc cctgcctcc aaatatgtga cttcctgta cctggccagc    8760
```

| | |
|---|---|
| cactatgaga agctgaaggg ctcccccgag ataatgagc agaaacagct gtttgtggaa | 8820 |
| cagcacaaac actacctgga cgagatcatc gagcagatca gcgagttctc caagagagtg | 8880 |
| atcctggccg acgctaatct ggacaaggtg ctgagcgcct acaacaagca cagagacaag | 8940 |
| cctatcagag agcaggccga gaatatcatc cacctgttta ccctgaccaa tctgggagcc | 9000 |
| cctgccgcct tcaagtactt tgacaccacc atcgaccgga gaggtacac cagcaccaaa | 9060 |
| gaggtgctgg acgccaccct gatccaccag agcatcaccg gcctgtacga gacacggatc | 9120 |
| gacctgtctc agctgggagg cgacgcggcc gcggagcaga aactcatctc tgaagaagat | 9180 |
| ctggaacaaa agttgatttc agaagaagat ctggaacaga agctcatctc tgaggaagat | 9240 |
| ctgtaataag gcgcgcctcc ttaatgggac ttgcagcctc ggtaccaaat tccagaaaag | 9300 |
| acacccgaaa gggtgttttt tcgttttggt cccacagaat gagcatcatg gcctagtcga | 9360 |
| catcggagaa gagtacggct cttttaaccg cctcaagaac cagataagtg aaatctagtt | 9420 |
| ccaaactatt ttgtcatttt taattttcgt attagcttac gacgctacac ccagttccca | 9480 |
| tctatttgt cactcttccc taaataatcc ttaaaaactc catttccacc cctcccagtt | 9540 |
| cccaactatt ttgtccgccc acagcggggc attttttcttc ctgttatgtt tgggcgctgc | 9600 |
| attaatgaat cggccaacgc gcggggagag gcggtttgcg tattgggcgc tcttccgctt | 9660 |
| cctcgctcac tgacccgctg cgctcggtcg ttcggctgcg gcgagcggta tcag | 9714 |

<210> SEQ ID NO 31
<211> LENGTH: 9714
<212> TYPE: DNA
<213> ORGANISM: Artificial sequence
<220> FEATURE:
<223> OTHER INFORMATION: Synthetic construct

<400> SEQUENCE: 31

| | |
|---|---|
| agcttatcgg ccagcctcgc agagcaggat tcccgttgag caccgccagg tgcgaataag | 60 |
| ggacagtgaa gaaggaacac ccgctcgcgg gtgggcctac ttcacctatc ctgcccggct | 120 |
| gacgccgttg gatacaccaa ggaaagtcta cacgaaccct ttggcaaaat cctgtatatc | 180 |
| gtgcgaaaaa ggatggatat accgaaaaaa tcgctataat gaccccgaag cagggttatg | 240 |
| cagcggaaag tataccttaa ggaatcccct gataacgcag gaaagaacat gtgagcaaaa | 300 |
| ggccagcaaa aggccaggaa ccgtaaaaag gccgcactcc ctgcctctgt catcacgata | 360 |
| ctgtgatgcc atggctaatt cccatgtcag ccgttaagtg ttcctgtgtc actcaaaatt | 420 |
| gctttgagag gctctaaggg cttctcagtg cgttacatcc ctggcttgtt gtccacaacc | 480 |
| gttaaacctt aaaagcttta aaagccttat atattctttt ttttcttata aacttaaaa | 540 |
| ccttagaggc tatttaagtt gctgatttat attaatttta ttgttcaaac atgagagctt | 600 |
| agtacgtgaa acatgagagc ttagtacgtt agccatgaga gcttagtacg ttagccatga | 660 |
| gggtttagtt cgttaaacat gagagcttag tacgttaaac atgagagctt agtacgtgaa | 720 |
| acatgagagc ttagtacgta ctatcaacag gttgaactgc tgatcttcag atcctctacg | 780 |
| ccggacgcat cgtggccgga tcttgcggcc gcaaaaatta aaatgaagt tttaaatcaa | 840 |
| tctaaagtat atatgagtaa acttggtctg acagttacca atgcttaatc agtgaggcac | 900 |
| caataactgc ctttgatctt ttctacgggg tctgacgctc agtggaacga aaactcacgt | 960 |
| taagggattt tggtcatgag attatcaaaa aggatcttca cctagatcct tttaaattaa | 1020 |
| aaatgaagtt ttaaatcaat ctaaagtata tatgagtaaa cttggtctga cagttaccaa | 1080 |
| tgcttaatca gtgaggcacc tatctcagcg atctgtctat ttcgttcatc catagttgcc | 1140 |

```
tgactccccg tcgtgtagat aactacgata cgggagggct taccatctgg ccccagtgct   1200
gcaatgatac cgcgggaccc acgctcaccg gctccagatt tatcagcaat aaaccagcca   1260
gccggaaggg ccgagcgcag aagtggtcct gcaactttat ccgcctccat ccagtctatt   1320
aattgttgcc gggaagctag agtaagtagt tcgccagtta atagtttgcg caacgttgtt   1380
gccattgcta caggcatcgt ggtgtcacgc tcgtcgtttg gtatggcttc attcagctcc   1440
ggttcccaac gatcaaggcg agttacatga tcccccatgt tgtgcaaaaa agcggttagc   1500
tccttcggtc ctccgatcgt tgtcagaagt aagttggccg cagtgttatc actcatggtt   1560
atggcagcac tgcataattc tcttactgtc atgccatccg taagatgctt ttctgtgact   1620
ggtgagtact caaccaagtc attctgagaa tagtgtatgc ggcgaccgag ttgctcttgc   1680
ccggcgtcaa tacgggataa taccgcgcca catagcagaa ctttaaaagt gctcatcatt   1740
ggaaaacgtt cttcggggcg aaaactctca aggatcttac cgctgttgag atccagttcg   1800
atgtaaccca ctcgtgcacc caactgatct tcagcatctt ttactttcac cagcgtttct   1860
gggtgagcaa aaacaggaag gcaaaatgcc gcaaaaaagg aataagggc gacacggaaa   1920 tgttgaatac tcatactctt ccttttcaa tattattgaa gcatttatca gggttattgt   1980
ctcatgagcg gatacatatt tgaatgtatt tagaaaaata aacaaatagg ggttccgcgc   2040
acatttcccc gaaaagtgcc acctgacgtc taagaaacca ttattatcat gacattaacc   2100
tataaaaata ggcgtatcac gaggcccttt cgtctcgcgc gtttcggtga tgacggtgaa   2160
aacctctgac acatgcagct cccggagacg gtcacagctt gtctgtaagc ggatgccggg   2220
agcagacaag cccgtcaggg cgcgtcagcg ggtgttggcg ggtgtcgggg ctggcttaac   2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt   2400
tgggaagggc gatcggtgcg ggcctcttcg ctattacgcc agctagagga ccagccgcgt   2460
aacctggcaa atcggttac ggttgagtaa taaatggatg ccctgcgtaa gcgggtgtgg    2520
gcggacaata aagtcttaaa ctgaacaaaa tagatctaaa ctatgacaat aaagtcttaa   2580
actagacaga atagttgtaa actgaaatca gtccagttat gctgtgaaaa agcatactgg   2640 actttttgtta tggctaaagc aaactcttca ttttctgaag tgcaaattgc ccgtcgtatt   2700
aaagaggggc gtggggttcg aggtcgacgg tatcgataag ctagcttaat tagctgagct   2760
tggactcctg ttgatagatc cagtaatgac ctcagaactc catctggatt tgttcagaac   2820
gctcggttgc cgccgggcgt ttttattgg tgagaatcca agctagactg cgatgagtgg   2880
cagggcgggg cgtaattttt ttaaggcagt tattggtgcc cttaaacgcc tggggtaatg   2940
actctctagc ttgaggcatc aaataaaacg aaaggctcag tcgaaagact gggcctttcg   3000
ttttatctgt tgtttgtcgg tgaacgctct cctgagtagg acaaatccgc cgctaggagc   3060
ttgcggcccg gacgatgagc tcgaattggg gatcttgaag tacctattcc gaagttccta   3120
ttctctagaa agtataggaa cttcagagcg cttttgaagc tgatgctcga gatctcggct   3180
tgaacgaatt gttaggtggc ggtacttggg tcgatatcaa agtgcatcac ttcttcccgt   3240
atgcccaact ttgtatagag agccactgcg ggatcgtcac cgtaatctgc ttgcacgtag   3300
atcacataag caccaagcgc gttggcctca tgcttgagga gattgatgag cgcggtggca   3360
atgccctgcc tccggtgctc tccggagact gcgagatcat agatatagat ctcactacgc   3420
ggctgctcaa acttgggcag aacgtaagcc gcgagagcgc caacaaccgc ttcttggtcg   3480
```

-continued

```
aaggcagcaa gcgcgatgaa tgtcttacta cggagcaagt tcccgaggta atcggagtcc   3540
ggctgatgtt gggagtaggt ggctacgtct ccgaactcac gaccgaaaag atcaagagca   3600
gcccgcatgg atttgacttg gtcagggccg agcctacatg tgcgaatgat gcccatactt   3660
gagccaccta actttgtttt agggcgactg ccctgctgcg taacatcgtt gctgctgcgt   3720
aacatcgttg ctgctccata acatcaaaca tcgacccacg gcgtaacgcg cttgctgctt   3780
ggatgcccga ggcatagact gtacaaaaaa acagtcataa caagccatga aaaccgccac   3840
tgcgccgtta ccaccgctgc gttcggtcaa ggttctggac cagttgcgtg agcgcatacg   3900
ctacttgcat tacagtttac gaaccgaaca ggcttatgtc aactgggttc gtgccttcat   3960
ccgtttccac ggtgtgcgtc catgggcaaa tattatacgc aaggcgacaa ggctcgagag   4020
ttcaacagac agccttcgtt cttatggccg ttcaggagga agttcctatt ccgaagttcc   4080
tattctctag aaagtatagg aacttcttga agagaaaaa gaaaaccgcc gatcctgtcc   4140
accgcattac tgcaaggtag tggacaagac cggcggtctt aagttttttg gctgaaacga   4200
atgacgaaaa ggctgtctga gcaaatccag gaggtcgttt aaaccgtatt agcccggtat   4260
tttggaaata gcggaagcac tgacttttgt tatcaataaa aaaggccccc cgttagggag   4320
gccttattgt tcgtctactc ggaagagcga gagacaacag aacggtcagc cacatgaatt   4380
caaaaaaaaa gcaccgactc ggtgccactt tttcaagttg ataacggact agccttattt   4440
aaacttgcta tgctgtttcc agcatagctc ttaaacagag accgaccgct atggtggaga   4500
ccaaagttgg tctcaactag aattatacga gccggatgat taattgtcaa cagctcattt   4560
cagaatattt gccagaaccg gaattctttc agctcagtcg ataggtagta ggcaagagta   4620
gtcgcacctt tggtcgaaaa aaaaagcccg cactgtcagg tgcgggcttt tttctgtgtt   4680
tccccaaaag taaaaaccg ccgaagcggg ttttttacgta aaacaggtga aactgaccag   4740
acgagaaggc tttggaggtg ataatggggc tcaaggaccc gggaggcaga taggtaggca   4800
tggcccccat tttcaataca agcaacgcat gagaaagccc ccggaagatc accttccggg   4860
ggctttttta ttgcgctccg gcaattaaaa aagcggctaa ccacgccgct ttttttacgt   4920
ctgcagacta gtgcgaattg atctggtttg acagcttatc accaagccag ttacctcggt   4980
tctttatagc tagctcagcc cttggtacaa tgctagcgat ctaaagagga gaaaactagt   5040
atggacaaga agtacagcat cggcctggcc atcggcacca actctgtggg ctgggccgtg   5100
atcaccgacg agtacaaggt gcccagcaag aaattcaagg tgctgggcaa caccgaccgg   5160
cacagcatca agaagaacct gatcggcgcc ctgctgttcg acagcggaga acagccgag   5220
gccacccggc tgaagagaac cgccagaaga agatacacca gacggaagaa ccggatctgc   5280
tatctgcaag agatcttcag caacgagatg gccaaggtgg acgacagctt cttccacaga   5340
ctggaagagt ccttcctggt ggaagaggat aagaagcacg agcggcaccc catcttcggc   5400
aacatcgtgg acgaggtggc ctaccacgag aagtacccca ccatctacca cctgagaaag   5460
aaactggtgg acagcaccga caaggccgac ctgcggctga tctatctggc cctggcccac   5520
atgatcaagt tccggggcca cttcctgatc gagggcgacc tgaaccccga caacagcgac   5580
gtggacaagc tgttcatcca gctggtgcag acctacaacc agctgttcga ggaaaacccc   5640
atcaacgcca gcggcgtgga cgccaaggcc atcctgtctg ccagactgag caagagcaga   5700
cggctggaaa atctgatcgc ccagctgccc ggcgagaaga gaatggcct gttcggcaac   5760
ctgattgccc tgagcctggg cctgaccccc aacttcaaga gcaacttcga cctggccgag   5820
gatgccaaac tgcagctgag caaggacacc tacgacgacg acctggacaa cctgctggcc   5880
```

```
cagatcggcg accagtacgc cgacctgttt ctggccgcca agaacctgtc cgacgccatc    5940
ctgctgagcg acatcctgag agtgaacacc gagatcacca aggccccccct gagcgcctct    6000 atgatcaaga gatacgacga gcaccaccag gacctgaccc tgctgaaagc tctcgtgcgg    6060
cagcagctgc ctgagaagta caaagagatt ttcttcgacc agagcaagaa cggctacgcc    6120
ggctacatcg atggcggagc cagccaggaa gagttctaca agttcatcaa gcccatcctg    6180
gaaaagatgg acggcaccga ggaactgctc gtgaagctga acagagagga cctgctgcgg    6240
aagcagcgga ccttcgacaa cggcagcatc ccccaccaga tccacctggg agagctgcac    6300
gccattctgc ggcggcagga agattttttac ccattcctga aggacaaccg ggaaaagatc    6360
gagaagatcc tgaccttccg catcccctac tacgtgggcc ctctggccag ggaaacagc     6420 agattcgcct ggatgaccag aaagagcgag gaaaccatca ccccctggaa cttcgaggaa    6480
gtggtggaca agggcgccag cgcccagagc ttcatcgagc ggatgaccaa cttcgataag    6540
aacctgccca cgagaaggt gctgcccaag cacagcctgc tgtacgagta cttcaccgtg     6600
tacaacgagc tgaccaaagt gaaatacgtg accgagggaa tgagaaagcc cgccttcctg    6660
agcggcgagc agaaaaaagc catcgtggac ctgctgttca agaccaaccg gaaagtgacc    6720
gtgaagcagc tgaaagagga ctacttcaag aaaatcgagt gcttcgactc cgtggaaatc    6780
tccggcgtgg aagatcggtt caacgcctcc ctgggcacat accacgatct gctgaaaatt    6840
atcaaggaca aggacttcct ggacaatgag gaaaacgagg acattctgga agatatcgtg    6900
ctgaccctga cactgtttga ggacagagag atgatcgagg aacggctgaa aacctatgcc    6960
cacctgttcg acgacaaagt gatgaagcag ctgaagcggc ggagatacac cggctggggc    7020
aggctgagcc ggaagctgat caacggcatc cgggacaagc agtccggcaa gacaatcctg    7080
gatttcctga agtccgacgg cttcgccaac agaaacttca tgcagctgat ccacgacgac    7140
agcctgacct ttaaagagga catccagaaa gcccaggtgt ccggccaggg cgatagcctg    7200
cacgagcaca ttgccaatct ggccggcagc cccgccatta agaagggcat cctgcagaca    7260
gtgaaggtgg tggacgagct cgtgaaagtg atgggccggc acaagcccga gaacatcgtg    7320
atcgaaatgg ccagagagaa ccagaccacc cagaagggac agaagaacag ccgcgagaga    7380
atgaagcgga tcgaagaggg catcaaagag ctgggcagcc agatcctgaa agaacacccc    7440
gtggaaaaca cccagctgca gaacgagaag ctgtacctgt actacctgca gaatgggcgg    7500
gatatgtacg tggaccagga actggacatc aaccggctgt ccgactacga tgtggacgct    7560
atcgtgcctc agagctttct gaaggacgac tccatcgata caaagtgct gactcggagc     7620 gacaagaacc ggggcaagag cgacaacgtg ccctccgaag aggtcgtgaa gaagatgaag    7680
aactactggc gccagctgct gaatgccaag ctgattaccc agaggaagtt cgacaatctg    7740
accaaggccg agagaggcgg cctgagcgaa ctggataagg ccggcttcat caagagacag    7800
ctggtggaaa cccggcagat cacaaagcac gtggcacaga tcctggactc ccggatgaac    7860
actaagtacg acgagaacga caaactgatc cgggaagtga aagtgatcac cctgaagtcc    7920
aagctggtgt ccgatttccg gaaggatttc cagttttaca agtgcgcga gatcaacaac     7980 taccaccacg cccacgacgc ctacctgaac gccgtcgtgg aaccgccct gatcaaaaag     8040 taccctaagc tggaaagcga gttcgtgtac ggcgactaca aggtgtacga cgtgcggaag    8100
atgatcgcca gagcgagca ggaaatcggc aaggctaccg ccaagtactt cttctacagc     8160
aacatcatga actttttcaa gaccgagatt accctggcca acggcgagat ccggaagcgg    8220
```

```
cctctgatcg agacaaacgg cgaaacaggc gagatcgtgt gggataaggg ccgggacttt    8280
gccaccgtgc ggaaagtgct gtctatgccc caagtgaata tcgtgaaaaa gaccgaggtg    8340
cagacaggcg gcttcagcaa agagtctatc ctgcccaaga ggaacagcga caagctgatc    8400
gccagaaaga aggactggga ccctaagaag tacggcggct cgacagccc caccgtggcc     8460 tattctgtgc tggtggtggc caaagtggaa aagggcaagt ccaagaaact gaagagtgtg    8520
aaagagctgc tgggatcac catcatggaa agaagcagct cgagaagaa tcccatcgac      8580 tttctggaag ccaagggcta caagaagtg aaaaaggacc tgatcatcaa gctgcctaag     8640
tactccctgt tcgagctgga aaacggccgg aagagaatgc tggcctctgc cggcgaactg    8700
cagaagggaa acgaactggc cctgccctcc aaatatgtga acttcctgta cctggccagc    8760
cactatgaga agctgaaggg ctcccccgag gataatgagc agaaacagct gtttgtggaa    8820
cagcacaaac actacctgga cgagatcatc gagcagatca gcgagttctc caagagagtg    8880
atcctggccg acgctaatct ggacaaggtg ctgagcgcct acaacaagca cagagacaag    8940
cctatcagag agcaggccga gaatatcatc cacctgttta cctgaccaa tctgggagcc    9000 cctgccgcct tcaagtactt tgacaccacc atcgaccgga gaggtacac cagcaccaaa    9060 gaggtgctgg acgccaccct gatccaccag agcataccg cctgtacga gacacggatc     9120 gacctgtctc agctgggagg cgacgcggcc gcggagcaga aactcatctc tgaagaagat    9180
ctggaacaaa agttgattc agaagaagat ctggaacaga gctcatctc tgaggaagat      9240 ctgtaataag gcgcgcctcc ttaatgggac ttgcagcctc ggtaccaaat tccagaaaag    9300
acacccgaaa gggtgttttt tcgtttttggt cccacagaat gagcatcatg gcctagtcga    9360
catcggagaa gagtacggct cttttaaccg cctcaagaac cagataagtg aaatctagtt    9420
ccaaactatt ttgtcatttt taattttcgt attagcttac gacgctacac ccagttccca    9480
tctattttgt cactcttccc taaataatcc ttaaaactc catttccacc cctcccagtt    9540
cccaactatt ttgtccgccc acagcggggc atttttcttc ctgttatgtt tgggcgctgc    9600
attaatgaat cggccaacgc gcggggagag gcggttttgcg tattgggcgc tcttccgctt    9660
cctcgctcac tgaccgctg cgctcggtcg ttcggctgcg gcgagcggta tcag            9714
```

<210> SEQ ID NO 32
<211> LENGTH: 35
<212> TYPE: DNA
<213> ORGANISM: Artificial sequence
<220> FEATURE:
<223> OTHER INFORMATION: Synthetic construct

<400> SEQUENCE: 32
ttgacagcta gctcagtcct agggattgtg ctagc                              35

<210> SEQ ID NO 33
<211> LENGTH: 35
<212> TYPE: DNA
<213> ORGANISM: Artificial sequence
<220> FEATURE:
<223> OTHER INFORMATION: Synthetic construct

<400> SEQUENCE: 33
tttatggcta gctcagtcct aggtacaatg ctagc                              35

<210> SEQ ID NO 34
<211> LENGTH: 35
<212> TYPE: DNA
<213> ORGANISM: Artificial sequence
<220> FEATURE:
<223> OTHER INFORMATION: Synthetic construct

<400> SEQUENCE: 34
tttatagcta gctcagccct tggtacaatg ctagc                                35

<210> SEQ ID NO 35
<211> LENGTH: 11801
<212> TYPE: DNA
<213> ORGANISM: Artificial Sequence
<220> FEATURE:
<223> OTHER INFORMATION: Synthetic construct

<400> SEQUENCE: 35
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc     180
gtgcgaaaaa ggatggatat accgaaaaaa tcgctataat gaccccgaag cagggttatg     240
cagcggaaag tataccttaa ggaatcccct gataacgcag gaaagaacat gtgagcaaaa     300
ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagccttat atattctttt ttttcttata aacttaaaa     540
ccttagaggc tatttaagtt gctgatttat attaattttat tgttcaaac atgagagctt     600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaatgaagt tttaaatcaa     840
tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140
tgactcccg tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860

```
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggcccttt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa atcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca agctagactg cgatgagtgg    2880
cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gtcatttcga    3180
accccagagt cccgctcaga agaactcgtc aagaaggcga tagaaggcga tgcgctgcga    3240
atcgggagcg gcgataccgt aaagcacgag gaagcggtca gcccattcgc cgccaagctc    3300
ttcagcaata tcacgggtag ccaacgctat gtcctgatag cggtccgcca cacccagccg    3360
gccacagtcg atgaatccag aaaagcggcc attttccacc atgatattcg gcaagcaggc    3420
atcgccatgg gtcacgacga gatcctcgcc gtcgggcatg cgcgccttga gcctggcgaa    3480
cagttcggct ggcgcgagcc cctgatgctc ttcgtccaga tcatcctgat cgacaagacc    3540
ggcttccatc cgagtacgtg ctcgctcgat gcgatgtttc gcttggtggt cgaatgggca    3600
ggtagccgga tcaagcgtat gcagccgccg cattgcatca gccatgatgg atactttctc    3660
ggcaggagca aggtgagatg acaggagatc ctgccccggc acttcgccca atagcagcca    3720
gtcccttccc gcttcagtga acaacgtcgag cacagctgcg caaggaacgc ccgtcgtggc    3780
cagccacgat agccgcgctg cctcgtcctg cagttcattc agggcaccgg acaggtcggt    3840
cttgacaaaa agaaccgggc gcccctgcgc tgacagccgg aacacggcgg catcagcagca    3900 gccgattgtc tgttgtgccc agtcatagcc gaatagcctc tccacccaag cggccggaga    3960
acctgcgtgc aatccatctt gttcaatcat gcgaaacgat cctcatcctg tctcttgatc    4020
agatcttgat cccctgcgcc atcagatcct ggcggcaag aaagccatcc agttttgagc    4080
gcatacgcta cttgcattac agtttacgaa ccgaacaggc ttatgtcaac tgggttcgtg    4140
ccttcatccg tttccacggt ctcgagagtt caacagacag ccttcgttct tatgccgtt    4200 caggaggaag ttcctattcc gaagttccta ttctctagaa agtataggaa cttcttgaga    4260
```

```
agagaaaaga aaaccgccga tcctgtccac cgcattactg caaggtagtg gacaagaccg   4320
gcggtcttaa gttttttggc tgaaacgaat gacgaaaagg ctgtctgagc aaatccagga   4380
ggtcgttttt attaagcacc ggtggagtga cgaccttcag cacgttcgta ctgttcaacg   4440
atggtgtagt cttcgttgtg ggaggtgatg tccagtttga tgtcggtttt gtaagcaccc   4500
ggcagctgaa ccggtttttt agccatgtag gtggttttaa cttcagcgtc gtagtgacca   4560
ccgtctttca gtttcagacg cattttgatt tcacctttca gagcaccgtc ttccgggtac   4620
atacgttcgg tggaagcttc ccaacccatg gttttttttct gcataaccgg accgtcggac   4680
gggaagttgg taccacgcag tttaactttg tagatgaact caccgtcttg cagggaggag   4740
tcctgggtaa cggtaacaac accaccgtct tcgaagttca taacacgttc ccatttgaaa   4800
ccttccggga aggacagttt caggtagtcc gggatgtcag ccgggtgttt aacgtaagct   4860
ttggaaccgt actggaactg cggggacagg atgtcccaag cgaacggcag cggaccacct   4920
ttggtaactt tcagtttagc ggtctgggta ccttcgtacg gacgaccttc accttcacct   4980
tcgatttcga actcgtgacc gttaacggaa ccttccatac gaactttgaa acgcatgaac   5040
tctttgataa cgtcttcgct actcgccatg gtacctttct cctctttaat taattcagat   5100
ctattatacc taggactgag ctagctgtca aattcaccac cctgaattga ctctcaaacc   5160
gtattagccc ggtattttgg aaatagcgga agcactgact tttgttatca ataaaaaagg   5220 cccccgtta gggaggcctt attgttcgtc tactcggaag agcgagagac aacagaacgg   5280
tcagccacat gaattctttc agctcagtcg ataggtagta ggcaagagta gtcgcacctt   5340
tggtcgaaaa aaaagcccg cactgtcagg tgcgggcttt tttctgtgtt tccccaaaag   5400
taaaaacccg ccgaagcggg tttttacgta aacaggtgaa actgaccag acgaaaggc    5460 tttggaggtg ataatggggc tcaaggaccc tggggtgcct aatgagtgag ctaactcaca   5520
ttaattgcgt tgcgctcact gcccgctttc cagtcgggaa acctgtcgtg ccagctgcat   5580
taatgaatcg gccaacgcgc ggggagaggc ggtttgcgta ttgggcgcca gggtggtttt   5640
tcttttcacc agtgagacgg gcaacagctg attgccctt accgcctggc cctgagagag   5700
ttgcagcaag cggtccacgc tggtttgccc cagcaggcga aaatcctgtt tgatggtggt   5760
taacggcggg atataacatg agctgtcttc ggtatcgtcg tatcccacta ccgagatatc   5820
cgcaccaacg cgcagcccgg actcggtaat ggcgcgcatt gcgcccagcg ccatctgatc   5880
gttggcaacc agcatcgcag tgggaacgat gccctcattc agcatttgca tggtttgttg   5940
aaaaccggac atggcactcc agtcgccttc ccgttccgct atcggctgaa tttgattgcg   6000
agtgagatat ttatgccagc cagccagacg cagacgcgcc gagacagaac ttaatgggcc   6060
cgctaacagc gcgatttgct ggtgacccaa tgcgaccaga tgctccacgc ccagtcgcgt   6120
accgtcttca tgggagaaaa taatactgtt gatgggtgtc tggtcagaga catcaagaaa   6180
taacgccgga acattagtgc aggcagcttc cacagcaatg gcatcctggt catccagcgg   6240
atagttaatg atcagcccac tgacgcgttg cgcgagaaga ttgtgcaccg ccgctttaca   6300
ggcttcgacg ccgcttcgtt ctaccatcga caccaccacg ctggcaccca gttgatcggc   6360
gcgagattta atcgccgcga caatttgcga cggcgcgtgc agggccagac tggaggtggc   6420
aacgccaatc agcaacgact gtttgcccgc cagttgttgt gccacgcggt tgggaatgta   6480
attcagctcc gccatcgccg cttccacttt ttcccgcgtt ttcgcagaaa cgtggctggc   6540
ctggttcacc acgcgggaaa cggtctgata agagacaccg gcatactctg cgacatcgta   6600
```

```
taacgttact ggtttcacat tcaccaccct gaattgactc tcttccgggc gctatcatgc   6660
cataccgcga aaggttttgc accattcgat ggtgtcaacg taaatgcatg ccgcttggga   6720
ggcagatagg taggcatggc ccccattttc aatacaagca acgcatgaga aagcccccgg   6780
aagatcacct tccggggggct tttttattgc gctccggcaa ttaaaaaagc ggctaaccac   6840
gccgcttttt ttacgtctgc aggcgaattg atctggtttg acagcttatc accaagccag   6900
ttacctcggt tcaaagagtt ggtagctcag agaaccttcg aaaaaccgcc ctgcaaggcg   6960
gttttttcgt tttcagagca agagattacg cgcagaccaa aacgatctca agaagatcat   7020
cttattaatc agataaaata ttataaatgt gagcggataa cattgacatt gtgagcggat   7080
aacaagatac tgagcacatc agcaggtttc acacaggaaa actagtatgg acaagaagta   7140
cagcatcggc ctggccatcg gcaccaactc tgtgggctgg gccgtgatca ccgacgagta   7200
caaggtgccc agcaagaaat tcaaggtgct gggcaacacc gaccggcaca gcatcaagaa   7260
gaacctgatc ggcgccctgc tgttcgacag cggagaaaca gccgaggcca ccgcgctgaa   7320
gagaaccgcc agaagaagat acaccagacg gaagaaccgg atctgctatc tgcaagagat   7380
cttcagcaac gagatggcca aggtggacga cagcttcttc cacagactgg aagagtcctt   7440
cctggtggaa gaggataaga agcacgagcg gcaccccatc ttcggcaaca tcgtggacga   7500
ggtggcctac cacgagaagt accccaccat ctaccacctg agaaagaaac tggtggacag   7560
caccgacaag gccgacctgc ggctgatcta tctggccctg gcccacatga tcaagttccg   7620
gggccacttc ctgatcgagg gcgacctgaa ccccgacaac agcgacgtgg acaagctgtt   7680
catccagctg gtgcagacct acaaccagct gttcgaggaa aacccccatca cgccagcgg   7740 cgtggacgcc aaggccatcc tgtctgccag actgagcaag agcagacggc tggaaaatct   7800
gatcgcccag ctgccggcg agaagaagaa tggcctgttc ggcaacctga ttgccctgag   7860
cctgggcctg acccccaact tcaagagcaa cttcgacctg gccgaggatg ccaaactgca   7920
gctgagcaag gacacctacg acgacgacct ggacaacctg ctggcccaga tcggcgacca   7980
gtacgccgac ctgtttctgg ccgccaagaa cctgtccgac gccatcctgc tgagcgacat   8040
cctgagagtg aacaccgaga tcaccaaggc ccccctgagc gcctctatga tcaagagata   8100
cgacgagcac caccaggacc tgaccctgct gaaagctctc gtgcggcagc agctgcctga   8160
gaagtacaaa gagattttct tcgaccagag caagaacggc tacgccggct acatcgatgg   8220
cggagccagc caggaagagt tctacaagtt catcaagccc atcctggaaa agatggacgg   8280
caccgaggaa ctgctcgtga agctgaacag agaggacctg ctgcggaagc agcggacctt   8340
cgacaacggc agcatccccc accagatcca cctgggagag ctgcacgcca ttctgcggcg   8400
gcaggaagat ttttacccat tcctgaagga caaccgggaa aagatcgaga agatcctgac   8460
cttccgcatc ccctactacg tgggccctct ggccagggga aacagcagat tcgcctggat   8520
gaccagaaag agcgaggaaa ccatcacccc ctggaacttc gaggaagtgg tggacaaggg   8580
cgccagcgcc cagagcttca tcgagcggat gaccaacttc gataagaacc tgcccaacga   8640
gaaggtgctg cccaagcaca gcctgctgta cgagtacttc accgtgtaca acgagctgac   8700
caaagtgaaa tacgtgaccg agggaatgag aaagcccgcc ttcctgagcg gcgagcagaa   8760
aaaagccatc gtggacctgc tgttcaagac caaccggaaa gtgaccgtga agcagctgaa   8820
agaggactac ttcaagaaaa tcgagtgctt cgactccgtg gaaatctccg gcgtggaaga   8880
tcggttcaac gcctccctgg gcacatacca cgatctgctg aaaattatca aggacaagga   8940
cttcctggac aatgaggaaa acgaggacat tctggaagat atcgtgctga ccctgacact   9000
```

```
gtttgaggac agagagatga tcgaggaacg gctgaaaacc tatgcccacc tgttcgacga   9060
caaagtgatg aagcagctga agcggcggag atacaccggc tggggcaggc tgagccggaa   9120
gctgatcaac ggcatccggg acaagcagtc cggcaagaca atcctggatt tcctgaagtc   9180
cgacggcttc gccaacagaa acttcatgca gctgatccac gacgcagcc tgacctttaa    9240
agaggacatc cagaaagccc aggtgtccgg ccagggcgat agcctgcacg agcacattgc   9300
caatctggcc ggcagccccg ccattaagaa gggcatcctg cagacagtga aggtggtgga   9360
cgagctcgtg aaagtgatgg gccggcacaa gcccgagaac atcgtgatcg aaatggccag   9420
agagaaccag accacccaga agggacagaa gaacagccgc gagagaatga gcggatcga   9480
agagggcatc aaagagctgg gcagccagat cctgaaagaa caccccgtgg aaaacaccca   9540
gctgcagaac gagaagctgt acctgtacta cctgcagaat gggcgggata tgtacgtgga   9600
ccaggaactg gacatcaacc ggctgtccga ctacgatgtg gacgctatcg tgcctcagag   9660
ctttctgaag gacgactcca tcgataacaa agtgctgact cggagcgaca gaaccgggg   9720
caagagcgac aacgtgccct ccgaagaggt cgtgaagaag atgaagaact actggcgcca   9780
gctgctgaat gccaagctga ttacccagag gaagttcgac aatctgacca aggccgagag   9840
aggcggcctg agcgaactgg ataaggccgg cttcatcaag agacagctgg tggaaacccg   9900
gcagatcaca aagcacgtgg cacagatcct ggactcccgg atgaacacta agtacgacga   9960
gaacgacaaa ctgatccggg aagtgaaagt gatcaccctg aagtccaagc tggtgtccga   10020
tttccggaag gatttccagt tttacaaagt gcgcgagatc aacaactacc accacgccca   10080
cgacgcctac ctgaacgccg tcgtgggaac cgccctgatc aaaaagtacc ctaagctgga   10140
aagcgagttc gtgtacggcg actacaaggt gtacgacgtg cggaagatga tcgccaagag   10200
cgagcaggaa atcggcaagg ctaccgccaa gtacttcttc tacagcaaca tcatgaactt   10260
tttcaagacc gagattaccc tggccaacgg cgagatccgg aagcggcctc tgatcgagac   10320
aaacggcgaa acaggcgaga tcgtgtggga taagggccgg gactttgcca ccgtgcggaa   10380
agtgctgtct atgccccaag tgaatatcgt gaaaaagacc gaggtgcaga caggcggctt   10440
cagcaaagag tctatcctgc ccaagaggaa cagcgacaag ctgatcgcca gaagaagga   10500
ctgggacccct aagaagtacg gcggcttcga cagccccacc gtggcctatt ctgtgctggt   10560
ggtggccaaa gtggaaaagg gcaagtccaa gaaactgaag agtgtgaaag agctgctggg   10620
gatcaccatc atggaaagaa gcagcttcga gaagaatccc atcgactttc tggaagccaa   10680
gggctacaaa gaagtgaaaa aggacctgat catcaagctg cctaagtact ccctgttcga   10740
gctggaaaac ggccggaaga atgctggc ctctgccggc gaactgcaga agggaaacga    10800
actggccctg ccctccaaat atgtgaactt cctgtacctg gccagccact atgagaagct   10860
gaagggctcc cccgaggata tgagcagaa acagctgttt gtggaacagc acaaacacta    10920
cctggacgag atcatcgagc agatcagcga gttctccaag agagtgatcc tggccgacgc   10980
taatctggac aaggtgctga gcgcctacaa caagcacaga gacaagccta tcagagagca   11040
ggccgagaat atcatccacc tgtttaccct gaccaatctg ggagccctg ccgccttcaa    11100
gtactttgac accaccatcg accggaagag gtacaccagc accaaagagg tgctggacgc   11160
caccctgatc caccagagca tcaccggcct gtacgagaca cggatcgacc tgtctcagct   11220
gggaggcgac gcgccgcgg agcagaaact catctctgaa gaagatctgg aacaaaagtt    11280
gatttcagaa gaagatctgg aacagaagct catctctgag gaagatctgt aataaggcgc   11340
```

```
gcctccttaa tgggacttgc agcctcggta ccaaattcca gaaaagacac ccgaaagggt    11400
gttttttcgt tttggtccca cagaatgagc atcatggctc tagtcgacat cggagaagag    11460
tacggctctt ttaaccgcct caagaaccag ataagtgaaa tctagttcca aactattttg    11520
tcatttttaa ttttcgtatt agcttacgac gctacaccca gttcccatct attttgtcac    11580
tcttccctaa ataatcctta aaaactccat ttccacccct cccagttccc aactattttg    11640
tccgcccaca gcggggcatt tttcttcctg ttatgtttgg gcgctgcatt aatgaatcgg    11700
ccaacgcgcg gggagaggcg gtttgcgtat gggcgctct tccgcttcct cgctcactga    11760
cccgctgcgc tcggtcgttc ggctgcggcg agcggtatca g                      11801
```

<210> SEQ ID NO 36
<211> LENGTH: 11653
<212> TYPE: DNA
<213> ORGANISM: Artificial Sequence
<220> FEATURE:
<223> OTHER INFORMATION: Synthetic construct

<400> SEQUENCE: 36

```
agcttatcgg ccagcctcgc agagcaggat tcccgttgag caccgccagg tgcgaataag      60
ggacagtgaa gaaggaacac ccgctcgcgg gtgggcctac ttcacctatc ctgcccggct     120
gacgccgttg gatacaccaa ggaaagtcta cacgaaccct ttggcaaaat cctgtatatc     180
gtgcgaaaaa ggatggatat accgaaaaaa tcgctataat daccccgaag cagggttatg     240
cagcggaaag tataccttaa ggaatcccct gataacgcag gaaagaacat gtgagcaaaa     300
ggccagcaaa aggccaggaa ccgtaaaaag gccgcactcc ctgcctctgt catcacgata     360
ctgtgatgcc atggctaatt cccatgtcag ccgttaagtg ttcctgtgtc actcaaaatt     420
gctttgagag gctctaaggg cttctcagtg cgttacatcc ctggcttgtt gtccacaacc     480
gttaaacctt aaaagcttta aaagccttat atattctttt ttttcttata aacttaaaa     540 ccttagaggc tatttaagtt gctgatttat attaattta ttgttcaaac atgagagctt      600
agtacgtgaa acatgagagc ttagtacgtt agccatgaga gcttagtacg ttagccatga     660
gggtttagtt cgttaaacat gagagcttag tacgttaaac atgagagctt agtacgtgaa     720
acatgagagc ttagtacgta ctatcaacag gttgaactgc tgatcttcag atcctctacg     780
ccggacgcat cgtggccgga tcttgcggcc gcaaaaatta aaatgaagt tttaaatcaa     840 tctaaagtat atatgagtaa acttggtctg acagttacca atgcttaatc agtgaggcac     900
caataactgc ctttgatctt ttctacgggg tctgacgctc agtggaacga aaactcacgt     960
taagggattt tggtcatgag attatcaaaa aggatcttca cctagatcct tttaaattaa    1020
aaatgaagtt ttaaatcaat ctaaagtata tatgagtaaa cttggtctga cagttaccaa    1080
tgcttaatca gtgaggcacc tatctcagcg atctgtctat ttcgttcatc catagttgcc    1140 tgactcccg tcgtgtagat aactacgata cgggagggct taccatctgg ccccagtgct    1200
gcaatgatac cgcgggaccc acgctcaccg gctccagatt tatcagcaat aaaccagcca    1260
gccggaaggg ccgagcgcag aagtggtcct gcaactttat ccgcctccat ccagtctatt    1320
aattgttgcc gggaagctag agtaagtagt tcgccagtta atagtttgcg caacgttgtt    1380
gccattgcta caggcatcgt ggtgtcacgc tcgtcgtttg gtatggcttc attcagctcc    1440
ggttcccaac gatcaaggcg agttacatga tcccccatgt tgtgcaaaaa agcggttagc    1500
tccttcggtc ctccgatcgt tgtcagaagt aagttggccg cagtgttatc actcatggtt    1560
atggcagcac tgcataattc tcttactgtc atgccatccg taagatgctt ttctgtgact    1620
```

```
ggtgagtact caaccaagtc attctgagaa tagtgtatgc ggcgaccgag ttgctcttgc    1680
ccggcgtcaa tacgggataa taccgcgcca catagcagaa ctttaaaagt gctcatcatt    1740
ggaaaacgtt cttcggggcg aaaactctca aggatcttac cgctgttgag atccagttcg    1800
atgtaaccca ctcgtgcacc caactgatct tcagcatctt ttactttcac cagcgtttct    1860
gggtgagcaa aaacaggaag gcaaaatgcc gcaaaaaagg gaataagggc gacacggaaa    1920
tgttgaatac tcatactctt cctttttcaa tattattgaa gcatttatca gggttattgt    1980
ctcatgagcg gatacatatt tgaatgtatt tagaaaaata aacaaatagg ggttccgcgc    2040
acatttcccc gaaaagtgcc acctgacgtc taagaaacca ttattatcat gacattaacc    2100
tataaaaata ggcgtatcac gaggcccttt cgtctcgcgc gtttcggtga tgacggtgaa    2160
aacctctgac acatgcagct cccggagacg gtcacagctt gtctgtaagc ggatgccggg    2220
agcagacaag cccgtcaggg cgcgtcagcg ggtgttggcg ggtgtcgggg ctggcttaac    2280
tatgcggcat cagagcagat tgtactgaga gtgcaccata tgcggtgtga ataccgcac    2340 agatgcgtaa ggagaaaata ccgcatcagg cgccattcgc cattcaggct gcgcaactgt    2400
tgggaagggc gatcggtgcg ggcctcttcg ctattacgcc agctagagga ccagccgcgt    2460
aacctggcaa aatcggttac ggttgagtaa taaatggatg ccctgcgtaa gcgggtgtgg    2520
gcggacaata aagtcttaaa ctgaacaaaa tagatctaaa ctatgacaat aaagtcttaa    2580
actagacaga atagttgtaa actgaaatca gtccagttat gctgtgaaaa agcatactgg    2640
acttttgtta tggctaaagc aaactcttca ttttctgaag tgcaaattgc ccgtcgtatt    2700 aaagagggc gtggggttcg aggtcgacgg tatcgataag ctagcttaat tagctgagct    2760
tggactcctg ttgatagatc cagtaatgac ctcagaactc catctggatt tgttcagaac    2820
gctcggttgc cgccgggcgt tttttattgg tgagaatcca gctagactg cgatgagtgg    2880 cagggcgggg cgtaattttt ttaaggcagt tattggtgcc cttaaacgcc tggggtaatg    2940
actctctagc ttgaggcatc aaataaaacg aaaggctcag tcgaaagact gggcctttcg    3000
ttttatctgt tgtttgtcgg tgaacgctct cctgagtagg acaaatccgc cgctaggagc    3060
ttgcggcccg gacgatgagc tcgaattggg gatcttgaag tacctattcc gaagttccta    3120
ttctctagaa agtataggaa cttcagagcg cttttgaagc tgatgctcga gatctcggct    3180
tgaacgaatt gttaggtggc ggtacttggg tcgatatcaa agtgcatcac ttcttcccgt    3240
atgcccaact ttgtatagag agccactgcg ggatcgtcac cgtaatctgc ttgcacgtag    3300
atcacataag caccaagcgc gttggcctca tgcttgagga gattgatgag cgcggtggca    3360
atgccctgcc tccggtgctc gccggagact gcgagatcat agatatagat ctcactacgc    3420
ggctgctcaa acctgggcag aacgtaagcc gcgagagcgc caacaaccgc ttcttggtcg    3480
aaggcagcaa gcgcgatgaa tgtcttacta cggagcaagt tcccgaggta atcggagtcc    3540
ggctgatgtt gggagtaggt ggctacgtct ccgaactcac gaccgaaaag atcaagagca    3600
gcccgcatgg atttgacttg gtcagggccg agcctacatg tgcgaatgat gcccatactt    3660
gagccaccta actttgtttt agggcgactg ccctgctgcg taacatcgtt gctgctgcgt    3720
aacatcgttg ctgctccata acatcaaaca tcgacccacg cgtaacgcg cttgctgctt    3780 ggatgcccga ggcatagact gtacaaaaaa acagtcataa caagccatga aaaccgccac    3840
tgcgccgtta ccaccgctgc gttcggtcaa ggttctggac cagttgcgtg agcgcatacg    3900
ctacttgcat tacagtttac gaaccgaaca ggcttatgtc aactgggttc gtgccttcat    3960
```

```
ccgtttccac ggtgtgcgtc catgggcaaa tattatacgc aaggcgacaa ggctcgagag    4020
ttcaacagac agccttcgtt cttatggccg ttcaggagga agttcctatt ccgaagttcc    4080
tattctctag aaagtatagg aacttcttga gaagagaaaa gaaaaccgcc gatcctgtcc    4140
accgcattac tgcaaggtag tggacaagac cggcggtctt aagttttttg gctgaaacga    4200
atgacgaaaa ggctgtctga gcaaatccag gaggtcgttt ttattaagca ccggtggagt    4260
gacgaccttc agcacgttcg tactgttcaa cgatggtgta gtcttcgttg tgggaggtga    4320
tgtccagttt gatgtcggtt ttgtaagcac ccggcagctg aaccggtttt ttagccatgt    4380
aggtggtttt aacttcagcg tcgtagtgac caccgtcttt cagtttcaga cgcattttga    4440
tttcaccttt cagagcaccg tcttccgggt acatacgttc ggtggaagct tcccaaccca    4500 tggtttttt ctgcataacc ggaccgtcgg acgggaagtt ggtaccacgc agtttaactt    4560
tgtagatgaa ctcaccgtct tgcagggagg agtcctgggt aacggtaaca acaccaccgt    4620
cttcgaagtt cataacacgt tcccatttga aaccttccgg gaaggacagt ttcaggtagt    4680
ccgggatgtc agccgggtgt ttaacgtaag ctttggaacc gtactggaac tgcggggaca    4740
ggatgtccca agcgaacggc agcggaccac cttggtaac tttcagttta gcggtctggg    4800
taccttcgta cggacgacct tcaccttcac cttcgatttc gaactcgtga ccgttaacgg    4860
aaccttccat acgaactttg aaacgcatga actctttgat aacgtcttcg ctactcgcca    4920
tggtaccttt ctcctctta attaattcag atctattata cctaggactg agctagctgt    4980
caaattcacc accctgaatt gactctcaaa ccgtattagc ccggtatttt ggaaatagcg    5040
gaagcactga cttttgttat caataaaaaa ggccccccgt tagggaggcc ttattgttcg    5100
tctactcgga agagcgagag acaacagaac ggtcagccac atgaattctt tcagctcagt    5160
cgataggtag taggcaagag tagtcgcacc tttggtcgaa aaaaaaagcc cgcactgtca    5220
ggtgcgggct tttttctgtg tttccccaaa agtaaaaacc cgccgaagcg ggttttttacg    5280 taaaacaggt gaaactgacc agacgagaag gctttggagg tgataatggg gctcaaggac    5340
cctggggtgc ctaatgagtg agctaactca cattaattgc gttgcgctca ctgcccgctt    5400
tccagtcgga aaacctgtcg tgccagctgc attaatgaat cggccaacgc gcggggagag    5460
gcggtttgcg tattgggcgc cagggtggtt tttcttttca ccagtgagac gggcaacagc    5520
tgattgccct tcaccgcctg gccctgagag agttgcagca agcggtccac gctggtttgc    5580
cccagcaggc gaaaatcctg tttgatggtg gttaacggcg ggatataaca tgagctgtct    5640
tcggtatcgt cgtatcccac taccgagata tccgcaccaa cgcgcagccc ggactcggta    5700
atggcgcgca ttgcgcccag cgccatctga tcgttggcaa ccagcatcgc agtgggaacg    5760
atgccctcat tcagcatttg catggtttgt tgaaaaccgg acatggcact ccagtcgcct    5820
tcccgttccg ctatcggctg aatttgattg cgagtgagat atttatgcca gccagccaga    5880
cgcagacgcg ccgagacaga acttaatggg cccgctaaca gcgcgatttg ctggtgaccc    5940
aatgcgacca gatgctccac gcccagtcgc gtaccgtctt catgggagaa aataatactg    6000
ttgatgggtg tctggtcaga gacatcaaga ataacgccg gaacattagt gcaggcagct    6060
tccacagcaa tggcatcctg gtcatccagc ggatagttaa tgatcagccc actgacgcgt    6120
tgcgcgagaa gattgtgcac cgccgcttta caggcttcga cgccgcttcg ttctaccatc    6180
gacaccacca gcgctggcac cagttgatcg cgcgagatt taatcgccgc gacaatttgc    6240 gacgcgcgt gcagggccag actggaggtg caacgccaa tcagcaacga ctgtttgccc    6300
gccagttgtt gtgccacgcg gttgggaatg taattcagct ccgccatcgc cgcttccact    6360
```

```
ttttcccgcg ttttcgcaga aacgtggctg gcctggttca ccacgcggga acggtctga      6420 taagagacac cggcatactc tgcgacatcg tataacgtta ctggtttcac attcaccacc      6480
ctgaattgac tctcttccgg gcgctatcat gccataccgc gaaaggtttt gcaccattcg      6540
atggtgtcaa cgtaaatgca tgccgcttgg gaggcagata ggtaggcatg gcccccattt      6600
tcaatacaag caacgcatga gaaagccccc ggaagatcac cttccggggg cttttttatt      6660
gcgctccggc aattaaaaaa gcggctaacc acgccgcttt ttttacgtct gcaggcgaat      6720
tgatctggtt tgacagctta tcaccaagcc agttacctcg gttcaaagag ttggtagctc      6780
agagaacctt cgaaaaaccg ccctgcaagg cggttttttc gttttcagag caagagatta      6840
cgcgcagacc aaaacgatct caagaagatc atcttattaa tcagataaaa tattataaat      6900
gtgagcggat aacattgaca ttgtgagcgg ataacaagat actgagcaca tcagcaggtt      6960
tcacacagga aaactagtat ggacaagaag tacagcatcg gcctggccat cggcaccaac      7020
tctgtgggct gggccgtgat caccgacgag tacaaggtgc ccagcaagaa attcaaggtg      7080
ctgggcaaca ccgaccggca cagcatcaag aagaacctga tcggcgccct gctgttcgac      7140
agcggagaaa cagccgaggc cacccggctg aagagaaccg ccagaagaag atacaccaga      7200
cggaagaacc ggatctgcta tctgcaagag atcttcagca acgagatggc caaggtggac      7260
gacagcttct tccacagact ggaagagtcc ttcctggtgg aagaggataa gaagcacgag      7320
cggcacccca tcttcggcaa catcgtggac gaggtggcct accacgagaa gtaccccacc      7380
atctaccacc tgagaaagaa actggtggac agcaccgaca aggccgacct gcggctgatc      7440
tatctggccc tggcccacat gatcaagttc cggggccact cctgatcga gggcgacctg       7500 aaccccgaca cagcgacgt ggacaagctg ttcatccagc tggtgcagac ctacaaccag       7560
ctgttcgagg aaaaccccat caacgccagc ggcgtggacg ccaaggccat cctgtctgcc      7620
agactgagca gagcagacg gctgaaaat ctgatcgccc agctgccgg cgagaagaag        7680 aatggcctgt tcggcaacct gattgccctg agcctgggcc tgacccccaa cttcaagagc      7740
aacttcgacc tggccgagga tgccaaactg cagctgagca aggacaccta cgacgacgac      7800
ctggacaacc tgctggccca gatcggcgac cagtacgccg acctgtttct ggccgccaag      7860
aacctgtccg acgccatcct gctgagcgac atcctgagag tgaacaccga gatcaccaag      7920 gccccctga gcgcctctat gatcaagaga tacgacgagc accaccagga cctgaccctg      7980
ctgaaagctc tcgtgcggca gcagctgcct gagaagtaca agagatttt cttcgaccag      8040 agcaagaacg gctacgccgg ctacatcgat ggcggagcca gccaggaaga gttctacaag      8100
ttcatcaagc ccatcctgga aaagatggac ggcaccgagg aactgctcgt gaagctgaac      8160
agagaggacc tgctgcggaa gcagcggacc ttcgacaacg gcagcatccc ccaccagatc      8220
cacctgggag agctgcacgc cattctgcgg cggcaggaag ttttttaccc attcctgaag      8280
gacaaccgga aaagatcga gaagatcctg accttccgca tccccactac cgtgggccct      8340
ctggccaggg gaaacagcag attcgcctgg atgaccagaa agagcgagga aaccatcacc      8400
ccctggaact tcgaggaagt ggtggacaag ggcgccagcg cccagagctt catcgagcgg      8460
atgaccaact tcgataagaa cctgcccaac gagaaggtgc tgcccaagca cagcctgctg      8520
tacgagtact tcaccgtgta caacgagctg accaaagtga aatacgtgac cgagggaatg      8580
agaaagcccg cctttctgag cggcgagcag aaaaaagcca tcgtgacct gctgttcaag      8640 accaaccgga agtgaccgt gaagcagctg aaagaggact acttcaagaa aatcgagtgc      8700
```

```
ttcgactccg tggaaatctc cggcgtggaa gatcggttca acgcctccct gggcacatac    8760
cacgatctgc tgaaaattat caaggacaag gacttcctgg acaatgagga aaacgaggac    8820
attctggaag atatcgtgct gaccctgaca ctgtttgagg acagagagat gatcgaggaa    8880
cggctgaaaa cctatgccca cctgttcgac gacaaagtga tgaagcagct gaagcggcgg    8940
agatacaccg gctggggcag gctgagccgg aagctgatca acggcatccg ggacaagcag    9000
tccggcaaga caatcctgga tttcctgaag tccgacggct cgccaacag aaacttcatg    9060 cagctgatcc acgacgacag cctgaccttt aaagaggaca tccagaaagc ccaggtgtcc    9120
ggccagggcg atagcctgca cgagcacatt gccaatctgg ccggcagccc cgccattaag    9180
aagggcatcc tgcagacagt gaaggtggtg gacgagctcg tgaaagtgat gggccggcac    9240
aagcccgaga acatcgtgat cgaaatggcc agagagaacc agaccaccca gaagggacag    9300
aagaacagcc gcgagagaat gaagcggatc gaagagggca tcaaagagct gggcagccag    9360
atcctgaaag aacaccccgt ggaaaacacc cagctgcaga acgagaagct gtacctgtac    9420
tacctgcaga atgggcggga tatgtacgtg gaccaggaac tggacatcaa ccggctgtcc    9480
gactacgatg tggacgctat cgtgcctcag agctttctga aggacgactc catcgataac    9540
aaagtgctga ctcggagcga caagaaccgg ggcaagagcg acaacgtgcc ctccgaagag    9600
gtcgtgaaga agatgaagaa ctactggcgc cagctgctga atgccaagct gattacccag    9660
aggaagttcg acaatctgac caaggccgag agaggcggcc tgagcgaact ggataaggcc    9720
ggcttcatca agagacagct ggtggaaacc cggcagatca caaagcacgt ggcacagatc    9780
ctggactccc ggatgaacac taagtacgac gagaacgaca aactgatccg ggaagtgaaa    9840
gtgatcaccc tgaagtccaa gctggtgtcc gatttccgga aggatttcca gttttacaaa    9900
gtgcgcgaga tcaacaacta ccaccacgcc cacgacgcct acctgaacgc cgtcgtggga    9960
accgccctga tcaaaaagta ccctaagctg gaaagcgagt tcgtgtacgg cgactacaag   10020
gtgtacgacg tgcggaagat gatcgccaag agcgagcagg aaatcggcaa ggctaccgcc   10080
aagtacttct tctacagcaa catcatgaac ttttttcaaga ccagattac cctggccaac   10140 ggcgagatcc ggaagcggcc tctgatcgag acaaacggcg aaacaggcga gatcgtgtgg   10200
gataagggcc gggactttgc caccgtgcgg aaagtgctgt ctatgcccca agtgaatatc   10260
gtgaaaaaga ccgaggtgca gacaggcggc ttcagcaaag agtctatcct gcccaagagg   10320
aacagcgaca agctgatcgc cagaaagaag gactgggacc ctaagaagta cggcggcttc   10380
gacagcccca ccgtggccta ttctgtgctg gtggtggcca aagtggaaaa gggcaagtcc   10440
aagaaactga agagtgtgaa agagctgctg gggatcacca tcatggaaag aagcagcttc   10500
gagaagaatc ccatcgactt tctggaagcc aagggctaca aagaagtgaa aaaggacctg   10560
atcatcaagc tgcctaagta ctccctgttc gagctggaaa acggccggaa gagaatgctg   10620
gcctctgccg cgaactgca gaagggaaac gaactggccc tgccctccaa atatgtgaac   10680
ttcctgtacc tggccagcca ctatgagaag ctgaagggct ccccgagga taatgagcag   10740 aaacagctgt ttgtggaaca gcacaaacac tacctggacg agatcatcga gcagatcagc   10800
gagttctcca agagagtgat cctggccgac gctaatctgg acaaggtgct gagcgcctac   10860
aacaagcaca gagacaagcc tatcagagag caggccgaga atatcatcca cctgtttacc   10920
ctgaccaatc tgggagcccc tgccgccttc aagtactttg acaccaccat cgaccggaag   10980
aggtacacca gcaccaaaga ggtgctggac gccacccctg accaccagag catcaccggc   11040
ctgtacgaga cacggatcga cctgtctcag ctgggaggcg acgcggccgc ggagcagaaa   11100
```

-continued

```
ctcatctctg aagaagatct ggaacaaaag ttgatttcag aagaagatct ggaacagaag    11160
ctcatctctg aggaagatct gtaataaggc gcgcctcctt aatgggactt gcagcctcgg    11220
taccaaattc cagaaaagac acccgaaagg gtgtttttc gttttggtcc cacagaatga    11280
gcatcatggc tctagtcgac atcggagaag agtacggctc ttttaaccgc ctcaagaacc    11340
agataagtga aatctagttc caaactattt tgtcattttt aattttcgta ttagcttacg    11400
acgctacacc cagttcccat ctattttgtc actcttccct aaataatcct taaaaactcc    11460
atttccaccc ctcccagttc ccaactattt tgtccgccca cagcggggca ttttcttcc     11520 tgttatgttt gggcgctgca ttaatgaatc ggccaacgcg cggggagagg cggtttgcgt    11580
attgggcgct cttccgcttc ctcgctcact gacccgctgc gctcggtcgt tcggctgcgg    11640
cgagcggtat cag                                                      11653
```